(12) United States Patent
Yamada et al.

(10) Patent No.: US 8,809,514 B2
(45) Date of Patent: Aug. 19, 2014

(54) TRIPARTITE OLIGONUCLEOTIDE COMPLEXES AND METHODS FOR GENE SILENCING BY RNA INTERFERENCE

(75) Inventors: Christina Yamada, Boulder, CO (US); Anastasia Khvorova, Boulder, CO (US); Rob Kaiser, Broomfield, CO (US); Emily Anderson, Lafayette, CO (US); Devin Leake, Denver, CO (US)

(73) Assignee: GE Healthcare Dharmacon, Inc., Lafayette, CO (US)

( * ) Notice: Subject to any disclaimer, the term of this patent is extended or adjusted under 35 U.S.C. 154(b) by 954 days.

(21) Appl. No.: 12/442,278

(22) PCT Filed: Sep. 20, 2007

(86) PCT No.: PCT/US2007/079074
§ 371 (c)(1),
(2), (4) Date: Dec. 9, 2009

(87) PCT Pub. No.: WO2008/036841
PCT Pub. Date: Mar. 27, 2008

(65) Prior Publication Data
US 2010/0093085 A1     Apr. 15, 2010

Related U.S. Application Data

(60) Provisional application No. 60/867,706, filed on Nov. 29, 2006, provisional application No. 60/826,702, filed on Sep. 22, 2006.

(51) Int. Cl.
*C07H 21/00* (2006.01)
*C12N 15/11* (2006.01)
*C12N 15/113* (2010.01)

(52) U.S. Cl.
CPC ............ *C12N 15/111* (2013.01); *C12N 15/113* (2013.01); *C12N 15/11* (2013.01)
USPC ........................................ 536/24.5; 536/23.1

(58) Field of Classification Search
CPC ..... C12N 15/111; C12N 15/113; C12N 15/11
See application file for complete search history.

(56) References Cited

U.S. PATENT DOCUMENTS

2003/0073640 A1   4/2003   Beigelman et al.
2005/0089902 A1   4/2005   Zheng et al.

FOREIGN PATENT DOCUMENTS

WO    WO2005019453    *   3/2005    ............. C12N 15/11

* cited by examiner

*Primary Examiner* — Jennifer McDonald
(74) *Attorney, Agent, or Firm* — Dorf & Nelson LLP; Scott D. Locke, Esq.

(57) ABSTRACT

Provided herein are tripartite oligonucleotide complexes which can be administered to a cell, tissue or organism to silence a target gene. The tripartite oligonucleotide complexes of the disclosure may include a conjugate moiety that facilitates delivery to a cell, tissue or organism without the aid of a transfection reagent.

25 Claims, 26 Drawing Sheets

- 16mer: 2'OMe C/U
- 19+2: Overhang: 2'OMe U (phosphodiester bonds)
- 35mer: always 5' phosphate
  - 2'F C/U in portion complementary to 19mer – unmod in portion complementary to 16mer (2'f)
  - 2'F C/U in portion complementary to 19mer – unmod in portion complementary to 16mer and UU – phosphorothioate (2'f 2'f)
  - 2'F C/U in whole strand – no mods on UU (2'f 2'f)
  - 2'F C/U in whole strand – phosphorothioate on UU (2'F PS 2'F)

TRIPARTITE OLIGONUCLEOTIDE COMPLEXES AND METHODS FOR GENE SILENCING BY RNA INTERFERENCE

This application is a National Stage Application of PCT/US2007/079074, filed Sep. 20, 2007, which claims the benefit of U.S. Provisional Application Ser. Nos. 60/826,702, filed Sep. 22, 2006, and 60/867,706 filed Nov. 29, 2006 and which applications are incorporated herein by reference. To the extent appropriate, a claim of priority is made to each of the above disclosed applications.

The present disclosure relates to the field of gene silencing using modified polynucleotides. Specifically, the disclosure provides tripartite oligonucleotide complexes that are linked to a molecule which facilitates delivery of the oligonucleotides into a cell, tissue or organism and methods of making and using them to silence a target gene.

BACKGROUND

RNA interference (RNAi) is a near-ubiquitous post-transcriptional gene regulatory mechanism that is mediated by microRNAs (miRNAs). Gene knockdown by these small, non-coding RNAs exploits the RNA Induced Silencing Complex (RISC) which utilizes the seed region (positions 2-7) of the miRNA guide strand to target the 3'UTR of mRNA for transcript cleavage and/or translational attenuation. Since the discovery that short, synthetic dsRNAs (referred to as small interfering RNAs, siRNAs) can enter the pathway, RNAi has been adopted as a tool for functional genomics.

SUMMARY

In one aspect, the present disclosure provides a tripartite oligonucleotide complex comprising:
  i) a first oligonucleotide between about 29 nucleotides and about 45 nucleotides in length having a target-dependent region and a target-independent region which is 5' to the target dependent region,
  ii) a second oligonucleotide between about 19 nucleotides and 28 nucleotides in length comprising an antisense region that has substantial complementarity to a target gene, and
  iii) a third oligonucleotide between about 8 nucleotides and about 18 nucleotides in length, The sequence of the target-dependent region of the first oligonucleotide is substantially complementary to that of the second nucleotide and the sequence of the target-independent region of the first oligonucleotide is substantially complementary to that of the third oligonucleotide, such that the first, second and third oligonucleotides are capable of forming a tripartite complex having at least two regions of duplex.

In one embodiment, the first oligonucleotide has a 3' overhang of 1-6 nucleotides, preferably a 3' overhang of 2 nucleotides.

In another embodiment, the first oligonucleotide is 37 nucleotides in length including a 3' overhang of 2 nucleotides, the second oligonucleotide is 21 nucleotides in length including a UU dinucleotide sequence at the 3' end, and the third oligonucleotide is 14 nucleotides in length.

In another embodiment, about 40% to about 90% of all nucleotides in each of the first, second and third oligonucleotides are chemically modified and the 5' terminus of the second oligonucleotide is phosphorylated. Preferably, all the Us and Cs in the first oligonucleotide are 2' O-methyl modified, all Us and Cs of the second oligonucleotide are 2' F modified, and all the nucleotides of the third oligonucleotide are 2' O-methyl modified.

In another embodiment, nucleotide positions in the target dependent region of the first oligonucleotide that are opposite nucleotide positions 18 and 19 of the second oligonucleotide counting from the 5' end are 2' O-methyl modified.

In another embodiment, a mismatch exists between position 10, 11, 12, 13, or 14 on the second oligonucleotide counting from the 5' end and the opposite nucleotide in the target dependent region of the first oligonucleotide, preferably between position 14 on the second oligonucleotide counting from the 5' end and the opposite nucleotide in the target dependent region of the first oligonucleotide.

In another embodiment, the sequence of the boundary between the target independent region of the first oligonucleotide and the target dependent of region of the first oligonucleotide is 5' G/AA 3'.

In another embodiment, the tripartite oligonucleotide complex further comprises at least one conjugate moiety attached to the third oligonucleotide. Preferably, the conjugate moiety is attached to the 3' terminus of the third oligonucleotide via a linker. The conjugate moiety is preferably selected from the group consisting of a steroid molecule, a vitamin, and a peptide. More preferably, the conjugate moiety is a steroid molecule selected from the group consisting of cholesterol, cholestanol, stigmasterol, cholanic acid, and ergosterol. More preferably, the conjugate moiety is cholesterol, the linker is a C5 linker molecule, and the third oligonucleotide has the structure:

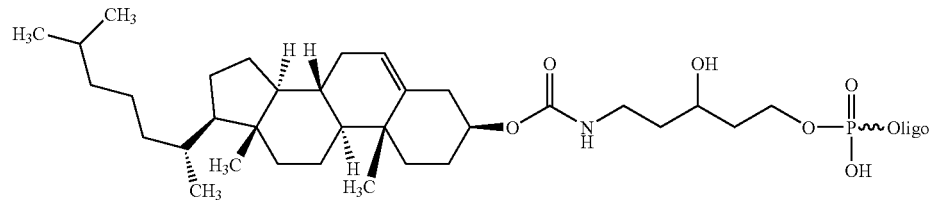

In another embodiment, the tripartite oligonucleotide complex further comprises at least one detectable label attached to the third oligonucleotide. Preferably, the detectable label is a dye molecule. In addition, the tripartite oligonucleotide complex may comprise both a conjugate moiety and a detectable label.

In another aspect, the disclosure provides a tripartite oligonucleotide complex comprising:
  i) a first oligonucleotide between about 29 nucleotides and about 45 nucleotides in length having a target-dependent region that has substantial complementarity to a target gene and a target-independent region which is 3' to the target dependent region, ii) a second oligonucleotide between about 19 nucleotides and 28 nucleotides in length comprising sequence that is substantially complementary to the target dependent region of the first oligonucleotide, iii) a third oligonucleotide between about 8 nucleotides and about 18 nucleotides in length comprising sequence that is substantially complementary to the target independent region of the first oligonucleotide, such that the first, second and third oligonucleotides are capable of forming a tripartite complex having at least two regions of duplex.

In another aspect, the disclosure provides a method for inhibiting expression of a target gene in a cell, the method comprising delivering to the cell a tripartite oligonucleotide complex of any of the preceeding embodiments. In one embodiment, the tripartite oligonucleotide complex is delivered to the cell by reverse transfection. In another embodiment, the tripartite oligonucleotide complex is delivered to the cell in vivo.

In another aspect, the disclosure provides a pharmaceutical composition comprising:
(a) a tripartite oligonucleotide complex of any of the preceeding embodiments; and
(b) at least one pharmaceutically acceptable carrier or diluent.

In another aspect, the disclosure provides a kit comprising a container, the container comprising:
(a) a tripartite oligonucleotide complex of any of the preceeding embodiments; and
(b) a reduced serum tissue culture medium.

Further aspects and embodiments will be apparent upon reading the disclosure.

BRIEF DESCRIPTION OF THE FIGURES

The preferred embodiments of the present disclosure have been chosen for purposes of illustration and description but are not intended to restrict the scope of the disclosure in any way. The benefits of the preferred embodiments of certain aspects of the disclosure are shown in the accompanying figures, wherein.

DETAILED DESCRIPTION

Figure 1:
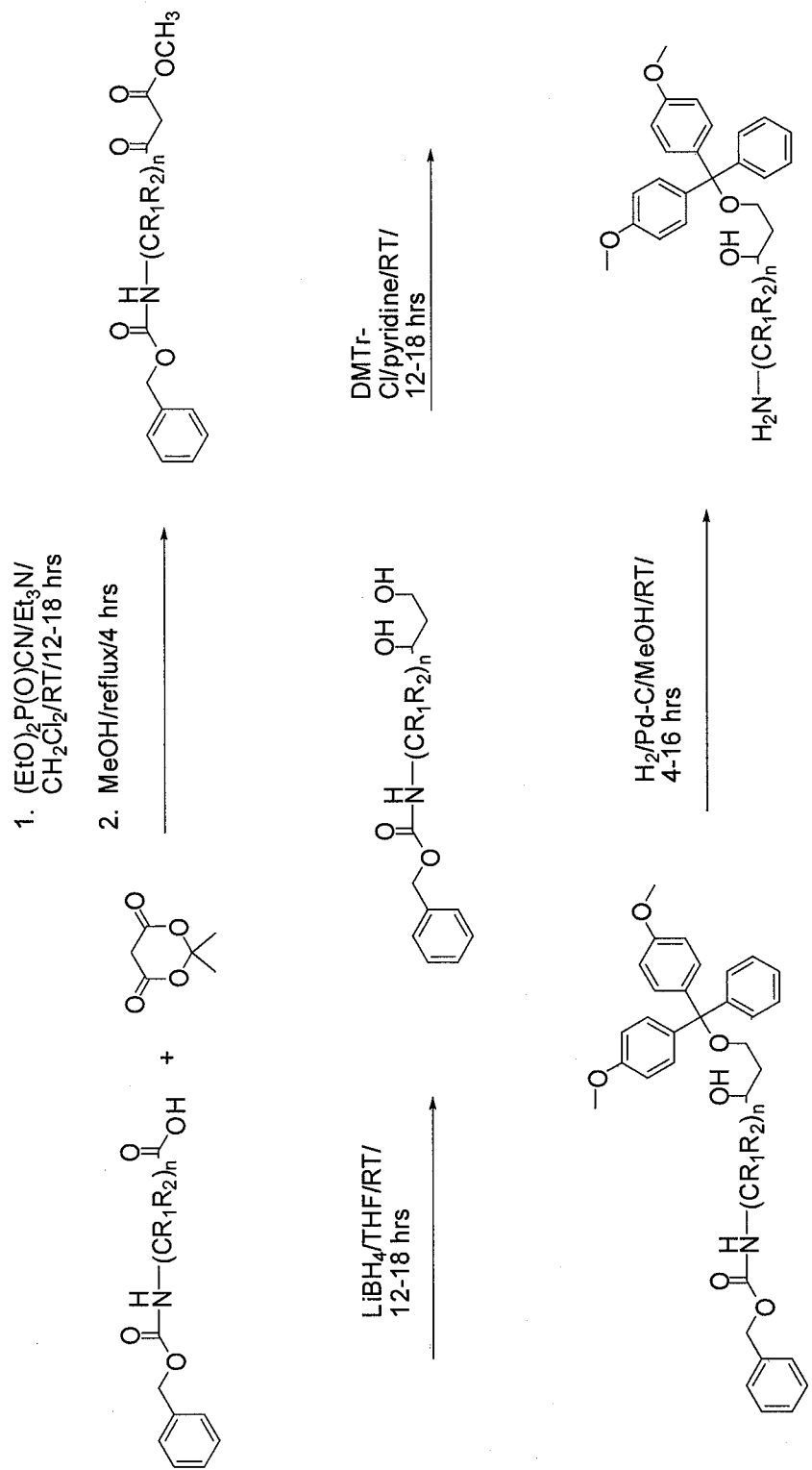
FIG. 1 shows a generalized synthesis scheme for the preparation of an ω-amino-1,3-diol linker compound.

The present disclosure will now be described in connection with preferred embodiments. These embodiments are presented to aid in an understanding of the present disclosure and are not intended, and should not be construed, to limit the disclosure in any way. All alternatives, modifications and equivalents that may become apparent to those of ordinary skill upon reading this disclosure are included within the spirit and scope of the present disclosure.

This disclosure is not a primer on compositions and methods for performing RNA interference. The present disclosure is directed to compositions and methods for performing RNA interference. Through the use of the present disclosure, modified polynucleotides, and derivatives thereof, one may improve the efficiency of RNA interference applications.

In general the terms and phrases used herein have art-recognized meanings, which can be found by reference to standard texts, journal references and contexts known to those skilled in the art. The following definitions are provided to clarify their specific use in the context of the disclosure.

The term "alkyl" refers to a hydrocarbyl moiety that can be saturated or unsaturated, and substituted or unsubstituted. It may comprise moieties that are linear, branched, cyclic and/or heterocyclic, and contain functional groups such as ethers, ketones, aldehydes, carboxylates, etc. Unless otherwise specified, alkyl groups are not cyclic, heterocyclic, or comprise functional groups.

Exemplary alkyl groups include but are not limited to substituted and unsubstituted groups of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and alkyl groups of higher number of carbons, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, and 2-ethylhexyl. The term alkyl also encompasses alkenyl groups, such as vinyl, allyl, aralkyl and alkynyl groups. Unless otherwise specified, alkyl groups are not substituted.

Substitutions within an alkyl group, when specified as present, can include any atom or group that can be tolerated in the alkyl moiety, including but not limited to halogens, sulfurs, thiols, thioethers, thioesters, amines (primary, secondary, or tertiary), amides, ethers, esters, alcohols and oxygen. The alkyl groups can by way of example also comprise modifications such as azo groups, keto groups, aldehyde groups, carboxyl groups, nitro, nitroso or nitrile groups, heterocycles such as imidazole, hydrazino or hydroxylamino groups, isocyanate or cyanate groups, and sulfur containing groups such as sulfoxide, sulfone, sulfide, and disulfide. Unless otherwise specified, alkyl groups do not comprise halogens, sulfurs, thiols, thioethers, thioesters, amines, amides, ethers, esters, alcohols, oxygen, or the modifications listed above.

Further, alkyl groups may also contain hetero substitutions, which are substitutions of carbon atoms, by for example, nitrogen, oxygen or sulfur. Heterocyclic substitutions refer to alkyl rings having one or more heteroatoms. Examples of heterocyclic moieties include but are not limited to morpholino, imidazole, and pyrrolidino. Unless otherwise specified, alkyl groups do not contain hetero substitutions or alkyl rings with one or more heteroatoms (i.e., heterocyclic substitutions).

The preferred alkyl group for a 2' modification is a methyl group with an O-linkage to the 2' carbon of a ribosyl moiety, i.e., a 2'-O-alkyl that comprises a 2'-O-methyl group.

The phrase "2'-O-alkyl modified nucleotide" refers to a nucleotide unit having a sugar moiety, for example a deoxyribosyl moiety that is modified at the 2' position such that an oxygen atom is attached both to the carbon atom located at the 2' position of the sugar and to an alkyl group. In various embodiments, the alkyl moiety consists essentially of carbons and hydrogens. A particularly preferred embodiment is one wherein the alkyl moiety is methyl.

The phrase "antisense strand" or "AS" as used herein, refers to a polynucleotide or region of a polynucleotide that is substantially (i.e., 80% or more) or 100% complementary to a target nucleic acid of interest. An antisense strand may be comprised of a polynucleotide region that is RNA, DNA or chimeric RNA/DNA. For example, an antisense strand may be complementary, in whole or in part, to a molecule of messenger RNA, an RNA sequence that is not mRNA (e.g., tRNA, rRNA and hnRNA) or a sequence of DNA that is either coding or non-coding. The phrase "antisense strand" includes the antisense region of the polynucleotides that are formed from two separate strands. The antisense strand can be modified with a diverse group of small molecules and/or conjugates.

The phrase "2' carbon modification" refers to a nucleotide unit having a sugar moiety, for example a moiety that is modified at the 2' position of the sugar subunit. A "2'-O-alkyl modified nucleotide" is modified at this position such that an oxygen atom is attached both to the carbon atom located at the 2' position of the sugar and to an alkyl group, e.g., 2'-O-methyl, 2'-O-ethyl, 2'-O-propyl, 2'-O-isopropyl, 2'-O-butyl, 2-O-isobutyl, 2'-O-ethyl-O-methyl (—OCH$_2$CH$_2$OCH$_3$), and 2'-O-ethyl-OH (—OCH$_2$CH$_2$OH). A "2' carbon sense modification" refers to a modification at the 2' carbon position of a nucleotide on the sense strand or within a sense region of polynucleotide. A "2' carbon antisense modification" refers to a modification at the 2' carbon position of a nucleotide on the antisense strand or within an antisense region of polynucleotide.

The term "complementary" refers to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G), or in any other manner that allows for the formation of stable duplexes.

Perfect complementarity or 100% complementarity refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other. For example, for two 20-mers, if only two base pairs on each strand can hydrogen bond with each other, the polynucleotide strands or regions exhibit 10% complementarity. In the same example, if 18 base pairs on each strand or each region can hydrogen bond with each other, the polynucleotide strands exhibit 90% complementarity. Substantial complementarity refers to polynucleotide strands or regions exhibiting 80% or greater complementarity.

The term "deoxynucleotide" refers to a nucleotide or polynucleotide lacking an OH group at the 2' or 3' position of a sugar moiety with appropriate bonding and/or 2',3' terminal dideoxy, instead having a hydrogen bonded to the 2' and/or 3' carbon.

The terms "deoxyribonucleotide" and "DNA" refer to a nucleotide or polynucleotide comprising at least one ribosyl moiety that has an H at its 2' position of a ribosyl moiety instead of an OH.

The term "gene" is defined to include both transcribed and non-transcribed elements. Thus, for instance, a gene can include any non-transcribed enhancer and/or promoter (i.e. genomic DNA) that plays a role in determining the level, timing, or tissue specificity of expression of a particular mRNA transcript or non-coding RNA. In addition, the 5' UTR, ORF, 3' UTR, introns, as well as non-coding RNAs such as miRNAs, piRNAs, tRNAs, rRNAs, and more, are included as elements of a gene.

The term "lipid-independent delivery reagent" refers to any number of molecules that can be conjugated to e.g. nucleic acids to enhance delivery in the absence of art-recognized nucleic acid delivery reagents (e.g. Lipofectamine, Lipofectamine 2000, DharmaFECTs). Such conjugates can themselves be lipid in nature, or consist of proteins, carbohydrates, or more.

The term "mismatch" includes a situation in where Watson-Crick base pairing does not take place between a nucleotide of a sense strand and a nucleotide of an antisense strand, where the nucleotides are flanked by a duplex comprising base pairs in the 5' direction of the mismatch beginning directly after (in the 5' direction) the mismatched position and in the 3' direction of the mismatch beginning directly after (in the 3' direction) the mismatched position. An example of a mismatch would be an A across from a G, a C across from an A, a U across from a C, an A across from an A, a G across from a G, a C across from a C, and so on. Mismatches are also meant to include an abasic residue across from a nucleotide or modified nucleotide, an acyclic residue across from a nucleotide or modified nucleotide, a gap, or an unpaired loop. In its broadest sense, a mismatch as used herein includes any alteration at a given position which decreases the thermodynamic stability at or in the vicinity of the position where the alteration appears, such that the thermodynamic stability of the duplex at the particular position is less than the thermodynamic stability of a Watson-Crick base pair at that position. Preferred mismatches include a G across from an A, and an A across from a C. A particularly preferred mismatch comprises an A across from an A, G across from a G, C across from a C, and U across from a U.

The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Preferably, a "nucleotide" comprises a cytosine, uracil, thymine, adenine, or guanine moiety.

Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, NH$_2$, NHR, NR$_2$, or CN, wherein R is an alkyl moiety as defined herein. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

Modified bases refer to nucleotide bases such as, for example, adenine, guanine, cytosine, thymine, and uracil, xanthine, inosine, and queuosine that have been modified by the replacement or addition of one or more atoms or groups. Some examples of types of modifications that can comprise nucleotides that are modified with respect to the base moieties, include but are not limited to, alkylated, halogenated, thiolated, aminated, amidated, or acetylated bases, in various combinations. More specific modified bases include, for example, 5-propynyluridine, 5-propynylcytidine, 6-methyladenine, 6-methylguanine, N,N-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4-thioribose, and other sugars, heterocycles, or carbocycles. The term nucleotide is also meant to include what are known in the art as universal bases. By way of example, universal bases include but are not limited to 3-nitropyrrole, 5-nitroindole, or nebularine.

Further, the term nucleotide also includes those species that have a detectable label, such as for example a radioactive or fluorescent moiety, or mass label attached to the nucleotide.

The term "overhang" refers to terminal non-base pairing nucleotide(s) resulting from one strand or region extending beyond the terminus of the complementary strand to which the first strand or region forms a duplex. One or more polynucleotides that are capable of forming a duplex through hydrogen bonding can have overhangs. The single-stranded region extending beyond the 3' and/or 5' end of the duplex is referred to as an overhang.

The term "ribonucleotide" and the phrase "ribonucleic acid" (RNA), refer to a modified or unmodified nucleotide or polynucleotide comprising at least one ribonucleotide unit. A ribonucleotide unit comprises an oxygen attached to the 2' position of a ribosyl moiety having a nitrogenous base attached in N-glycosidic linkage at the 1' position of a ribosyl moiety, and a moiety that either allows for linkage to another nucleotide or precludes linkage.

The phrase "RISC" is synonymous with "RNA induced silencing complex" and represents a complex of proteins that mediate RNAi (Hutvagner, G. FEBS Letters, 2005 579(26): 5850-7).

The phrase "RNA interference" and the term "RNAi" are synonymous and refer to the process by which a single, double, or tripartite molecule (e.g. an siRNA, an shRNA, an miRNA, a piRNA) exerts an effect on a biological process by interacting with one or more components of the RNAi pathway including but not limited to Drosha, RISC, Dicer, etc. The process includes, but is not limited to, gene silencing by degrading mRNA, attenuating translation, interactions with tRNA, rRNA, hnRNA, cDNA and genomic DNA, inhibition of as well as methylation of DNA with ancillary proteins. In addition, molecules that modulate RNAi (e.g. siRNA, piRNA, or miRNA inhibitors) are included in the list of molecules that enhance the RNAi pathway (Tomari, Y. et al. Genes Dev. 2005, 19(5):517-29).

The phrase "sense strand" refers to a polynucleotide or region that has the same nucleotide sequence, in whole or in part, as a target nucleic acid such as a messenger RNA or a sequence of DNA. When a sequence is provided, by convention, unless otherwise indicated, it is the sense strand (or region), and the presence of the complementary antisense strand (or region) is implicit.

The phrase "silencing" is defined as an RNAi-mediated reduction in gene expression that can be measured by any number of methods including PCR-based methods, Northern blot analysis, Branched DNA, western blot analysis, and other art recognized techniques.

The term "siRNA" and the phrase "short interfering RNA" refer to unimolecular nucleic acids and to nucleic acids comprised of two separate strands that are capable of performing RNAi and that have a duplex region that is between 18 and 30 base pairs in length. Additionally, the term siRNA and the phrase "short interfering RNA" include nucleic acids that also contain moieties other than ribonucleotide moieties, including, but not limited to, modified nucleotides, modified internucleotide linkages, non-nucleotides, deoxynucleotides and analogs of the aforementioned nucleotides.

The terms "target dependent" region or "target-independent" region, as used herein, are meant to indicate that a specified nucleotide sequence of the region has either a substantial homology to a target gene to be silenced or insubstantial levels of homology to any known sequences available in the databases describing the organism being targeted, respectively. In some embodiments, the target-dependent region of the first oligonucleotide becomes the sense strand following processing of a tripartite oligonucleotide complex by Dicer. In other embodiments, the target-dependent region of the first oligonucleotide becomes the antisense strand following processing of a tripartite oligonucleotide complex by Dicer.

The phrase "pharmaceutically acceptable carrier" means a pharmaceutically acceptable salt, solvent, suspending agent or vehicle for delivering a composition of the present disclosure to the animal or human. The carrier may be liquid, semisolid or solid, and is often synonymously used with diluent, excipient or salt. The phrase "pharmaceutically acceptable" means that an ingredient, excipient, carrier, diluent or component disclosed is one that is suitable for use with humans and/or animals without undue adverse side effects (such as toxicity, irritation, and allergic response) commensurate with a reasonable benefit/risk ratio. See Remington's Pharmaceutical Sciences 16th edition, Osol, A. Ed. (1980).

The term "tripartite molecule" or "tripartite oligonucleotide complex" refers to a reagent that is capable of silencing gene expression through the RNAi pathway and comprises three separate oligonucleotides. Tripartite oligonucleotide complexes can contain modified nucleotides, conjugate moieties, as well as mismatches, that enhance functionality, specificity, or delivery.

The following embodiments are presented in order to aid in an understanding of the present disclosure and are not intended, and should not be construed, to limit the disclosure in any way. All alternatives, modifications and equivalents that may become apparent to those of ordinary skill upon reading this disclosure are included within the spirit and scope of the present disclosure. Furthermore, it should be noted that while much of the following describes the disclosure in the context of siRNA, the embodiments of the disclosure can be applied to other nucleic acids including, but not limited to, miRNA, piRNA, miRNA and piRNA inhibitors, tRNA, and more.

According to a first aspect, the present disclosure is directed to a tripartite oligonucleotide complex comprising:
  i) a first oligonucleotide having a target-dependent region and a target-independent region which is 5' to the target dependent region,
  ii) a second oligonucleotide comprising an antisense region that has substantial complementarity to a target gene, and
  iii) a third oligonucleotide.

The sequence of the target-dependent region (sometimes referred to herein as "region one" or "region 1") of the first oligonucleotide is substantially complementary to the sequence of the second oligonucleotide. The sequence of the target-independent region (sometimes referred to as "the non-targeting region", "region 2" or "region two") of the first oligonucleotide is substantially complementary to the sequence of the third oligonucleotide. Thus, the first, second and third oligonucleotides (sometimes referred to herein "oligonucleotide 1", "oligonucleotide 2", and "oligonucleotide 3", respectively) are capable of forming a tripartite complex with at least two duplex regions having target dependent and target independent sequences separated by a gap or a break.

Optionally, at least one of the three oligonucleotides is linked via a linker molecule to at least one conjugate moiety that facilitates delivery of the oligonucleotide complex into a cell, tissue or organism.

Optionally, at least one of the three oligonucleotides is attached to a detectable label such as a dye molecule, a radiolabel, or a mass label.

The tripartite oligonucleotide complex of the disclosure is designed such that a functional silencing molecule is generated after entry into a cell. Dicer processing of a tripartite oligonucleotide complex of the disclosure produces a functional silencing molecule in which the sense strand is formed by at least a portion of the target dependent region of the first oligonucleotide, and in which the antisense strand is formed by at least a portion of the second oligonucleotide.

The First Oligonucleotide

In preferred embodiments, the first oligonucleotide is from about 29 to about 45 nucleotides in length with a minimum of about 19 nucleotides of the first oligonucleotide being dedicated to the target dependent region. The first oligonucleotide may also include a nucleotide overhang at the 3' end (i.e. nucleotides that extend beyond the end of the duplex formed between the first oligonucleotide and the second oligonucleotide). The overhang can include modified internucleotide linkages, such as phosphorothioate linkages. In one preferred embodiment the first oligonucleotide is 37 nucleotides in length with the target dependent region being 21 nucleotides, the target independent region (which is 5' of the target dependent region) being 14 nucleotides, and with a 2 (non-pairing) nucleotide overhang on the 3' terminus. In another embodiment, the first oligonucleotide is 35 nucleotides in length with the target dependent region being 19 nucleotides, the target independent region being 14 nucleotides, and with a 2 (non-pairing) nucleotide overhang on the 3' terminus. In yet another embodiment, the first oligonucleotide is 35 nucleotides in length with the target dependent region being 21 nucleotides, the target independent region being 12 nucleotides, and with a 2 (non-pairing) nucleotide overhang on the 3' terminus.

Both the target dependent and the target independent regions of the first oligonucleotide can vary in the degree of complementarity they have with their respective annealing partners (i.e. the degree of complementary between the target dependent region of the first oligonucleotide and the second oligonucleotide, and the degree of complementarity between the target independent region of the first oligonucleotide and the third oligonucleotide). Preferably, the degree of complementarity between the target dependent and target independent regions of the first oligonucleotide with the second and third oligonucleotides (respectively) is greater than 80%. More preferably the level of complementarity is greater than 90%. Most preferably, the degree of complementarity is greater than 95%.

Less than perfect complementarity might be desired include instances where bulges and/or base pair mismatches between the target dependent region of the first oligonucleotide and the second oligonucleotide are desired in order to optimize e.g. Dicer processing or RISC strand selection or processing of the molecule. In this case of mismatches, preferably a mismatch is formed between position 10, 11, 12, 13, or 14 of oligonucleotide 2 (counting from the 5' end and not including any 5' overhang which may present) and the opposite nucleotide in oligonucleotide 1. Most preferably, a mismatch is formed between position 14 of oligonucleotide 2 (counting from the 5' end and not including any 5' overhang which may present) and the opposite nucleotide in oligonucleotide 1. Relative to the same tripartite oligonucleotide complex which does not contain a mismatch, a tripartite oligonucleotide complex with a mismatch has a base substitution on oligonucleotide 1. For example, if position 14 of oligonucleotide 2 is "A" (which would base-pair with a "U" in a target mRNA), then the opposite position of the target dependent region of oligonucleotide 1 may be "U" (no mismatch) or "G" (mismatch), "C" (mismatch), or "A" (mismatch). In this way, complementarity is maintained between the target mRNA and oligonucleotide 2 at the site of the mismatch. Similarly, a bulge may be formed by one or more nucleotides of oligonucleotide 1. Relative to the same tripartite oligonucleotide complex which does not contain a bulge, a tripartite oligonucleotide complex with a bulge has one or more bases inserted on oligonucleotide 1. In this way, as with the mismatches, perfect complementarity is maintained between the target mRNA and oligonucleotide 2.

Any nucleotide of the first oligonucleotide can contain one or more modifications to enhance stability, functionality, processing, or to minimize activation of one or more proteins involved in the innate immune response pathway(s). Preferably, the modifications include, but are not limited to 2'-O-alkyl modifications of nucleotides 1 and 2 of a post-Dicer processed tripartite oligonucleotide complex i.e., nucleotides 1 and 2 of the sense strand resulting from Dicer processing of the tripartite complex (counting from the 5' end of the post-Dicer processed sense strand). In the case where the full length of the first oligonucleotide is 35 nts (not including possible 3' overhangs) and the target independent region of the first oligonucleotide is 14 nts in length, the modifications would be on nucleotides 17 and 18 counting from the 5' end of the first oligonucleotide (Dicer cuts the first oligonucleotide in this example between nucleotides 16 and 17). Following Dicer processing of this tripartite oligonucleotide complex, the resulting sense-antisense strand duplex (a functional silencing molecule) would contain 2'-O-alkyl modifications on positions 1 and 2 of the sense strand, a modification pattern that enhances specificity by preventing the sense strand from entering RISC. It is within the abilities of one skilled in the art to determine which nucleotide positions in the first oligonucleotide will form nucleotides 1 and 2 of the sense strand that results from Dicer processing of a tripartite oligonucleotide complex according to the disclosure. For example, tripartite molecules can be end-labeled with a radio-isotope and subsequently digested in vitro with Dicer (see Vermeulen et al., (2005) RNA 11: 6740682). The products of digestion can then be analyzed on a polyacrylamide gel to determine the exact position of Dicer cleavage. Based on these data, positions 1 and 2 (of oligonucleotide 1) of the post-Dicer processed molecule can be determined and modified with e.g., 2'-O-methyl moieties in subsequent tripartite synthesis.

Figure 15:
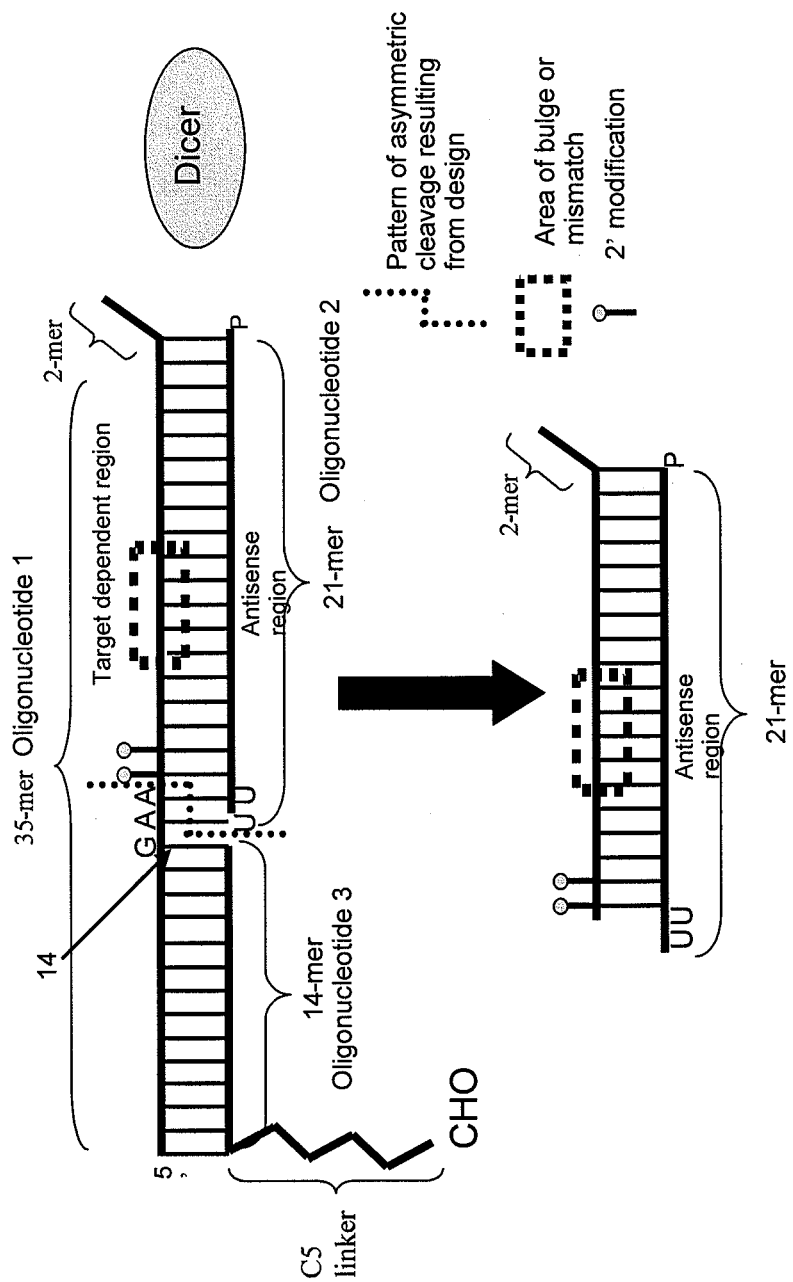
FIG. 15 shows a tripartite oligonucleotide complex in which oligonucleotide 1 has a 14 nucleotide target independent region 5' of a 21 nucleotide target dependent region. Oligonucleotide 1 also includes a 2 nucleotide overhang at the 3' end, thus making the total length of oligonucleotide 1 equal to 37 nucleotides. The nucleotides in oligonucleotide 1 which become nucleotides 1 and 2 of the sense strand following Dicer processing (which are opposite nucleotides 19 and 18 respectively of oligonucleotide 2) are 2' modified as indicated. Oligonucleotide 2 (which forms the antisense strand following Dicer processing) is 21 nucleotides in length, including a UU dinucleotide at the 3' end. Oligonucleotide 2 also includes a 5' phosphate. Bulges and mismatches between oligonucleotide 1 and 2 may be formed at the indicated position. Oligonucleotide 3 is 14 nucleotides in length and includes a cholesterol molecule attached to the 3' end via a C5 linker. Dicer asymmetrically cleaves the tripartite molecule at the indicated location to yield a duplex molecule in which the antisense strand has a UU 3' overhang and the sense strand strand (formed by the target dependent region of oligonucleotide 1) has a 2 nucleotide 3' overhang.

In preferred embodiments, the sequence of the boundary between the target independent region and the target dependent region of the first oligonucleotide is 5' G/AAX$_1$X$_2$ 3' i.e. the 3' most nucleotide in the target independent region is "G" and the nucleotides 1 and 2 of the target dependent region (counting from the 5' end of the target dependent region) are both "A." X$_1$ and X$_2$ are nucleotides 3 and 4 of the target dependent region (counting from the 5' end of the target dependent region) which becomes nucleotides 1 and 2 of the sense strand following Dicer processing (counting from the 5' end of the sense strand following Dicer processing). As described above, X$_1$ and X$_2$ are preferably 2'-O-alkyl modified. See FIG. 15.

In preferred embodiments, the sequence of the target independent region of the first nucleotide is a non-targeting sequence. Non-targeting sequences have limited levels of homology with any genes, particularly the transcribed regions of a gene, in the target organism and as such, have limited ability (preferably no ability) to modulate gene expression by the RNAi pathway. Sequences can be assessed for their value as a non-targeting sequence by submitting them for nucleotide analysis (BLASTN analysis) using the NCBI database. A preferred non-targeting sequence for use in the context of the human genome (i.e. when the tripartite oligonucleotide complexes are used in human cells) is 5'-AGCUCUCAUCCAUG. SEQ ID NO:1

In preferred embodiments, the target independent region of the first oligonucleotide is less than 19 nucleotides and longer than 8 nucleotides in length. For example, the target independent region of the first oligonucleotide may be 14 nucleotides in length. Sequences that are less than 19 nucleotides in length exhibit poor entry and/or affinity toward RISC and other proteins that mediate RNAi, and as such, are poor gene modulators.

In particularly preferred embodiments, the sequence of the target independent region of the first oligonucleotide is a non-targeting sequence that is less than 19 nucleotides but more than 8 nucleotides in length. Such target independent region sequences have a drastically limited ability to alter gene expression by the RNAi pathway.

The Second Oligonucleotide

The second oligonucleotide can also be referred to as the antisense strand or the targeting strand since following Dicer processing of a tripartite oligonucleotide complex, the second oligonucleotide enters RISC and targets one or more transcripts. The sequence of the antisense strand is complementary to the target dependent region of the first oligonucleotide as well as a target gene sequence. The level of complementarity with the target dependent region of the first oligonucleotide and/or the target gene sequence need not be identical and can vary considerably. Preferably, the level of complementarity is greater than 70%. More preferably, the level of complementarity is greater than 80%. Even more preferably, the level of complementarity is greater than 90%. Most preferably still, the level of complementarity is greater than 95%.

In preferred embodiments, the second oligonucleotide is from about 19 nucleotides to about 28 nucleotides in length. More preferably, the second oligonucleotide is from about 19 nucleotides to about 23 nuncleotides in length and contains a phosphate group on the 5' terminus. Most preferably, the second oligonucleotide is 21 nucleotides in length and contains a phosphate group on the 5' terminus. Duplex regions formed by the target dependent region of the first oligonucleotide and the second oligonucleotide can include bulges and mismatches that enhance RISC entry (and thus functionality), alter specificity, and/or alter and/or enhance the position or efficiency of Dicer processing (as described above). Duplex regions formed by the second oligonucleotide and the target gene sequence (e.g. between the second oligonucleotide and a target mRNA) can also include bulges and mismatches.

The sequence of the second oligonucleotide can be selected by a variety of art-recognized methods including random selection based on the sequence of the gene. Preferably, one or more rational design and/or neural networking algorithms that select sequences on the basis of position-specific nucleotide preferences, differential end stability, internal stability profiles, and the like, can be employed. Detailed descriptions of the criteria for the rational design of antisense strands for efficient gene silencing can be found in WO 2004/045543, WO 2006/006948, WO 2005/078095, WO 2005/097992, and WO 2005/090606As recent studies have demonstrated a correlation between the size of an off-target signature and the number of different transcripts that contain a 3' UTR complement to the siRNA seed region (positions ~2-7 of the RISC entering strand), processes that select sequences on the basis of seed complement frequency (SCF) can also be incorporated into the selection process. Lastly, sequences that can induce particular phenotypes (e.g. toxic sequences such as GUCCUUCAA, see Judge, A. D. Nat. Biotechnology, 23:457-62; or sequences that have miRNA seed regions) can be eliminated from second oligonucleotide sequences (see US2005/0203043). All of these procedures can be performed with or without the aid of computer hardware and software.

As was the case with the first oligonucleotide, chemical modifications can be incorporated into the second oligonucleotide to enhance specificity, stability, and/or Dicer processing. In one embodiment, the modifications are 2'-O-alkyl modifications and are located in the seed region (positions 2-7 of the antisense strand) of the second oligonucleotide. More preferably, the 2'-O-alkyl modifications are on the first and second, first, second and third, the second, or the second and third nucleotides, counting from the 5' terminus of the strand. In addition, or alternatively, all of the Cs and Us of the second oligonucleotide can be 2' halogen modified, preferably 2'F modified. In addition, or alternatively, internucleotide linkage modifications (e.g. phosphorothioate of 3' terminal nucleotides) can be included to enhance stability of the pre- and post-Dicer processed molecule.

In some embodiments, the tripartite oligonucleotide complex is designed such that Dicer processing of the tripartite oligonucleotide complex yields a duplex RNAi silencing molecule in which the 3' end of the antisense strand (formed by the second oligonucleotide) has an overhang. Preferably, the overhang is a 2 nucleotide overhang, more preferably a UU overhang. For example, in one embodiment, the 3' end of the second oligonucleotide contains a UU dinucleotide sequence which base pairs with a AA dinucleotide sequence located at the 5' end of the target dependent region of the first oligonucleotide. The most 3' base in the target independent region of the first oligonucleotide is G (i.e. the sequence of the boundary between the target independent region and the target dependent region of the first oligonucleotide is 5' G/AA 3' as described above). Upon Dicer processing of this tripartite oligonucleotide complex, a duplex is formed in which the antisense strand (formed by the second oligonucleotide) has a UU overhang at the 3' end, and in which the sense strand lacks the AA dinucleotide (thus, position 1 of the Dicer-processed sense strand, counting from the 5' end of the Dicer-processed sense strand, corresponds to position 3 of the second oligonucleotide in the tripartite complex). See FIG. 15. In preferred embodiments, the overhang comprises modified internucleotide linkages such as, for example, phosphorothioate linkages. For detailed description, see Vermeulen, RNA, 2005 May; 11(5):674-82.

In another embodiment, the 3' end of the second oligonucleotide forms an "internal" overhang, preferably a dinucleotide overhang, within the tripartite oligonucleotide complex. For example, oligonucleotide 2 may be 21 nucleotides in length, including 19 nucleotides that base pair with the target dependent region of oligonucleotide 1 and further including a 2 nucleotide 3' overhang (nucleotides 20 and 21 of oligonucleotide 2). In this embodiment, nucleotide 19 of oligonucleotide 2 base pairs with the 5'-most nucleotide of the target dependent region of oligonucleotide 1; and the 3'-most nucleotide in the target independent region of oligonucleotide 1 base pairs with nucleotide 1 of the third oligonucleotide. Thus, the 3' overhang in oligonucleotide 2 in this example is located at the point at which oligonucleotide 3 and oligonucleotide 2 abutt.

The Third Oligonucleotide

The third oligonucleotide comprises a sequence that is the reverse complement of the target-independent region of the first oligonucleotide. Preferably, the length of the third oligonucleotide is less than 19 nts but longer than 8 nucleotides (again, to minimize possible entry into the RNAi pathway). More preferably, the third oligonucleotide is 14 nucleotides in length. In preferred embodiments, the sequence of the third nucleotide is a non-targeting sequence. More preferably, the third oligonucleotide is fourteen bases in length and has the sequence of 5'-CAUGGAUGAGAGCU. SEQ ID NO:2

All of the variant structural attributes (e.g. bulges, mismatches) as well as modifications described for the first and second oligonucleotides are equally applicable for the third oligonucleotide in order to enhance functionality, processing, stability, and to minimize the recognition and activation of components of the innate immune response pathway. For example, all nucleotides in the third oligonucleotide may be 2' O-methyl modified to prevent incorporation of this oligonucleotide into RISC.

Conjugate Moieties

As detailed above, the tripartite oligonucleotide complexes of the disclosure optionally include at least one conjugate moiety. Thus, in some embodiments a tripartite oligonucleotide complex comprises a conjugate moiety, and in other embodiments a tripartite oligonucleotide complex does not include a conjugate moiety.

Conjugate moieties of the disclosure (also referred to simply as "conjugates") can vary widely and target entry into the cell by a variety of means. For instance, conjugate moieties can be lipid in nature and deliver their payload (e.g. siRNA or other nucleic acid), by inserting themselves into the membrane and being absorbed into the cell by one of several mechanisms including endocytosis. As such, lipid-based conjugate moieties can include cationic lipids, neutral lipids, sphingolipids, and fatty acids including stearic, oleic, elaidic, linoleic, linoleaidic, linolenic, and myristic acids. Alternatively, the conjugate moieties can be proteinaceous in nature including peptides that are membrane translocating (e.g. TAT, penetratin, MAP) or cationic (e.g. poly(lys), poly(arg), poly (his), poly(lys/arg/his), or protamine).

Alternatively, the conjugate moiety can be a small molecule that, for instance, targets a particular receptor or (again) is capable of inserting itself into the membrane and being absorbed by endocytic pathways. Thus, small molecules based on adamantanes, polyaromatic hydrocarbons (e.g. napthalenes, phenanthrenes, or pyrenes), macrocyles, steroids, or other chemical scaffolds, are all potential conjugates for the disclosure.

In yet another alternative, conjugate moieties can be based on cationic polymers. Numerous studies have demonstrated that cationic polymers such as cationic albumin can greatly enhance delivery to particular cell types and/or tissues (e.g. brain delivery, see Lu, W. et. al. (2005) J of Control Release 107:428-448). Given the benefits of these molecules, the conjugate moieties can be cationic polymers such as polyethyleneimine, dendrimers, poly(alkylpyridinium) salts, or cationic albumin.

In some cases, the conjugate moieties are ligands for receptors or can associate with molecules that (in turn) associate with receptors. Included in this class are bile acids, small molecule drug ligands, vitamins, aptamers, carbohydrates, peptides (including but not limited to hormones, proteins, protein fragments, antibodies or antibody fragments), viral proteins (e.g. capsids), toxins (e.g. bacterial toxins), and more. Also included in this class are conjugates that are steroidal in nature e.g. cholesterol, cholestanol, cholanic acid, stigmasterols, pregnolones, progesterones, corticosterones, aldosterones, testosterones, estradiols, ergosterols, and more), Preferred conjugate moieties of the disclosure are cholesterol (CHOL), cholestanol (CHLN), cholanic acid (CHLA), stigmasterol (STIG), and ergosterol (ERGO). In certain preferred embodiments, the conjugate moiety is cholesterol.

In the case of cholesterol, the molecule can associate with one or more proteins or protein complexes in e.g. the blood (e.g. albumin, LDLs, HDLs, IDLs, VLDLs, chylomicron remnants, and chylomicrons) and be delivered to the cell through association with the appropriate receptor for that complex (e.g. the LDLR, low density lipoprotein receptor). The example of delivery via the cholesterol-LDL association is particularly attractive since the opportunity for dozens or hundreds of siRNA to be delivered in a single LDL particle is feasible. For that reason, the inventors can envision packaging cholesterol conjugated siRNAs or siRNA conjugated to derivatives of cholesterol, in one or more natural carriers (e.g. LDLs) in vitro, and using this as an in vivo delivery system.

In yet another embodiment, the molecules that target a particular receptor are modified to eliminate the possible loss of conjugated siRNAs to other sources. For instance, when cholesterol-conjugated siRNAs are placed in the presence of normal serum, a significant fraction of this material will associate with the albumin and/or other proteins in the serum, thus making the siRNA unavailable for e.g. interactions with desired molecules. For this reason, the conjugate moieties of the disclosure can be modified in such a way that they continue to bind or associate with their intended target but have lesser affinities with unintended binding partners (e.g. serum albumin).

It is also envisioned that the tripartite oligonucleotide complexes of the disclosure are associated with two or more conjugates of different nature, which can provide different functions. For example, the tripartite molecule can be linkered to both cholesterol and a targeting molecule (e.g. receptor ligand or a binding fragment thereof) which can selectively deliver the tripartite complex to a specific cell or tissue so that the tripartite oligonucleotide can silence a target gene in the specific cell or tissue only.

The Linker

As detailed above, the tripartite oligonucleotide complexes of the disclosure optionally include at least one conjugate moiety which is attached to at least one oligonucleotide via a linker. Though not wishing to be limited by definitions or conventions, in this application the length of the linker is described by counting the number atoms that represents the shortest distance between the atom that joins the conjugate moiety to the linker and the oxygen atom of the terminal phosphate moiety associated with the oligonucleotide through which the linker is attached to the oligonucleotide (preferably to the third oligonucleotide). For example, in embodiments where the conjugate moiety is joined to the linker via a carbamate linkage, the length of the linker is described as the number of atoms that represents the shortest distance between the nitrogen atom of the carbamate linkage and the oxygen atom of the phosphate linkage. In cases where ring structures are present, counting the atoms around the ring that represent the shortest path is used to define the linker length.

Non-limiting examples of structures of the conjugate-linker which may be used in the compositions and methods of the disclosure are provided in Table 1. Alternative chemistries can be used and provide a similar length linker to linkers exemplified in Table 1. for example, linkers/linker chemistries that are based on ω-amino-1,3-diols, ω-amino-1,2-diols, hydroxyprolinols, ω-amino-alkanols, diethanolamines, ω-hydroxy-1,3-diols, ω-hydroxy-1,2-diols, ω-thio-1,3-diols, ω-thio-1,2-diols, ω-carboxy-1,3-diols, ω-carboxy-1,2-diols, ω-hydroxy-alkanols, ω-thio-alkanols, ω-carboxy-alkanols, functionalized oligoethylene glycols, allyl amine, acrylic acid, alyl alcohol, propargyl amine, propargyl alcohol, and more, can be applied in this context to generate linkers of the appropriate length.

In some embodiments a linker not only provides a site of attachment to the conjugate moiety, but also provides functional sites for attachment to the support and for initiation of oligonucleotide synthesis. Preferably, these sites are hydroxyl groups; most preferably, they are a primary hydroxyl group and a secondary hydroxyl group, to allow them to be chemically distinguished during synthesis of the conjugate-modified solid support. One hydroxyl group, preferably the primary hydroxyl group, is protected with a protecting group that can be removed as the first step in the synthesis of the oligonucleotide, according to methods well understood by those of ordinary skill in the art. Preferably, this protecting group is chromophoric and can be used to estimate the amount of the conjugate moiety attached to the solid support; most preferably, the group is chosen from triphenylmethyl (Tr), monomethoxytriphenylmethyl (MMTr), dimethoxytriphenylmethyl (DMTr) and trimethoxytriphenylmethyl (TMTr). Another hydroxyl group, preferably a secondary hydroxyl group, is derivatized with a functionalized tether that can covalently react with a functional group on the solid synthesis support, according to methods well understood by those of ordinary skill in the art. Preferable tethers are, by way of example, dicarboxylic acids such as succinic, glutaric, terephthalic, oxalic, diglycolic, and hydroquinone-O,O'-diacetic. One of the carboxylic acid functionalities of the tether is reacted with the hydroxyl to provide an ester linkage that is cleavable using basic reagents (hydroxide, carbonate or amines), while the other carboxylic acid functionality is reacted with the synthesis support, usually through formation of an amide bond with an amine functionality on the support.

The linker may also confer other desirable properties on the oligonucleotide conjugate: improved aqueous solubility, optimal distance of separation between the conjugate moiety and the oligonucleotide, flexibility (or lack thereof), specific orientation, branching, and others.

Preferably, the chemical bond between the linker and the conjugate moiety is a carbamate linkage; however, alternative chemistries are also within the scope of the disclosure. examples of functional groups on linkers which form a chemical bond with a conjugate moiety include, but are not limited to, hydroxyl, amine, carboxylic acid, carboxylic acid halide, carboxylic acid active ester, carbonyl, chlorocarbonyl, imidazolylcarbonyl, thiol, maleimide, haloalkyl, sulfonyl, allyl and propargyl. examples of chemical bonds that are formed between a linker and a cojugate include, but are not limited to, those based on carbamates, ethers, esters, amides, disulfides, thioethers, phosphodiesters, phosphorothioates, phorphorodithioate, sulfonamides, sulfonates, fulfones, sulfoxides, ureas, hydrazide, oxime, photolabile linkages, C—C bond forming groups such as Diels-Alder cyclo-addition pairs or ring-closing metathesis pairs, and Michael reaction pairs. In general, the conjugate moiety will have an appropriate functional group either naturally or chemically installed; the linker will then be synthesized with a functional group chosen to efficiently and stably react with the functional group on the conjugate moiety.

Linkers that have the same length, but are capable of associating with two or more conjugates, are also specifically contemplated.

In another embodiment, the linker may be a nucleoside derivative. The nucleoside may be, for example, a ribonucleoside, 2'-deoxyribonucleoside, or 2'-modified-2'-deoxyribonucleoside, such as 2'-O-methyl or 2'-fluoro. The nucleoside may be, for example, an arabinonucleoside or a 2'-modified arabinonucleoside. Using methods well known to those of ordinary skill in the art, purine and pyrimidine nucleosides may be modified at particular sites on the base to provide linkers and functional groups for attachment of conjugate moieties. For example, pyrimidine nucleosides, such as uridine and cytidine, may be modified at the 5-position of the uracil or cytosine base using mercuric acetate, a palladium catalyst, and an allylic reagent such as allylamine, allyl alcohol, or acrylic acid. Alternatively, 5-iodopyrimidines may be modified at the 5-position with a palladium catalyst and a propargylic reagent such as propargyl amine, propargyl alcohol or propargylic acid. Alternatively, uridine may be modified at the 4-position through activation with triazole or a sulfonyl chloride and subsequent reaction with a diamine, amino alcohol or amino acid. Cytidine may be similarly modified at the 4-position by treatment with bisulfite and subsequent reaction with a diamine, amino alcohol or amino acid. Purines may be likewise modified at the 7, 8 or 9 positions using similar types of reaction sequences.

In preferred embodiments, the linker is from about 3 to about 9 atoms in length. Thus, the linker may be 3, 4, 5, 6, 7, 8, or 9 atoms in length using the terms and definitions provided above. Preferably, the linker is 5, 6, 7, or 8 atoms in length. More preferably, the linker is 5 or 8 atoms in length. Most preferably the linker is a straight chain C5 linker i.e., there are 5 carbon atoms between the atom that joins the conjugate moiety to the linker and the oxygen atom of the terminal phosphate moiety associated with the oligonucleotide through which the linker is attached to the oligonucleotide. Thus, where the conjugate moiety is joined to a C5 linker via a carbamate linkage, there are 5 carbon atoms between the nitrogen atom of the carbamate linkage and the oxygen atom of the phosphate linkage. Note that the term "5 atom linker" or "8 atom linker" refers to at least the number of atoms separating two points, e.g., the conjugate and the oligonucleotide, and is not intended to suggest that there are only, e.g., 5 or 8 atoms in the entire linker molecule.

In one preferred embodiment, the conjugate moiety is cholesterol and the linker is a C5 linker (a 5 atom linker) attached to the cholesterol via a carbamate group, thus forming a Chol-C5 conjugate-linker (see Table 1). When attached via a phosphodiester linkage to the 5' and/or 3' terminus of an oligonucleotide (preferably to the 3' end of oligonucleotide 3) the resulting conjugate-linker-oligonucleotide can have the structure:

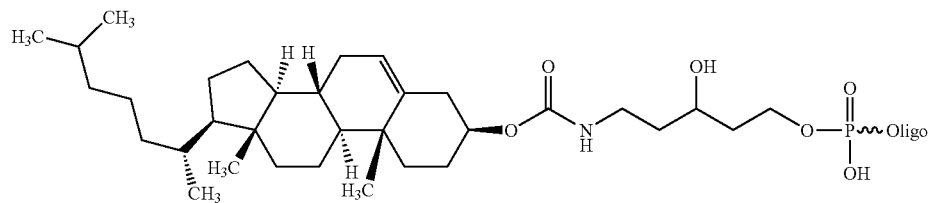

In another preferred embodiment, the conjugate moiety is cholesterol and the linker is a C3 linker attached to the cholesterol via a carbamate group, thus forming a Chol-C3 conjugate-linker (see Table 1). When attached via a phosphodiester linkage to the 5' and/or 3' terminus of an oligonucleotide (preferably to the 3' end of oligonucleotide 3) the resulting conjugate-linker-oligonucleotide can have the structure:

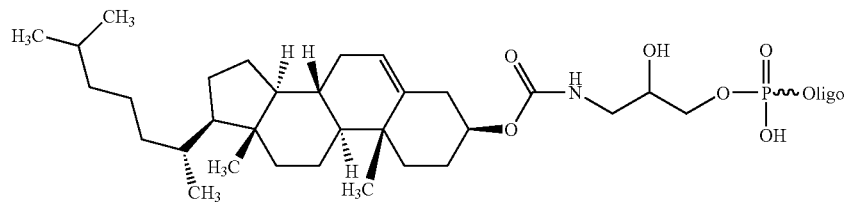

In another preferred embodiment, the conjugate moiety is cholesterol and the linker is a C8 linker (a 8 atom linker) attached to the cholesterol via a carbamate group, thus forming a Chol-C8 conjugate-linker (see Table 1). When attached via a phosphodiester linkage to the 5' and/or 3' terminus of an oligonucleotide (preferably to the 3' end of oligonucleotide 3) the resulting conjugate-linker-oligonucleotide can have the structure:

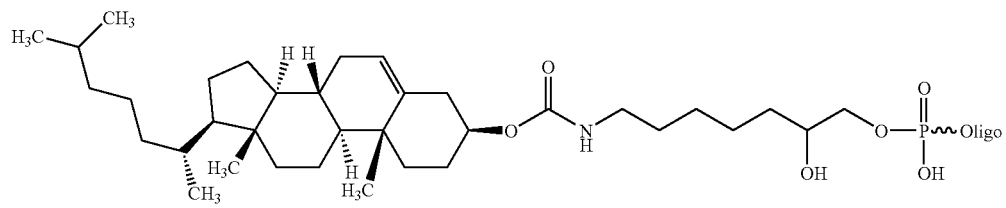

In another preferred embodiment, the conjugate moiety is cholesterol and the linker is a PRO linker (a 4 atom linker) attached to the cholesterol via a carbamate group, thus forming a Chol-PRO conjugate-linker (see Table 1). When attached via a phosphodiester linkage to the 5' and/or 3' terminus of an oligonucleotide (preferably to the 3' end of oligonucleotide 3) the resulting conjugate-linker-oligonucleotide can have the structure:

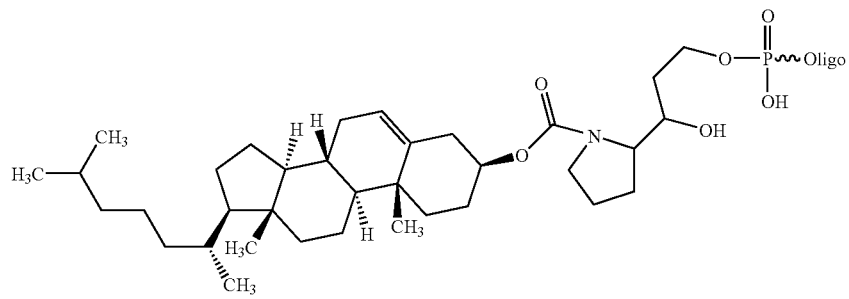

In another preferred embodiment, the conjugate moiety is cholesterol and the linker is a PIP linker (a 6 atom linker) attached to the cholesterol via a carbamate group, thus forming a Chol-PIP conjugate-linker (see Table 1). When attached via a phosphodiester linkage to the 5' and/or 3' terminus of an oligonucleotide (preferably to the 3' end of oligonucleotide 3) the resulting conjugate-linker-oligonucleotide can have the structure:

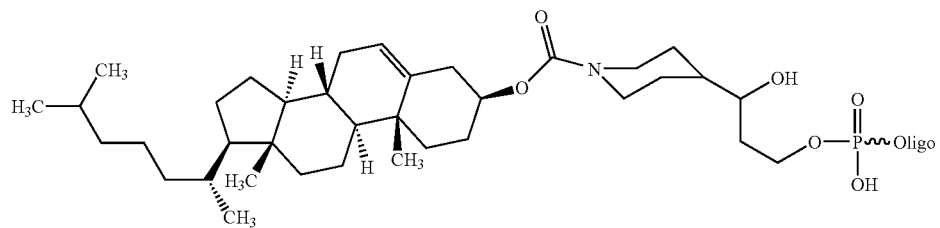

In another preferred embodiment, the conjugate moiety is cholesterol and the linker is a C6-HP (also referred to as "HP6") linker (a 9 atom linker) attached to the cholesterol via a carbamate group, thus forming a Chol-C6-HP conjugate-linker (see Table 1). When attached via a phosphodiester linkage to the 5' and/or 3' terminus of an oligonucleotide (preferably to the 3' end of oligonucleotide 3) the resulting conjugate-linker-oligonucleotide can have the structure:

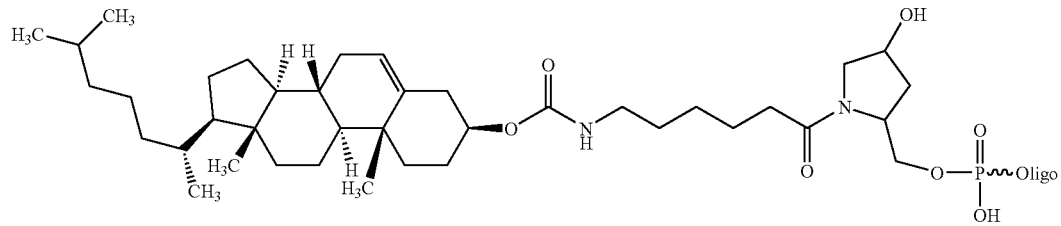

It is explicitly contemplated that the C5, C3, C8, PRO, C6-HP and PIP linkers in the foregoing embodiments (along with the additional linkers shown attached to cholesterol in Table 1) can be used with conjugate moieties other than cholesterol, including, for example, cholestanol (CHLN), cholanic acid (CHLA), stigmasterol (STIG), and ergosterol (ERGO). It will also be understood that while the C5, C3, C8, PRO, C6-HP, and PIP linkers exemplified above (and the additional linkers shown in Table 1) are shown with a carbamate group attaching the conjugate to the linker, other attachment chemistries may be used (see below). Finally, while the C5, C3, C8, PRO, C6-HP, and PIP linkers in the foregoing embodiments are shown attached to oligonucleotides via a phosphodiester linkage, it will be appreciated that other sites of attachment to oligonucleotides, and other chemistries for attachment to oligonucleotides, may be used (see below).

Linker-Conjugate Positions on the Tripartite Design

The position of the linker-conjugate moiety (if present) on the tripartite oligonucleotide complex can vary with respect to the strand or strands that are conjugated (e.g. oligonucleotide 1, 2, and/or 3 in the present disclosure), the position or positions within the strand that are modified (i.e. the nucleotide positions within the strand or strands), and the position on the nucleotide(s) that are modified (e.g. the sugar, the base).

Linker-conjugates can be placed on the 5' and/or 3' terminus of one or more of the strands of the tripartite oligonucleotide molecule of the present disclosure, and/or be conjugated to internal positions (e.g. nucleotide 18 of the second oligonucleotide). In addition, multiple positions on the nucleotides including the 5-position of uridine, 5-position of cytidine, 4-position of cytidine, 7-position of guanosine, 7-position of adenosine, 8-position of guanosine, 8-position of adenosine, 6-position of adenosine, 2'-position of ribose, 5'-postion of ribose, 3'-position of ribose, can be employed for attachment of the conjugate to the nucleic acid.

It is important that the position of the linker-conjugate does not interfere with 1) the ability of Dicer to accurately process the tripartite molecule, or 2) the ability of RISC to load and utilize the antisense strand to target the gene of interest. Furthermore, conjugates should not interfere with the ability of other modifications to fulfill their intended functions. For instance, the conjugate should not be placed in positions that interfere with modifications that enhance specificity or stability. One skilled in the art can readily determine the positions at which a conjugate moiety would have such undesired effects. Preferably, the linker-conjugate is positioned at the 3' end of oligonucleotide 3.

Modifications

A broad range of modifications can be included in the disclosure to enhance stability, Dicer or RISC processing, functionality, and/or specificity. In addition, modifications can be used to minimize the innate immune response that cells typically have against dsRNAs that are longer than e.g. 23 bp (see Reynolds, A. et al (2006) RNA. 12(6):988-930). Modifications to the internucleotide linkages that can enhance overall stability or enzymatic processing can include phosphorothioates, phosphorodithioates, alkylphosphonates, phosphonoacetates, phosphonoacetamides, phosphonoacetic acid esters, phosphonamidates, phosphonoalcohols, phosphonoalcohol esters, phosphonoformates, boranophosphonoates, peptide nucleic acids, and more. Similarly, modifications to the sugar structures can be included in the disclosure to enhance or alter oligonucleotide stability, functionality, enzymatic processing, and specificity. Possible modifications to the sugar ring structure include 2'-O-alkylribose, 2'-halo-2'-deoxyribose, 2'-deoxyribose, 2'amino-2'-deoxyribose, 2'-thio-2'-deoxyribose, arabinose, L-ribose, 2'-halo-2'-deoxyarabinose, 2'-O-alkylarabinose, 2'-amino-2'-deoxyarabinose, 2'-thio-2'-deoxyarabinose, 2'-O, 4'-C-methylene bicyclo ("locked nucleic acid"), 4'-aminoalkylribose, 5'-aminoalkylribose, 4-thioribose, and more. Preferred sets of chemical modifications include 1) 2'-O-methyl modification of nucleotides 1 and 2 of the post-Dicer processed oligonucleotide 1 (which correspond to nucleotides 3 and 4 of the target dependent region of oligonucleotide 1, counting from the 5' end), 2) 2'-O methyl modification of positions 1, 2, and/or 3 of oligonucleotide 2, 3) 2'-O methyl modification of some or all of the Cs and Us of oligonucleotide 1, 4) 2' halogen modification of some or all of the Cs and Us of oligonucleotide 2, 5) 2' halogen or 2'-O methyl modification of some or all of the Cs and Us of oligonucleotide 3. Preferably, between about 40% and about 90% of the nucleotides in oligonucleotides 1, 2, and 3 are chemically modified nucleotides.

In addition to internucleotide and sugar modifications, a number of base analogs can be included in the oligonucleotides of the disclosure. Such analogs can be included to enhance, or minimize base pairing at desired positions so as to increase specificity or functionality, enhance or minimize interaction with one or more proteins in the RNAi pathway or targets, and to minimize activation of the innate immune response. Base analogs include iso-cytidine/iso-guanosine, 2-aminopurine, pseudouridine, 5-methyluridine, 3-methyluridine, nitroindoles, imidazoles, pyridines, 5-azapyrimidines, 6-azapyrimidines, 7-deazapurines, 5-halopyriomidines, 8-halopurines, 8-oxopurines, 2-thiopyrimidines, 6-thioguanosine, 4-thiouridine, 2,6-diaminopurine, and more. Lastly, in addition to the three classes of modifications described above, nucleoside modifications that include morpholino nucleosides, 1',5'-anhydrohexitol nucleosides, 2,3-dideoxyhexopyranosyl nucleoside, carbocyclic nucleosides, C-nucleosides, and acyclic nucleosides (e.g. acyclovir, ganciclovir, penciclovir, and deciclovir), and any number of chemistries that can lead to universal base pairing, can be included in the disclosure.

In one embodiment, a tripartite oligonucleotide complex is provided which includes a first oligonucleotide that contains 37 nucleotides. The first 14 nucleotides (counting from the 5' terminus of the oligo) are the target independent region and anneal with oligonucleotide 3. The next 21 nucleotides are the target dependent region and anneal with oligonucleotide 2. The final 2 nucleotides of the first oligonucleotide represent a 2 nucleotide 3' overhang. The 2 nucleotide overhang ensures Dicer entry and processing from that end of the molecule. Optionally, the first oligonucleotide contains one or more of the following additional attributes:

a. One or more modified internucleotide linkages associated with the nucleotides of the 3' overhang. Preferably the internucleotide modifications are phosphorothioate modifications;

b. One or more of the nucleotides associated with the overhang are 2'-O alkylated, preferably 2'-O methylated. Such modifications enhance the stability of the overhang and thus increase the likelihood that Dicer will enter and process the molecule from that end of the tripartite molecule.

c. The 2 nucleotide 3' overhang consists of two Us;

d. A "G" at position 14, counting from the 5' end of the strand (which is the 3' terminal nucleotide of the target independent region);

e. An "A" at position 15 counting from the 5' end of the strand (which is also the first nucleotide of the target dependent region, counting from the 5' end of the target dependent region);

f. An "A" at position 16, counting from the 5' end of the strand (which is also the second nucleotide of the target dependent region, counting from the 5' end of the target dependent region);

g. A modified nucleotide, preferably a 2' modified nucleotide, more preferably a 2'-O-alkyl modified nucleotide, and most preferably a 2'-O-methyl modified nucleotide at position 17, counting from the 5' end of the strand (which is also the third nucleotide of the target dependent region, counting from the 5' end of the target dependent region);

h. A modified nucleotide, preferably a 2' modified nucleotide, more preferably a 2'-O-alkyl modified nucleotide, and most preferably a 2'-O-methyl modified nucleotide at position 18, counting from the 5' end of the strand (which is also the fourth nucleotide of the target dependent region, counting from the 5' end of the target dependent region);

i. A bulge or mismatch between oligonucleotide 1 and 2, at position(s) 11, 12, 13, or 14 counting from the 5' terminus of oligonucleotide 2;

j. The target dependet region of oligonucleotide 1 (positions 15-35) is 2'-O alkylated (preferably 2'-O-methylated) on any or all Cs and Us;

k. All the Cs and Us of the first oligonucleotide (including any of those associated with the overhang) are 2'-O alkylated, preferably 2'-O methylated;

l. One or more linker molecules having any of the previously described properties associated with the 3' or 5' terminus or internal positions of the first oligonucleotide;

m. A conjugate that is covalently linked to the distal end of the linker (i.e. the end which is not associated with the oligonucleotide 1). Preferably, the conjugate is a sterol or derivative of a sterol. More preferably, the conjugate is a cholesterol molecule The second oligonucleotide in this embodiment is 21 nucleotides in length and optionally contains one or more of the following additional attributes, a. A 5' phosphate group on the first nucleotide, counting from the 5' terminus.
   b. A "U" at position 20, counting from the 5' terminus.
   c. A "U" at position 21, counting from the 5' terminus.
   d. Some or all of the "Cs" and "Us" in the strand are modified. Preferably the modification is a 2' halogen. More preferably, the modification is a 2' F.
   e. The first, second, and/or third nucleotides (counting from the 5' terminus) contain 2'-O alkyl modifications. Preferably the 2'-O alkyl modification is a 2'-O methyl modification.
   f. An internucleotide modification, preferably a phosphorothioate modification, exists between nucleotide 19 and nucleotide 20, counting from the 5' terminus of the molecule.
   g. An internucleotide modification, preferably a phosphorothioate modification exists between nucleotide 20 and 21, counting from the 5' terminus of the molecule.
   h. One or more linker molecules having any of the previously described properties conjugated to the 3' terminus or internal position(s) of the second oligonucleotide.
   i. A conjugate that is covalently linked to the distal end of the linker(s) (i.e. the end which is not associated with the oligonucleotide 2). Preferably, the conjugate is a sterol or derivative of a sterol. More preferably, the conjugate is, for example, a cholesterol molecule.

The third oligonucleotide in this embodiment is 14 nucleotides in length, non-targeting, and optionally contains one or more of the following properties a. A linker molecule having any of the previously described properties conjugated to the 3' terminus of the third oligonucleotide.
   b. A linker molecule having any of the previously described properties conjugated to the 5' terminus of the third oligonucleotide.
   c. A linker molecule having any of the previously described properties conjugated to one or more internal positions of the third oligonucleotide.
   d. A conjugate that is covalently linked to the distal end of the linker (i.e. the end which is not associated with oligonucleotide 3). Preferably, the conjugate is a sterol or derivative of a sterol. More preferably, the conjugate is a cholesterol molecule
   e. An internucleotide modification associated with nucleotides 12 and 13, counting from the 5' terminus of oligonucleotide 3.
   f. Internucleotide linkages associated with nucleotides 13 and 14, counting from the 5' terminus of oligonucleotide 3.
   g. 2'-carbon modification of some or all of the nucleotides of oligonucleotide 3. Preferably the modifications are 2'-O alkyl modifications. More preferably, the modifications are 2'-O methyl modifications.

The modifications 1) enhance strand stability, and/or 2) promote the formation of desired products following Dicer processing, and/or 3) enhance delivery, and/or 4) promote efficient RISC entry, and/or 5) hinder the entrance of Dicer of that end of the tripartite molecule. In addition, while the variants described above specifically pertain to a particular tripartite design (37:21:14) it is anticipated that equivalent sets of modifications can be applied to comparable positions on tripartite designs that differ in length (e.g. 35:19:14).

Specific Examples of Tripartite Oligonucleotide Complexes

The following, non-limiting, examples of tripartite oligonucleotide complexes are provided to illustrate the design principles disclosed herein.

In one example, a tripartite oligonucleotide complex has the following features:

a. oligonucleotide 1 is 35 nucleotides in length (not including the 3' overhang), having a target independent region of 14 nucleotides and a target dependent region of 21 nucleotides; oligonucleotide 1 is 2'-O-methylated on all Cs and Us, contains 2'-O-methyl on nucleotide positions 17 and 18 (counting from the 5' end of the molecule), and has a 2'-O-methyl modified UU overhang;
   b oligonucleotide 2 is 21 nucleotides in length, is the reverse complement of the target dependent region of oligonucleotide 1, with all Cs and Us being 2' F modified, and has phosphorothioate internucleotide linkages between the last three nucleotides on the 3' terminus, and
   c. oligonucleotide 3 is 14 nucleotides in length, is the reverse complement of the target independent region of oligonucleotide 1, is fully 2'-O-methylated, has phosphorothioate internucleotide linkages between the last three nucleotides on the 3' terminus, and optionally has cholesterol linked to the 3' terminus of the oligonucleotide using a C5 linker.

In another example, a tripartite oligonucleotide complex has the following features:

a. oligonucleotide 1 is 35 nucleotides in length (not including the 3' overhang), having a target independent region of 14 nucleotides and a target dependent region of 21 nucleotides; oligonucleotide 1 is 2'-O-methylated on all Cs and Us, contains 2'-O-methyl on nucleotide positions 17 and 18 (counting from the 5' end of the molecule), and has a 2'-O-methyl modified UU overhang,
   b. oligonucleotide 2 is 21 nucleotides in length, is the reverse complement of the target dependent region of oligonucleotide 1, with all Cs and Us being 2' F modified, and
   c. oligonucleotide 3 is 14 nucleotides in length, is the reverse complement of the target independent region of oligonucleotide 1, is fully 2'-O-methylated, and optionally has cholesterol linked to the 3' terminus of the oligonucleotide using a C5 linker.

In another example, a tripartite oligonucleotide complex has the following features:

a. oligonucleotide 1 is 35 nucleotides in length (not including the 3' overhang), having a target independent region of 14 nucleotides and a target dependent region of 21 nucleotides; oligonucleotide 1 is 2'-O-methylated on all Cs and Us, contains 2'-O-methyl on nucleotide positions 17 and 18 (counting from the 5' end of the molecule), and has a 2'-O-methyl modified UU overhang,
   b. oligonucleotide 2 is 21 nucleotides in length, is the reverse complement of the target dependent region of oligonucleotide 1, with all Cs and Us being 2' F modified, and has phosphorothioate internucleotide linkages between the last three nucleotides on the 3' terminus, and
   c. oligonucleotide 3 is 14 nucleotides in length, is the reverse complement of the target independent region of oligonucleotide 1, is fully 2'-O-methylated, and optionally has cholesterol linked to the 3' terminus of the oligonucleotide using a C5 linker.

In another example, a tripartite oligonucleotide complex has the following features:

a. oligonucleotide 1 is 35 nucleotides in length (not including the 3' overhang), having a target independent region of 14 nucleotides and a target dependent region of 21 nucleotides; oligonucleotide 1 is 2'-O-methylated on all Cs and Us, contains 2'-O-methyl on nucleotide positions 17 and 18 (counting from the 5' end of the molecule), and has a 2'-O-methyl modified UU overhang, b. oligonucleotide 2 is 21 nucleotides in length, is the reverse complement of the target dependent region of oligonucleotide 1, with all Cs and Us being 2' F modified, and has phosphorothioate internucleotide linkages between the last three nucleotides on the 3' terminus, and c. oligonucleotide 3 is 14 nucleotides in length, is the reverse complement of the target independent region of oligonucleotide 1, and optionally has cholesterol linked to the 3' terminus of the oligonucleotide using a C5 linker.

Embodiments in which the Target Dependent Region of the First Oligonucleotide Becomes the Antisense Strand Following Dicer Processing All of the foregoing embodiments are directed to tripartite oligonucleotide complexes in which oligonucleotide 2 comprises an antisense region that has substantial complementarity to a target gene. Upon processing by Dicer, such tripartite oligonucleotide complexes yield a duplex in which the sense strand is formed by the target dependent region of oligonucleotide 1 and the antisense strand is formed by oligonucleotide 2. In another series of embodiments, the roles of oligonucleotide 1 and oligonucleotide 2 are reversed such that the resulting tripartite complex yields a duplex upon Dicer processing in which oligonucleotide 2 forms the sense strand and the target dependent region of oligonucleotide 1 forms the antisense strand. Such tripartite oligonucleotide complexes comprise:

i) a first oligonucleotide having a target-dependent region that has substantial complementarity to a target gene and a target-independent region which is 3' to the target dependent region, ii) a second oligonucleotide comprising sequence that is substantially complementary to the target dependent region of the first oligonucleotide; and iii) a third oligonucleotide.

The sequence of the target-independent region of the first oligonucleotide is substantially complementary to the sequence of the third oligonucleotide. Optionally, at least one of the three oligonucleotides is linked via a linker molecule to at least one conjugate moiety that facilitates delivery of the oligonucleotide complex into a cell, tissue or organism. For example, a C5 linker may be used to attach cholesterol to the 5' end of oligonucleotide 3 or to the 3' end of oligonucleotide 1. Optionally, at least one of the oligonucleotides is attached to a detectable label, such as a dye molecule, a radiolabel, or a mass label. All of the design considerations disclosed in connection with the first series of embodiments (i.e., the embodiments in which the second oligonucleotide forms the antisense strand following Dicer processing) are equally applicable. One skilled in the art, in view of the instant disclosure, will understand that the position of overhangs, modified nucleotides, modified internucleotide linkages etc will differ with respect to the first series of embodiments as a result of the reversed roles of the oligonucleotides 1 and 2. For example, in one embodiment a tripartite oligonucleotide complex has the following features:

a. oligonucleotide 1 is 35 nucleotides in length and comprises a 19 nucleotide target dependent region (i.e antisense region) that is located 5' to a 16 nucleotide target independent region. The 5' terminus of oligonucleotide 1 is phosphorylated. Nucleotides 20 and 21 (which are the first two nucleotides of the target independent region, counting from the 5' end of the target dependent region) are U's. All C's and U's in the target dependent region are 2' F modified;

b. oligonucleotide 2 is 21 nucleotides in length, including a 19 nucleotide region that is complementary to the target dependent region of oligonucleotide 1 and a UU overhang at the 3' terminus (which may be 2' O-methylated).

c. oligonucleotide 3 is 16 nucleotides in length, fully 2' O-methylated, and optionally has a cholesterol attached to the 5' terminus via a C5 linker.

Figure 14A:
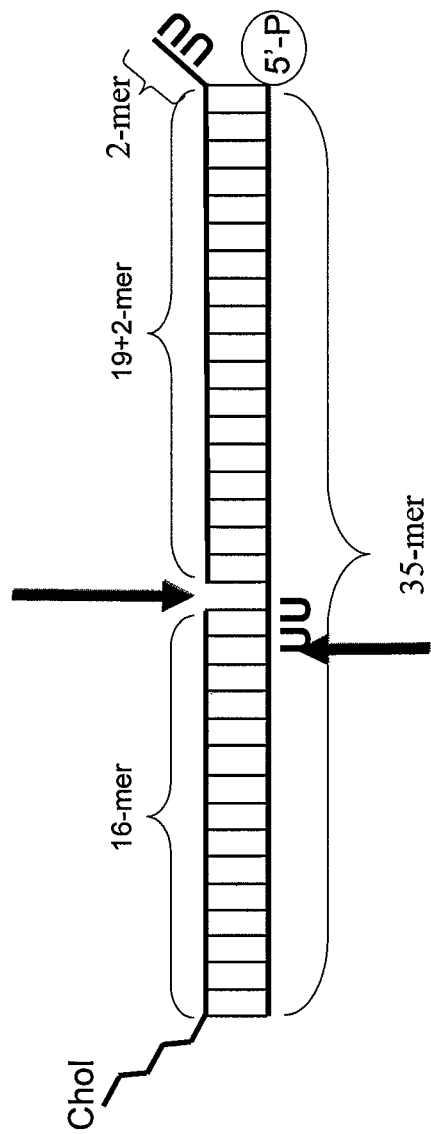
FIG. 14A shows an alternate tripartite design targeting PPIB. Cholesterol is now associated with the 5' terminus of oligonucleotide 3. Arrows indicate positions of Dicer cleavage.

FIG. 14A depicts an example of this configuration. Example 60 below provides additional disclosure relating to such tripartite oligonucleotide complexes.

Conjugates and Formulations

A number of conjugates can be used in conjunction with any of the targeting molecules described above. Thus, any of the embodiments previously described can be used jointly with protein (e.g. antibody) fusion constructs, polycations, cationic peptides, zinc fingers, aptamers, histones, dsRNA binding proteins, single stranded nucleic acid binding proteins, heparin binding domains, KH domains, PAZ domains, viral capsid proteins and transcription factors or domains. Formulations based on peptides, lipo- or poly-plexes, dendrimers, heparin, cholesterol, albumin, LDL blocking molecules, receptor blocking molecules, endosomal disrupting compounds or mixtures, neutral lipids, poly histidines, protamine, amino acids, taxol, time-released formulations, and nanoparticles (e.g. quantum dots, calcium phosphate or carbon based nanotubes) are all compatible with the compositions of the disclosure.

Methods of Delivery

The tripartite oligonucleotide complexes of the disclosure (with or without the optional conjugate moiety) may be employed in methods related to RNAi. As stated previously, methods related to RNAi include, but are not limited to targeting a gene or genes with siRNA, shRNA, miRNAs, or piRNAs. In addition, the targeting of miRNAs, siRNAs, shRNAs, or piRNAs with inhibitors are included as methods related to RNAi.

The tripartite oligonucleotide complexes of the disclosure are particularly potent in silencing genes by the RNAi pathway. Tripartite oligonucleotide complexes of the disclosure which comprise cholesterol (CHOL), cholestanol (CHLN), cholanic acid (CHLA), stigmasterol (STIG), or ergosterol (ERGO) as a conjugate, especially when linked to the 3' end of oligonucleotide 3 via a C5 linker (see FIG. 15), are particularly useful because they can be used to passively deliver (i.e., deliver without additional transfection reagents) their attached tripartite oligonucleotide to cells in culture or other environments in order to silence or knockdown genes. It is expressly contemplated that such molecules are passively delivered to cells in culture (e.g., in cuture plates, culture dishes, multiwell plates etc without limitation) under reduced serum conditions, including under 0% serum conditions. Such conditions include cells cultured in standard, art-tested reduced-serum media that are commercially available from numerous companies including Invitrogen, and HyClone. In one example, cells are first plated in serum medium, then the serum medium is replaced with reduced serum medium comprising a tripartite oligonucleotide complex of the disclosure for 24 hours, then the reduced serum medium is replaced with serum medium.

The tripartite oligonucleotide complexes of the disclosure may be conveniently supplied to end-users premixed in reduced serum media (including serum-free media). The tripartite oligonucleotide complexes of the disclosure can be stored in such media at 4° C. for extended periods of time without significant loss of gene silencing activity. Thus, in one aspect, the disclosure provides a kit comprising one or more containers, each container comprising reduced serum media and a tripartite oligonucleotide complex(es) of the disclosure. In this way, the tripartite oligonucleotide complexes of the disclosure may be purchased by a consumer in a stable and ready-to-use formulation. Gene silencing may then be carried out by simply culturing cells in the supplied formulation without additional transfection steps. In addition, if the supplied formulation comprises a plurality of tripartite oligonucleotide complexes, each specific for a particular gene, then a single supplied formulation may be used for the simultaneous silencing of a plurality of genes. If a single gene is to be silenced, then the supplied formulation may comprise a single tripartite oligonucleotide complex of the disclosure, or it may comprise a pool of tripartite oligonucleotide complexes, each targeting a different region of, for example, a single target mRNA of interest.

In another embodiment, the tripartite oligonucleotide complexes of the disclosure are used to silence genes in cultured cells in a "reverse transfection" format. In this format, the tripartite oligonucleotide complexes of the disclosure are first dispensed onto a solid support (such as a glass slide) and then cells are grown on the solid support. Cells that grow on the solid support take up the tripartite oligonucleotide complexes through passive delivery if a conjugate moiety is present; if a conjugate moiety is not present, then additional transfection reagents may be included in the growth medium to allow delivery of the tripartite oligonucleotide complex. In preferred embodiments, a plurality of different tripartite oligonucleotide complexes are attached at a plurality of spatially defined addresses on a solid support (for example, by printing or pipetting spots of tripartite oligonucleotide complexes on the support), thus forming a microarray of tripartite oligonucleotide complexes. Cells that are grown on the solid support thereby come into contact with different tripartite oligonucleotide complexes in a position-dependent manner. The support can be unmodified or can be modified (e.g., with one or more polymers) that enhance retention or delivery of the duplex, or enhance adhesion of the cell population to the solid support.

Tripartite oligonucleotide complexes of the disclosure, especially those which comprise cholesterol (CHOL), cholestanol (CHLN), cholanic acid (CHLA), stigmasterol (STIG), or ergosterol (ERGO) as a conjugate, are particularly useful for continuous dosing of cells. Continuous dosing with the tripartite oligonucleotide complexes of the disclosure is useful for achieving long term knockdown of a gene target. Moreover, cells continuously dosed with tripartite oligonucleotide complexes which include conjugate moieties remain amenable to conventional lipid-mediated transfection. Thus, it is possible to use the conjugate moiety-containing tripartite oligonucleotide complexes of the disclosure to knockdown a specific gene and then to use conventional lipid-mediated delivery of additional reagents that mediate RNAi (e.g., additional siRNAs) in order simultaneously to knockdown additional genes. In this way, it is possible to screen a panel of different siRNAs for a phenotype of interest in a "background" of a continuous knockdown of one specific gene.

In one embodiment, the compositions of the disclosure are used in basic research settings, in drug discovery settings, in ADME-tox applications, and in therapeutic/prophylactic applications.

In yet another embodiment, a method by which different combinations of linkers, conjugates, and delivery payloads are combined to screen for functional arrangement is described.

In yet another embodiment, a combi-chem approach to screen for conjugate structures that enhance nucleic acid delivery, preferably delivery of siRNAs, miRNAs, miRNA mimics, piRNAs, miRNA and piRNA inhibitors, is described.

In yet another embodiment, one or more compositions of the disclosure are used in combination with a small molecule libarary to perform small molecule screening.

In yet another embodiment, one or more compositions and/or methods of the disclosure are used to identify molecules that are capable of blocking the interaction of the molecules of the disclosure with another entity, such as a serum protein.

In yet another embodiment, one or more compositions and/or methods of the disclosure are used to optimize the backbone for universal attachment of ligands.

In yet another embodiment, one or more compositions of the disclosure are used in kits developed for transfection procedures. Such procedures can include 1) plating cells in e.g. a well and adding one or more compositions of the disclosure to the well for passive delivery or 2) depositing one or more compositions of the disclosure in a well or on a slide and adding cell cells to initiate passive delivery of the molecules of the disclosure. In both cases, such methods can be employed to introduce a homogeneous population of molecules into cells, or can be arrayed in such a way as to introduce larger collections (e.g. a genome wide collection of siRNA) into cells.

In another embodiment, the compositions of the disclosure are applied in high throughput screening methods.

In yet another embodiment, the compositions of the disclosure are employed to introduce nucleic acids e.g. tripartite molecules into hard-to-transfect cells such as Jurkat cells, stem cells, cells of neuronal origin, and cells of a myeloid origin.

In another embodiment, the compositions of the disclosure are employed to introduce nucleic acids, e.g. tripartite molecules into primary cells.

In another embodiment, the compositions of the disclosure are employed to introduce nucleic acids, e.g. siRNA into non-adherent, suspension cells.

In another embodiment, the compositions of the disclosure are employed to deliver a wide array of nucleic acids including but not limited to tripartite molecules, siRNA, miRNAs, miRNA inhibitors, piRNAs, piRNA inhibitors, plasmids, antisense molecules, modified and unmodified nucleic acids, hybrid nucleic acids (e.g. DNA-RNA hybrids), and more. Importantly, the present disclosure can be used to deliver miRNAs, siRNAs, and piRNAs of the human genome implicated in diseases such as diabetes, Alzheimer's, and cancer, as well as those associated with the genomes of pathogens (e.g. pathogenic viruses), or host-encoded genes that play a role in pathogen entry, replication, packaging, release, or any other critical step in pathogen replication.

In another embodiment, the compositions of the disclosure are used to deliver collections of nucleic acids such as pools of siRNA targeting multiple sites on a single gene, pools of siRNA targeting multiple genes, pools of miRNA or piRNA mimics, pools of miRNA or piRNA inhibitors, and more. Alternatively, pools of miRNA mimics or miRNA inhibitors, particularly those that are related to a particular disease, can be simultaneously delivered using the compositions of the disclosure.

In another embodiment, the compositions of the disclosure are used to deliver one or more randomly selected nucleic acids e.g. siRNA.

In another embodiment, the compositions of the disclosure are used to deliver one or more nucleic acids that have been selected by rational design methods.

In another embodiment, the compositions of the disclosure are associated with control molecules that, for instance, are incapable of entering RISC, or can cause toxicity, or are labeled and can be used to assess transfection efficiency.

In another embodiment, the compositions of the disclosure are used to deliver molecules that target a specific gene or set of genes for RNAi. For instance, the set of genes might include a set of siRNA that target e.g. the kinome or GPCRs, or genes associated with membrane remodelling, or the druggable genome set, or an entire genome.

In another embodiment, the compositions of the disclosure and related methods are used for diagnostic applications, prophylactics, therapeutics, agricultural applications, veterinary applications, research tools, cosmetic applications, and more. In the case of therapeutics and prophylactics, the compositions of the disclosure can be used in the manufacture of a medicament in animals, preferably mammals, more preferably humans in the treatment of diseases. Dosages of medicaments manufactured in accordance with the present disclosure may vary from micrograms per kilogram to hundreds of milligrams per kilogram of a subject. As is known in the art, dosage will vary according to the mass of the mammal receiving the dose, the nature of the mammal receiving the dose, the severity of the disease or disorder, and the stability of the medicament in the serum of the subject, among other factors well known to persons of ordinary skill in the art. For these applications, an organism suspected of having a disease or disorder that is amenable to modulation by manipulation of a particular target nucleic acid of interest is treated by administering compositions of the disclosure. Results of the treatment may be ameliorative, palliative, prophylactic, and/or diagnostic of a particular disease or disorder.

Furthermore, in the case of therapeutic or prophylactic applications, the present disclosure can be combined with a variety of therapeutic compositions, delivery agents, and methods of administration. Pharmaceutically acceptable carriers, excipients, and diluents are known to persons skilled in the art. Methods of administration to cells and organisms are also known to persons skilled in the art. Dosing regimens, for example, are known to depend on the severity and degree of responsiveness of the disease or disorder to be treated, with a course of treatment spanning from days to months, or until the desired effect on the disorder or disease state is achieved. Chronic administration of molecules of the disclosure may be required for lasting desired effects with some diseases or disorders. Suitable dosing regimens can be determined by, for example, administering varying amounts of one or more molecules of the disclosure in a pharmaceutically acceptable carrier or diluent, by a pharmaceutically acceptable delivery route, and amount of drug accumulated in the body of the recipient organism can be determined at various times following administration. Similarly, the desired effect can be measured at various times following administration of the molecule(s) of the disclosure, and this data can be correlated with other pharmacokinetic data, such as body or organ accumulation. Those of ordinary skill can determine optimum dosages, dosing regimens, and the like. Those of ordinary skill may employ $EC_{50}$ data from in vivo and in vitro animal models as guides for human studies.

In another embodiment, the compositions and methods of the disclosure are used in combinational therapies, in particular, combinational therapies directed toward alleviating or minimizing the effects of human diseases including cancer, Alzheimer's and other neural diseases such as epilepsy, and more.

In another embodiment, the compositions and methods of the disclosure are employed in structure/function studies to design and test alternative targeting scaffolds.

Because the molecules of the disclosure act independent of the cell type or species into which they are introduced, in another embodiment the present disclosure is used to deliver nucleic acids to a broad range of organisms, including but not limited to plants, animals, protozoa, bacteria, viruses and fungi. The present disclosure is particularly advantageous for use in mammals such as cattle, horse, goats, pigs, sheep, canines, rodents such as hamsters, mice, and rats, and primates such as, gorillas, bush babies, chimpanzees, and humans.

In another embodiment, the compositions and methods of the disclosure can be used to target specific tissues, particularly diseased tissues including heart tissues, neural tissues, tissues of the gastrointestinal tract, muscle tissues, pulmonary tissues, cancerous tissues, tissues infected with pathogens, and more. The present disclosure may be used advantageously with diverse cell types, including but not limited to primary cells, germ cell lines and somatic cells. For example, the cell types may be embryonic cells, oocytes, sperm cells, adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes and cells of the endocrine or exocrine glands.

In another embodiment, the compositions of the disclosure are delivered to e.g. a subject by intravenous, inhalation, intramuscular, dermal, sub-dermal, cutaneous, subcutaneous, intranasal, oral, rectal, by eye drops, by tissue implantation of a device that releases the molecule(s) at an advantageous location, such as near an organ or tissue or cell type harboring e.g. a target nucleic acid of interest, or other art recognized methods for introducing nucleic acids to a subject. The molecules of the disclosure can be administered in a cream or ointment topically, an oral preparation such as a capsule or tablet or suspension or solution, and the like.

Methods of Synthesizing Tripartite Oligonucleotide Complexes

In another aspect, the disclosure provides methods for preparing tripartite oligonucleotide complexes. In one embodiment, chemical derivatives of the conjugate moiety are incorporated at the desired position in an oligonucleotide chain while still attached to the solid synthesis support. Preferably, this is accomplished using the same chemistry as that used to assemble the oligonucleotide (e.g., phosphoramidite, H-phosphonate, etc.) or by using a solid synthesis support comprising the desired conjugate moiety as the initiation site for assembly of the oligonucleotide. Alternatively, protected chemical functionalities may be incorporated into the oligonucleotide during its synthesis, deprotected at an appropriate point in the synthesis under conditions compatible with the oligonucleotide protecting groups and the linkage to the solid support, and then covalently reacted with a suitably activated form of the conjugate moiety.

In another embodiment, completed oligonucleotides are reacted following cleavage and deprotection with a suitable derivative of the conjugate moiety of interest. This reaction can either be non-specific, that is, the conjugate moiety can either covalently react randomly with sites on the oligonucleotide or interact non-covalently (e.g., through ionic interactions, hydrogen bonding, or hydrophobic interactions) with the oligonucleotide; or specific, if a particular chemical functionality has been incorporated in to the oligonucleotide for reaction with a suitably reactive derivative of the conjugate moiety. In this embodiment, duplexed oligonucleotides may be utilized in the conjugation reactions as well as single strands.

As described above, conjugate moieties can be attached to solid oligonucleotide synthesis supports to act as the initiation site for oligonucleotide synthesis. In one embodiment, a linker is appended to the conjugate moiety to provide functional sites for attachment to the support and for initiation of oligonucleotide synthesis. Preferably, as described above, these sites are hydroxyl groups; most preferably, they are a primary hydroxyl group and a secondary hydroxyl group, to allow them to be chemically distinguished during synthesis of the conjugate-modified solid support.

In one embodiment, a conjugate moiety is incorporated into an oligonucleotide at sites other than the 3'-end by employing a derivative of the conjugate moiety that utilizes the same chemistry for its incorporation as the chemistry used to assemble the oligonucleotide chain. For example, the conjugate derivative may be placed in a reagent position on the automated synthesis instrument that is unused by the four standard nucleotide monomers, and then programmed into the desired sequence at the appropriate position(s). The addition of the conjugate is thus treated the same way as the other monomers, except perhaps for adjustments to the solution concentration or coupling time as needed for maximum efficiency of incorporation. Since the most common oligonucleotide chemistry currently in practice today is the phosphoramidite method, preferably the derivative of the conjugate moiety is a phosphoramidite.

Linkers of the sort described in the previous sections can be used as the scaffold on which to build the requisite phosphoramidite derivatives of the conjugate moiety. Similarly, covalent bonds of the sort described in the previous sections can be used to bond the linker and the conjugate moiety. One hydroxyl group of the linker, preferably a primary hydroxyl group, is protected with a protecting group suitable for use in oligonucleotide synthesis (e.g., dimethoxytrityl or silyl), according to methods well understood by those of ordinary skill in the art. Another hydroxyl group, preferably a secondary hydroxyl group, is reacted with an appropriately protected chlorophosphine in the presence of a tertiary base, or with an appropriately protected phosphorodiamidite in the presence of a tetrazole, triazole or imidazole derivative, to product the desired phosphoramidite, according to methods well understood by those of ordinary skill in the art. Such linker-conjugate moiety phosphoramidite derivatives may be used to place the conjugate moiety a virtually any position in the oligonucleotide sequence that does not impair the resulting utility of the oligonucleotide conjugate in the desired application.

In another embodiment, the linker may be a nucleoside derivative, as described above.

In another embodiment, the site of conjugation is the 5'-end of the oligonucleotide and the linker has only the functional group for covalent bond formation with the conjugate moiety and a hydroxyl group for conversion into the phosphoramidite derivative. This is because the conjugation at the 5'-end is the final step in the assembly of the oligonucleotide; no further monomers are added past this point. As such, the following types of linkers, by way of example, may be used in this case (in addition to those previously described): ω-aminoalkanols, ω-hydroxyalkanols, ω-hydroxyalkane thiols, and ω-hydroxyalkyl carboxylic acids.

Whenever a range is given in the specification, for example, a temperature range, a time range, a percent sequence identity, a sequence complementarity range, a length range, or a composition or concentration range, all intermediate ranges and subranges, as well as all individual values included in the ranges given are intended to be included in the disclosure.

All patents and publications mentioned in the specification are indicative of the levels of skill of those skilled in the art to which the disclosure pertains. References cited herein are incorporated by reference herein in their entirety to indicate the state of the art as of their filing date and it is intended that this information can be employed herein, if needed, to exclude specific embodiments that are in the prior art. For example, when a compound is claimed, it should be understood that compounds known and available in the art prior to Applicant's disclosure, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The disclosure illustratively described herein suitably may be practiced in the absence of any element or elements, limitation or limitations which is not specifically disclosed herein.

All references cited in the present application are incorporated in their entirety herein by reference to the extent not inconsistent herewith.

EXAMPLES

The following Examples are intended to illustrate but not to limit the invention as described previously.

Example 1

General Preparation of an ω-amino-1,3-diol Linker Compound

In Examples 1-51, all raw materials and solvents are available from commercial sources or were prepared using methods well known to those of ordinary skill in the art. The products of all reactions in Examples 1-51 were analyzed and the structures confirmed by $^1$H NMR spectroscopy and ESI-TOF mass spectrometry.

FIG. 1 describes a general synthetic scheme for preparing a class of linkers based upon an ω-amino-1,3-diol. Those of ordinary skill in the art will realize that the particular methods and materials described subsequently could be varied to produce the same product compounds. A benzyloxycarbonyl-protected (Cbz) amino acid is treated with 2,2-dimethyl-1,3-dioxane-4,6-dione (Meldrum's acid), diethyl cyanophosphonate, and triethylamine in methylene chloride solution at ambient temperature for 12-18 hours followed by refluxing in methanol for 4 hours. The resulting Cbz-protected ω-amino-β-ketoester is then treated with excess lithium borohydride in tetrahydrofuran solution for at ambient temperature 12-18 hours. The resulting Cbz-protected ω-amino-1,3-diol is treated with 4,4'-dimethoxytritylchloride in pyridine solution at ambient temperature 12-18 hours. The resulting Cbz-protected 1-O-DMTr-ω-amino-1,3-diol is treated with hydrogen and palladium on carbon catalyst in methanol solution at ambient temperature 4-16 hours. The resulting product is a 1-O-DMTr-ω-amino-1,3-diol.

Figure 2A:
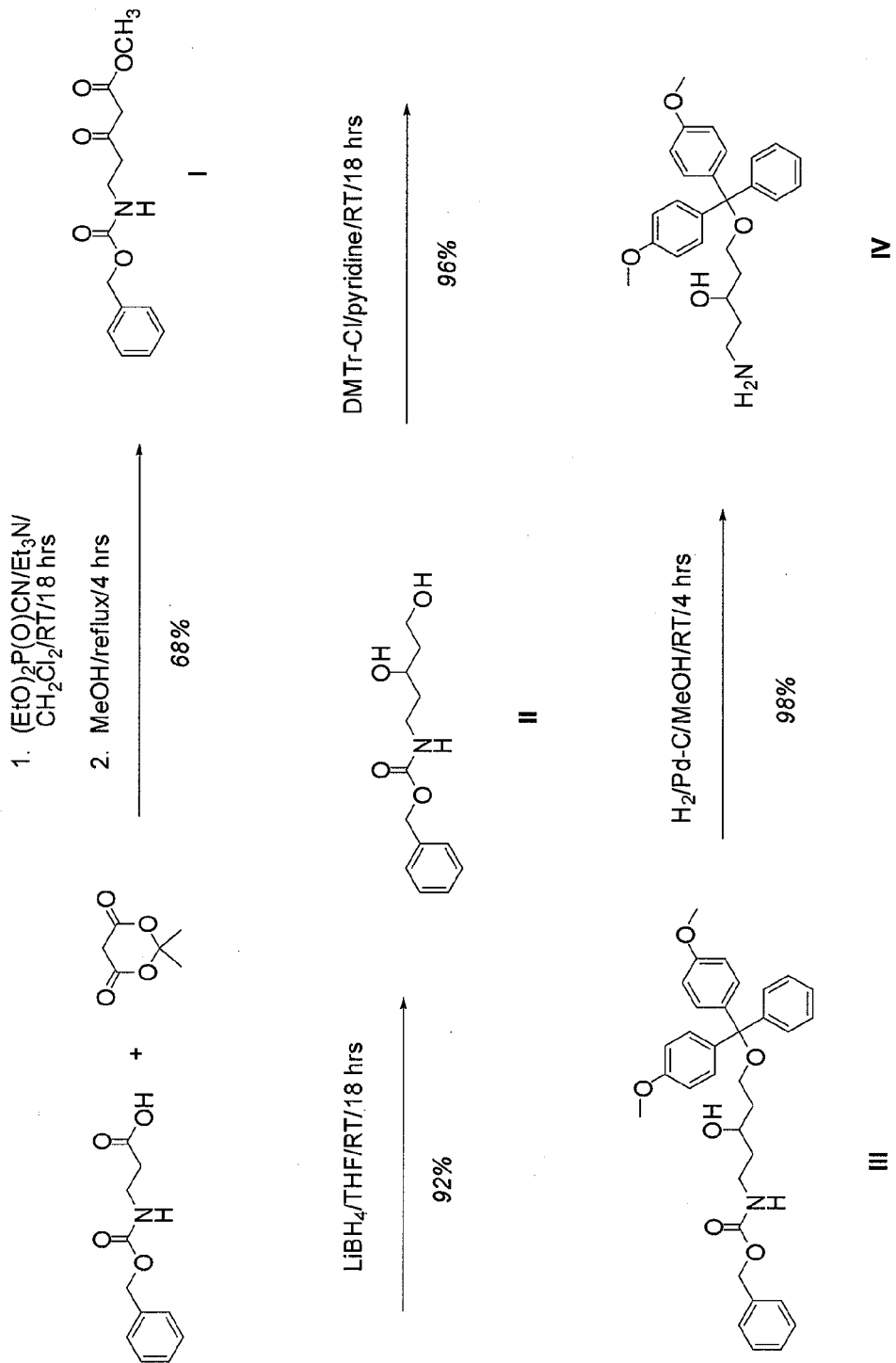
FIG. 2A is a synthetic scheme for the preparation of 1-amino-5-(bis(4-methoxyphenyl)(phenyl)methoxy)pentan-3-ol ("C5" linker).

The details of the preparation of 1-amino-5-(bis(4-methoxyphenyl)-(phenyl)methoxy)pentan-3-ol according to the above general scheme are given in the following Examples 2-5, and are illustrated in FIG. 2A.

Example 2

Preparation of methyl 5-(benzyloxycarbonylamino)-3-oxopentanoate (I)

3-(Benzyloxycarbonylamino)propanoic acid [N-Cbz-β-alanine] (5.0 g, 22.4 mmoles) is suspended in methylene chloride (100 mL) and 2,2-dimethyl-1,3-dioxane-4,6-dione (3.3 g, 22.9 mmoles), triethylamine (8.5 mL, 61.0 mmoles) and diethyl cyanophosphonate (3.7 mL, 22.8 mmoles) are added. All solids dissolve quickly, and the reaction quickly turns yellow. The solution is stirred for 16 hours at ambient temperature. The reaction mixture is then diluted with methylene chloride (100 mL) and carefully washed three times with aqueous hydrochloric acid (3 $\underline{M}$, 50 mL each), three times with water (50 mL each) and once with saturated aqueous sodium chloride (50 mL). The reaction mixture is then dried over anhydrous sodium sulfate, filtered and evaporated to an orange syrup. The syrup is dissolved in anhydrous methanol (200 mL) and heated to reflux for 16 hours. The methanol is evaporated and the crude product purified on silica gel (150 mL bed volume) eluting with methylene chloride (500 mL) then methylene chloride:methanol (99.5:0.5 [v/v], 500 mL then 99:1 [v/v], 1000 mL). Fractions containing pure product by thin layer chromatography are pooled and evaporated to a pale yellow oil. The oil is dried well in vacuo. The yield is 4.5 g (68%).

Similarly, the following compounds are prepared:
  i) Methyl 8-(benzyloxycarbonylamino)-3-oxooctanoate from 6-(Benzyloxycarbonyl-amino)-hexanoic acid.
  ii) Methyl 10-(benzyloxycarbonylamino)-3-oxooctanoate from 8-(Benzyloxycarbonyl-amino)-octanoic acid.
  iii) Methyl 14-(benzyloxycarbonylamino)-3-oxooctanoate from 10-(Benzyloxycarbonyl-amino)-decanoic acid.
  iv) Methyl 3-(4-(benzyloxycarbonylamino)phenyl)-3-oxopropanoate from 4-(benzyloxy-carbonylamino)benzoic acid.
  v) Benzyl 4-(3-methoxy-3-oxopropanoyl)piperidine-1-carboxylate from 1-(benzyloxy-carbonyl)piperidine-4-carboxylic acid.
  vi) Benzyl 2-(3-methoxy-3-oxopropanoyl)pyrrolidine-1-carboxylate from 1-(benzyloxy-carbonyl)pyrrolidine-2-carboxylic acid.

Example 3

Preparation of benzyl 3,5-dihydroxypentylcarbamate (II)

Methyl 5-(benzyloxycarbonylamino)-3-oxopentanoate (4.5 g, 15.3 mmoles) is dissolved in anhydrous tetrahydrofuran (25 mL) and this solution is added slowly dropwise to an ice-cooled solution of lithium borohydride in anhydrous tetrahydrofuran (2 $\underline{M}$, 25 mL, 50 mmoles). When the addition is complete, the cooling bath is removed and the reaction is stirred at ambient temperature for 16 hours. The clear, colorless solution is again cooled in an ice bath, and aqueous hydrochloric acid (1 $\underline{M}$, 50 mL) is added slowly dropwise to decompose the excess reducing agent (gas is evolved). When a homogeneous solution is obtained, the mixture is concentrated to remove tetrahydrofuran. Ethyl acetate (100 mL) is added; the mixture is shaken well and poured into a separatory funnel. The layers are allowed to separate and the bottom aqueous layer is drawn off. The aqueous layer is then washed twice more with ethyl acetate (100 mL each), and the combined ethyl acetate solutions are washed with saturated aqueous sodium chloride (50 mL). The ethyl acetate solution is then dried over anhydrous sodium sulfate, filtered and evaporated to a pale brown syrup. The crude product is purified on silica gel (200 mL bed volume) eluting with ethyl acetate (500 mL) then ethyl acetate:methanol (99:1 [v/v], 500 mL then 95:5 [v/v], 1000 mL). Fractions containing pure product by thin layer chromatography are pooled and evaporated to a pale yellow oil. The oil is dried well in vacuo. The yield is 3.6 g (92%). The oil solidifies on standing at 4° C.

Similarly, the following compounds are prepared:
  i) Benzyl 6,8-dihydroxyoctylcarbamate from methyl 8-(benzyloxycarbonylamino)-3-oxo-octanoate.
  ii) Benzyl 8,10-dihydroxydodecylcarbamate from methyl 10-(benzyloxycarbonyl-amino)-3-oxo-octanoate.
  iii) Benzyl 12,14-dihydroxytetradecylcarbamate from methyl 14-(benzyloxy-carbonylamino)-3-oxo-octanoate.
  iv) Benzyl 4-(1,3-dihydroxypropyl)phenylcarbamate from methyl 3-(4-(benzyloxy-carbonylamino)phenyl)-3-oxopropanoate.
  v) Benzyl 4-(1,3-dihydroxypropyl)piperidine-1-carboxylate from benzyl 4-(3-methoxy-3-oxopropanoyl)piperidine-1-carboxylate.
  vi) Benzyl 2-(1,3-dihydroxypropyl)pyrrolidine-1-carboxylate from benzyl 2-(3-methoxy-3-oxopropanoyl)pyrrolidine-1-carboxylate.

Example 4

Preparation of benzyl 5-(bis(4-methoxyphenyl)(phenyl)methoxy)-3-hydroxy-pentylcarbamate (III)

Benzyl 3,5-dihydroxypentylcarbamate (7.3 g, 28.8 mmoles) is co-evaporated twice with anhydrous pyridine (100 mL each) and then is dissolved in anhydrous pyridine (300 mL). The solution is chilled in an ice bath, and 4,4'-dimethoxytritylchloride (9.8 g, 28.9 mmoles) is added. The reaction is allowed to warm to ambient temperature and is stirred for 16 hours. The yellow solution is then evaporated to near dryness, and the residue is dissolved in dry toluene (250 mL). The toluene mixture is chilled for 1 hour at 4° C., then filtered. The collected solid is washed with toluene (50 mL) and the combined toluene filtrates are evaporated to a dark yellow syrup. The syrup is dried in vacuo for at least 24 hours at ambient temperature. The crude product is purified on silica gel (500 mL bed volume) eluting with hexanes:ethyl acetate:triethylamine (90:5:5 [v/v/v], 300 mL, then 85:10:5 [v/v/v], 1000 mL, then 80:15:5 [v/v/v], 1000 mL, then 75:20:5 [v/v/v], 1000 mL, then 70:25:5 [v/v/v], 2000 mL, then 50:45:5 [v/v/v], 2000 mL). Fractions containing pure product by thin layer chromatography are pooled and evaporated to a pale yellow syrup. The syrup is dried well in vacuo. The yield is 15.4 g (96%).

Similarly, the following compounds are prepared:

i) Benzyl 8-(bis(4-methoxyphenyl)(phenyl)methoxy)-6-hydroxyoctylcarbamate from benzyl 6,8-dihydroxypentylcarbamate.

ii) Benzyl 10-(bis(4-methoxyphenyl)(phenyl)methoxy)-8-hydroxydodecylcarbamate from benzyl 8,10-dihydroxypentylcarbamate.

iii) Benzyl 14-(bis(4-methoxyphenyl)(phenyl)methoxy)-12-hydroxytetradecylcarbamate from benzyl 12,14-dihydroxypentylcarbamate.

iv) Benzyl 4-(3-(bis(4-methoxyphenyl)(phenyl)methoxy)-1-hydroxypropyl)phenyl-carbamate from benzyl 4-(1,3-dihydroxypropyl)phenylcarbamate.

v) Benzyl 4-(3-(bis(4-methoxyphenyl)(phenyl)methoxy)-1-hydroxypropyl)piperidine-1-carboxylate from benzyl 4-(1,3-dihydroxypropyl)piperidine-1-carboxylate.

vi) Benzyl 2-(3-(bis(4-methoxyphenyl)(phenyl)methoxy)-1-hydroxypropyl)pyrrolidine-1-carboxylate from benzyl 2-(1,3-dihydroxypropyl)pyrrolidine-1-carboxylate.

Example 5

Preparation of 1-amino-5-(bis(4-methoxyphenyl)(phenyl)methoxy)pentan-3-ol (IV)

Benzyl 5-(bis(4-methoxyphenyl)(phenyl)methoxy)-3-hydroxypentylcarbamate (15.4 g, 27.7 mmoles) is dissolved in methanol (250 mL) and the solution is poured into a hydrogenation flask. 10% Palladium on carbon (1.5 g, 50% water by weight) is added, and the flask is sealed. The atmosphere in the flask is evacuated using a diaphragm pump, and replaced with dry argon to 10 psi. This cycle of evacuation/argon purging is repeated four more times. The flask is then evacuated once more and filled with hydrogen to 30 psi. The suspension is stirred briskly at ambient temperature for 16 hours. Hydrogen is replaced to 30 psi as necessary during the first four hours of reaction. The flask is then evacuated to remove hydrogen, and refilled with argon to atmospheric pressure. The catalyst is removed by filtration using a 0.45 μm nylon membrane, and washed with methanol (100 mL). The combined methanol filtrates are evaporated to dryness to give a white glassy foam, which is further dried in vacuo. The yield is 11.4 g (98%).

Similarly, the following compounds are prepared:

i) 8-Amino-1-(bis(4-methoxyphenyl)(phenyl)methoxy)-octan-3-ol from benzyl 8-(bis(4-methoxyphenyl)(phenyl)methoxy)-6-hydroxyoctylcarbamate.

ii) 10-Amino-1-(bis(4-methoxyphenyl)(phenyl)methoxy)-dodecan-3-ol from benzyl 10-(bis(4-methoxyphenyl)(phenyl)methoxy)-8-hydroxydodecylcarbamate.

iii) 14-Amino-1-(bis(4-methoxyphenyl)(phenyl)methoxy)-tetradecan-3-ol from benzyl 14-(bis(4-methoxyphenyl)(phenyl)methoxy)-12-hydroxytetradecylcarbamate.

iv) 1-(4-Aminophenyl)-3-(bis(4-methoxyphenyl)(phenyl)methoxy)propan-1-ol from benzyl 4-(3-(bis(4-methoxyphenyl)(phenyl)methoxy)-1-hydroxypropyl)phenylcarbamate.

v) 3-(Bis(4-methoxyphenyl)(phenyl)methoxy)-1-(piperidin-4-yl)propan-1-ol from benzyl 4-(3-(bis(4-methoxyphenyl)(phenyl)methoxy)-1-hydroxypropyl)piperidine-1-carboxylate.

vi) 3-(Bis(4-methoxyphenyl)(phenyl)methoxy)-1-(pyrrolidin-2-yl)propan-1-ol from benzyl 2-(3-(bis(4-methoxyphenyl)(phenyl)methoxy)-1-hydroxypropyl)pyrrolidine-1-carboxylate.

Example 6

General Preparation of a Conjugate moiety-ω-amino-1,3-diol Linker Compound

Covalent attachment of a conjugate moiety to an ω-amino-1,3-diol linker requires a derivative of the conjugate moiety that is reactive with the amine functionality on the linker. Suitable reactive derivatives include carboxylic acid anydrides, carboxylic acid chlorides, activated carboxylic acid esters such as N-hydroxysuccinimidyl, N-hydroxybenzotriazolyl, or pentafluorophenyl, chloroformates, 4-nitrophenyl carbonates and sulfonyl chlorides, to list a few Examples. Such reactive derivatives can be prepared and isolated as pure compounds, or can be prepared in situ immediately prior to use. In general, equivalent molar quantities of the reactive conjugate derivative and the aminated linker are dissolved together in an appropriate solvent and allowed to react at ambient temperature for 1 to 24 hours. Typical solvents depend on the solubility of the reagents and the type of reaction; for example, N,N-dimethylformamide is a useful solvent for the condensation of activated carboxylic acid esters with ω-amino-1,3-diol linkers, while pyridine is more appropriate for carboxylic acid anhydrides, chlorides or chloroformates where acid byproducts are produced.

Figure 2B:
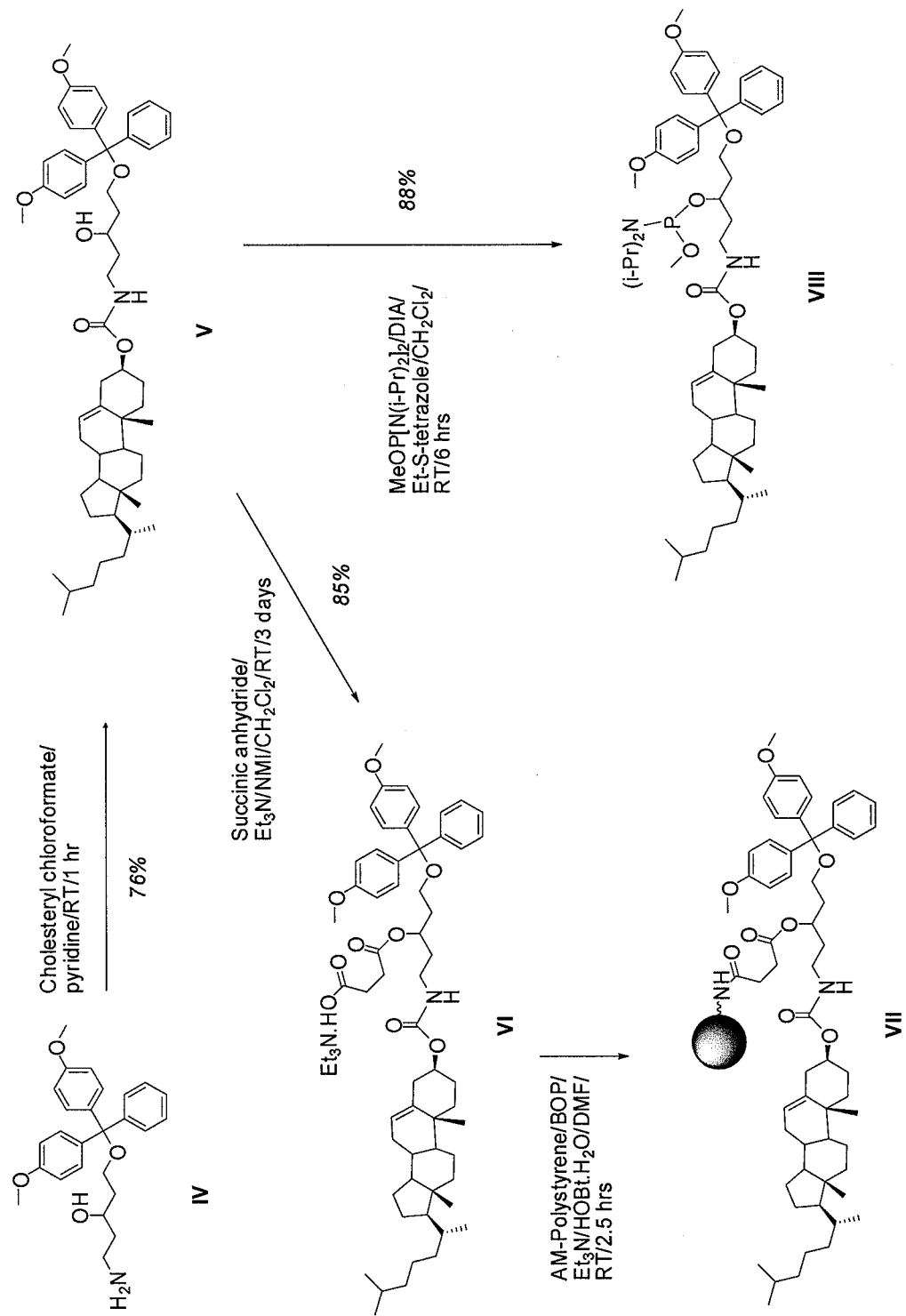
FIG. 2B is a synthetic scheme for the preparation of cholesteryl 5-(bis(4-methoxyphenyl)(phenyl)methoxy)-3-hydroxypentylcarbamate ("CHOL-C5"), a preferred embodiment of the present invention. Also, synthetic schemes for the preparation of a solid support and a phosphoramidite (cholesteryl 5-(bis(4-methoxyphenyl)-(phenyl)methoxy)-3-((diisopropylamino)(methoxy)phosphinooxy)pentylcarbamate) useful for oligonucleotide synthesis from CHOL-C5.

The details of the preparation of cholesteryl 5-(bis(4-methoxyphenyl)(phenyl)methoxy)-3-hydroxypentylcarbamate according to the above general scheme are given in the following Example 7, and are illustrated in FIG. 2B. In this case cholesterol is the conjugate moiety and cholesteryl chloroformate its reactive derivative. Examples 7-16 provide preparative details for steroidal conjugate moieties other than cholesterol.

Example 7

Preparation of cholesteryl 5-(bis(4-methoxyphenyl)(phenyl)methoxy)-3-hydroxypentylcarbamate (V)

1-amino-5-(bis(4-methoxyphenyl)(phenyl)methoxy)pentan-3-ol (4.3 g, 10.3 mmoles) is co-evaporated twice with anhydrous pyridine (50 mL each) and then is dissolved in anhydrous pyridine (70 mL). The solution is chilled in an ice bath, and cholesteryl chloroformate (4.8 g, 10.8 mmoles) in dry toluene (15 mL) is added slowly dropwise. The reaction is allowed to warm to ambient temperature and is stirred for 1 hour. Methanol (25 mL) is added, and the mixture is evaporated to near dryness. The residue is co-evaporated twice with dry toluene (50 mL each). The crude product is purified on silica gel (250 mL bed volume) eluting with hexanes:acetone:triethylamine (93:5:2 [v/v/v], 500 mL, then 88:10:2 [v/v/v], 1000 mL, then 78:20:2 [v/v/v], 1000 mL). Fractions containing pure product by thin layer chromatography are pooled and evaporated to a pale yellow resin. The resin is dried well in vacuo. The yield is 6.6 g (76%).

Similarly, the following compounds are prepared:

i) Cholesteryl 8-(bis(4-methoxyphenyl)(phenyl)methoxy)-6-hydroxyoctylcarbamate from 8-amino-1-(bis(4-methoxyphenyl)(phenyl)methoxy)-octan-3-ol and cholesteryl chloroformate in pyridine.

ii) Cholesteryl 10-(bis(4-methoxyphenyl)(phenyl)methoxy)-8-hydroxydodecylcarbamate from 10-amino-1-(bis(4-methoxyphenyl)(phenyl)methoxy)-dodecan-3-ol and cholesteryl chloroformate in pyridine.

iii) Cholesteryl 14-(bis(4-methoxyphenyl)(phenyl)methoxy)-12-hydroxytetradecylcarbamate from 14-amino-1-(bis (4-methoxyphenyl)(phenyl)methoxy)-octan-3-ol and cholesteryl chloroformate in pyridine.

iv) Cholesteryl 4-(3-(bis(4-methoxyphenyl)(phenyl)methoxy)-1-hydroxypropyl)phenylcarbamate from 1-(4-aminophenyl)-3-(bis(4-methoxyphenyl)(phenyl)methoxy)propan-1-ol and cholesteryl chloroformate in pyridine.

v) Cholesteryl 4-(3-(bis(4-methoxyphenyl)(phenyl)methoxy)-1-hydroxypropyl)piperidine-1-carboxylate from 3-(bis(4-methoxyphenyl)(phenyl)methoxy)-1-(piperidin-4-yl)propan-1-ol and cholesteryl chloroformate in pyridine.

vi) Cholesteryl 2-(3-(bis(4-methoxyphenyl)(phenyl)methoxy)-1-hydroxypropyl)pyrrolidine-1-carboxylate from 3-(bis(4-methoxyphenyl)(phenyl)methoxy)-1-(pyrrolidin-2-yl)propan-1-ol and cholesteryl chloroformate in pyridine.

vii) N-(8-(bis(4-methoxyphenyl)(phenyl)methoxy)-6-hydroxyoctyl)acetamide from 8-amino-1-(bis(4-methoxyphenyl)(phenyl)methoxy)-octan-3-ol and 4-nitrophenylacetate in N,N-dimethylformamide.

viii) Cholesteryl 6-(8-(bis(4-methoxyphenyl)(phenyl)methoxy)-6-hydroxyoctylamino)-6-oxo-hexylcarbamate from 8-amino-1-(bis(4-methoxyphenyl)(phenyl)methoxy)-octan-3-ol and 1H-benzo[d][1,2,3]triazol-1-yl 6-(benzyloxycarbonylamino)hexanoate in N,N-dimethylformamide. 1H-benzo[d][1,2,3]triazol-1-yl 6-(benzyloxycarbonylamino)hexanoate is prepared in situ from 6-(cholesteryloxycarbonylamino)hexanoic acid, 1-hydroxybenzotriazole hydrate and N,N'dicyclohexyl carbodiimide in N,N-dimethylformamide. 6-(Cholesteryloxycarbonylamino)-hexanoic acid is prepared from 6-aminohexanoic acid and cholesteryl chloroformate in pyridine.

ix) Cholesteryl 12-(8-(bis(4-methoxyphenyl)(phenyl)methoxy)-6-hydroxyoctylamino)-12-oxo-dodecylcarbamate from 8-amino-1-(bis(4-methoxyphenyl)(phenyl)methoxy)-octan-3-ol and 1H-benzo[d][1,2,3]triazol-1-yl 12-(cholesteryloxycarbonylamino)dodecanoate in N,N-dimethylformamide. 1H-benzo[d][1,2,3]triazol-1-yl 12-(cholesteryloxycarbonylamino)dodecanoate is prepared in situ from 12-(cholesteryloxycarbonylamino) dodecanoic acid, 1-hydroxy-benzotriazole hydrate and N,N'dicyclohexylcarbodiimide in N,N-dimethylformamide. 12-(Cholesteryloxycarbonylamino)-dodecanoic acid is prepared from 12-aminododecanoic acid and cholesteryl chloroformate in pyridine.

Example 8

Preparation of 5α-cholestan-3β-ol 4-nitrophenyl carbonate

5α-cholestan-3β-ol (3.9 g, 10.0 mmoles) is co-evaporated with dry toluene (50 mL) and then is dissolved in dry toluene (100 mL). The solution is stirred at ambient temperature, and triethylamine (1.4 mL, 10.0 mmoles) is added, followed by 4-nitrophenyl chloroformate (2.0 g, 9.9 mmoles). The reaction mixture is stirred overnight, during which time a white precipitate of triethylammonium chloride forms. The mixture is evaporated to near dryness. The crude product is purified on silica gel (200 mL bed volume) eluting with hexanes:ethyl acetate (95:5 [v/v], 2000 mL). Fractions containing pure product by thin layer chromatography are pooled and evaporated to an amorphous white solid. The solid is dried well in vacuo. The yield is 3.5 g (63%).

Similarly, the following compounds are prepared:
i) Stigmasterol 4-nitrophenyl carbonate from stigmasterol and 4-nitrophenyl chloroformate and triethylamine in toluene.

ii) Ergosterol 4-nitrophenyl carbonate from ergosterol and 4-nitrophenyl chloroformate and triethylamine in toluene.

iii) Trans-androstenone 4-nitrophenyl carbonate from trans-adrosterone and 4-nitrophenyl chloroformate and triethylamine in ethyl acetate.

iv) Pregnenolone 4-nitrophenyl carbonate from pregnenolone and 4-nitrophenyl chloroformate and triethylamine in tetrahydrofuran. A catalytic quantity (10 mole percent) of N,N-dimethylaminopyridine was added to this reaction.

v) 5α-Androstan-3β-ol 4-nitrophenyl carbonate from 5α-androstan-3β-ol and 4-nitrophenyl chloroformate and triethylamine in toluene.

vi) 5α-Androstan-17β-ol 4-nitrophenyl carbonate from 5α-androstan-17β-ol and 4-nitrophenyl chloroformate and triethylamine in toluene.

Example 9

Preparation of 5α-cholestan-3β-yl 5-(bis(4-methoxyphenyl)(phenyl)methoxy)-3-hydroxypentylcarbamate 1-amino-5-(bis(4-methoxyphenyl)(phenyl)methoxy)pentan-3-ol (1.2 g, 2.8 mmoles) is dissolved in dry toluene (20 mL). The solution is stirred at room temperature, and triethylamine (0.4 mL, 2.9 mmoles) is added, followed by a solution of 5α-cholestan-3β-ol 4-nitrophenyl carbonate (1.6 g, 2.8 mmoles) in toluene (25 mL). The reaction is stirred at ambient temperature overnight. The mixture is evaporated to near dryness to give a yellow glassy foam. The crude product is purified on silica gel (150 mL bed volume) eluting with hexanes:ethyl acetate:triethylamine (80:20:2 [v/v/v], 700 mL, then 70:30:2 [v/v/v], 1000 mL). Fractions containing pure product by thin layer chromatography are pooled and evaporated to a white glassy foam. The foam is dried well in vacuo. The yield is 2.0 g (87%).

Similarly, the following compounds are prepared:
i) Stigmasteryl 5-(bis(4-methoxyphenyl)(phenyl)methoxy)-3-hydroxypentylcarbamate from 1-amino-5-(bis(4-methoxyphenyl)(phenyl)methoxy)-pentan-3-ol and stigmasterol 4-nitrophenyl carbonate in toluene and triethylamine.

ii) Ergosteryl 5-(bis(4-methoxyphenyl)(phenyl)methoxy)-3-hydroxypentylcarbamate from 1-amino-5-(bis(4-methoxyphenyl)(phenyl)methoxy)-pentan-3-ol and ergosterol 4-nitrophenyl carbonate in toluene and triethylamine.

iii) Trans-androsteronyl 5-(bis(4-methoxyphenyl)(phenyl)methoxy)-3-hydroxypentylcarbamate from 1-amino-5-(bis(4-methoxyphenyl)(phenyl)methoxy)-pentan-3-ol and trans-androsterone 4-nitrophenyl carbonate in toluene and triethylamine.

iv) Pregnenolonyl 5-(bis(4-methoxyphenyl)(phenyl)methoxy)-3-hydroxypentylcarbamate from 1-amino-5-(bis(4-methoxyphenyl)(phenyl)methoxy)-pentan-3-ol and pregnenolone 4-nitrophenyl carbonate in toluene and triethylamine.

v) 5α-Androstan-3β-yl 5-(bis(4-methoxyphenyl)(phenyl)methoxy)-3-hydroxypentylcarbamate from 1-amino-5-(bis(4-methoxyphenyl)(phenyl)methoxy)-pentan-3-ol and 5α-androstan-3β-ol 4-nitrophenyl carbonate in toluene and triethylamine.

v) 5α-Androstan-17β-yl 5-(bis(4-methoxyphenyl)(phenyl)methoxy)-3-hydroxypentylcarbamate from 1-amino-5-(bis(4-methoxyphenyl)(phenyl)methoxy)-pentan-3-ol and 5α-androstan-17β-ol 4-nitrophenyl carbonate in toluene and triethylamine.

Example 10

Preparation of cholanic acid 4-nitrophenyl ester

Cholanic acid (3.6 g, 10.0 mmoles) is suspended in methylene chloride (200 mL) and stirred well at ambient temperature. 4-Nitrophenol (1.4 g, 10.1 mmoles) and N,N'-dicylcohexylcarbodiimide (2.1 g, 10.2 mmoles) are added, and the mixture is stirred overnight. The mixture is then filtered, the solid washed with a little methylene chloride, and the filtrate is evaporated to dryness to give a yellow solid. The crude product is dissolved in ethyl acetate (100 mL). The solution is filtered and the filtrate si evaporated to give an off-white solid. The solid is crystallized from hot hexanes. The yield is 3.9 g (80%).

Example 11

Preparation of cholanyl 5-(bis(4-methoxyphenyl)(phenyl)methoxy)-3-hydroxypentylamide 1-amino-5-(bis(4-methoxyphenyl)(phenyl)methoxy)pentan-3-ol (1.2 g, 2.8 mmoles) is dissolved in dry toluene (20 mL). The solution is stirred at room temperature, and triethylamine (0.4 mL, 2.9 mmoles) is added, followed by a solution of cholanic acid 4-nitrophenyl ester (1.4 g, 2.9 mmoles) in toluene (25 mL). The reaction is stirred at ambient temperature overnight. The mixture is evaporated to near dryness to give a yellow syrup. The crude product is purified on silica gel (200 mL bed volume) eluting with hexanes:ethyl acetate:triethylamine (60:40:2 [v/v/v], 1500 mL). Fractions containing pure product by thin layer chromatography are pooled and evaporated to a pale yellow glassy foam. The foam is dried well in vacuo. The yield is 1.7 g (80%).

Example 12

Preparation of 3-O-acetyl-lithocholic acid

Lithocholic acid (5.5 g, 14.6 mmoles) is suspended in acetic anhydride (55 mL) and the mixture is stirred overnight while heating at 90-95° C. During this period, all solid dissolves. The mixture is then cooled to ambient temperature and evaporated to dryness to give a white solid. The solid is crystallized from hot methanol. The yield is 4.3 g. Approximately 35% of the solid obtained is 3'-O-acetyl-lithocholic acid methyl ester, presumably arising from some 3'-O-acetyl-lithocholic-acetic mixed anhydride in the crude product during the crystallization from methanol. This mixed product was carried forward in subsequent reactions without additional purification.

Example 13

3'-O-acetyl-lithocholic acid 4-nitrophenyl ester

The mixed product from Example 12 (4.3 g) is dissolved in methylene chloride (100 mL) and the solution is stirred at ambient temperature. 4-Nitrophenol (1.4 g, 10.1 mmoles) and N,N'-dicylcohexylcarbodiimide (2.1 g, 10.2 mmoles) are added, and the mixture is stirred overnight. The mixture is then filtered, the solid washed with a little methylene chloride, and the filtrate is evaporated to dryness to give a yellow syrup. The crude product is purified on silica gel (200 mL bed volume) eluting with hexanes:ethyl acetate (90:10 [v/v], 1500 mL). Fractions containing pure product by thin layer chromatography are pooled and evaporated to a white solid. The solid is crystallized from hot acetonitrile. The yield is 3.9 g. The product is a 70:30 (mole:mole) mixture of the desired 4-nitrophenyl ester and the methyl ester, and is carried forward in subsequent reactions without further purification.

Example 14

Preparation of 3-O-acetyl-lithocholyl 5-(bis(4-methoxyphenyl)(phenyl)methoxy)-3-hydroxypentylamide 1-amino-5-(bis(4-methoxyphenyl)(phenyl)methoxy)pentan-3-ol (1.0 g, 2.4 mmoles) is dissolved in dry toluene (20 mL). The solution is stirred at room temperature, and triethylamine (0.4 mL, 2.9 mmoles) is added, followed by a solution of 3-O-acetyl lithocholic acid 4-nitrophenyl ester (product of Example 13, 1.8 g, 2.4 mmoles) in toluene (25 mL). The reaction is stirred at ambient temperature overnight. The mixture is evaporated to near dryness to give a yellow syrup. The crude product is purified on silica gel (200 mL bed volume) eluting with hexanes:ethyl acetate:triethylamine (60:40:2 [v/v/v], 600 mL, then 50:50:2 [v/v/v], 1500 mL). Fractions containing pure product by thin layer chromatography are pooled and evaporated to a white glassy foam. The foam is dried well in vacuo. The yield is 1.4 g (71%).

Example 15

Preparation of lithocholic acid methyl amide

3'-O-acetyl-lithocholic acid 4-nitrophenyl ester (product of Example 13, 2.0 g) is suspended in cold 33% [w/v] methylamine:ethanol, and methylene chloride (20 mL) is added. The reaction flask is tightly stoppered, and the reaction mixture is allowed to stir at ambient temperature for three days. The yellow solution thus obtained is evaporated to dryness, and the residue is partitioned between methylene chloride (300 mL) and 1 $\underline{M}$ aqueous sodium hydroxide (200 mL). The layers are separated, and the methylene chloride solution is washed with additional 1 $\underline{M}$ aqueous sodium hydroxide (200 mL), followed by saturated aqueous sodium chloride (200 mL). The methylene chloride solution is dried over anhydrous sodium sulfate, filtered and evaporated to a pale yellow foam. $^1$H NMR (CDCl$_3$) indicates that the acetyl group is incompletely removed, so that the crude product is dissolved in chloroform (30 mL) and methanol (10 mL), and 10 M aqueous sodium hydroxide (1 mL) is added. The mixture is stirred for 4 hours at ambient temperature, after which time glacial acetic acid is added (1 mL) followed by ethyl acetate (50 mL). The solution is washed three times with water (50 mL each time), dried over anhydrous sodium sulfate, filtered, and evaporated to a white solid. The yield is 1.9 g. It should be noted that the treatment with methylamine in ethanol smoothly converted not only the 4-nitrophenyl ester, but also the methyl ester, to the methyl amide.

Example 16

Preparation of lithocholic acid methyl amide 4-nitrophenyl carbonate

Lithocholic acid methyl amide (1.4 g, 3.6 mmoles) is co-evaporated with dry toluene (50 mL) and then is dissolved in dry toluene (50 mL) and chloroform (50 mL). The solution is stirred at ambient temperature, and triethylamine (0.6 mL, 4.3 mmoles) is added, followed by 4-nitrophenyl chloroformate (0.7 g, 3.5 mmoles). The reaction mixture is stirred overnight. Thin layer chromatography (1:1 [v/v] methylene chloride:

ethyl acetate) indicates the reaction is incomplete, so additional triethylamine (0.6 mL, 4.3 mmoles) and 4-nitrophenyl chloroformate (0.7 g) are added, and the reaction is allowed to proceed for two days more. The mixture is evaporated to near dryness. The crude product is purified on silica gel (200 mL bed volume) eluting with methylene chloride (500 mL) then methylene chloride:ethyl acetate (3:1 [v/v], 1000 mL). Fractions containing pure product by thin layer chromatography are pooled and evaporated to an amorphous white solid. The solid is dried well in vacuo. The yield is 1.7 g (85%).

Example 17

Preparation of lithocholic acid methyl amide 5-(bis (4-methoxyphenyl)(phenyl)methoxy)-3-hydroxypentylcarbamate 1-amino-5-(bis(4-methoxyphenyl)(phenyl)methoxy)pentan-3-ol (1.2 g, 2.8 mmoles) is dissolved in dry toluene (20 mL). The solution is stirred at room temperature, and triethylamine (0.4 mL, 2.9 mmoles) is added, followed by lithocholic acid methyl amide 4-nitrophenyl carbonate (1.4 g, 2.9 mmoles) and toluene (25 mL). The reaction is stirred at ambient temperature for three days. The mixture is evaporated to near dryness to give a yellow syrup. The crude product is purified on silica gel (200 mL bed volume) eluting with methylene chloride:triethylamine (100:2 [v/v], 500 mL) then methylene chloride:ethyl acetate:triethylamine (80:20:2 [v/v/v], 1000 mL). Fractions containing pure product by thin layer chromatography are pooled and evaporated to a white glassy foam. The foam is dried well in vacuo. The yield is 2.5 g. $^1$H NMR (CDCl$_3$) indicates the product is contaminated with about 25% (mole:mole) of starting lithocholic acid methyl amide 4-nitrophenyl carbonate. The mixture is carried forward in subsequent steps without further purification.

For additional clarity and ease of discussion in subsequent sections, Table 1 presents the structures of the above compounds and the abbreviated nomenclature associated therewith.

Example 18

General Preparation of a Conjugate moiety-ω-amino-1,3-diol Linker Compound Attached to a Solid Support Useful for Oligonucleotide Synthesis A conjugate moiety-ω-amino-1,3-diol linker compound may be attached to a solid synthesis support by providing a molecular tether between the compound and the support. As described previously, the most common tethers are dicarboxylic acids. For dicarboxylic acids that form cyclic anhydrides, approximately equivalent molar quantities of the conjugate moiety-ω-amino-1,3-diol linker compound and the cyclic anhydride are dissolved in methylene chloride containing triethylamine and 1-methylimidazole. The solution is stirred at ambient temperature for 12 hours to several days. For dicarboxylic acids that do not form cyclic anhydrides, the dicarboxylic acid is first activated with a carbodiimide reagent and then reacted in slight molar excess with the conjugate moiety-ω-amino-1,3-diol linker compound in the presence of a catalytic quantity of N,N-dimethylaminopyridine at ambient temperature for 12 hours to several days. In either case, the conjugate moiety-ω-amino-1,3-diol linker compound comprising a dicarboxylic acid tether is isolated as its triethylamine salt following chromatography.

The conjugate moiety-ω-amino-1,3-diol linker compound comprising a dicarboxylic acid tether is then attached to the solid synthesis support. Typical solid supports for oligonucleotide synthesis are either amine-functionalized controlled pore glass or cross-linked aminomethyl polystyrene. The free carboxylic acid moiety is activated using any of several carboxylic acid activating reagents corn conjugate moiety-ω-amino-1,3-diol linker compound inium hexafluorophosphate [HBTU] or benzotriazol-1-yl-oxy-tris(dimethylamino)phosphonium hexafluorophosphate [BOP], in N,N-dimethylformamide solution in the presence of a tertiary amine and 1-hydroxybenzotriazole hydrate. An aliquot of the activated carboxylic acid solution is added to a suspension of the solid synthesis support in N,N-dimethylformamide and the mixture shaken at ambient temperature for 1-2 hours. The quantity of the conjugate moiety-ω-amino-1,3-diol linker compound comprising a dicarboxylic acid tether attached to the solid support (the "loading") is then assayed by washing a small sample of the support with appropriate solvents, treating the sample with anhydrous acid solution (for example, 3% [v/v] dichloroacetic acid in methylene chloride) to remove the DMTr-protecting group, measuring the absorbance at 498 nm of the obtained acid solution, and calculating the quantity of DMTr-cation present using Beer's Law and a molar extinction coefficient of 70,000 M$^{-1}$ cm$^{-1}$. This analytical procedure is well known to those of ordinary skill in the art. Additional aliquots of the activated carboxylic acid solution are added as necessary to the solid support until the desired loading is obtained. Typical loadings are from about 5 to about 35 μmoles of conjugate moiety-ω-amino-1,3-diol linker compound per gram of solid support.

The details of the preparation of 4-(1-(cholesteryloxycarbonylamino)-5-(bis(4-methoxyphenyl)-(phenyl)methoxy) pentan-3-yloxy)-4-oxobutanoic acid attached to a solid polystyrene support according to the above general scheme are given in the following Examples 19 and 20, and are illustrated in FIG. 2B. In this case the dicarboxylic acid tether is succinic acid.

Example 19

Preparation of 4-(1-(cholesteryloxycarbonylamino)-5-(bis(4-methoxyphenyl)-(phenyl)methoxy)pentan-3-yloxy)-4-oxobutanoic acid triethylamine salt (VI)

Cholesteryl 5-(bis(4-methoxyphenyl)(phenyl)methoxy)-3-hydroxypentylcarbamate (6.6 g, 7.9 mmoles), succinic anhydride (0.8 g, 8.0 mmoles), triethylamine (3.3 mL, 23.7 mmoles) and 1-methylimidazole (0.3 mL, 3.9 mmoles) are dissolved in methylene chloride (60 mL). The reaction is stirred at ambient temperature for three days, during which time the solution darkened. The solution is then diluted with methylene chloride (100 mL) and washed twice with ice-cold aqueous citric acid (10% [w/v], 50 mL) and once with saturated aqueous sodium chloride (50 mL). The methylene chloride solution is dried over anhydrous sodium sulfate, filtered and evaporated to a dark resin. The crude product is purified on silica gel (175 mL bed volume) eluting with methylene chloride:triethylamine (95:5 [v/v], 1000 mL), then methylene chloride:methanol:triethylamine (90:5:5 [v/v/v], 1000 mL). Fractions containing pure product by thin layer chromatography are pooled and evaporated to a pale yellow resin. The resin is dried well in vacuo to give an off-white glassy foam. The yield is 6.3 g (85%).

Similarly, the following compounds are prepared:
i) 4-(8-(Cholesteryloxycarbonylamino)-1-(bis(4-methoxyphenyl)-(phenyl)methoxy)octan-3-yloxy)-4-oxobutanoic acid triethylamine salt from cholesteryl 8-(bis(4-methoxyphenyl)(phenyl)methoxy)-6-hydroxyoctylcarbamate.

ii) 4-(10-(Cholesteryloxycarbonylamino)-1-(bis(4-methoxyphenyl)-(phenyl)methoxy)octan-3-yloxy)-4-oxobutanoic acid triethylamine salt from cholesteryl 10-(bis(4-methoxyphenyl)(phenyl)methoxy)-8-hydroxydodecylcarbamate.

iii) 4-(14-(Cholesteryloxycarbonylamino)-1-(bis(4-methoxyphenyl)-(phenyl)methoxy)octan-3-yloxy)-4-oxobutanoic acid triethylamine salt from cholesteryl 14-(bis(4-methoxyphenyl)(phenyl)methoxy)-12-hydroxytetradecylcarbamate.

iv) 4-(1-(4-(Cholesteryloxycarbonylamino)phenyl)-3-(bis(4-methoxyphenyl)(phenyl)methoxy)-propoxy)-4-oxobutanoic acid triethylamine salt from cholesteryl 4-(3-(bis(4-methoxy-phenyl)(phenyl)methoxy)-1-hydroxypropyl)phenylcarbamate.

v) 4-(1-(1-(Cholesteryloxycarbonyl)piperidin-4-yl)-3-(bis(4-methoxyphenyl)(phenyl)methoxy)-propoxy)-4-oxobutanoic acid triethylamine salt from cholesteryl 4-(3-(bis(4-methoxy-phenyl)(phenyl)methoxy)-1-hydroxypropyl)piperidine-1-carboxylate.

vi) 4-(1-(1-(Cholesteryloxycarbonyl)pyrrolidin-2-yl)-3-(bis(4-methoxyphenyl)(phenyl)-methoxy)propoxy)-4-oxobutanoic acid triethylamine salt from cholesteryl 2-(3-(bis(4-methoxy-phenyl)(phenyl)methoxy)-1-hydroxypropyl)pyrrolidine-1-carboxylate.

vii) 4-(8-Acetamido-1-(bis(4-methoxyphenyl)(phenyl)methoxy)octan-3-yloxy)-4-oxobutanoic acid triethylamine salt from N-(8-(bis(4-methoxyphenyl)(phenyl)methoxy)-6-hydroxyoctyl)-acetamide.

viii) 4-(8-((6-Cholesteryloxycarbonyl)aminohexanamido)-1-(bis(4-methoxyphenyl)(phenyl)-methoxy)octan-3-yloxy)-4-oxobutanoic acid triethylamine salt from cholesteryl 6-(8-(bis(4-methoxyphenyl)(phenyl)methoxy)-6-hydroxyoctylamino)-6-oxo-hexylcarbamate.

ix) 4-(8-((12-Cholesteryloxycarbonyl)aminododecanamido)-1-(bis(4-methoxyphenyl)(phenyl)-methoxy)octan-3-yloxy)-4-oxobutanoic acid triethylamine salt from cholesteryl 12-(8-(bis(4-methoxyphenyl)(phenyl)methoxy)-6-hydroxyoctylamino)-12-oxododecyl-carbamate.

Example 20

Preparation of 4-(1-(cholesteryloxycarbonylamino)-5-(bis(4-methoxyphenyl)-(phenyl)methoxy)pentan-3-yloxy)-4-oxobutanoic acid Attached to Cross-Linked aminomethyl-polystyrene (VII)

AM-Polystyrene (5.0 g, ~33 μmoles amino groups per gram; Applied Biosystems) is suspended in dry, amine-free N,N-dimethylformamide (37.5 mL) in a single neck round bottom flask (250 mL) capped with a rubber septum. The flask is placed on a wrist-action shaker and shaken at ambient temperature to gently but thoroughly agitate the solid. In another flask (50 mL) are placed 4-(1-(cholesteryloxycarbonylamino)-5-(bis(4-methoxyphenyl)-(phenyl)methoxy)pentan-3-yloxy)-4-oxobutanoic acid triethylamine salt (105 mg, 113 μmoles), dry, amine-free N,N-dimethylformamide (25.0 mL), triethylamine (31 μL, 225.0 μmoles), 1-hydroxybenzotriazole hydrate (18 mg, 117.5 μmoles) and BOP (55 mg, 124 μmoles). The mixture is shaken well until all solids dissolve and then allowed to sit for five minutes at ambient temperature to activate the carboxylic acid. An aliquot of the activated carboxylic acid solution (16.7 mL, 75.4 μmoles) is added via syringe to the shaking solid support suspension. The mixture is shaken for 1.5 hours and a 40 mg aliquot of the solid is then removed and a loading of 11.0 μmoles/gram determined using the method outlined above. An additional aliquot of activated carboxylic acid (4.5 mL, 20.3 μmoles) is added and the suspension shaken for another hour. A loading of 14.5 μmoles/gram is determined. The solid suspension is poured into a coarse fitted glass funnel and the liquid drained under vacuum. The solid is then washed well with N,N-dimethylformamide (200 mL), acetone (200 mL) and acetonitrile (200 mL). It is dried overnight in vacuo. Residual amino groups on the support are capped by suspending the dried solid in a mixture of acetic anhydride in acetonitrile (10% [v/v], 25 mL) and 1-methylimidazole in acetonitrile (10% [v/v], 25 mL) and shaking for 2.5 hours at ambient temperature. The solid suspension is poured into a coarse fritted glass funnel and the liquid drained under vacuum. The solid is then washed well with acetonitrile (500 mL) and dried overnight in vacuo.

Solid supports having the compounds listed in Example 19 (i)-(ix) attached and loadings of approximately 15.0±1.0 μmoles/gram are prepared similarly.

The details of the preparation of 4-(1-(cholestanyloxycarbonylamino)-5-((bis(4-methoxyphenyl)-(phenyl)methoxy)pentan-3-yloxy)-2-oxoethoxy)acetic acid attached to a solid polystyrene support according to the above general scheme are given in the following Examples 21 and 22. In this case the dicarboxylic acid tether is diglycolic acid.

Example 21

Preparation of 4-(1-(cholestanyloxycarbonylamino)-5-((bis(4-methoxyphenyl)-(phenyl)methoxy)pentan-3-yloxy)-2-oxoethoxy)acetic acid triethylamine salt Cholestanyl 5-(bis(4-methoxyphenyl)(phenyl)methoxy)-3-hydroxypentylcarbamate (2.0 g, 2.4 mmoles), diglycolic anhydride (0.4 g, 3.6 mmoles), triethylamine (1.0 mL, 7.2 mmoles) and 1-methylimidazole (0.2 mL, 2.4 mmoles) are dissolved in methylene chloride (25 mL). The reaction is stirred at ambient temperature for three days, during which time the solution darkened. The solution is then diluted with methylene chloride (200 mL) and washed with 5% (w/v) aqueous dipotassium phosphate (50 mL). The methylene chloride solution is dried over anhydrous sodium sulfate, filtered and evaporated to a brown syrup. The crude product is purified on silica gel (100 mL bed volume) eluting with methylene chloride:triethylamine (95:5 [v/v], 400 mL), then methylene chloride:methanol:triethylamine (93:2:5 [v/v/v], 1000 mL). Fractions containing pure product by thin layer chromatography are pooled and evaporated to a pale tan glassy foam. The foam is dried well in vacuo. The yield is 2.0 g (79%).

Similarly, the following compounds are prepared:

i) 4-(1-(cholesteryloxycarbonylamino)-5-((bis(4-methoxyphenyl)-(phenyl)methoxy)pentan-3-yloxy)-2-oxoethoxy)acetic acid triethylamine salt from cholesteryl 5-(bis(4-methoxyphenyl)(phenyl)methoxy)-3-hydroxypentylcarbamate.

ii) 4-(1-(stigmasteryloxycarbonylamino)-5-((bis(4-methoxyphenyl)-(phenyl)methoxy)pentan-3-yloxy)-2-oxoethoxy)acetic acid triethylamine salt from stirmasteryl 5-(bis(4-methoxyphenyl)(phenyl)methoxy)-3-hydroxypentylcarbamate.

iii) 4-(1-(ergosteryloxycarbonylamino)-5-((bis(4-methoxyphenyl)-(phenyl)methoxy)pentan-3-yloxy)-2-oxoethoxy)acetic acid triethylamine salt from ergosteryl 5-(bis(4-methoxyphenyl)(phenyl)methoxy)-3-hydroxypentylcarbamate.

iv) 4-(1-(trans-androsteronyloxycarbonylamino)-5-((bis(4-methoxyphenyl)-(phenyl)methoxy)-pentan-3-yloxy)-2- oxoethoxy)acetic acid triethylamine salt from trans-androsteronyl 5-(bis(4-methoxyphenyl)(phenyl)methoxy)-3-hydroxypentylcarbamate.

v) 4-(1-(pregnenolonyloxycarbonylamino)-5-((bis(4-methoxyphenyl)-(phenyl)methoxy)pentan-3-yloxy)-2-oxoethoxy)acetic acid triethylamine salt from pregnenolonyl 5-(bis(4-methoxyphenyl)(phenyl)methoxy)-3-hydroxypentylcarbamate.

vi) 4-(1-(5α-androstan-3β-yloxycarbonylamino)-5-((bis(4-methoxyphenyl)-(phenyl)methoxy)-pentan-3-yloxy)-2-oxoethoxy)acetic acid triethylamine salt from 5α-androstan-3β-yl 5-(bis(4-methoxyphenyl)(phenyl)methoxy)-3-hydroxypentylcarbamate.

vii) 4-(1-(5α-androstan-17β-yloxycarbonylamino)-5-((bis(4-methoxyphenyl)-(phenyl)methoxy)-pentan-3-yloxy)-2-oxoethoxy)acetic acid triethylamine salt from 5α-androstan-17β-yl 5-(bis(4-methoxyphenyl)(phenyl)methoxy)-3-hydroxypentylcarbamate.

viii) 4-(1-(cholanylamido)-5-((bis(4-methoxyphenyl)-(phenyl)methoxy)pentan-3-yloxy)-2-oxoethoxy)acetic acid triethylamine salt from cholanyl 5-(bis(4-methoxyphenyl)(phenyl)methoxy)-3-hydroxypentylamide.

ix) 4-(1-(3-O-acetyllithocholylamido)-5-((bis(4-methoxyphenyl)-(phenyl)methoxy)pentan-3-yloxy)-2-oxoethoxy)acetic acid triethylamine salt from 3-O-acetyl-lithocholyl 5-(bis(4-methoxyphenyl)(phenyl)methoxy)-3-hydroxypentylamide.

x) 4-(1-N-methylamidolithocholylamido)-5-((bis(4-methoxyphenyl)-(phenyl)methoxy)pentan-3-yloxy)-2-oxoethoxy)acetic acid triethylamine salt from lithocholic acid methyl amide 5-(bis(4-methoxyphenyl)(phenyl)methoxy)-3-hydroxypentylcarbamate.

Example 22

Preparation of 4-(1-(cholestanyloxycarbonylamino)-5-(bis(4-methoxyphenyl)-(phenyl)methoxy)pentan-3-yloxy)-2-oxoethoxy)acetic acid Attached to Cross-Linked aminomethyl-polystyrene AM-Polystyrene (5.0 g, ~33 µmoles amino groups per gram; Applied Biosystems) is suspended in dry, amine-free N,N-dimethylformamide (37.5 mL) in a single neck round bottom flask (250 mL) capped with a rubber septum. The flask is placed on a wrist-action shaker and shaken at ambient temperature to gently but thoroughly agitate the solid. In another flask (50 mL) are placed 4-(1-(cholestanyloxycarbonylamino)-5-((bis(4-methoxyphenyl)-(phenyl)methoxy) pentan-3-yloxy)-2-oxoethoxy)acetic acid triethylamine salt (50 mg, 50 µmoles), dry, amine-free N,N-dimethylformamide (12.5 mL), triethylamine (10 µL, 90 µmoles), 1-hydroxybenzotriazole hydrate (10 mg, 50 µmoles) and BOP (20 mg, 50 µmoles). The mixture is shaken well until all solids dissolve and then allowed to sit for five minutes at ambient temperature to activate the carboxylic acid. An aliquot of the activated carboxylic acid solution (9.0 mL, 36 µmoles) is added via syringe to the shaking solid support suspension. The mixture is shaken for 1.5 hours and a 40 mg aliquot of the solid is then removed and a loading of 5.2 µmoles/gram determined using the method outlined above. An additional aliquot of activated carboxylic acid (1.3 mL, 5.2 µmoles) is added and the suspension shaken for another hour. A loading of 6.0 µmoles/gram is determined. The solid suspension is poured into a coarse fritted glass funnel and the liquid drained under vacuum. The solid is then washed well with N,N-dimethylformamide (200 mL), acetone (200 mL) and acetonitrile (200 mL). It is dried overnight in vacuo. Residual amino groups on the support are capped by suspending the dried solid in a mixture of acetic anhydride in acetonitrile (10% [v/v], 25 mL) and 1-methylimidazole in acetonitrile (10% [v/v], 25 mL) and shaking for 2.5 hours at ambient temperature. The solid suspension is poured into a coarse fritted glass funnel and the liquid drained under vacuum. The solid is then washed well with acetonitrile (500 mL) and dried overnight in vacuo.

Solid supports having the compounds listed in Example 21 (i)-(x) attached and loadings of approximately 6.0±0.5 µmoles/gram are prepared similarly.

Example 23

General Preparation of a Conjugate moiety-ω-amino-1,3-diol Linker Compound phosphoramidite A conjugate moiety-ω-amino-1,3-diol linker compound may be converted into a phosphoramidite derivative using methods well known to those of ordinary skill in the art.

The details of the preparation of cholesteryl 5-(bis(4-methoxyphenyl)(phenyl)methoxy)-3-((diisopropylamino)(methoxy)phosphinooxy)pentylcarbamate according to the above general scheme are given in the following Example 24, and are illustrated in FIG. 2B.

Example 24

Preparation of cholesteryl 5-(bis(4-methoxyphenyl)(phenyl)methoxy)-3-((diisopropylamino)(methoxy)phosphinooxy)pentylcarbamate (VIII)

Cholesteryl 5-(bis(4-methoxyphenyl)(phenyl)methoxy)-3-hydroxypentylcarbamate (1.3 g, 1.6 mmoles) is dissolved in dry methylene chloride (3.2 mL) containing N,N-diisopropylamine (224 µL, 1.6 mmoles). The solution is stirred at ambient temperature. In a separate flask, methyl N,N,N',N'-tetraisopropylphosphorodiamidite (0.6 g, 2.4 mmoles) is dissolved in a mixture of methylene chloride (3.2 mL), N,N-diisopropylamine (224 µL, 1.6 mmoles), and 5-ethylthio-1H-tetrazole in acetonitrile (0.5 M, 1.6 mL, 0.8 mmoles). This solution is stirred at ambient temperature for 5 minutes, then added in one portion to the first solution. The mixture is stirred for 6 hours. Methanol (5 mL) is added, and the solution is evaporated to a thick syrup. The crude product is purified on silica gel (75 mL bed volume) eluting with hexanes:acetone:triethylamine (95:5:2 [v/v/v], 500 mL). Fractions containing pure product by thin layer chromatography are pooled and evaporated to a clear colorless syrup. The syrup is co-evaporated twice with toluene (50 mL each). The resulting white glassy foam is dried well in vacuo. The yield is 1.4 g (88%).

Example 25

General Preparation of a Conjugate moiety-ω-amino-alcohol Linker Compound

Covalent attachment of a conjugate moiety to an ω-amino-alcohol linker requires a derivative of the conjugate moiety that is reactive with the amine functionality on the linker. Suitable reactive derivatives include carboxylic acid anydrides, carboxylic acid chlorides, activated carboxylic acid esters such as N-hydroxysuccinimidyl, N-hydroxybenzotriazolyl, or pentafluorophenyl, chloroformates, 4-nitrophenyl carbonates and sulfonyl chlorides, to list a few Examples. Such reactive derivatives can be prepared and isolated as pure compounds, or can be prepared in situ immediately prior to use. In general, equivalent molar quantities of the reactive conjugate derivative and the ω-amino-alcohol linker are dissolved together in an appropriate solvent and allowed to react at ambient temperature for 1 to 24 hours. Typical solvents depend on the solubility of the reagents and the type of reaction; for example, N,N-dimethylformamide is a useful solvent for the condensation of activated carboxylic acid esters with ω-amino-alcohol linkers, while pyridine is more appropriate for carboxylic acid anhydrides, chlorides or chloroformates where acid byproducts are produced.

Figure 3A:
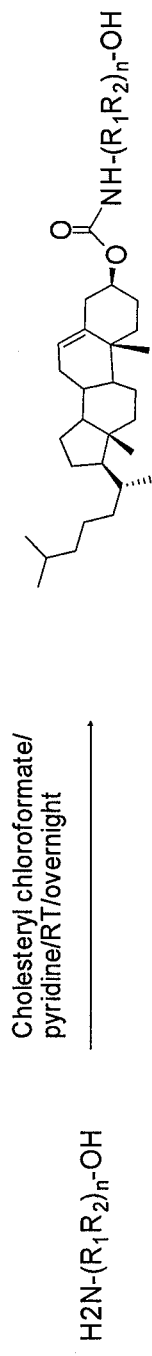
FIG. 3A is a generalized synthetic scheme for the preparation of a conjugate moiety-ω-amino-alcohol linker compound.

FIG. 3A describes a general synthetic scheme for preparing a conjugate moiety-ω-amino-alcohol linker compound. The details of the preparation of cholesteryl 2-hydroxyethylcarbamate according to the above general scheme are given in the following Example 26. In this case cholesterol is the conjugate moiety and cholesteryl chloroformate its reactive derivative.

Example 26

Preparation of cholesteryl 2-hydroxyethylcarbamate

2-Aminoethanol (0.4 mL, 6.7 mmoles) is dissolved in dry pyridine (150 mL) and cholesteryl chloroformate (3.0 g, 6.7 mmoles) is added. The reaction mixture is stirred overnight at ambient temperature. The mixture is evaporated to dryness. The crude product is purified on silica gel (500 mL bed volume) eluting with methylene chloride:methanol (100:4 [v/v], 2000 mL). Fractions containing pure product by thin layer chromatography are pooled and evaporated to a white glassy foam. The foam is dried well in vacuo. The yield is 2.8 g (87%).

Similarly, the following compounds are prepared:
 i) Cholesteryl 3-hydroxypropylcarbamate from cholesteryl chloroformate and 3-aminopropan-1-ol.
 ii) Cholesteryl 4-hydroxybutylcarbamate from cholesteryl chloroformate and 4-aminobutan-1-ol.
 iii) Cholesteryl 5-hydroxypentylcarbamate from cholesteryl chloroformate and 5-aminopentan-1-ol.
 iv) Cholesteryl 6-hydroxyhexylcarbamate from cholesteryl chloroformate and 6-aminohexan-1-ol.
 v) Cholesteryl 8-hydroxyoctylcarbamate from cholesteryl chloroformate and 8-aminooctan-1-ol. 8-Aminooctan-1-ol is prepared from 8-bromooctan-1-ol and sodium azide in refluxing 95% ethanol, followed by catalytic hydrogenation (10% Pd/C catalyst, 30 psi hydrogen) in methanol.
 vi) Cholesteryl 12-hydroxydodecylcarbamate from cholesteryl chloroformate and 12-aminododecan-1-ol. 12-Aminododecanl-1-ol is prepared from 12-bromododecan-1-ol and sodium azide in refluxing 95% ethanol, followed by catalytic hydrogenation (10% Pd/C catalyst, 30 psi hydrogen) in methanol.
 vii) Cholesteryl 4-(hydroxymethyl)phenylcarbamate from cholesteryl chloroformate and 4-aminobenzyl alcohol.
 viii) Cholesteryl 4-hydroxypiperidine-1-carboxylate from cholesteryl chloroformate and 4-hydroxypiperidine.

For additional clarity and ease of discussion in subsequent sections, Table 2 presents the structures of the above compounds and the abbreviated nomenclature associated therewith.

Example 27

General Preparation of a Conjugate moiety-ω-amino-alcohol Linker Compound phosphoramidite A conjugate moiety-ω-amino-alcohol linker compound may be converted into a phosphoramidite derivative using methods well known to those of ordinary skill in the art.

Figure 3B:
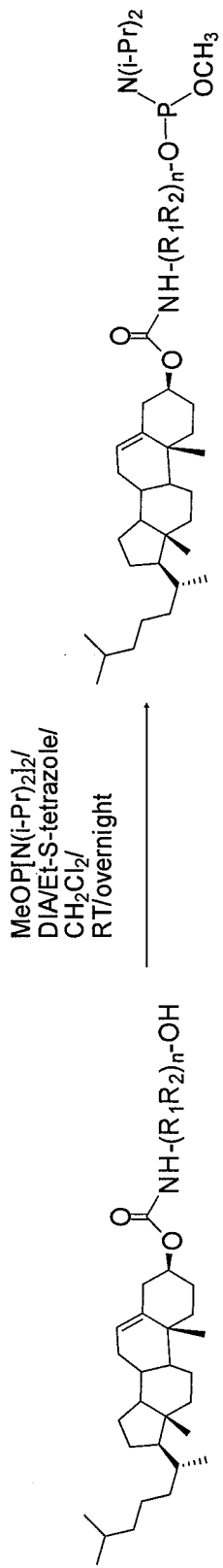
FIG. 3B is a generalized scheme for the preparation of a conjugate moiety-ω-amino-alcohol linker compound phosphoramidite.

FIG. 3B describes a general synthetic scheme for preparing a conjugate moiety-ω-amino-alcohol linker compound phosphoramidite. The details of the preparation of cholesteryl 2-((diisopropylamino)(methoxy)phosphinooxy)-ethylcarbamate according to the above general scheme are given in the following Example 28.

Example 28

Preparation of cholesteryl 2-((diisopropylamino)(methoxy)phosphinooxy)-ethylcarbamate Cholesteryl 2-hydroxyethylcarbamate (2.8 g, 5.8 mmoles) is dissolved in dry methylene chloride (11.6 mL) containing N,N-diisopropylamine (810 μL, 5.8 mmoles). The solution is stirred at ambient temperature. In a separate flask, methyl N,N,N',N'-tetraisopropylphosphorodiamidite (2.3 g, 8.7 mmoles) is dissolved in a mixture of methylene chloride (11.6 mL), N,N-diisopropylamine (810 μL, 5.8 mmoles), and 5-ethylthio-1H-tetrazole in acetonitrile (0.5 M, 5.8 mL, 2.9 mmoles). This solution is stirred at ambient temperature for 5 minutes, and then added in one portion to the first solution. The mixture is stirred overnight at ambient temperature, and then evaporated to a thick syrup. The crude product is purified on silica gel (400 mL bed volume) eluting with hexanes: acetone:triethylamine (94:3:3 [v/v/v], 1000 mL). Fractions containing pure product by thin layer chromatography are pooled and evaporated to a clear colorless syrup. The syrup is co-evaporated twice with toluene (50 mL each). The resulting syrup is dried well in vacuo. The yield is 3.1 g (85%).

Similarly, the following compounds are prepared:
 i) Cholesteryl 3-((diisopropylamino)(methoxy)phosphinooxy)propylcarbamate from cholesteryl 3-hydroxypropylcarbamate.
 ii) Cholesteryl 4-((diisopropylamino)(methoxy)phosphinooxy)butylcarbamate from cholesteryl 4-hydroxybutylcarbamate.
 iii) Cholesteryl 5-((diisopropylamino)(methoxy)phosphinooxy)pentylcarbamate from cholesteryl 5-hydroxypentylcarbamate.
 iv) Cholesteryl 6-((diisopropylamino)(methoxy)phosphinooxy)hexylcarbamate from cholesteryl 6-hydroxyhexylcarbamate.
 v) Cholesteryl 8-((diisopropylamino)(methoxy)phosphinooxy)octylcarbamate from cholesteryl 8-hydroxyoctylcarbamate.
 vi) Cholesteryl 12-((diisopropylamino)(methoxy)phosphinooxy)dodecylcarbamate from cholesteryl 12-hydroxydodecylcarbamate.
 vii) Cholesteryl 4-(((diisopropylamino)(methoxy)phosphinooxy)methyl)phenylcarbamate from cholesteryl 4-(hydroxymethyl)phenylcarbamate.
 viii) Cholesteryl 4-((diisopropylamino)(methoxy)phosphinooxy)piperidine-1-carboxylate from cholesteryl 4-hydroxypiperidine-1-carboxylate.
 ix) Cholesteryl methyl diisopropylphosphoramidite from cholesterol.

Example 29

General Preparation of a hydroxymethylpyrrolidinol Linker Compound

Figure 4:
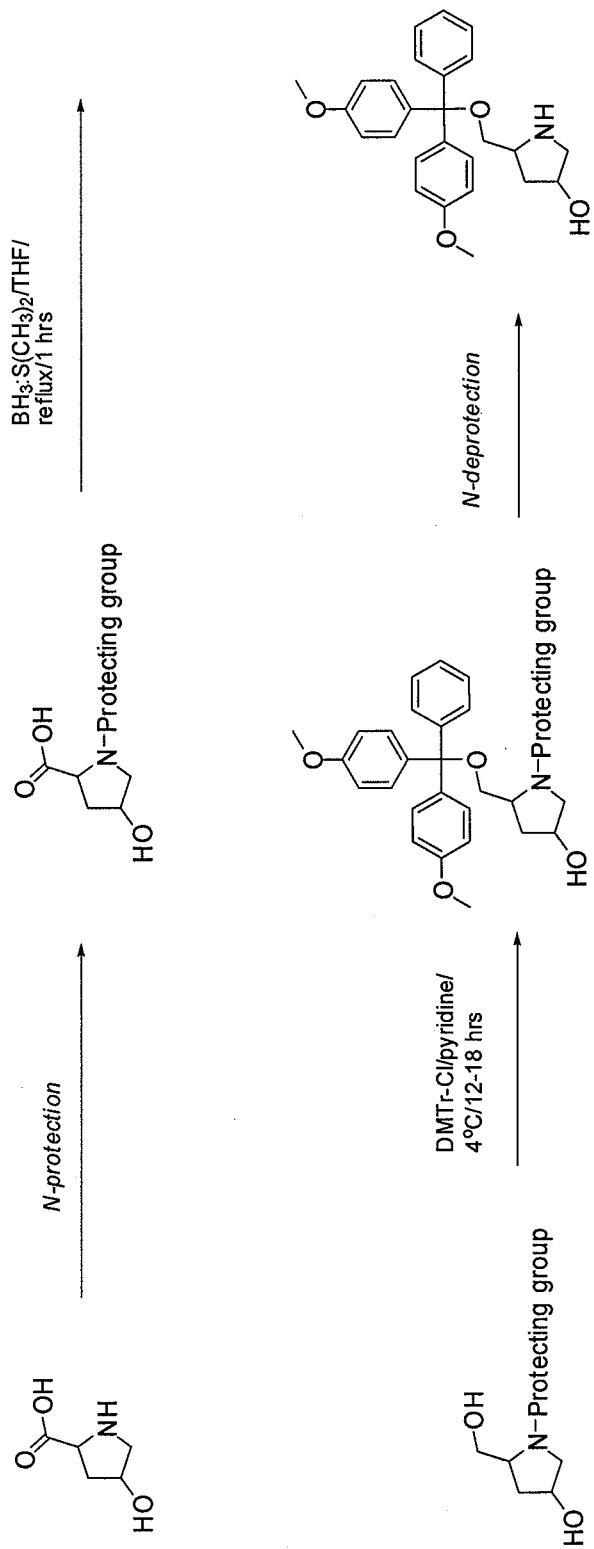
FIG. 4 is a generalized synthetic scheme for the preparation of a hydroxymethylpyrrolidinol linker compound.

FIG. 4 describes a general synthetic scheme for preparing a class of linkers based upon a hydroxymethylpyrrolidinol. Those of ordinary skill in the art will realize that the particular methods and materials described subsequently could be varied to produce the same product compounds. A hydroxyproline compound is reacted with a suitable N-protecting group (e.g., Fmoc, Boc, Cbz) to produce an N-protected hydroxyproline. This compound is reduced using borane-methyl sulfide complex in anhydrous tetrahydrofuran under reflux for 1 hour to produce the N-protected hydroxymethylpyrrolidinol. This compound is treated with 4,4'-dimethoxytritylchloride in pyridine solution at ambient temperature 12-18 hours to produce the N-protected O-DMT-protected hydroxymethylpyrrolidinol. The N-protecting group is then removed using a suitable reaction to yield the desired hydroxymethylpyrrolidinol linker compound.

Figure 5A:
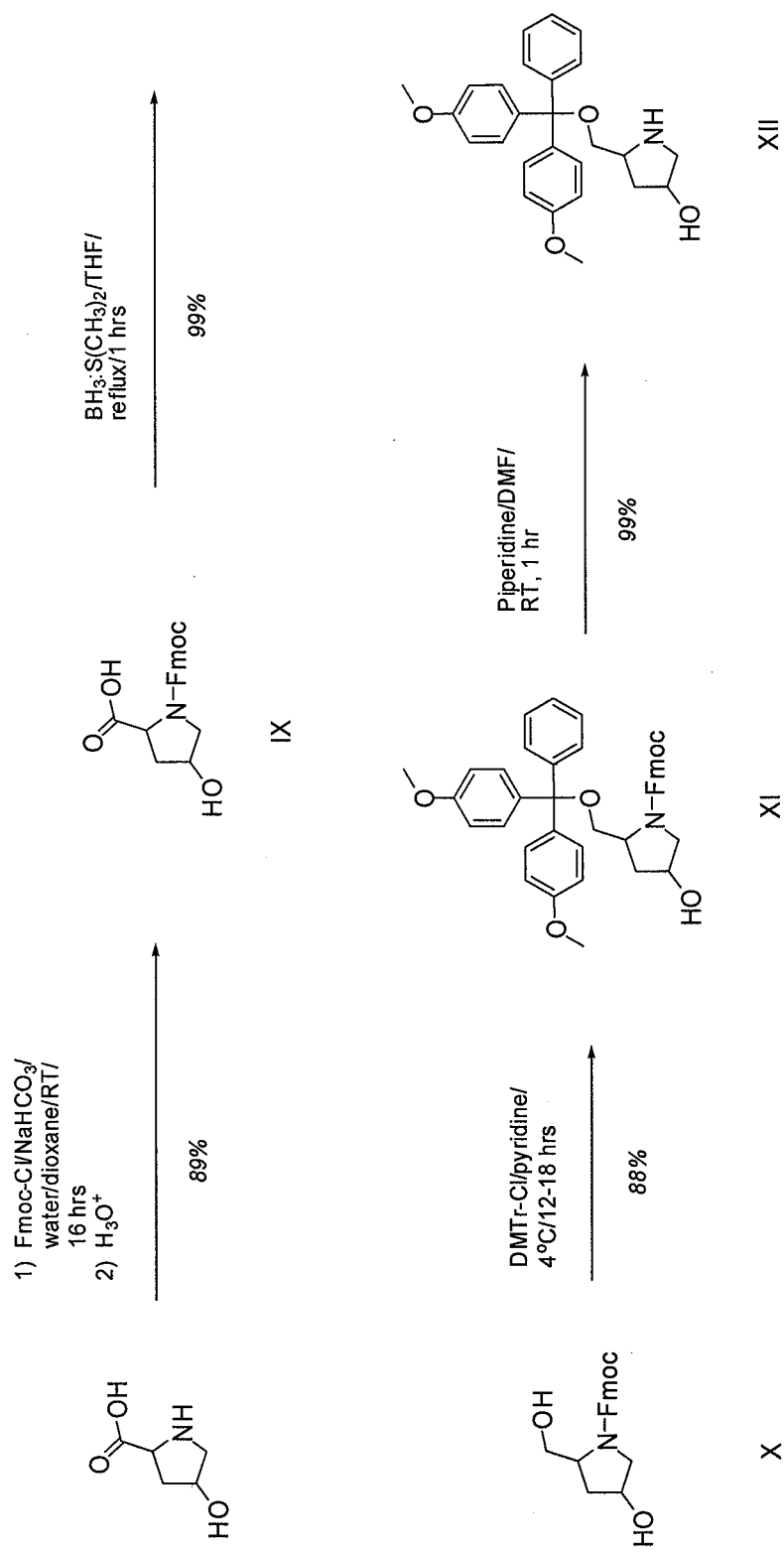
FIG. 5A is a synthetic scheme for the preparation of 5-((bis(4-methoxyphenyl)-(phenyl)methoxy)methyl)pyrrolidin-3-ol.

The details of the preparation of 5-((bis(4-methoxyphenyl) (phenyl)methoxy)methyl)pyrrolidin-3-ol according to the above general scheme are given in the following Examples 30-33, and are illustrated in FIG. 5A.

Example 30

Preparation of 1-(((9H-fluoren-9-yl)methoxy)carbonyl)-4-hydroxypyrrolidine-2-carboxylic acid (IX)

Trans-4-hydroxyproline (5.0 g, 38.1 mmoles) is suspended in a mixture of dioxane (75 mL) and water (75 mL), and stirred briskly at ambient temperature. Sodium bicarbonate (8.0 g, 95.2 mmoles) is added. And the mixture is stirred until all solids dissolve. A solution of 9-fluorenylmethyl chloroformate (11.4 g, 44.0 mmoles) in toluene (25 mL) is added slowly dropwise. The mixture is then stirred for 16 hours. Water (50 mL) and saturated aqueous sodium bicarbonate (50 mL) are added to the reaction mixture, which is then poured into a separatory funnel and washed with diethyl ether (100 mL). The layers are separated, and the aqueous layer is titrated to a pH of about 2 (as determined using pH paper) with concentrated aqueous hydrochloric acid. Ethyl acetate (150 mL) is added to the acidic solution; the mixture is shaken well, and then poured into a separatory funnel. The layers are separated and the aqueous layer extracted again with ethyl acetate (150 mL). The combined ethyl acetate extracts are dried over anhydrous sodium sulfate, filtered and evaporated to a white glassy foam. The crude product is purified on silica gel (400 mL bed volume) eluting with ethyl acetate:acetic acid (100:2 [v/v], 1800 mL), then ethyl acetate:methanol: acetic acid (95:5:2 [v/v/v], 1000 mL). Fractions containing pure product by thin layer chromatography are pooled and evaporated to a clear colorless syrup. The syrup is co-evaporated three time with toluene (150 mL each) to remove residual acetic acid. The resulting amorphous white solid is dried well in vacuo. The yield is 12.0 g (89%).

Example 31

Preparation of (9H-fluoren-9-yl)methyl 4-hydroxy-2-(hydroxymethyl)pyrrolidine-1-carboxylate (X)

1-(((9H-Fluoren-9-yl)methoxy)carbonyl)-4-hydroxypyrrolidine-2-carboxylic acid (13.3 g, 37.6 mmoles) is dissolved in anhydrous tetrahydrofuran (250 mL). The solution is stirred at ambient temperature, and borane-methyl sulfide complex in tetrahydrofuran (2 M, 40 mL, 80 mmoles) is added slowly via syringe. When the evolution of gas ceases, the flask is fitted with a condenser and Drierite drying tube and the solution is refluxed for 1 hour. During this time a white precipitate forms. Methanol (15 mL) is carefully added to the hot reaction mixture, which is refluxed for an additional 15 minutes, during which time the solid dissolves. The mixture is cooled and evaporated to a clear syrup. The syrup is coevaporated three times with methanol (100 mL each) to remove borate salts. The resulting brittle white solid is dried in vacuo. The yield is 12.7 g (99%).

Example 32

Preparation of (9H-fluoren-9-yl)methyl 2-((bis(4-methoxyphenyl)(phenyl)-methoxy)methyl)-4-hydroxypyrrolidine-1-carboxylate (XI)

(9H-Fluoren-9-yl)methyl 4-hydroxy-2-(hydroxymethyl) pyrrolidine-1-carboxylate (10.6 g, 31.2 mmoles) is coevaporated twice with anhydrous pyridine (50 mL each) and then dissolved in anhydrous pyridine (200 mL). The stirred solution is chilled in an ice bath, and 4,4'-dimethoxytritylchloride (11.0 g, 32.5 mmoles) is added in three approximately equal portions at thirty minute intervals. When the addition is complete, the flask is stoppered and place at 4° C. for 16 hours. The mixture is then evaporated to a thick yellow syrup, which is dissolved in toluene (100 mL), filtered and evaporated. The residue is dissolved in methylene chloride (350 mL) and washed successively with cold aqueous citric acid (10% [w/v], 150 mL), saturated aqueous sodium bicarbonate (150 mL) and saturated aqueous sodium chloride (150 mL). The methylene chloride solution is dried over anhydrous sodium sulfate, filtered and evaporated to a yellow foam. The crude product is purified on silica gel (500 mL bed volume) eluting with ethyl acetate:hexanes:triethylamine (50:50:1 [v/v/v], 1300 mL; then 67:33:1 [v/v/v], 1800 mL), then ethyl acetate: triethylamine (99:1 [v/v], 1000 mL). Fractions containing pure product by thin layer chromatography are pooled and evaporated to an off-white amorphous solid which is dried well in vacuo. The yield is 17.7 g (88%).

Example 33

Preparation of 5-((bis(4-methoxyphenyl)(phenyl) methoxy)methyl)pyrrolidin-3-ol (XII)

(9H-Fluoren-9-yl)methyl 2-((bis(4-methoxyphenyl)(phenyl)-methoxy)methyl)-4-hydroxypyrrol-idine-1-carboxylate (3.4 g, 5.3 mmoles) is dissolved in anhydrous N,N-dimethylformamide (15 mL). The solution is stirred at ambient temperature, and piperidine (1.1 mL, 11. mmoles) is added. After 1 hour, a copious white precipitate has formed. Water (100 mL) and ethyl acetate (75 mL) are added, and the mixture is stirred until all of the solid has dissolved. The layers are separated and the aqueous layer is extracted with ethyl acetate (75 mL). The combined ethyl acetate layers are washed with saturated aqueous sodium bicarbonate (50 mL) then saturated aqueous sodium chloride (50 mL), dried over anhydrous sodium sulfate and filtered. The filtrate is evaporated to an amorphous white solid. The crude product is purified on silica gel (150 mL bed volume) eluting with methylene chloride: methanol:triethylamine (94:1:5 [v/v/v], 700 mL; then 90:5:5 [v/v/v], 700 mL). Fractions containing pure product by thin layer chromatography are pooled and evaporated to a white glassy foam, which is dried well in vacuo. The yield is 2.2 g (99%).

Example 34

General Preparation of a Conjugate moiety-hydroxymethylpyrrolidinol Linker Compound The considerations for the preparation of these compounds are similar to those discussed previously for the case of conjugate moiety-ω-amino-1,3-diol linker compounds.

Figure 5B:
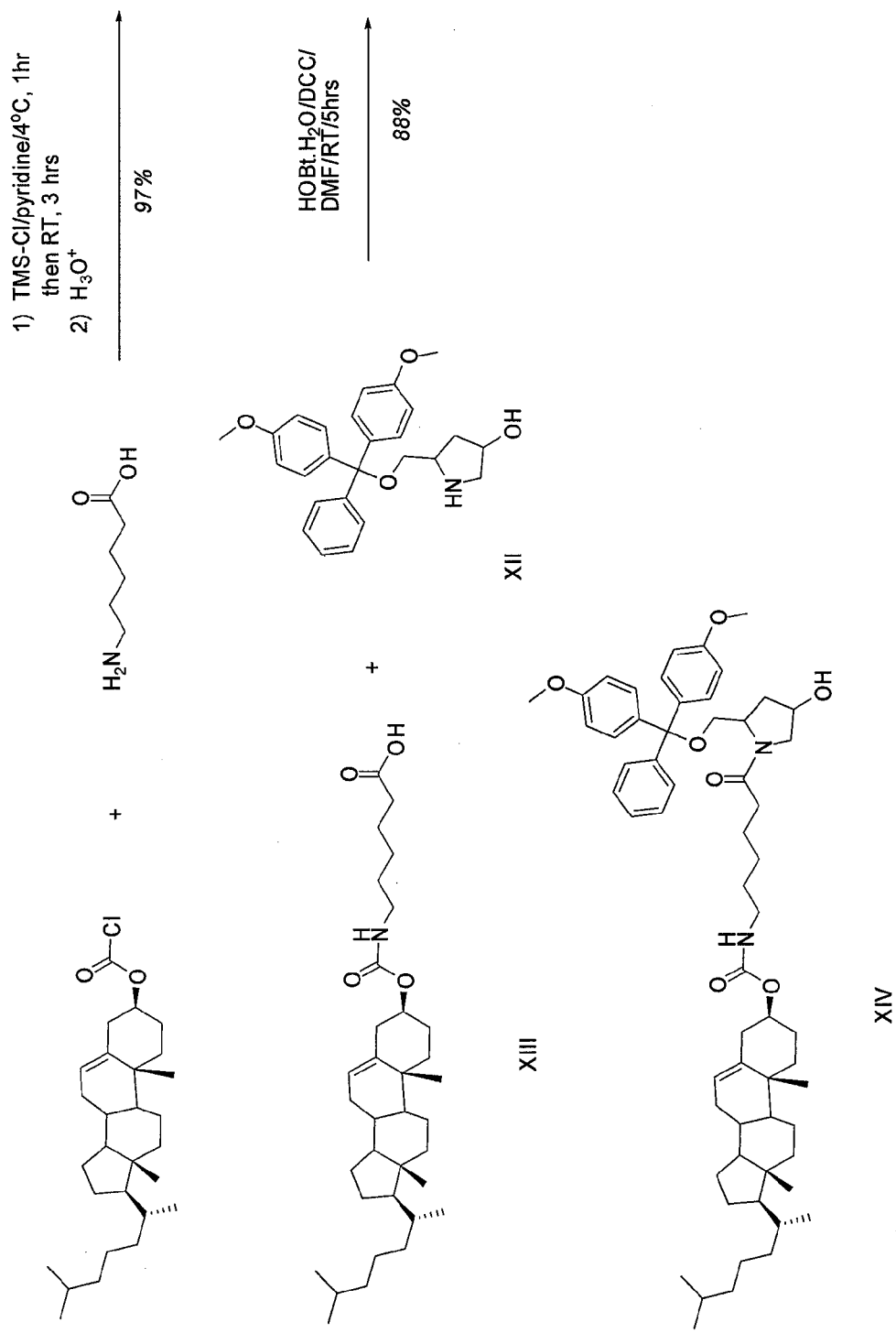
FIG. 5B is a synthetic scheme for the preparation of cholesteryl 6-(2-((bis(4-methoxyphenyl)(phenyl)methoxy)-methyl)-4-hydroxypyrrolidin-1-yl)-6-oxohexylcarbamate ("CHOL-C6-HP").

The details of the preparation of cholesteryl 6-(2-((bis(4-methoxyphenyl)(phenyl)methoxy)-methyl)-4-hydroxypyrrolidin-1-yl)-6-oxohexylcarbamate according to the above general scheme are given in the following Examples 35 and 36, and are illustrated in FIG. 5B. In this case cholesterol is the conjugate moiety and 6-cholesteryloxycarbonylaminohexanoic acid its reactive derivative.

Example 35

Preparation of
6-cholesteryloxycarbonylaminohexanoic acid (XIII)

6-Aminohexanoic acid (3.9 g, 29.7 mmoles) is suspended in dry pyridine (60 mL) and the stirred suspension is chilled in an ice bath. Chlorotrimethylsilane (15 mL, 118.6 mmoles) is added via syringe and the mixture is stirred for 1 hour, during which time all solids dissolve. Cholesteryl chloroformate (7.0 g, 15.6 mmoles) is added to the cold solution, followed 1 hour later by a further portion of cholesteryl chloroformate (6.5 g, 14.5 mmoles). The ice bath is then removed and the mixture stirred at ambient temperature for 3 hours. The reaction is again chilled in an ice bath, and cold aqueous hydrochloric acid (0.7 $\underline{M}$, 150 mL) is added slowly. After 15 minutes, the mixture is poured into a separatory funnel and methylene chloride is added (200 mL). The contents of the flask are shaken well and the layers separated. The aqueous layer is extracted further with methylene chloride (200 mL). The combined methylene chloride extracts are washed with aqueous hydrochloric acid (0.7 $\underline{M}$, 200 mL) then saturated aqueous sodium chloride (200 mL), dried over anhydrous sodium sulfate, and filtered. The filtrate is evaporated to an amorphous white solid. The solid is dissolved in acetone (150 mL) and the product precipitated by the addition of aqueous hydrochloric acid (1 $\underline{M}$, 200 mL). The solid is collected by filtration, washed with water, and dried well in vacuo. The yield is 15.8 g (97%).

Example 36

Preparation of cholesteryl 6-(2-((bis(4-methoxyphenyl)(phenyl)methoxy)-methyl)-4-hydroxypyrrolidin-1-yl)-6-oxohexylcarbamate (XIV)

6-cholesteryloxycarbonylaminohexanoic acid (2.9 g, 5.3 mmoles) is dissolved in methylene chloride (50 mL), and 1-hydroxybenzotriazole hydrate (0.9 g, 5.6 mmole) is added, followed by N,N'-dicyclohexylcarbodiimide (1.1 g, 5.3 mmoles). The mixture is stirred at ambient temperature for 1 hour, during which time a white precipitate of N,N'-dicyclohexylurea forms. 5-((bis(4-methoxyphenyl)(phenyl)methoxy)methyl)pyrrolidin-3-ol (2.2 g, 5.2 mmoles) is added, and the mixture is stirred for four hours. The mixture is then filtered and the filtrate is concentrated to a small volume (about 25 mL). Ethyl acetate (200 mL) is added, and the solution is washed three times with saturated aqueous sodium bicarbonate (100 mL each) and once with saturated aqueous sodium chloride (100 mL). The ethyl acetate solution is dried over anhydrous sodium sulfate, filtered and evaporated to a pale yellow glassy foam. The crude product is purified on silica gel (250 mL bed volume) eluting with methylene chloride:hexanes:triethylamine (75:20:5 [v/v/v], 1000 mL) then methylene chloride:triethylamine (95:5 [v/v], 500 mL). Fractions containing pure product by thin layer chromatography are pooled and evaporated to an off-white glassy foam, which is dried well in vacuo. The yield is 4.4 g (88%).

Example 37

General Preparation of a Conjugate
moiety-hydroxymethylpyrrolidinol Linker
Compound Attached to a Solid Support Useful for
Oligonucleotide Synthesis The considerations for the preparation of these compounds are similar to those discussed previously for the case of conjugate moiety-ω-amino-1,3-diol linker compounds.

Figure 5C:
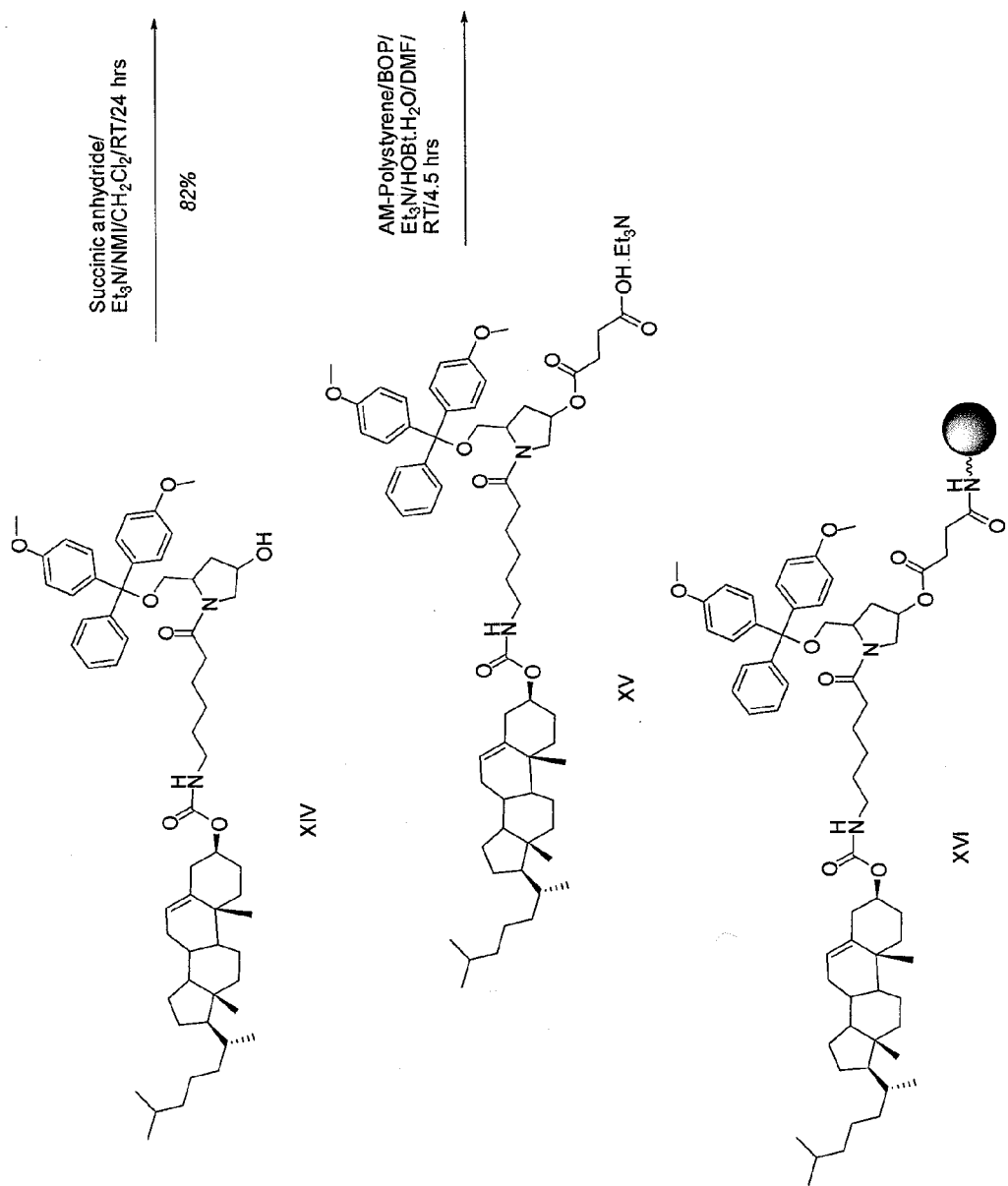
FIG. 5C is a synthetic scheme for preparation of a solid support useful for oligonucleotide synthesis from CHOL-C6-HP.

The details of the preparation of 4-(5-((bis(4-methoxyphenyl)(phenyl)methoxy)methyl)-1-(6-((cholesteryloxy)carbonylamino)hexanoyl)-pyrrolidin-3-yloxy)-4-oxobutanoic acid attached to a solid polystyrene support according to the above general scheme are given in the following Example 38 and 39, and are illustrated in FIG. 5C. In this case the dicarboxylic acid tether is succinic acid.

Example 38

Preparation of 4-(5-((bis(4-methoxyphenyl)(phenyl)methoxy)methyl)-1-(6-((cholesteryloxy)carbonylamino)hexanoyl)-pyrrolidin-3-yloxy)-4-oxobutanoic acid triethylamine salt (XV)

Cholesteryl 6-(2-((bis(4-methoxyphenyl)(phenyl)methoxy)-methyl)-4-hydroxypyrrolidin-1-yl)-6-oxohexylcarbamate (4.3 g, 4.6 mmoles), succinic anhydride (0.5 g, 5.0 mmoles), triethylamine (1.9 mL, 13.6 mmoles) and 1-methylimidazole (0.2 mL, 2.3 mmoles) are dissolved in methylene chloride (50 mL). The reaction is stirred at ambient temperature for 24 hours. The solution is then diluted with methylene chloride (100 mL) and washed twice with ice-cold aqueous citric acid (10% [w/v], 50 mL) and once with saturated aqueous sodium chloride (50 mL). The methylene chloride solution is dried over anhydrous sodium sulfate, filtered and evaporated to yellow resin. The crude product is purified on silica gel (150 mL bed volume) eluting with methylene chloride:triethylamine (95:5 [v/v], 500 mL), then methylene chloride:methanol:triethylamine (90:5:5 [v/v/v], 1000 mL). Fractions containing pure product by thin layer chromatography are pooled and evaporated to an off-white glassy foam which is dried well in vacuo. The yield is 4.3 g (82%).

Example 39

Preparation of 4-(5-((bis(4-methoxyphenyl)(phenyl)methoxy)methyl)-1-(6-((cholesteryloxy)carbonylamino)hexanoyl)-pyrrolidin-3-yloxy)-4-oxobutanoic acid Attached to Cross-Linked aminomethyl-polystyrene (XVI)

AM-Polystyrene (5.0 g, ~33 μmoles amino groups per gram; Applied Biosystems) is suspended in dry, amine-free N,N-dimethylformamide (37.5 mL) in a single neck round bottom flask (250 mL) capped with a rubber septum. The flask is placed on a wrist-action shaker and shaken at ambient temperature to gently but thoroughly agitate the solid. In another flask (50 mL) are placed 4-(5-((bis(4-methoxyphenyl)(phenyl)methoxy)methyl)-1-(6-((cholesteryloxy)carbonyl-amino)hexanoyl)-pyrrolidin-3-yloxy)-4-oxobutanoic acid triethylamine salt (241 mg, 210 μmoles), dry, amine-free N,N-dimethylformamide (25.0 mL), triethylamine (58 μL, 420 μmoles), 1-hydroxybenzotriazole hydrate (34 mg, 252 μmoles) and BOP (102 mg, 231 μmoles). The mixture is shaken well until all solids dissolve and then allowed to sit for five minutes at ambient temperature to activate the carboxylic acid. An aliquot of the activated carboxylic acid solution (9.0 mL, 75.6 µmoles) is added via syringe to the shaking solid support suspension. The mixture is shaken for 2.5 hours and a 40 mg aliquot of the solid is then removed and a loading of 12.2 µmoles/gram determined using the method outlined above. An additional aliquot of activated carboxylic acid (2.5 mL, 21.0 µmoles) is added and the suspension shaken for another 2 hours. A loading of 15.0 µmoles/gram is determined. The solid suspension is poured into a coarse fritted glass funnel and the liquid drained under vacuum. The solid is then washed well with N,N-dimethylformamide (200 mL), acetone (200 mL) and acetonitrile (200 mL). It is dried overnight in vacuo. Residual amino groups on the support are capped by suspending the dried solid in a mixture of acetic anhydride in acetonitrile (10% [v/v], 25 mL) and 1-methylimidazole in acetonitrile (10% [v/v], 25 mL) and shaking for 2.5 hours at ambient temperature. The solid suspension is poured into a coarse fitted glass funnel and the liquid drained under vacuum. The solid is then washed well with acetonitrile (500 mL) and dried overnight in vacuo.

Example 40

General Preparation of a Conjugate moiety-ω-amino-1,2-diol Linker Compound

The considerations for the preparation of these compounds are similar to those discussed previously for the case of conjugate moiety-ω-amino-1,3-diol linker compounds.

Figure 6A:
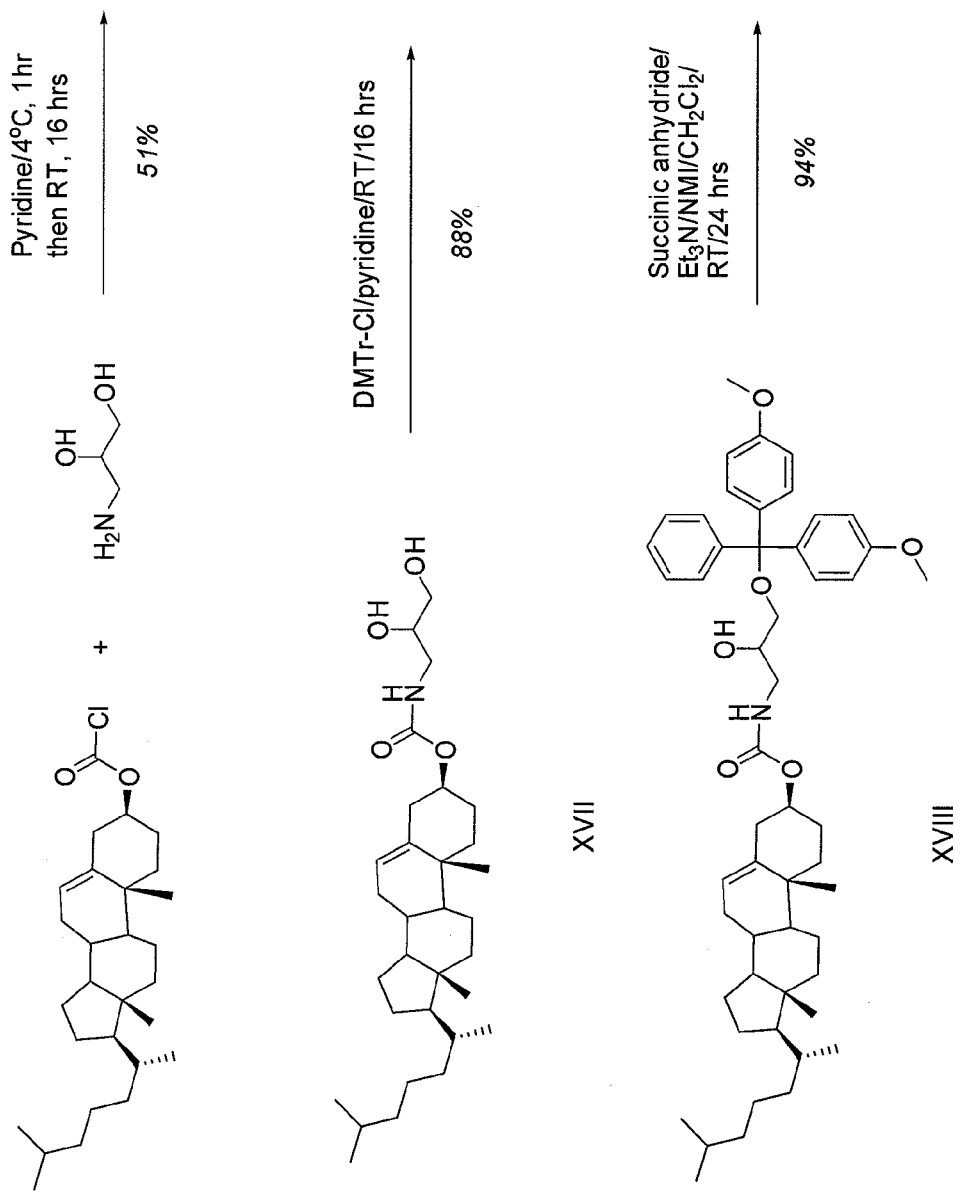
FIGS. 6A-6B depicts a synthetic scheme for the preparation of cholesteryl 3-(bis(4-methoxyphenyl)(phenyl)methoxy)-2-hydroxypropylcarbamate ("CHOL-C3") and preparation of a solid support useful for oligonucleotide synthesis from CHOL-C3.

The details of the preparation of cholesteryl 3-(bis(4-methoxyphenyl)(phenyl)methoxy)-2-hydroxypropylcarbamate according to the above general scheme are given in the following Examples 41 and 42, and are illustrated in FIG. 6A. In this case cholesterol is the conjugate moiety, and cholesteryl chloroformate its reactive derivative.

Example 41

Preparation of cholesteryl 2,3-dihydroxypropylcarbamate (XVII)

3-Amino-1,2-propanediol (2.0 g, 22.0 mmoles) is coevaporated twice with dry pyridine (50 mL each) then dissolved in dry pyridine (147 mL). The solution is stirred in an ice bath, and a solution of cholesteryl chloroformate (10.4 g, 23.1 mmoles) in toluene (50 mL) is added dropwise over 30 minutes. After addition, the ice bath is removed and the reaction mixture is stirred at ambient temperature for 16 hours. The solution is then evaporated, and the residue is coevaporated twice with toluene (50 mL each). The crude product is purified on silica gel (300 mL bed volume) eluting with hexanes:acetone (90:10 [v/v], 1000 mL; then 85:15 [v/v], 1000 mL; then 70:30 [v/v], 1000 mL; then 65:35 [v/v], 1000 mL). Fractions containing pure product by thin layer chromatography are pooled and evaporated to syrup which is dried well in vacuo. The yield is 5.7 g (51%).

Example 42

Preparation of cholesteryl 3-(bis(4-methoxyphenyl)(phenyl)methoxy)-2-hydroxypropylcarbamate (XVIII)

Cholesteryl 2,3-dihydroxypropylcarbamate (5.7 g, 11.4 mmoles) is dissolved in dry pyridine (50 mL) and stirred in an ice bath. A solution of 4,4'-dimethoxytritylchloride (4.1 g, 12.1 mmoles) in pyridine (26 mL) is added slowly dropwise. When the addition is complete, the cooling bath is removed and the mixture is stirred at ambient temperature for 16 hours. The mixture is then evaporated to a thick yellow syrup. The crude product is purified on silica gel (250 mL bed volume) eluting with hexanes:acetone:triethylamine (95:5:2 [v/v/v], 1000 mL; then 90:10:2 [v/v/v], 2000 mL). Fractions containing pure product by thin layer chromatography are pooled and evaporated to a resin which is dried well in vacuo. The yield is 8.1 g (88%).

Example 43

General Preparation of a Conjugate moiety-ω-amino-1,2-diol Linker Compound Attached to a Solid Support Useful for Oligonucleotide Synthesis The considerations for the preparation of these compounds are similar to those discussed previously for the case of conjugate moiety-ω-amino-1,3-diol linker compounds.

Figure 6B:
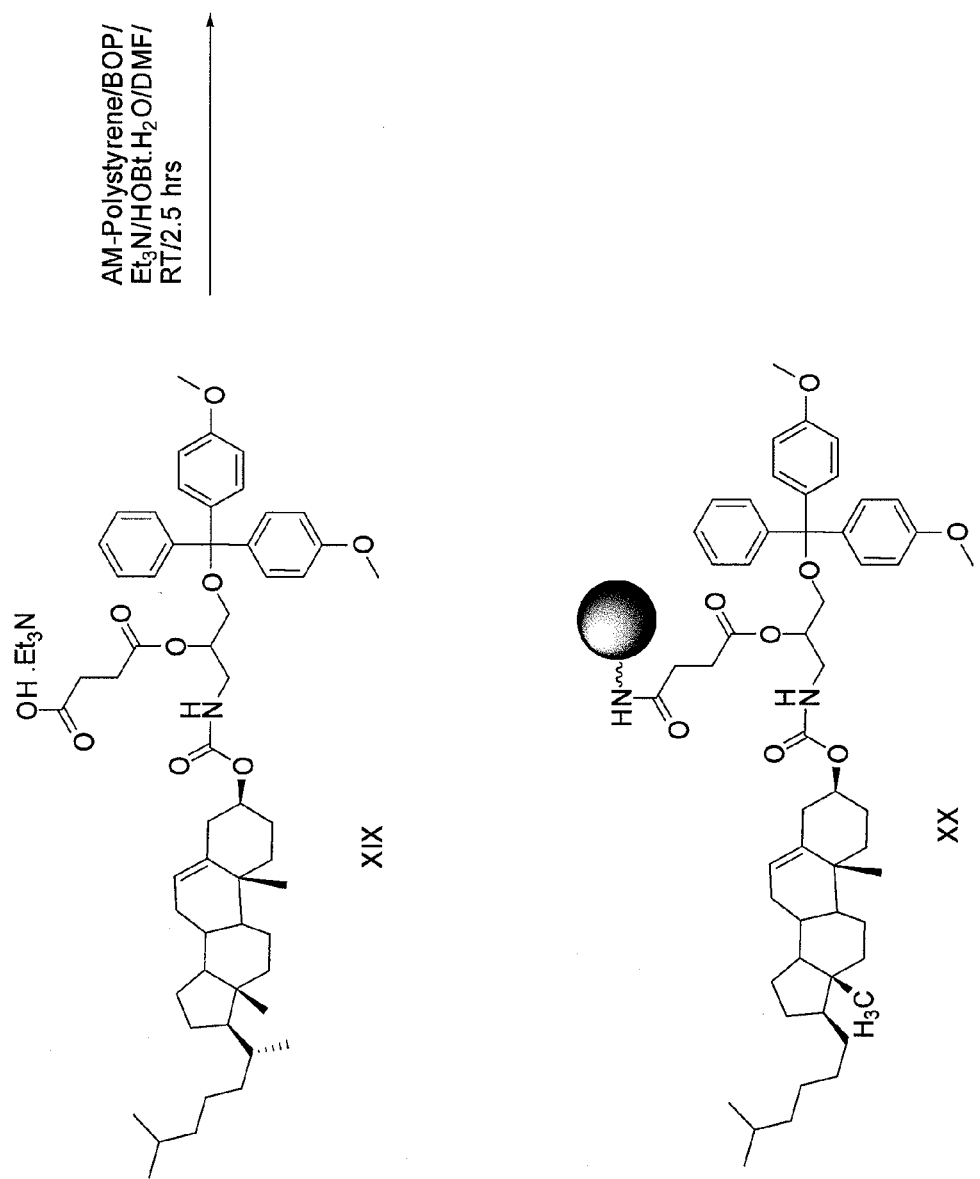

The details of the preparation of 4-(1-(bis(4-methoxyphenyl)(phenyl)methoxy)-3-((cholesteryloxy)carbonylamino) propan-2-yloxy)-4-oxobutanoic acid attached to a solid polystyrene support according to the above general scheme are given in the following Examples 44 and 45, and are illustrated in FIG. 6B. In this case the dicarboxylic acid tether is succinic acid.

Example 44

Preparation of 4-(1-(bis(4-methoxyphenyl)(phenyl) methoxy)-3-((cholesteryloxy)-carbonylamino)propan-2-yloxy)-4-oxobutanoic acid triethylamine salt (XIX)

Cholesteryl 3-(bis(4-methoxyphenyl)(phenyl)methoxy)-2-hydroxypropylcarbamate (8.1 g, 10.0 mmoles), succinic anhydride (1.0 g, 10.0 mmoles), triethylamine (4.2 mL, 30.0 mmoles) and 1-methylimidazole (0.4 mL, 5.0 mmoles) are dissolved in methylene chloride (81 mL). The reaction is stirred at ambient temperature for 24 hours. The solution is then diluted with methylene chloride (100 mL) and washed twice with ice-cold aqueous citric acid (10% [w/v], 50 mL) and once with saturated aqueous sodium chloride (50 mL). The methylene chloride solution is dried over anhydrous sodium sulfate, filtered and evaporated to yellow resin. The crude product is purified on silica gel (200 mL bed volume) eluting with methylene chloride:triethylamine (95:5 [v/v], 1000 mL), then methylene chloride:methanol:triethylamine (93:2:5 [v/v/v], 1000 mL). Fractions containing pure product by thin layer chromatography are pooled and evaporated to a glassy foam which is dried well in vacuo. The yield is 8.6 g (94%).

Example 45

Preparation of 4-(1-(bis(4-methoxyphenyl)(phenyl) methoxy)-3-((cholesteryloxy)-carbonylamino)propan-2-yloxy)-4-oxobutanoic acid Attached to Cross-Linked aminomethyl-polystyrene (XX)

AM-Polystyrene (5.0 g, ~33 µmoles amino groups per gram; Applied Biosystems) is suspended in dry, amine-free N,N-dimethylformamide (37.5 mL) in a single neck round bottom flask (250 mL) capped with a rubber septum. The flask is placed on a wrist-action shaker and shaken at ambient temperature to gently but thoroughly agitate the solid. In another flask (50 mL) are placed 4-(1-(bis(4-methoxyphenyl) (phenyl)methoxy)-3-((cholesteryloxy)-carbonylamino)-propan-2-yloxy)-4-oxobutanoic acid triethylamine salt (113 mg, 113 µmoles), dry, amine-free N,N-dimethylformamide (25.0 mL), triethylamine (31 µL, 225 µmoles), 1-hydroxybenzotriazole hydrate (18 mg, 135 µmoles) and BOP (55 mg, 124 µmoles). The mixture is shaken well until all solids dissolve and then allowed to sit for five minutes at ambient temperature to activate the carboxylic acid. An aliquot of the activated carboxylic acid solution (16.7 mL, 75.4 µmoles) is added via syringe to the shaking solid support suspension. The mixture is shaken for 1.5 hours and a 40 mg aliquot of the solid is then removed and a loading of 12.5 µmoles/gram determined using the method outlined above. An additional aliquot of activated carboxylic acid (2.7 mL, 12.2 µmoles) is added and the suspension shaken for another hour. A loading of 14.7 µmoles/gram is determined. The solid suspension is poured into a coarse fitted glass funnel and the liquid drained under vacuum. The solid is then washed well with N,N-dimethylformamide (200 mL), acetone (200 mL) and acetonitrile (200 mL). It is dried overnight in vacuo. Residual amino groups on the support are capped by suspending the dried solid in a mixture of acetic anhydride in acetonitrile (10% [v/v], 25 mL) and 1-methylimidazole in acetonitrile (10% [v/v], 25 mL) and shaking for 2.5 hours at ambient temperature. The solid suspension is poured into a coarse fitted glass funnel and the liquid drained under vacuum. The solid is then washed well with acetonitrile (500 mL) and dried overnight in vacuo.

Example 46

General Preparation of a Conjugate moiety-1,3-diol Linker Compound Attached to a Solid Support Useful for Oligonucleotide Synthesis Certain desirable conjugate moieties of this invention will have functional groups inherent in their structure that may be converted to provide linker capabilities directly. For example, conjugate moieties having a carboxylic acid group not critical to the function of the conjugate moiety can be directly converted into conjugate moiety-linker compounds using the same chemical transformations described previously for preparing ω-amino-1,3-diol linker compounds. Similarly, conjugate moieties having a hydroxyl group not critical to the function of the conjugate moiety can be directly converted into phosphoramidite derivatives using the same chemical transformations described previously.

Figure 7:
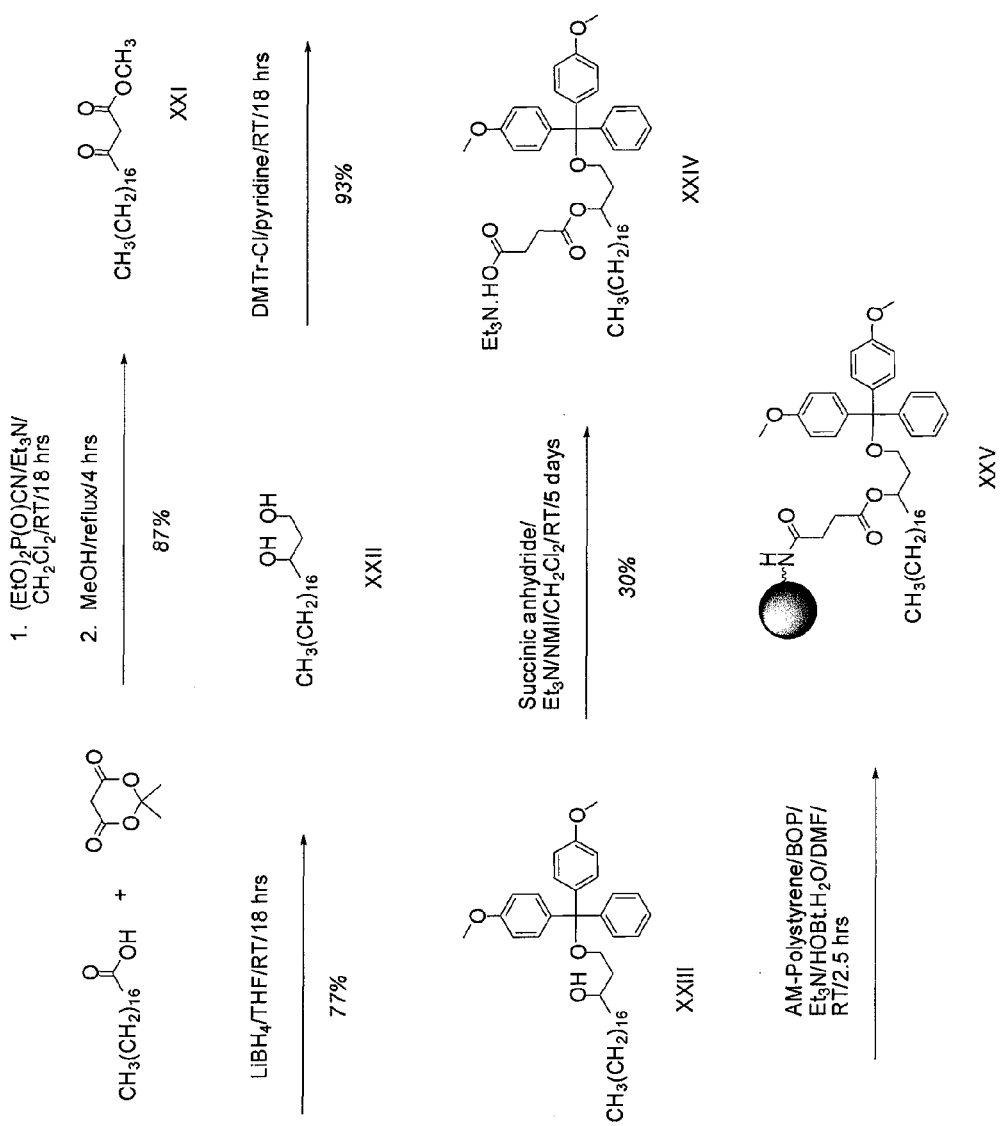
FIG. 7 is a generalized synthetic scheme for the preparation of a conjugate moiety-1,3-diol linker compound attached to a solid support useful for oligonucleotide synthesis.

The details of the preparation of 4-(1-(bis(4-methoxyphenyl)(phenyl)methoxy)icosan-3-yloxy)-4-oxobutanoic acid attached to a solid polystyrene support according to the above general scheme are given in the following Examples 47-51, and are illustrated in FIG. 7. In this case the dicarboxylic acid tether is succinic acid.

Example 47

Preparation of methyl 3-oxoicosanoate (XXI)

Stearic acid (5.0 g, 17.6 mmoles) is suspended in methylene chloride (88 mL) and 2,2-dimethyl-1,3-dioxane-4,6-dione (2.7 g, 18.5 mmoles), triethylamine (6.7 mL, 48.0 mmoles) and diethyl cyanophosphonate (2.7 mL, 17.6 mmoles) are added. All solids dissolve quickly. The solution is stirred for 16 hours at ambient temperature. The reaction mixture is then diluted with methylene chloride (100 mL) and carefully washed three times with aqueous hydrochloric acid (3 M, 50 mL each), three times with water (50 mL each) and once with saturated aqueous sodium chloride (50 mL). The reaction mixture is then dried over anhydrous sodium sulfate, filtered and evaporated. The resulting syrup is dissolved in anhydrous methanol (100 mL) and heated to reflux for 16 hours. The methanol is evaporated and the crude product dissolved in hexanes with slight heating. The crude product was then loaded on silica gel (150 mL bed volume) eluting with hexanes (500 mL) then hexane:acetone (98:2 [v/v], 1000 mL). Fractions containing pure product by thin layer chromatography are pooled and evaporated to dryness. The resulting oil is dried well in vacuo. The yield is 5.2 g (87%).

Similarly, the following compounds are prepared:
i) Methyl 3-oxodecanote from caprylic acid.
ii) (E)-Methyl 3-oxoicos-11-enoate from elaidic acid.
iii) (Z)-Methyl 3-oxoicos-11-enoate from oleic acid.
iv) (11Z,14Z)-Methyl 3-oxoicosa-11,14-dienoate from linoleic acid.

Example 48

Preparation of icosane-1,3-diol (XXII)

Methyl 3-oxoicosanoate (5.2 g, 15.3 mmoles) is dissolved in anhydrous tetrahydrofuran (31 mL) and this solution is added slowly dropwise to an ice-cooled solution of lithium borohydride in anhydrous tetrahydrofuran (2 M, 31 mL, 61.2 mmoles). When the addition is complete, the cooling bath is removed and the reaction is stirred at ambient temperature for 16 hours. The clear, colorless solution is again cooled in an ice bath, and aqueous hydrochloric acid (1 M, 62 mL) is added slowly dropwise to decompose the excess reducing agent (gas is evolved). When a homogeneous solution is obtained, the mixture is concentrated to remove tetrahydrofuran. Methylene chloride (100 mL) is added; the mixture is shaken well and poured into a separatory funnel. The layers are allowed to separate and the bottom aqueous layer is drawn off. The aqueous layer is then washed once more with methylene chloride (100 mL), and the combined methylene chloride solutions are washed with saturated aqueous sodium chloride (50 mL). The methylene chloride solution is then dried over anhydrous sodium sulfate, filtered and co-evaporated five times with methanol (50 mL each) to dryness. The oil is dried well in vacuo. The yield is 3.7 g (77%).

Similarly, the following compounds are prepared:
i) Decane-1,3-diol from methyl 3-oxodecanote.
ii) (E)-Icos-11-ene-1,3-diol from (E)-methyl 3-oxoicos-11-enoate.
iii) (Z)-Icos-11-ene-1,3-diol from (Z)-methyl 3-oxoicos-11-enoate.
iv) (11Z,14Z)-Icosa-11,14-diene-1,3-diol from (11Z,14Z)-methyl 3-oxoicosa-11,14-dienoate.

Example 49

Preparation of 1-(bis(4-methoxyphenyl)(phenyl)methoxy)icosan-3-ol (XXIII)

Icosane-1,3-diol (3.7 g, 11.8 mmoles) is co-evaporated twice with anhydrous pyridine (50 mL each) and then is dissolved in anhydrous pyridine (60 mL). The solution is chilled in an ice bath, and 4,4'-dimethoxytritylchloride (4.2 g, 12.4 mmoles) is added. The reaction is allowed to warm to ambient temperature and is stirred for 16 hours. The remaining 4,4'-dimethoxytritylchloride is quenched with methanol (10 mL), and the yellow solution is then evaporated to near dryness. The residue is co-evaporated twice to dryness with toluene (50 mL each). The crude product is purified on silica gel (150 mL bed volume) eluting with hexanes:acetone:triethylamine (95.5:5:0:5 [v/v/v], 500 mL). Fractions containing pure product by thin layer chromatography are pooled and evaporated to a pale yellow syrup. The syrup is dried well in vacuo. The yield is 6.8 g (93%).

Similarly, the following compounds are prepared:
i) 1-(Bis(4-methoxyphenyl)(phenyl)methoxy)decan-3-ol from decane-1,3-diol.
ii) (E)-1-(Bis(4-methoxyphenyl)(phenyl)methoxy)icos-11-en-3-ol from (E)-icos-11-ene-1,3-diol.
iii) (Z)-1-(Bis(4-methoxyphenyl)(phenyl)methoxy)icos-11-en-3-ol from (Z)-icos-11-ene-1,3-diol.
iv) (11Z,14Z)-1-(Bis(4-methoxyphenyl)(phenyl)methoxy)icosa-11,14-dien-3-ol from (11Z,14Z)-icosa-11,14-diene-1,3-diol.

Example 50

Preparation of 4-(1-(bis(4-methoxyphenyl)(phenyl)methoxy)icosan-3-yloxy)-4-oxobutanoic acid triethylamine salt (XXIV)

1-(bis(4-methoxyphenyl)(phenyl)methoxy)icosan-3-ol (6.8 g, 11.0 mmoles), succinic anhydride (1.1 g, 11.0 mmoles), triethylamine (4.6 mL, 33.0 mmoles) and 1-methylimidazole (0.44 mL, 5.5 mmoles) are dissolved in methylene chloride (68 mL). The reaction is stirred at ambient temperature for five days, during which time the solution darkened. The solution is then diluted with methylene chloride (100 mL) and washed twice with ice-cold aqueous citric acid (10% [w/v], 50 mL) and once with saturated aqueous sodium chloride (50 mL). The methylene chloride solution is dried over anhydrous sodium sulfate, filtered and evaporated to a dark resin. The crude product is purified on silica gel (200 mL bed volume) eluting with methylene chloride:triethylamine (95:5 [v/v/v], 500 mL), then methylene chloride:methanol:triethylamine (93:2:5 [v/v/v], 1000 mL). Fractions containing pure product by thin layer chromatography are pooled and evaporated to a resin. The resin is dried well in vacuo. The yield is 2.4 g (30%).

Similarly, the following compounds are prepared:
i) 1-(Bis(4-methoxyphenyl)(phenyl)methoxy)decan-3-yloxy)-4-oxobutanoic acid triethylamine salt from 1-(bis(4-methoxyphenyl)(phenyl)methoxy)decan-3-ol.
ii) (E)-1-(Bis(4-methoxyphenyl)(phenyl)methoxy)icos-11-en-3-yloxy)-4-oxobutanoic acid triethylamine salt from (E)-1-(bis(4-methoxyphenyl)(phenyl)methoxy)icos-11-en-3-ol.
iii) (Z)-1-(Bis(4-methoxyphenyl)(phenyl)methoxy)icos-11-en-3-yloxy)-4-oxobutanoic acid triethylamine salt from (Z)-1-(bis(4-methoxyphenyl)(phenyl)methoxy)icos-11-en-3-ol.
iv) (11Z,14Z)-1-(Bis(4-methoxyphenyl)(phenyl)methoxy)icosa-11,14-dien-3-yloxy)-4-oxobutanoic acid triethylamine salt from (11Z,14Z)-1-(bis(4-methoxyphenyl)-(phenyl)methoxy)icosa-11,14-dien-3-ol.

Example 51

Preparation of 4-(1-(bis(4-methoxyphenyl)(phenyl)methoxy)icosan-3-yloxy)-4-oxobutanoic acid Attached to Cross-Linked aminomethyl-polystyrene (XV)

AM-Polystyrene (5.0 g, ~33 µmoles amino groups per gram; Applied Biosystems) is suspended in dry, amine-free N,N-dimethylformamide (37.5 mL) in a single neck round bottom flask (250 mL) capped with a rubber septum. The flask is placed on a wrist-action shaker and shaken at ambient temperature to gently but thoroughly agitate the solid. In another flask (50 mL) are placed 4-(1-(bis(4-methoxyphenyl)(phenyl)methoxy)icosan-3-yloxy)-4-oxobutanoic acid triethylamine salt (49 mg, 60 µmoles), dry, amine-free N,N-dimethylformamide (25.0 mL), triethylamine (17 µL, 120.0 µmoles), 1-hydroxybenzotriazole hydrate (10 mg, 72 µmoles) and BOP (29 mg, 66 µmoles). The mixture is shaken well until all solids dissolve and then allowed to sit for five minutes at ambient temperature to activate the carboxylic acid. An aliquot of the activated carboxylic acid solution (16.7 mL, 40.0 µmoles) is added via syringe to the shaking solid support suspension. The mixture is shaken for 1.5 hours and a 40 mg aliquot of the solid is then removed and a loading of 11.9 µmoles/gram determined using the method outlined above. An additional aliquot of activated carboxylic acid (1.0 mL, 2.4 µmoles) is added and the suspension shaken for another hour. A loading of 16 µmoles/gram is determined. The solid suspension is poured into a coarse fitted glass funnel and the liquid drained under vacuum. The solid is then washed well with N,N-dimethylformamide (200 mL), acetone (200 mL) and acetonitrile (200 mL). It is dried overnight in vacuo. Residual amino groups on the support are capped by suspending the dried solid in a mixture of acetic anhydride in acetonitrile (10% [v/v], 25 mL) and 1-methylimidazole in acetonitrile (10% [v/v], 25 mL) and shaking for 2.5 hours at ambient temperature. The solid suspension is poured into a coarse fitted glass funnel and the liquid drained under vacuum. The solid is then washed well with acetonitrile (500 mL) and dried overnight in vacuo.

Solid supports having the compounds listed in Example 50 (i)-(iv) attached and loadings of approximately 15.0±1.0 µmoles/gram are prepared similarly.

TABLE 1

| Compound Name | Structure | Abbreviation |
|---|---|---|
| Cholesteryl 5-(bis(4-methoxyphenyl)(phenyl)methoxy)-3-hydroxypentylcarbamate | 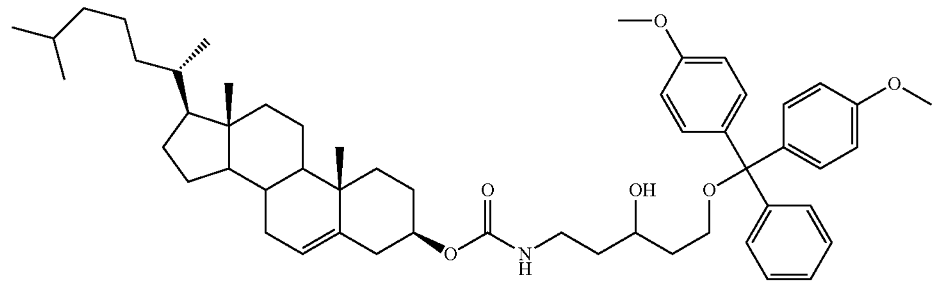 [SMILES: COc1ccc(C(OCCC(O)CCNC(=O)O[C@@H]2CC[C@]3(C)C(=CCC4C3CC[C@]3(C)C4CC[C@H]3[C@@H](C)CCCC(C)C)C2)(c2ccccc2)c2ccc(OC)cc2)cc1] | CHOL-C5 |
| Cholesteryl 8-(bis(4-methoxyphenyl)(phenyl)methoxy)-6-hydroxyoctylcarbamate | 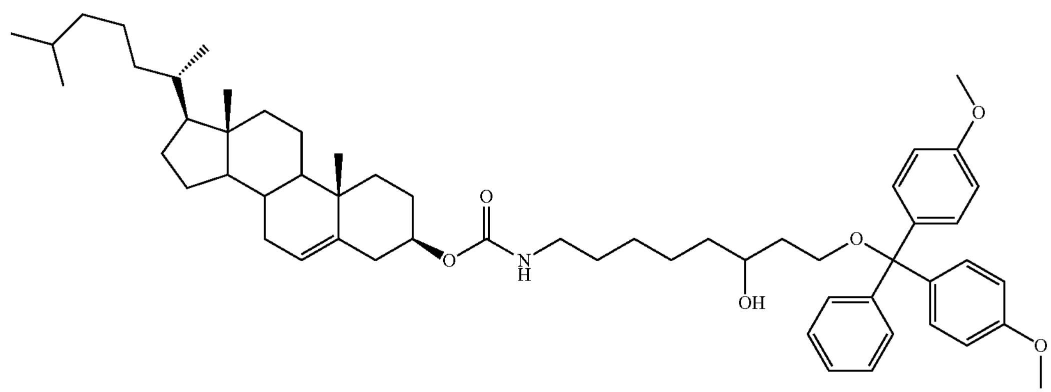 [SMILES: COc1ccc(C(OCCC(O)CCCCCNC(=O)O[C@@H]2CC[C@]3(C)C(=CCC4C3CC[C@]3(C)C4CC[C@H]3[C@@H](C)CCCC(C)C)C2)(c2ccccc2)c2ccc(OC)cc2)cc1] | CHOL-C8 |

TABLE 1-continued
| Compound Name | Structure | Abbreviation |
|---|---|---|
| Cholesteryl 10-(bis(4-methoxyphenyl)(phenyl)methoxy)-8-hydroxydodecylcarbamate | 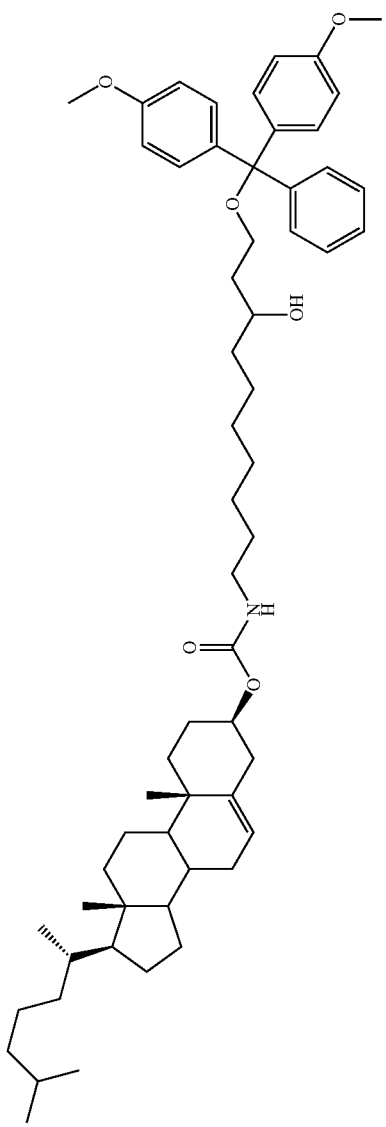 | CHOL-C10 |
| Cholesteryl 14-(bis(4-methoxyphenyl)(phenyl)methoxy)-12-hydroxytetradecylcarbamate | 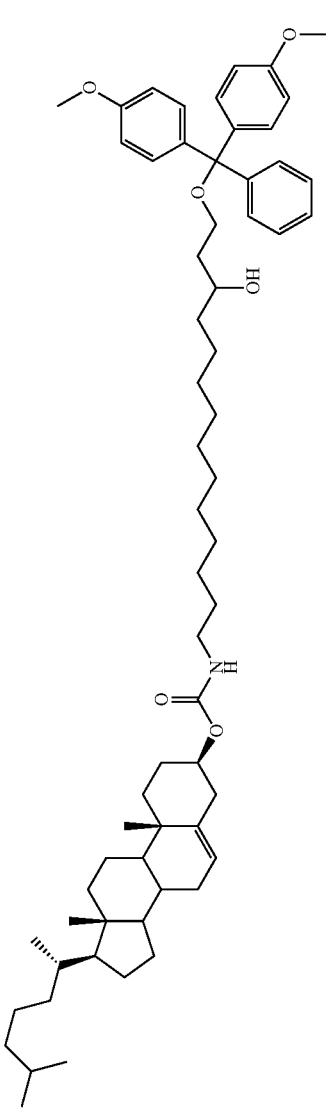 | CHOL-C14 |

TABLE 1-continued

| Compound Name | Structure | Abbreviation |
|---|---|---|
| Cholesteryl 4-(3-(bis(4-methoxyphenyl)(phenyl)methoxy)-1-hydroxypropyl)phenylcarbamate | 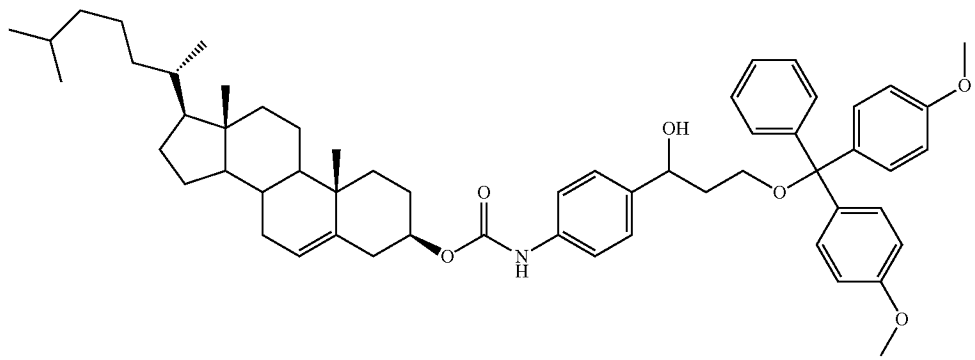 [SMILES: COc1ccc(C(OCCC(O)c2ccc(NC(=O)O[C@@H]3CC[C@]4(C)C(=CCC5C4CC[C@]4(C)C5CC[C@H]4[C@@H](C)CCCC(C)C)C3)cc2)(c2ccccc2)c2ccc(OC)cc2)cc1] | CHOL-ABA |
| Cholesteryl 4-(3-(bis(4-methoxyphenyl)(phenyl)methoxy)-1-hydroxypropyl)piperidine-1-carboxylate | 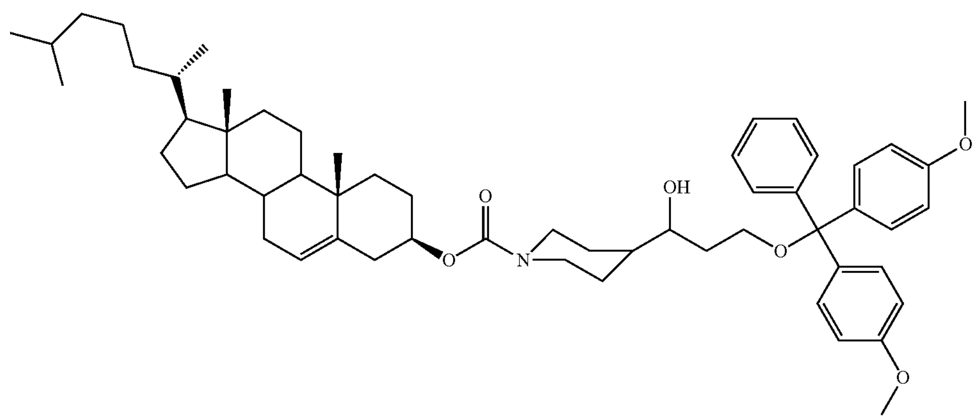 [SMILES: COc1ccc(C(OCCC(O)C2CCN(C(=O)O[C@@H]3CC[C@]4(C)C(=CCC5C4CC[C@]4(C)C5CC[C@H]4[C@@H](C)CCCC(C)C)C3)CC2)(c2ccccc2)c2ccc(OC)cc2)cc1] | CHOL-PIP |

TABLE 1-continued

| Compound Name | Structure | Abbreviation |
|---|---|---|
| Cholesteryl 2-(3-(bis(4-methoxyphenyl)(phenyl)methoxy)-1-hydroxypropyl)pyrrolidine-1-carboxylate | 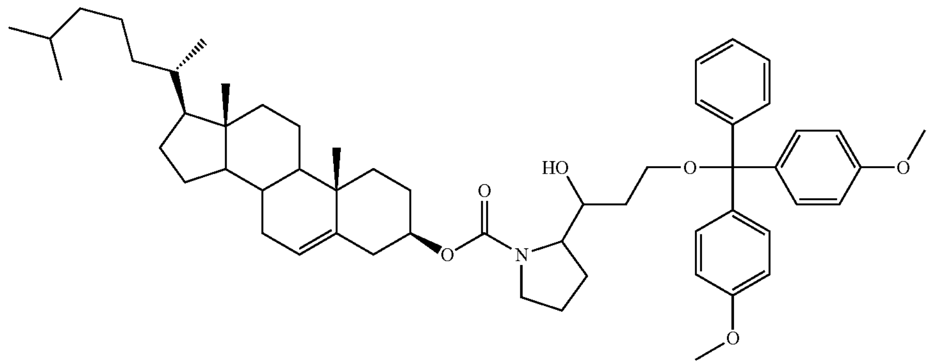 [SMILES: COc1ccc(C(OCCC(O)C2CCCN2C(=O)O[C@@H]2CC[C@]3(C)C(=CCC4C3CC[C@]3(C)C4CC[C@H]3[C@@H](C)CCCC(C)C)C2)(c2ccccc2)c2ccc(OC)cc2)cc1] | CHOL-PRO |
| N-(8-(bis(4-methoxyphenyl)(phenyl)methoxy)-6-hydroxyoctyl)acetamide | 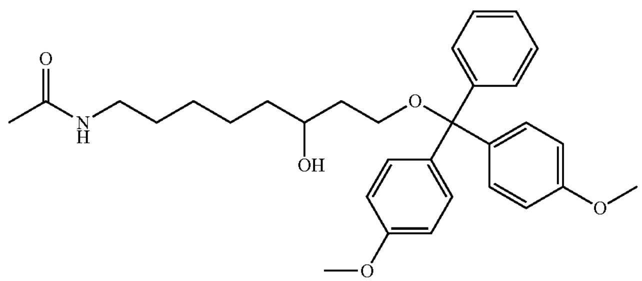 [SMILES: COc1ccc(C(OCCC(O)CCCCCNC(C)=O)(c2ccccc2)c2ccc(OC)cc2)cc1] | Ac-C8 |
| Cholesteryl 6-(8-(bis(4-methoxyphenyl)(phenyl)methoxy)-6-hydroxyoctylamino)-6-oxohexylcarbamate | | CHOL-C8 + C6 |

TABLE 1-continued

| Compound Name | Structure | Abbreviation |
|---|---|---|
| Cholesteryl 12-(8-(bis(4-methoxyphenyl)(phenyl)methoxy)-6-hydroxyoctylamino)-12-oxo-dodecylcarbamate | 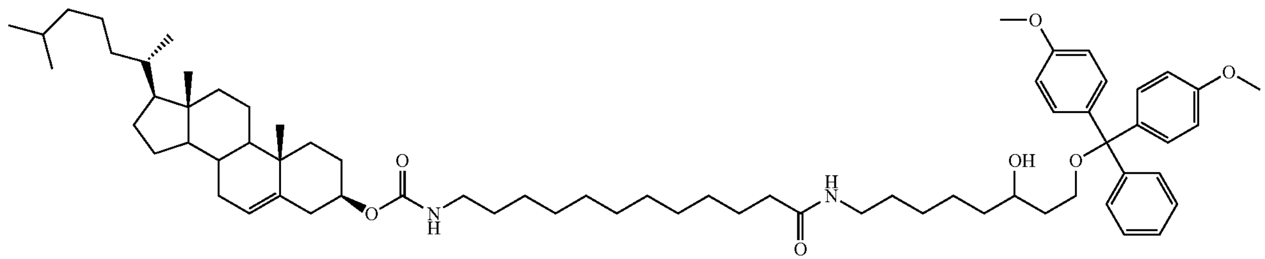 [SMILES: COc1ccc(C(OCCC(O)CCCCCNC(=O)CCCCCCCCCCCNC(=O)O[C@@H]2CC[C@]3(C)C(=CCC4C3CC[C@]3(C)C4CC[C@H]3[C@@H](C)CCCC(C)C)C2)(c2ccccc2)c2ccc(OC)cc2)cc1] | CHOL-C8 + C12 |
| Cholesteryl 6-(2-((bis(4-methoxyphenyl)(phenyl)methoxy)methyl)-4-hydroxypyrrolidin-1-yl)-6-oxohexylcarbamate | | CHOL-C6-Hp |
| Cholesteryl 3-(bis(4-methoxyphenyl)(phenyl)methoxy)-2-hydroxypropylcarbamate | 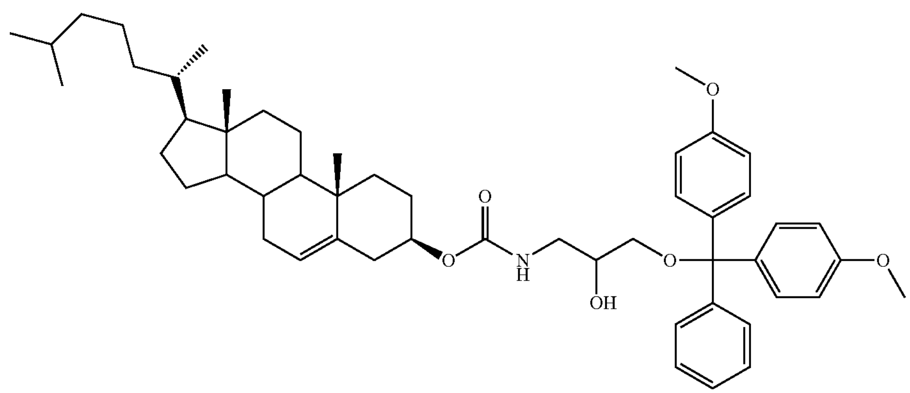 [SMILES: COc1ccc(C(OCC(O)CNC(=O)O[C@@H]2CC[C@]3(C)C(=CCC4C3CC[C@]3(C)C4CC[C@H]3[C@@H](C)CCCC(C)C)C2)(c2ccccc2)c2ccc(OC)cc2)cc1] | CHOL-C3 |

TABLE 1-continued

| Compound Name | Structure | Abbreviation |
|---|---|---|
| 5α-cholestan-3β-yl 5-(bis(4-methoxyphenyl)(phenyl)methoxy)-3-hydroxypentylcarbamate | 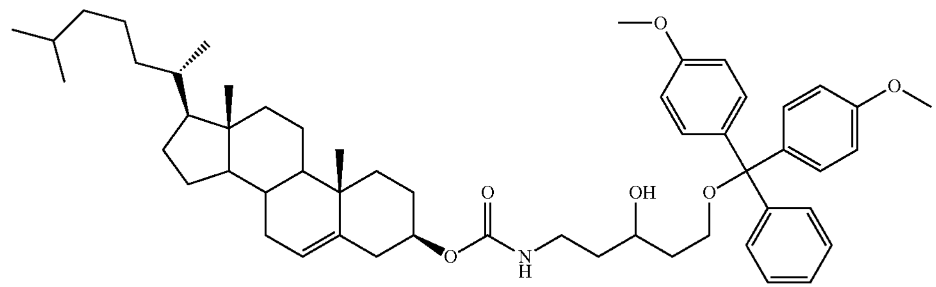 [SMILES: COc1ccc(C(OCCC(O)CCNC(=O)O[C@@H]2CC[C@]3(C)C(=CCC4C3CC[C@]3(C)C4CC[C@H]3[C@@H](C)CCCC(C)C)C2)(c2ccccc2)c2ccc(OC)cc2)cc1] | CHLN-C5 |
| Stigmasteryl 5-(bis(4-methoxyphenyl)(phenyl)methoxy)-3-hydroxypentylcarbamate | 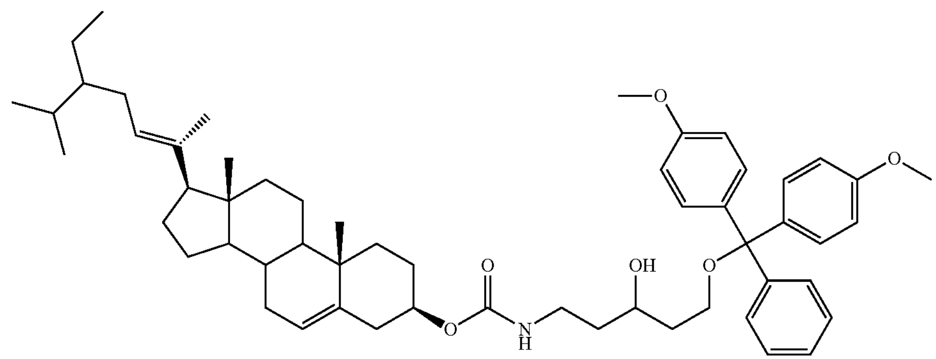 | STIG-C5 |
| Ergosteryl 5-(bis(4-methoxyphenyl)(phenyl)methoxy)-3-hydroxypentylcarbamate | 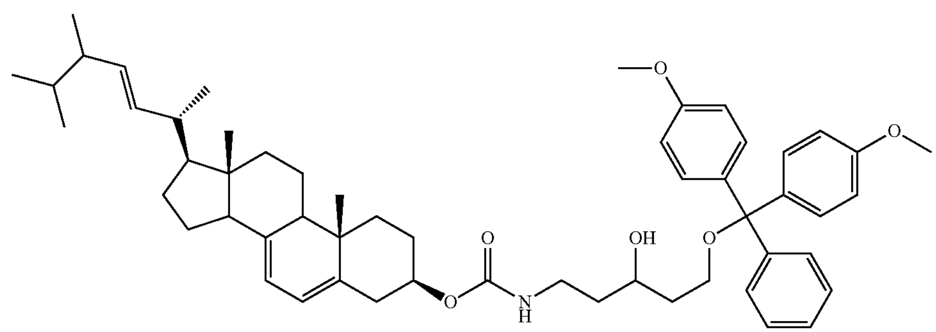 [SMILES: COc1ccc(C(OCCC(O)CCNC(=O)O[C@@H]2CC[C@]3(C)C(=CC=C4C3CC[C@]3(C)C4CC[C@H]3[C@@H](C)/C=C/C(C)C(C)C)C2)(c2ccccc2)c2ccc(OC)cc2)cc1] | ERGO-C5 |

TABLE 1-continued

| Compound Name | Structure | Abbreviation |
|---|---|---|
| Trans-androsteronyl 5-(bis(4-methoxyphenyl)(phenyl)methoxy)-3-hydroxypentylcarbamate | 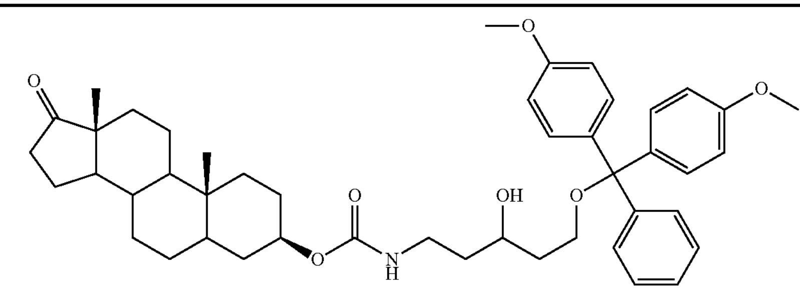 | ANDR-C5 |
| Pregnenolonyl 5-(bis(4-methoxyphenyl)(phenyl)methoxy)-3-hydroxypentylcarbamate | 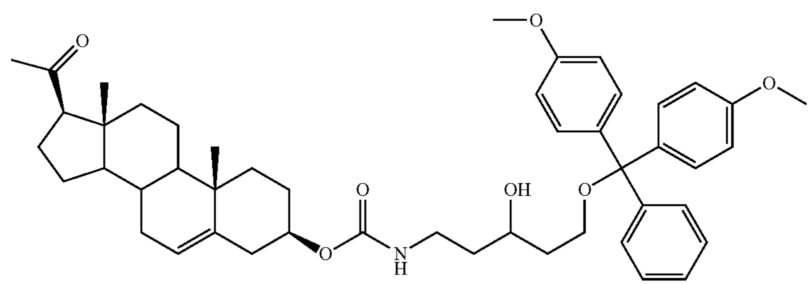 [SMILES: COc1ccc(C(OCCC(O)CCNC(=O)O[C@@H]2CC[C@]3(C)C(=CCC4C3CC[C@]3(C)C4CC[C@H]3C(C)=O)C2)(c2ccccc2)c2ccc(OC)cc2)cc1] | PREG-C5 |
| Cholanyl 5-(bis(4-methoxyphenyl)(phenyl)methoxy)-3-hydroxypentylamide | | CHLA-C5 |

TABLE 1-continued
| Compound Name | Structure | Abbreviation |
|---|---|---|
| 5α-Androstan-3β-yl 5-(bis(4-methoxyphenyl)(phenyl)methoxy)-3-hydroxypentylcarbamate | 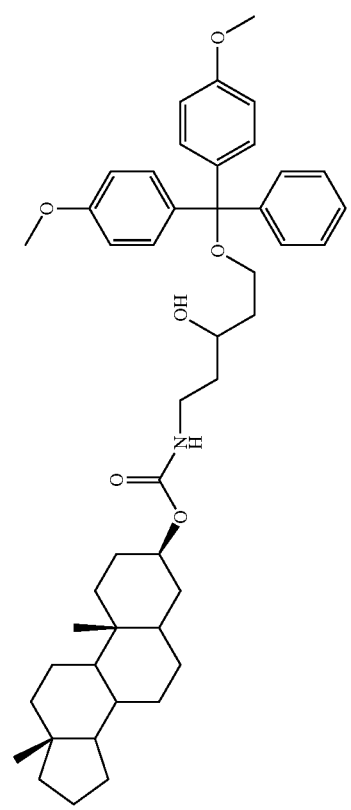 | 3BAND-C5 |
| 5α-Androstan-17β-yl 5-(bis(4-methoxyphenyl)(phenyl)methoxy)-3-hydroxypentylcarbamate | 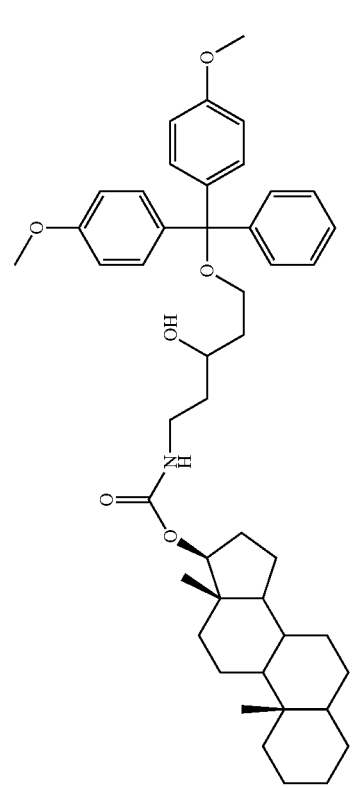 | 17BAND-C5 |

TABLE 1-continued
| Compound Name | Structure | Abbreviation |
|---|---|---|
| 3-O-acetyl-lithocholyl 5-(bis(4-methoxyphenyl)(phenyl)methoxy)-3-hydroxypentylamide | 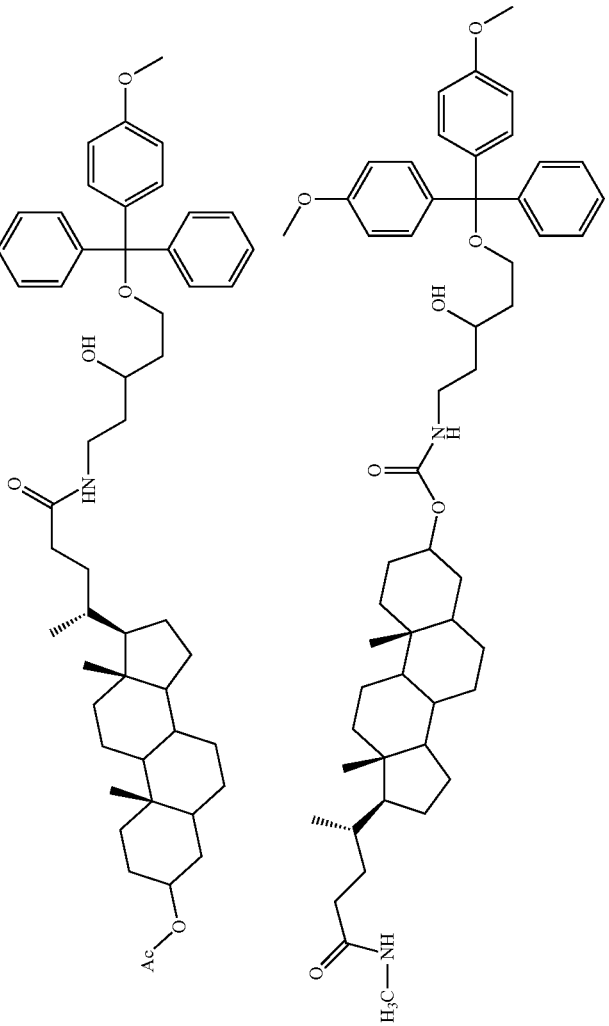 | ACLITH-C5 |
| Lithocholic acid methyl amide 5-(bis(4-methoxyphenyl)(phenyl)-methoxy)-3-hydroxypentyl-carbamate | 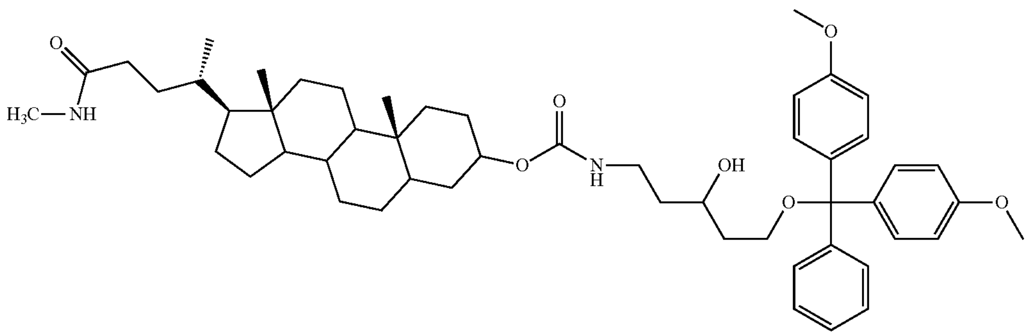 | LITHNM-C5 |

TABLE 2

| Compound Name | Structure | Abbreviation |
|---|---|---|
| Cholesterol | 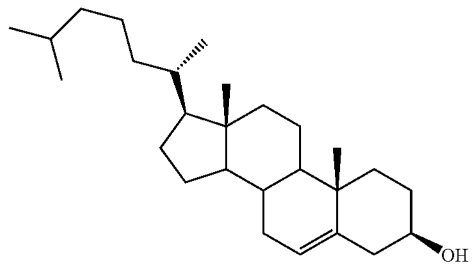 [SMILES: CC(C)CCC[C@H](C)[C@@H]1CCC2C3CC=C4C[C@H](O)CC[C@@]4(C)C3CC[C@]21C] | 5'C0 |
| Cholesteryl 2-hydroxyethylcarbamate | 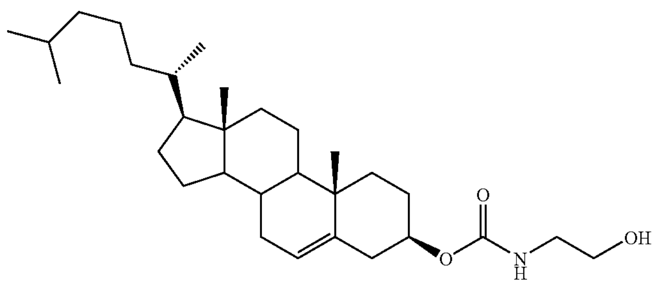 [SMILES: CC(C)CCC[C@H](C)[C@@H]1CCC2C3CC=C4C[C@H](OC(=O)NCCO)CC[C@@]4(C)C3CC[C@]21C] | 5'C2 |
| Cholesteryl 3-hydroxypropylcarbamate | 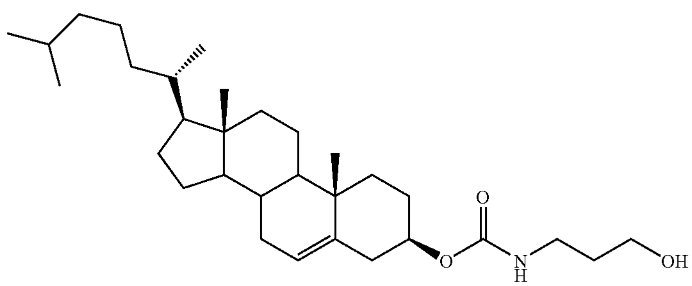 [SMILES: CC(C)CCC[C@H](C)[C@@H]1CCC2C3CC=C4C[C@H](OC(=O)NCCCO)CC[C@@]4(C)C3CC[C@]21C] | 5'C3 |
| Cholesteryl 4-hydroxybutylcarbamate | 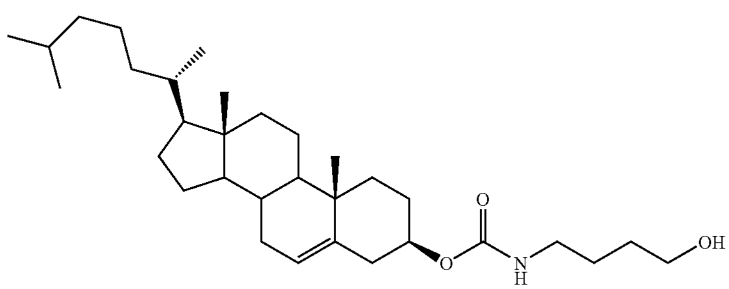 [SMILES: CC(C)CCC[C@H](C)[C@@H]1CCC2C3CC=C4C[C@H](OC(=O)NCCCCO)CC[C@@]4(C)C3CC[C@]21C] | 5'C4 |
| Cholesteryl 5-hydroxypentylcarbamate | 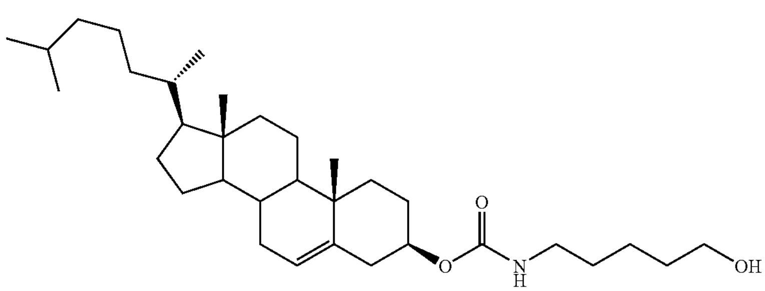 [SMILES: CC(C)CCC[C@H](C)[C@@H]1CCC2C3CC=C4C[C@H](OC(=O)NCCCCCO)CC[C@@]4(C)C3CC[C@]21C] | 5'C5 |

TABLE 2-continued

| Compound Name | Structure | Abbreviation |
|---|---|---|
| Cholesteryl 6-hydroxyhexylcarbamate | 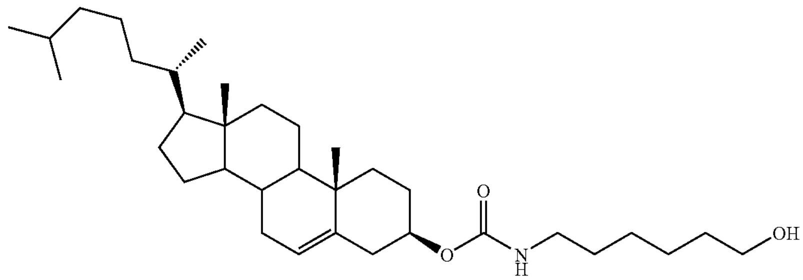 [SMILES: CC(C)CCC[C@H](C)[C@@H]1CCC2C3CC=C4C[C@H](OC(=O)NCCCCCCO)CC[C@@]4(C)C3CC[C@]21C] | 5'C6 |
| Cholesteryl 8-hydroxyoctylcarbamate | 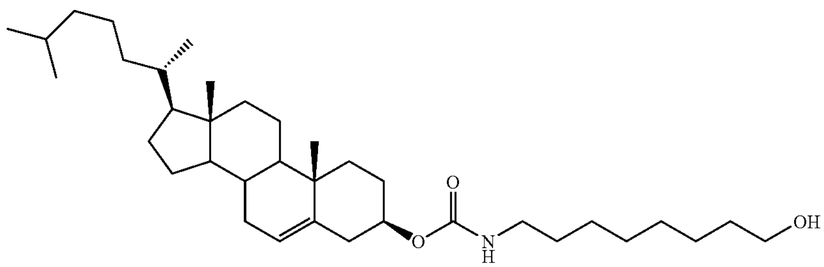 [SMILES: CC(C)CCC[C@H](C)[C@@H]1CCC2C3CC=C4C[C@H](OC(=O)NCCCCCCCCO)CC[C@@]4(C)C3CC[C@]21C] | 5'C8 |
| Cholesteryl 12-hydroxydodecylcarbamate | 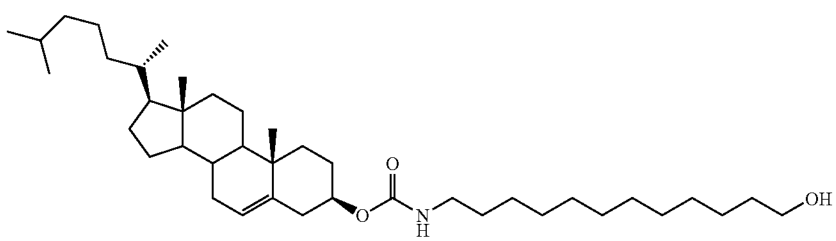 [SMILES: CC(C)CCC[C@H](C)[C@@H]1CCC2C3CC=C4C[C@H](OC(=O)NCCCCCCCCCCCCO)CC[C@@]4(C)C3CC[C@]21C] | 5'C12 |
| Cholesteryl 4-(hydroxymethyl)phenylcarbamate | 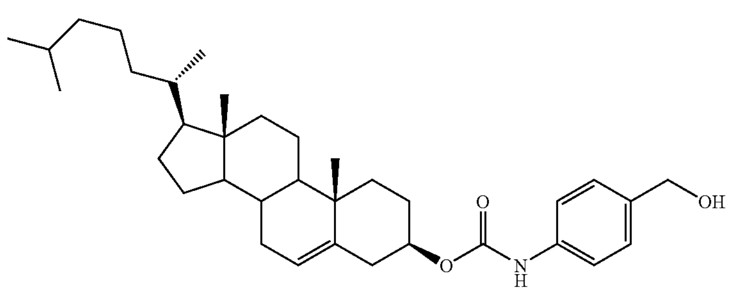 [SMILES: CC(C)CCC[C@H](C)[C@@H]1CCC2C3CC=C4C[C@H](OC(=O)Nc5ccc(CO)cc5)CC[C@@]4(C)C3CC[C@]21C] | 5'ABA |
| Cholesteryl 4-hydroxypiperidine-1-carboxylate | 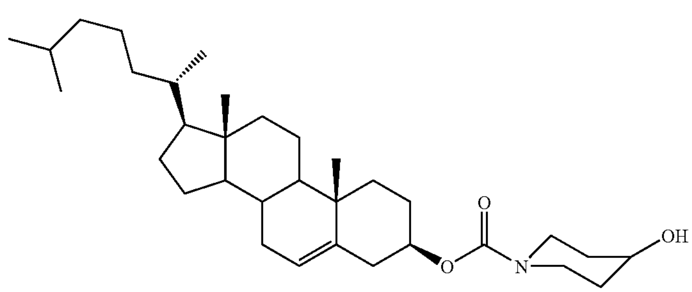 [SMILES: CC(C)CCC[C@H](C)[C@@H]1CCC2C3CC=C4C[C@H](OC(=O)N5CCC(O)CC5)CC[C@@]4(C)C3CC[C@]21C] | 5'PIP |

Table 3 lists alternative abreviations used for linker structures and the number of atoms separating the phosphate moiety of the oligonucleotide from the carbamate linkage of the conjugate.

TABLE 3

| Compound | Alternate Name | Number of Atoms between the siRNA and conjugate |
|---|---|---|
| C3 | Chol-C3 | 3 |
| PRO | Chol-PRO | 4 |
| C5 | Chol-C5 | 5 |
| PIP | Chol-PIP | 6 |
| ABA | Chol-ABA | 7 |
| C8 | Chol-C8 | 8 |
| Ac-C8 | | 8 |
| Chol-C6-Hp | HP6 | 9 |
| C10 | Chol-C10 | 10 |
| C14 | Chol-C14 | 14 |
| C14-Ac | | 14 |
| C8 + C6 | Chol-C8 + C6 | 15 |
| PEG | Dharm | 16 |
| C8 + C12 | Chol-C8 + C12 | 22 |

Note:
"Ac" represents an acetyl group substituted for the cholesterol group

Example 52

General Techniques

In order to identify optimal modification and conjugation patterns that will enhance nucleic acid delivery, stability and silencing specificity of the inventive tripartite complex molecules, the following studies were carried out. Given the universiality of these studies and thus the direct applicability to nucleic acids in many forms (i.e. duplexes, tripartite molecules), several of these experiments have been performed with duplexes (i.e. siRNA) with the expectation that what is learned can be directly extrapolated to tripartite molecules.

The following general techniques were used in examples 53-59.

For most of the passive delivery studies, cells were plated a density of 2,500 cells per well in a 96 well plate and exposed to molecules at given concentrations in a reduced serum media. Transfections took place for 72 hours.

Target genes assessed in many of these studies were (in human cell lines) PPIB (NM_011149) and, GAPDH (NM_001001303) in mouse cell lines. Sequences used in these studies included (for duplexes) hPPIB#3 (sense: 5'ACAG-CAAAUUCCAUCGUGU) (SEQ ID NO: 3), and mGAPDH (sense; 5' CACUCAAGAUUGUCAGCAA) (SEQ ID NO: 4).

In all experiments, overall culture viability was compared with untreated or mock treated cells by Alamar blue (Biosource International) and assessed for target knockdown using branched DNA (BDNA, Genospectra). Tripartite molecules were tested in human HeLa-S3 cells. For mouse cell line studies, 3T3 NIH and ES-D3 cells (both adherent cell types) were employed.

Conditions for delivery included 1) passive delivery: 2,500 cells, HyQ MEM-RS media (HyClone), 100 nanomolar siRNA→5 micromolar, and 72 hr incubation; 2) lipid delivery: 10,000 cells, DMEM, 0.2 ug/well of DharmaFECT 1, 24 hr incubation, 1-100 nanomolar siRNA; and 3) electroporation, 20,000 cells, DMEM, square wave protocol, 24 hr incubation 133 nanomolar siRNA.

Example 53

Identifying Preferred Linker Lengths for Cholesterol-Mediated Delivery of Nucleic Acids To identify the preferred linker length for cholesterol mediated delivery of nucleic acids, siRNA duplexes targeting mouse GAPDH were synthesized with 3' sense strand cholesterol conjugate having a range of linker lengths. Linker sequences included those listed in Tables 1 and 2 (see above). Sequences were then compared by transfecting them into cells by passive, lipid-mediated, and electroporation protocols. In addition, to measure the contribution of the cholesterol to passive transfection (as compared to the linker alone) a C14-acetyl group linker was included in the study (GAPDH SOS, no chol).

Figure 8:
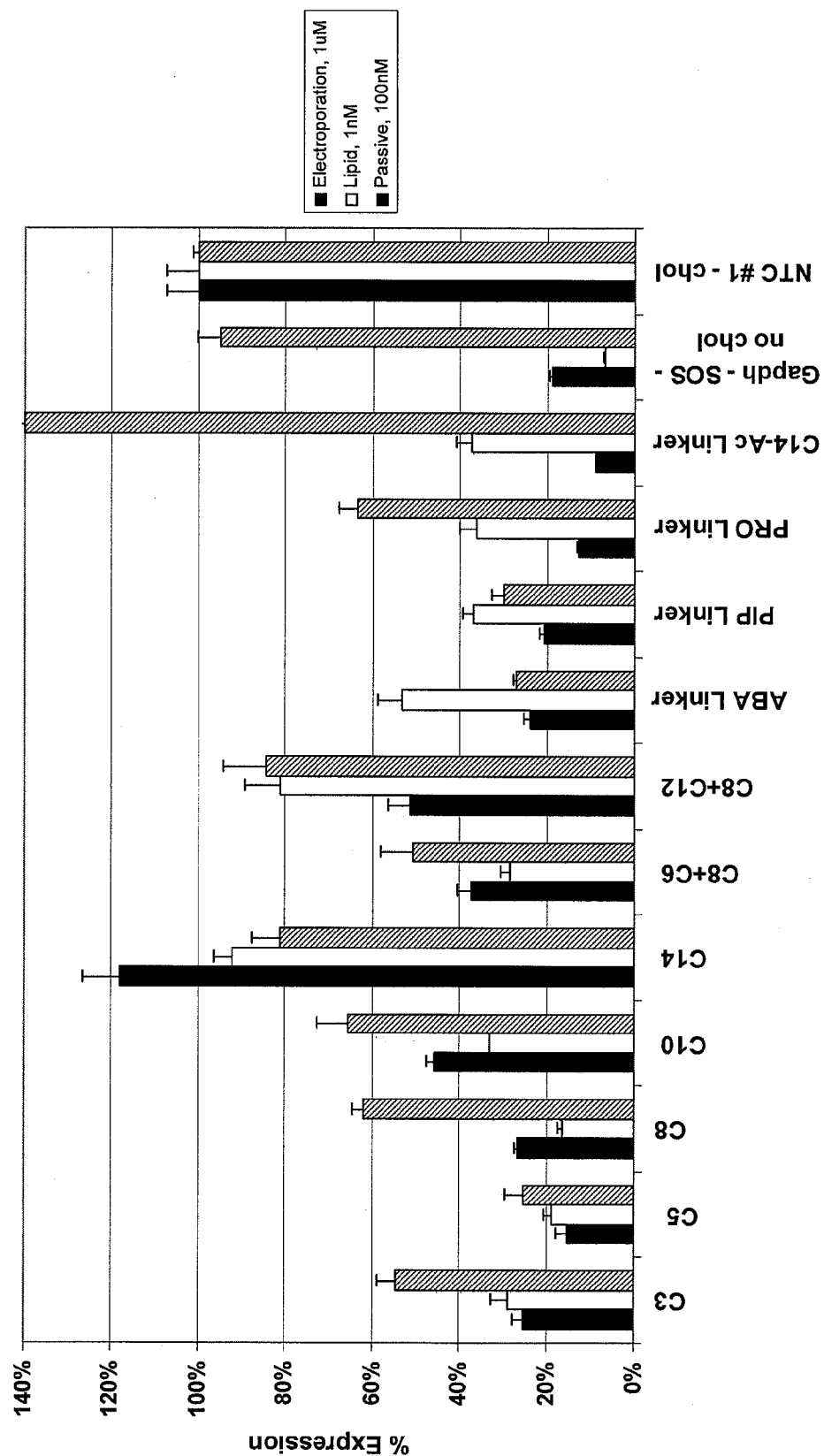
FIG. 8 shows a comparison of linkers of varying lengths (Tables 1 and 2 provide detailed descriptions of molecules). Linkers with 5 (C5), 6 (PIP) and 7 (ABA) atoms separating the oligonucleotide and the conjugate, exhibit greater performance (see arrows). Linker lengths were tested in the context of a duplex siRNA targeting GAPDH. Molecules were introduced into cells by 1) electroporation, 2) lipid mediated delivery, and 3) passive delivery.

Data presented in FIG. 8 shows that a small window of linker lengths performed best in all three delivery systems. Specifically, the C5 linker, the PIP (C6) linker, and the ABA (C7) linker exhibited superior performance. C3 and C8 linkers also performed well under certain conditions. These studies identify linkers that have atom lengths of 4-8, and particularly lengths of 5-7, as the preferred lengths for nucleic acid-cholesterol applications.

The double stranded molecules described above have been successfully tested in a range of cell types including: Human Adherent Cells: SH-SY5Y: Neuroblastoma, IMR32: Neuroblastoma, LAN5: Neuroblastoma, HeLa: Cervix; Adenocarcinoma, HeLa S3: Cervix; Adenocarcinoma, LNCap: Prostate; Metastatic, MCF10A: Epithelial; mammary gland, 293T: Epithelial; kidney, MCF-7: Breast Cancer, SK-BR3: Breast Cancer, Huh7: Hepatoma, DU145: Prostate; mets: brain carcinoma, GTM-3: Glaucomatour trabecular meshwork, HT1080: Connective Tissue; Fibrosarcoma, U2OS: Bone, osteosarcoma, epithelial, DLD-1: Epithelial, colon, colorectal adenocarcinoma, A-375: Epithelial, skin, malignant melanoma, HepG2: Liver, Hepatocellular carcinoma, THP-1: Monocyte; Acute Monocytic Leukemia, Jurkat: T-Lymphocyte, Acute T cell Leukemia, Human Differentiated Stem Cells: Osteoblasts: From hMSC, Adipocytes: From hMSC, Primary Cells:HUVEC: Primary cells; Umbilical vein; endothelial, HUASMC (60% KD): Primary Smooth Muscle, Hepatocytes: Mouse, Liver, hMSC: Undifferentiated mesenchymal, PBMC: Peripheral blood mononuclear cells, NHA: Human astrocytes, Other Species:3T3 NIH: Mouse, Embryo; Fibroblast, 3T3 L1: Mouse, Embryo; Fibroblast, ES-D3: Mouse, Pluripotent embryonic stem cells, C2C12: Mouse, muscle myoblast, and H9c2: Rat, Heart, Myocardium. Based on these data, it is expected that the tripartite molecules disclosed herein will have equivalent efficacy.

Example 54

Identifying Key Attributes Associated with the Tripartite Design

To identify optimal attributes associate with the tripartite oligonucleotide complex design, the following features were evaluated:
1. oligonucleotide 1 with
   a. lengths of 28 nts, 31 nts, and 33 nts (2 nucleotide UU included)
   b. with and without 2'-O-methyl modification on
      i. the entire strand
      ii. region 1 (the target dependent region)

2. oligonucleotide 2 with
   a. 19 nts
   b. 5' phosphate
   c. With and without phosphorothioate modifications on the last two nucleotides
   d. With and without 2' F modifications on the Cs and Us.
3. oligonucleotide 3 with
   a. 7, 10, and 12 nts in length
   b. With and without fully 2'-O-methylated sequences
   c. With a 3' C8 linker associated with cholesterol The following test sets of oligonucleotides 1, 2, and 3 were synthesized:

Test Set #1
Oligonucleotide 1
   a. 28 mer-s: A 28 nucleotide oligonucleotide #1 (includes 2 nucleotide UU 3' overhang)
   b. 28 mer-s, 2OME: A 28 nucleotide oligonucleotide #1 (includes 2 nucleotide UU 3' overhang) with 2'-O-methyl modifications on all Cs and Us of region 1 (the target dependent region)
Oligonucleotide 2
   a. 19 mer-AS: A 19 nucleotide oligonucleotide 2.
   b. 19 mer-AS 2'F PS: A 19 nucleotide oligonucleotide 2, with 2' F on Cs and Us, with two phosphorothioate modifications associated with the last two nucleotides of the strand, counting from the 5' terminus
   c. 19 mer-AS 2'F: A 19 nucleotide oligonucleotide 2, with 2' F on Cs and Us.
Oligonucleotide 3
   a. 7-mer-2'-OME-chol: A 7 nucleotide oligonucleotide 3 with 2'-O-methyl at all positions (except the first nucleotide counting from the 5' end), with the 3' cholesterol conjugate
   b. 7-mer-chol: A 7 nucleotide oligonucleotide 3 with the 3' cholesterol conjugate Test Set #2
Oligonucleotide 1
   a. 31 mer-s: A 31 nucleotide oligonucleotide #1 (includes 2 nucleotide UU 3' overhang)
   b. 31 mer-s, 2OME: A 31 nucleotide oligonucleotide #1 (includes 2 nucleotide UU 3' overhang) with 2'-O-methyl modifications on all Cs and Us in region 1. (the target dependent region)
Oligonucleotide 2
   a. 19 mer-AS: A 19 nucleotide oligonucleotide 2.
   b. 19 mer-AS 2'F PS: A 19 nucleotide oligonucleotide 2, with 2' F on Cs and Us, with two phosphorothioate modifications associated with the last two nucleotides of the strand, counting from the 5' terminus
   c. 19 mer-AS 2'F: A 19 nucleotide oligonucleotide 2, with 2' F on Cs and Us.
Oligonucleotide 3
   a. 10-mer-2'-OME-chol: A 10 nucleotide oligonucleotide 3 with 2'-O-methyl at all positions (except the first nucleotide counting from the 5' end), with the 3'-cholesterol conjugate
   b. 10-mer-chol: A 10 nucleotide oligonucleotide 3 with the 3'-cholesterol conjugate Test Set #3
Oligonucleotide 1
   a. 33 mer-s: A 33 nucleotide oligonucleotide #1 (includes 2 nucleotide UU 3' overhang)
   b. 33 mer-s, 2OME: A 33 nucleotide oligonucleotide #1 (includes 2 nucleotide UU 3' overhang) with 2'-O-methyl modifications on all Cs and Us of region 1 (the target dependent region)

Oligonucleotide 2
   19 mer-AS: A 19 nucleotide oligonucleotide 2.
   19 mer-AS 2'F PS: A 19 nucleotide oligonucleotide 2, with 2' F on Cs and Us, with two phosphorothioate modifications associated with the last two nucleotides of the strand, counting from the 5' terminus
   19 mer-AS 2'F: A 19 nucleotide oligonucleotide 2, with 2' F on Cs and Us.
Oligonucleotide 3
   12-mer-2'-OME-chol: A 12 nucleotide oligonucleotide 3 with 2'-O-methyl at all positions except the first oligonucleotide counting from the 5' terminus, with the 3'-cholesterol conjugate
   12-mer-chol: A 12 nucleotide oligonucleotide 3 with the 3'-cholesterol conjugate Sequences targeting the human PPIB gene were synthesized with the appropriate modification set using chemistries described above and annealed using standard procedures. Subsequently, HeLa cells were exposed to either 100 nM or 500 nM concentrations and tested for gene knockdown by bDNA on days 3 and 6.

Figure 9A:
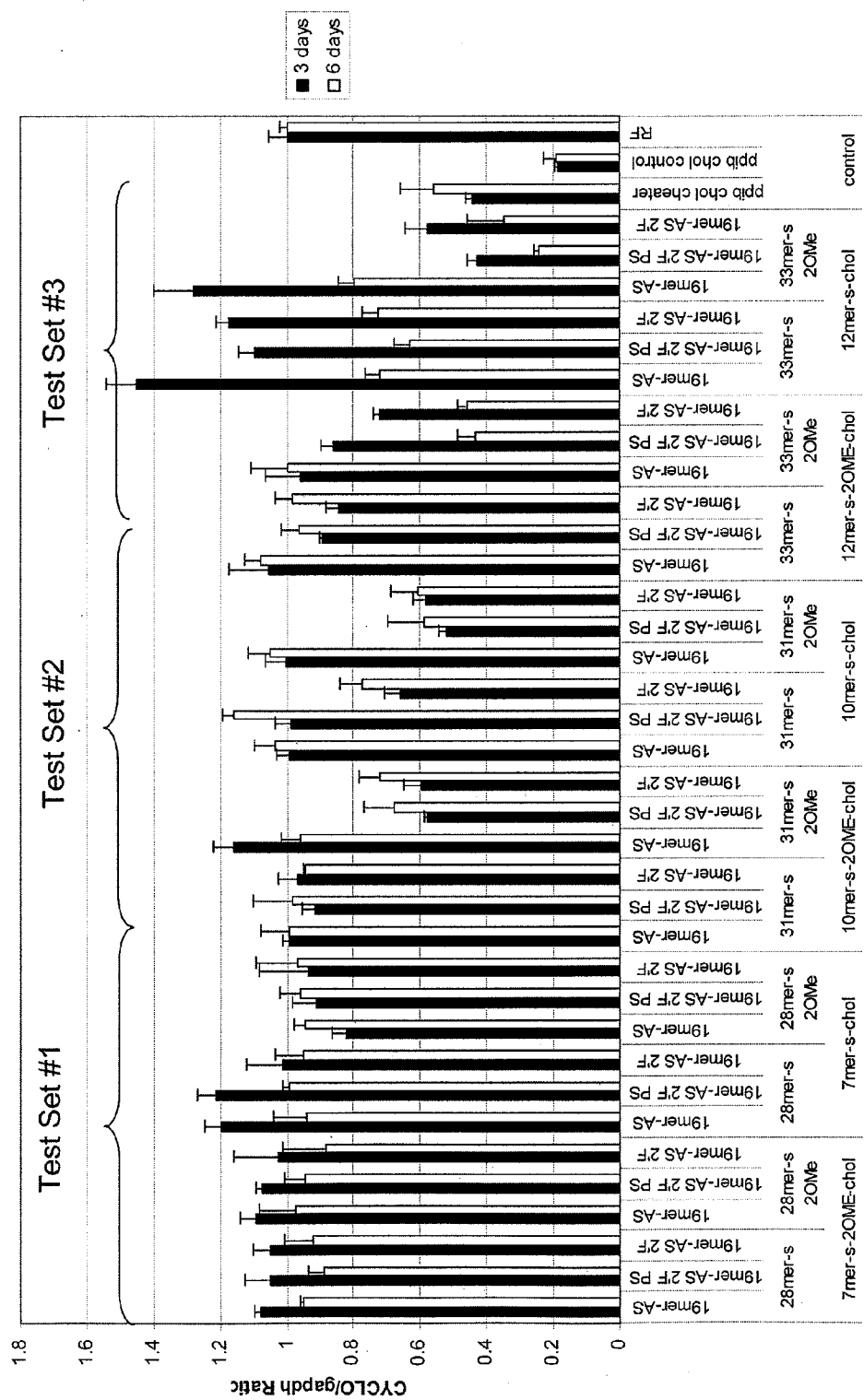
FIG. 9A-9B compares a variety of tripartite designs targeting PPIB (cyclophilin B) on day 3 and day 6 after lipid-independent transfection. Concentrations used in these experiments include A. 100 nM, and B. 500 nM in HeLa cells (2,500 cells per well in a 96 well format). All the designs include a 19 nt AS strand (oligonucleotide 2), a 28-33 nucleotide oligonucleotide 1, and a 7-12 nucleotide oligonucleotide 3. Cholesterol was linked to the oligonucleotide using a C8 linker. Results demonstrate that all designs having oligonucleotide 3 lengths of 7 nucleotides, failed to provide adequate silencing. In contrast, when oligonucleotide 3 was 10 nts or longer, functionality increased when it was combined with oligonucleotides 1 and 2 containing unique patterns of modifications.
Figure 9B:
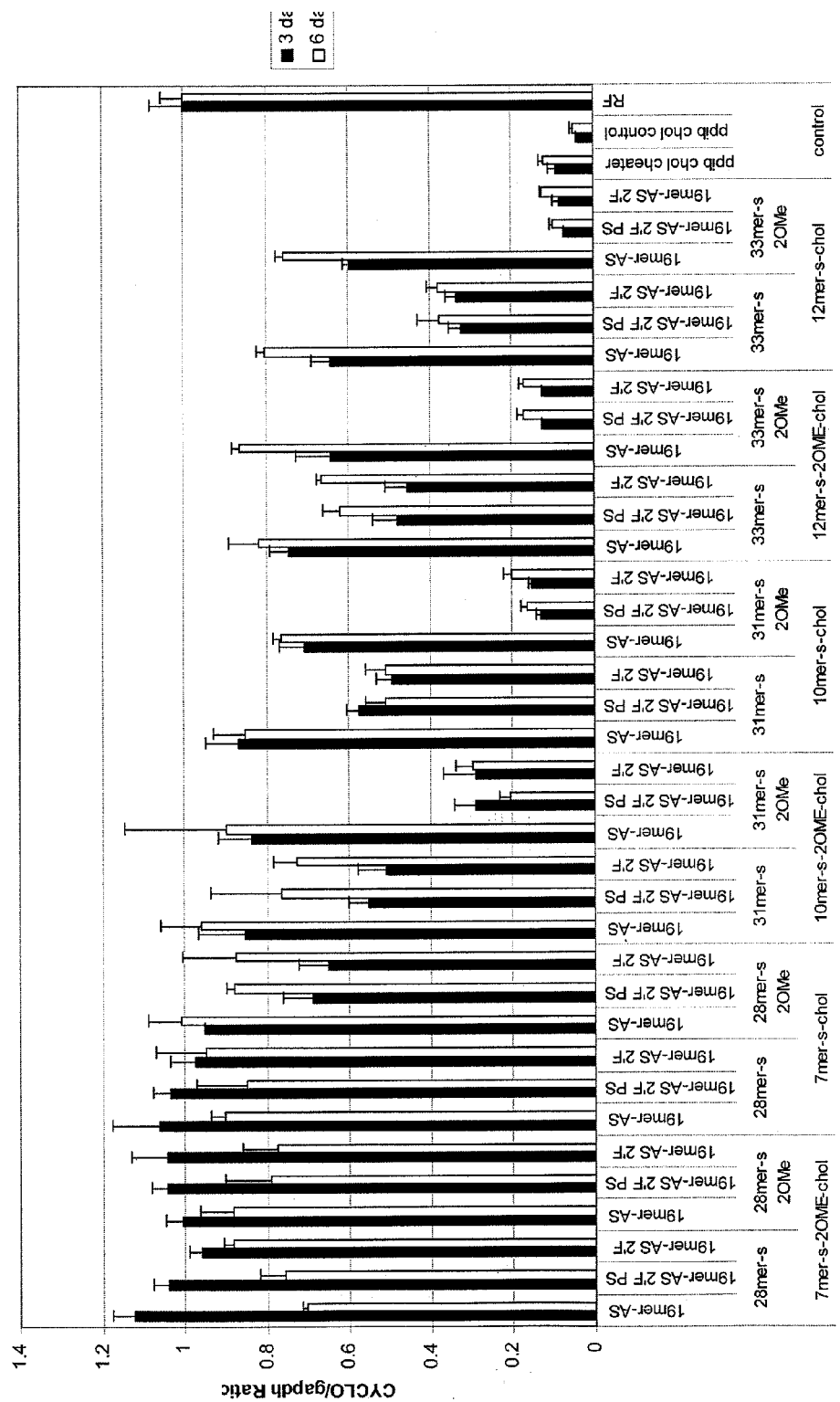

The results of these experiments are presented in FIGS. 9A and 9B. Results from the 100 nM studies demonstrate that designs that utilize a short 7 nucleotide oligonucleotide 3 provided little knockdown at either time points.

Increasing the length of oligonucleotide 3 to 10 nts and incorporating modifications that enhanced the stability of oligonucleotide 2 (e.g. PS and F) enhanced the functionality of the design. Addition of 2'-O-methyl modifications to oligonucleotide 1 did not interfere with this enhanced functionality. Similar or better performance was observed for molecules having similar modification patterns when the length of oligonucleotide 1 was extended to 33 nts (including the 2 nucleotide 3' overhang) along with an increase in the length of oligonucleotide 3 (12 nts).

Increasing the concentration of these molecules from 100 nM to 500 nM provided similar or better results in all the previously highlighted categories, inducing greater than 90% knockdown with certain designs.

Example 55

Further Demonstration of Efficacy of Tripartite Design Using C5 Linker

To further define optimal design parameters for the tripartite molecule, the following attributes were tested Oligonucleotide 1: a 35 nucleotide oligonucleotide 1 (including 2 nucleotide, 3' overhang) having 2'-O-methyl modifications on all Cs and Us of region 1 and unmodified nucleotides on the 14 nucleotide span of region 2.

Oligonucleotide 2: 19 nucleotide AS strand carrying a 5' phosphate group and 2'F modifications on all Cs and Us. Tested with and without phosphorothioate modifications on the last two linkages of the 3' end of the molecule.

Oligonucleotide 3: 14 nts in length and carrying 2'-O methyl modifications on all nucleotides. Tested with and without phosphorothioate modifications on the last two nucleotides of the 3' terminus, with and without a C5 linker attached to cholesterol on the 3' terminus.

Samples were passively introduced into HeLa cells (2,500 cells per well) in reduced serum media (HyClone Reduced serum media) and gene knockdown was measured by BDNA at 72 hrs. Viability studies designed to determine overall toxicity of the molecules was assessed by Alamar blue.

Figure 10:
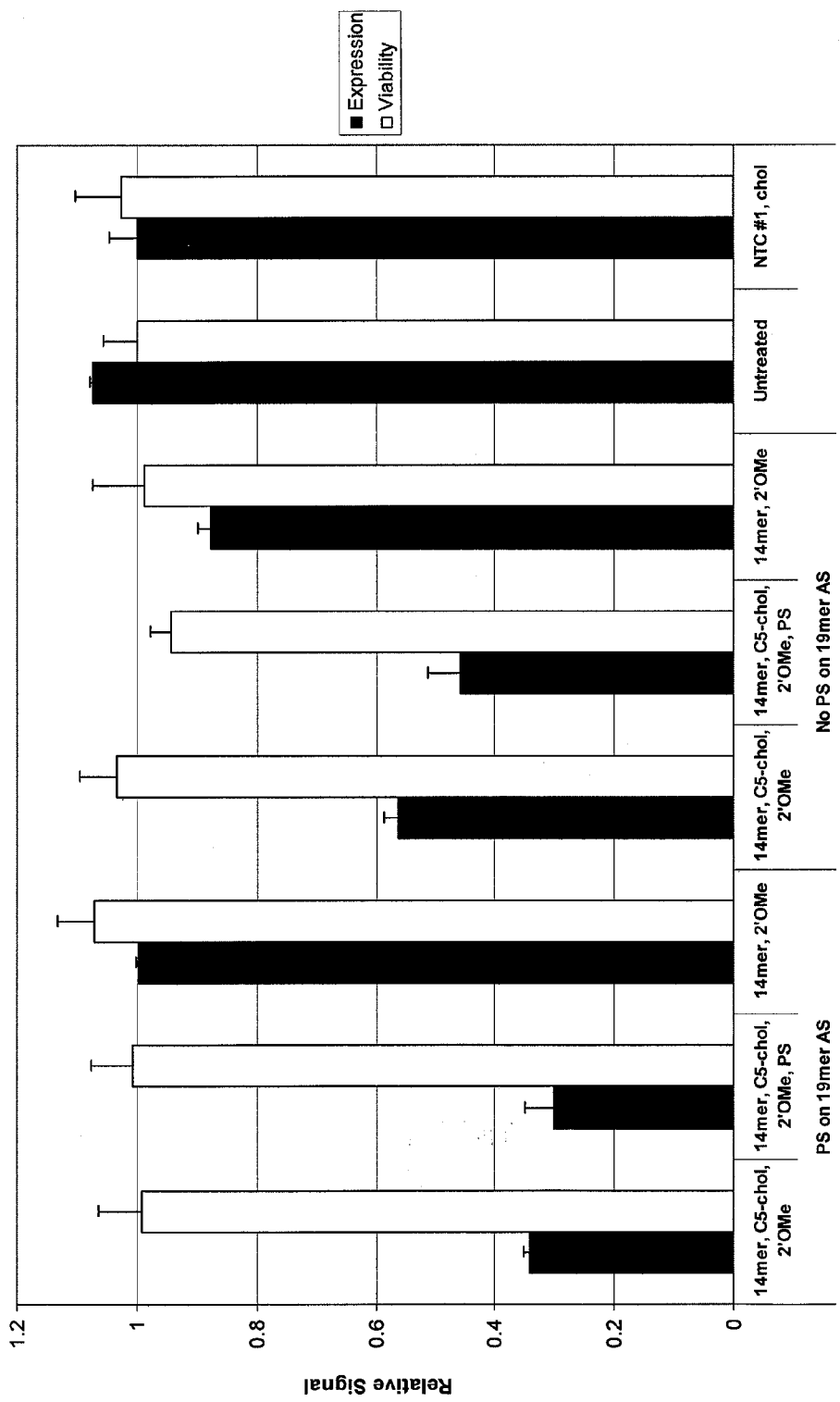
FIG. 10 describes studies performed on a variety of tripartite designs using gene knockdown and viability to assess overall functionality. All conjugates employed a C5 linker. Oligonucleotide 2 is a 19 nucleotide. Studies show a clear benefit by adding phosphorothioate internucleotide modifications in the 3' overhang of the antisense (oligonucleotide 2) strand. For details, see Example 57.

The results of these experiments are presented in FIG. 10 and demonstrate: 1) the C5 linker is compatible with the tripartite design and enhances delivery of the molecule in the absence of e.g. lipid transfection agents, 2) addition of phosphorothioate modifications to the 3' end of the antisense strand enhances overall functionality over designs that do not contain the modification pattern, and 3) none of the designs dramatically alter the viability of cells over untreated controls.

Example 56

Identifying Secondary Structures that Enhance Functionality

As tripartite molecules are designed to generate duplexes capable of entering RISC, we synthesized siRNAs with mismatches at various positions to determine whether the incorporation of secondary structures could enhance overall functionality. To achieve this, a poorly functional GAPDH-targeting siRNA was synthesized with all possible sense-antisense strand mismatches at positions 6-10 of the sense strand. All of the molecules tested contain a 3' sense strand C5 linker and conjugated to cholesterol. Subsequently, the ability of each of these molecules to induce GAPDH knockdown via passive delivery was assessed via branched DNA assay (passive delivery conditions: 2.5K HeLa cells plated, siRNA concentration=0.1 uM or 1 uM, reduced serum media, knockdown assessed at 72 hr).

Figure 11A:
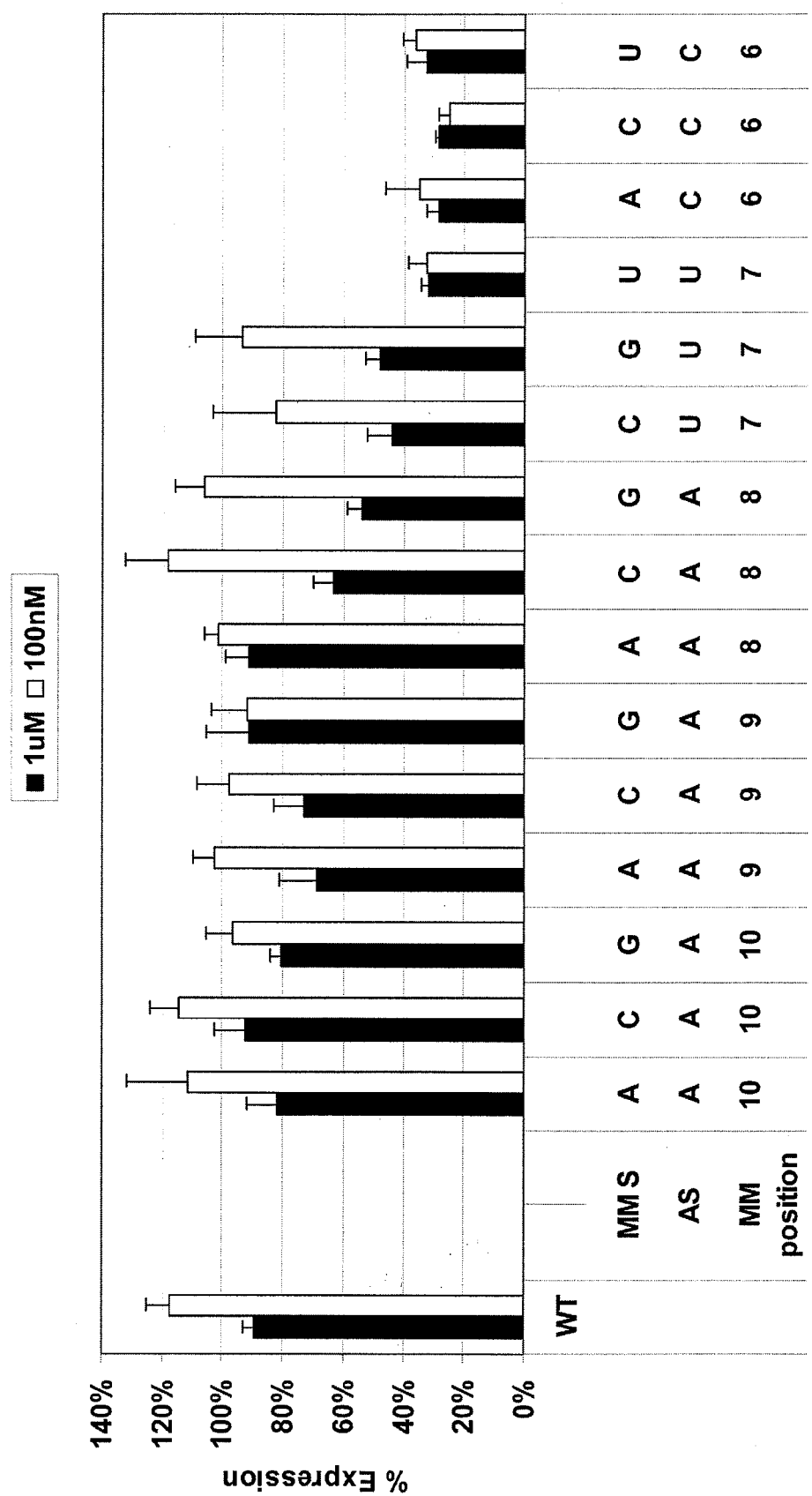
FIG. 11A provides a graph depicting the effects of single mismatches between the sense and antisense strand at sense positions 6-10 (numbered from the 5' end of the sense strand, equivalent to antisense positions 10-14) of G4 modified molecules. "G4" represents duplex molecules containing the following modification pattern: the sense strand has 2'-O-methyl modifications on positions 1 and 2 (counting from the 5' terminus of the molecule), and 2-O-methyl modifications on all Cs and Us. In addition, the sense strand has a C5 linker on the 3' terminus and is conjugated to cholesterol. Sequence changes occur in the sense strand, thus preserving perfect complementarity between the antisense strand and the target mRNA. Results show that incorporation of a mismatch at sense strand positions 6 or 7 greatly enhances gene knockdown. Studies performed at both 0.1 and 1.0 uM.

The results of these experiments are shown in FIG. 11A and demonstrate that incorporation of a mismatch at positions 6 and/or 7 of the sense strand greatly enhance the functionality of the cholesterol modified molecule. This enhancement appears to be unrelated to the type of mismatch (e.g., C-A=C-C) suggesting that this trait is sequence independent. For a 19 nucleotide sense strand and a 19 nucleotide antisense strand, positions 6 and 7 on the sense strand (numbered from the 5' end) are opposite positions 14 and 13 respectively on the antisense strand (numbered from the 5' end).

Figure 11B:
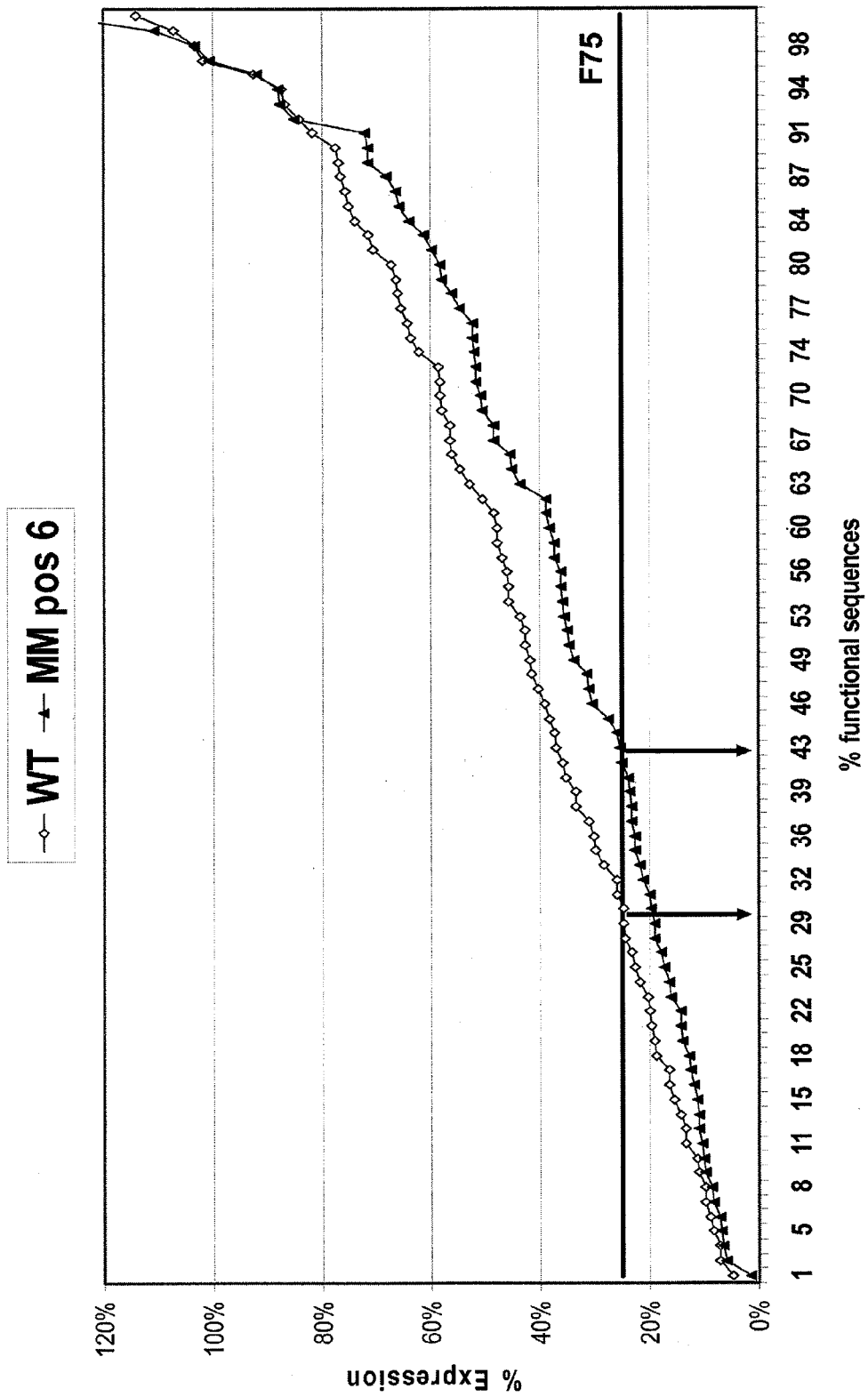
FIG. 11B provides a graph that represents a broad study of the effects of position 6 mismatch on G4-siRNA functionality. Eighty-seven siRNAs synthesized as G4 (−mm) or G4(+mm) duplexes were transfected into cells at 1 uM concentrations. For these experiments, the mismatch incorporated at position 6 always consisted of replacing the native nucleotide in the sense strand with the nucleotide that was found in pairing position in the antisense strand (e.g. A-A, G-G, C-C, or U-U mismatches). Branched DNA assays were used to assess gene knockdown. The results demonstrate that incorporation of a mismatch at position 6 enhances functionality of a significant fraction of G4 molecules. G4 duplex oligonucleotide complexes are described in great detail in the co-pending and commonly assigned assigned PCT application entitled "Duplex Oligonucleotide Complexes And Methods For Gene Silencing By RNA Interference," filed Sep. 20, 2007.

To further study the effects of position 6 mismatches, 87 different sequences containing the following modifications [sense strand: 2'-O methyl modification of positions 1 and 2 (counting from the 5' terminus), 2'-O methyl modification of all Cs and Us, a 3' C5 linker conjugated to cholesterol; antisense strand: a 5' phosphate, 2' F modification of all Cs and Us, a 2 nucleotide 3' overhang containing internucleotide linkage phosphorothioate modifications]. These molecules target hPPIB and were synthesized with or without a position 6 mismatch. In all cases, the mismatch consists of substituting the position 6 (sense) nucleotide with the nucleotide that is present at position 14 on the antisense strand. As shown in FIG. 11B, incorporation of the mismatch enhances overall gene silencing within the population, increasing the number of duplexes that silence gene expression by 75% from 30% to 43%.

Example 57

Demonstration that the Increase in Functionality is the Result of the Conjugate and Not the Linker To determine whether the observed lipid-independent delivery of duplexes having linkers and cholesterol was the consequence of the linker alone, the functionality of siRNA targeting GAPDH and having a C8-Cholesterol (3' terminus of the sense strand) were compared with identical siRNA having the C8 or C14 linkers terminated with an acetyl group (i.e. no cholesterol). Conditions for transfection were similar to those previously described (2.5 k 3T3 NIH, 72 hours, Hy-MEM-RS) and gene knockdown was measured by branched DNA using ACTB for normalization.

Figure 12:
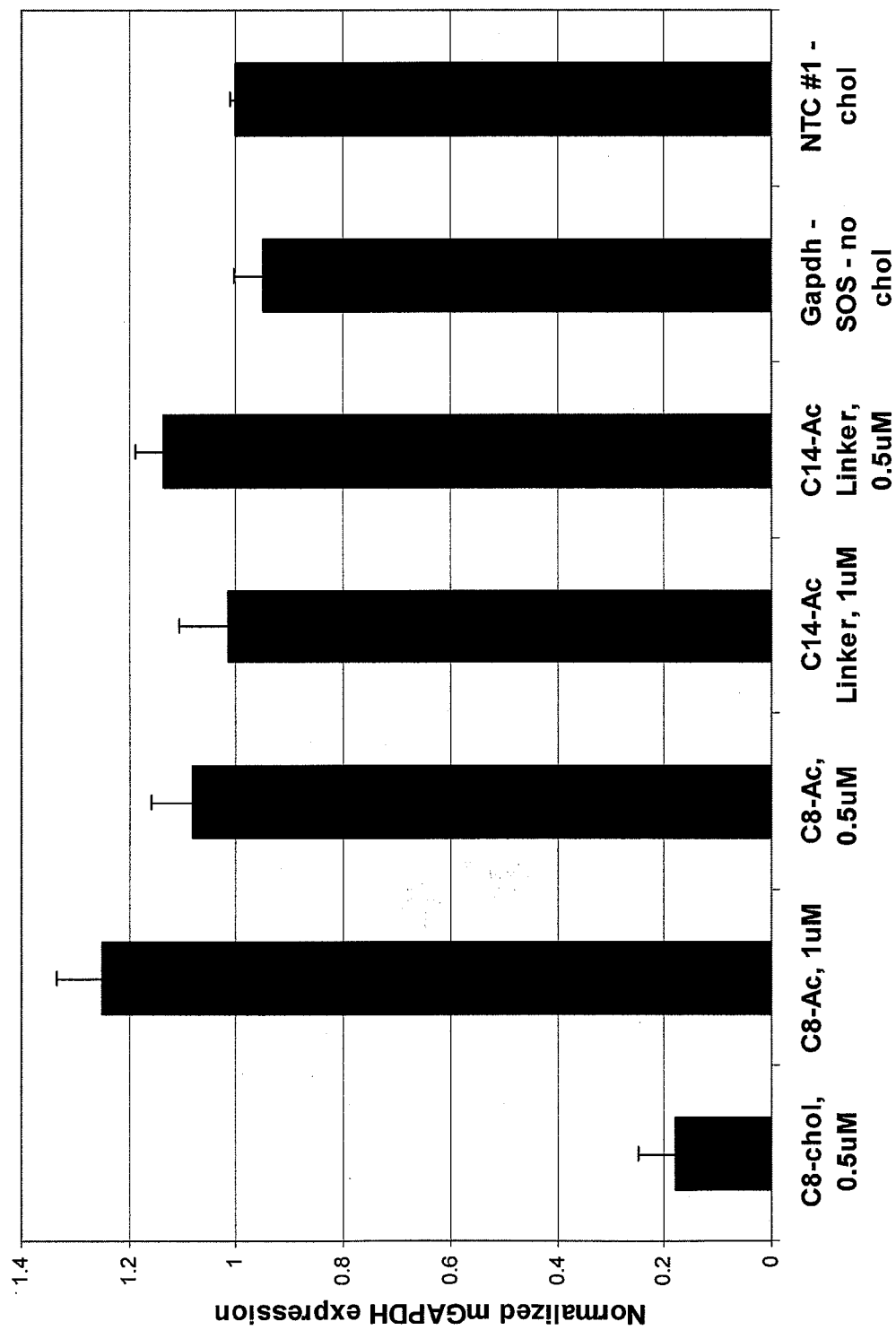
FIG. 12 compares the performance of duplex molecules having C8 or C14 linkers (capped with acetyl groups) with duplexes that have a C8 linker conjugated to cholesterol. Results clearly demonstrate that cholesterol conjugation is necessary for delivery and gene silencing.

Results of these studies are shown in FIG. 12 and show that while cholesterol linked GAPDH siRNA provide strong knockdown (~80%) at 0.5 micromolar, duplexes having the linker alone (e.g. C8-Ac, C14-Ac) provide no knockdown at either 0.5-1.0 micromolar concentrations. These results clearly show that it is the combination of the linker molecule and the conjugate (cholesterol) that are responsible for the observed non-lipid mediated delivery.

Example 58

Identification of Preferred Chemical Modification Patterns in Tripartite Designs To identify chemical modification patterns that enhance functionality of tripartite designs, having a 35 nucleotide oligonucleotide 1, a 19+2 oligonucleotide 2 (19 nucleotides being complementary to the target gene PPIB and 2 U nucleotides on the 3' terminus), and a 14 nucleotide oligonucleotide 3 having a C5 linker conjugated to cholesterol on the 3' end of the strand, molecules were synthesized with the chemical modifications described in Table 4. The unmodified nucleotide sequences of the oligonucleotides were:

```
Oligonucleotide 1 (target dependent region which
forms sense strand upon Dicer processing is
underlined):
                                        SEQ ID NO: 5
5'UGCUCUCAUCCAUGAAACAGCAAAUUCCAUCGUGU3'

Oligonucleotide 2:
                                        SEQ ID NO: 6
5'ACACGAUGGAAUUUGCUGUUU 3'

Oligonucleotide 3
                                        SEQ ID NO: 7
5' CAUGGAUGAGAGCU 3'
```

All of the oligo symbol descriptions are preceded by a number (e.g. (1), (2), or (3)) which depicts which strand (oligo 1, 2, or 3) which is being described. "2OMe" refers to a 2'-O methyl group on the 2' position of the ribose ring, "35+2" refers to a 35 nucleotide strand with a 2 nucleotide 3' overhang, "PS" refers to a phosphorothioate. "5 pMi Arm RC" refers to oligonucleotide 3 which is the reverse complement of region 2 of oligonucleotide 1, "19+2" refers to a 21 nucleotide oligonucleotide 2 in which 19 nts are complementary to the PPIB target and 2 nucleotides (typically UU) remain as a 3' AS overhang after Dicer processing. Oligonucleotides 1, 2, and 3 described in Table 4 were then annealed in different combinations to generate 128 different tripartite configurations. Each design was then introduced into HeLa cells using previously described procedures and tested for the ability to knockdown the PPIB target.

TABLE 4

| Oligo Symbol | Modification Pattern |
| --- | --- |
| (1)PPIB3__35+2__2OMe__UU | 2'OMe UU overhang/2'OMe on C's and U's on target dependent region |
| (1)PPIB3__35+2__unmod__UU | unmodUU overhang/2'OMe on target dependent region |

TABLE 4-continued

| Oligo Symbol | Modification Pattern |
|---|---|
| (1)PPIB3_35+2_PS_UU | Phosphorothioate UU overhang/2'OMe on target dependent region |
| (1)PPIB3_35+2OMe_2OMe_UU | 2'OMe UU overhang/2'OMe on C's and U's in entire 35mer |
| (3)5pmiR_arm_RC_PS | Unmodified except for 2 phosphorothioate linkages on 3' end/C5-cholesterol on 3' |
| (3)5pmiR_arm_RC_naked | Unmodified/C5-cholesterol on 3' |
| (3)5pmiR_arm_RC_2OMe_PS | Fully 2'OME/2 phosphorothioate linkages on 3' end/C5-cholesterol on 3' |
| (3)5pmiR_arm_RC_2OMe | Fully 2'OME/C5-cholesterol on 3' |
| (2)PPIB3_19+2_2F_PS | 2'F on C's and U's/Two Phosphorothioate linkages on 3' end/5'phosphate |
| (2)PPIB3_19+2_PS | Two Phosphorothioate linkages on 3' end/5'phosphate |
| (2)PPIB3_19+2_2F_OTP_PS | 2'F on C's and U's/One 2'OMe on 2nd position from 5'end/Two Phosphorothioate linkages on 3' end/5'phosphate |
| (2)PPIB3_19+2_OTP_PS | One 2'OMe on 2nd position from 5'end/Two Phosphorothioate linkages on 3' end/5'phosphate |
| (2)PPIB3_19+2_2F | 2'F on C's and U's/5'phosphate |
| (2)PPIB3_19+2 | 5' phosphate |
| (2)PPIB3_19+2_2F_OTP | 2'F on C's and U's/One 2'OMe on 2nd position from 5'end/5'phosphate |
| (2)PPIB3_19+2_OTP | One 2'OMe on 2nd position from 5'end/5'phosphate |

The list of combinations and performance of each design are provided in Table 5. The 128 tripartite molecules tested are divided into six groups according to the percentage of target gene knowdown (KD), Group 1: provides ~70% or greater silencing, Group 2 provides 60-70% silencing, Group 3 provides 50-60% silencing, Group 4 provides 40-50% silencing, Group 5 provides 30-40% silencing, and Group 6 provides less than 30% silencing. The descriptions provided in Table 5 include specific chemical modification patterns for each of the three oligonucleotides associated with the tripartite molecule.

For oligonucleotide 1, the description "35+2OMe_2OMe_UU" refers to a 35 base oligonucleotide (not including the 2 nucleotide 3' overhang) that is 2'-O-methylated on all Cs and Us, contains 2'-O-methyl groups on positions 17 and 18 (counting from the 5' end of the molecule), and has 2'-O-Me on the UU overhangs.

For oligonucleotide 1, the description "35+2_2OMe_UU" refers to a 35 base oligonucleotide (not including the 2 nucleotide 3' overhang) that is 2'-O-methylated on all Cs and Us of region 1, contains 2'-O-methyl groups on positions 17 and 18 (counting from the 5' end of the molecule), and has 2'-O-Me on the UU overhangs.

For oligonucleotide 1, the description "35+2_PS_UU" refers to a 35 base oligonucleotide (not including the 2 nucleotide 3' overhang) that is 2'-O-methylated on all Cs and Us of region 1, contains 2'-O-methyl groups on positions 17 and 18 (counting from the 5' end of the molecule), and has (2) internucleotide phosphorothioate modifications on the UU overhangs.

For oligonucleotide 1, the description "35+2_unmod_UU" refers to a 35 base oligonucleotide (not including the 2 nucleotide 3' overhang) that is 2'-O-methylated on all Cs and Us of region 1, contains 2'-O-methyl groups on positions 17 and 18 (counting from the 5' end of the molecule), and has no modifications associated with the UU overhangs.

For oligonucleotide 2, the description "19+2_2F_PS" refers to a 21 nucleotide oligonucleotide with all Cs and Us being 2' F modified, and has phosphorothioate internucleotide linkages between the last three nucleotides on the 3' terminus, For oligonucleotide 2, the description "19+2_2F" refers to a 21 nucleotide oligonucleotide with all Cs and Us being 2' F modified, For oligonucleotide 3, the description "5pmiR_arm_RC_2OMe_PS" refers to a 14 base oligonucleotide that is the reverse complement of the non-targeting region of oligonucleotide 1, that is 2'-O-methylated at all positions, contains (2) phosphorothioate internucleotide linkages on the 3' end of the oligonucleotide, and is conjugated to cholesterol via a C5 linker at the 3' end of the molecule.

For oligonucleotide 3, the description "5pmiR_arm_RC_2OMe" refers to a 14 base oligonucleotide that is the reverse complement of the non-targeting region of oligonucleotide 1, that is 2'-O-methylated at all positions, and is conjugated to cholesterol via a C5 linker at the 3' end of the molecule.

For oligonucleotide 3, the description "5pmiR_arm_RC_naked" refers to a 14 base oligonucleotide that is the reverse complement of the non-targeting region of oligonucleotide 1, that is conjugated to cholesterol via a C5 linker at the 3' end of the molecule.

The results of these studies identified multiple designs that provided strong (greater than 70%) silencing. The top four molecules of this collection included:

A. A tripartite molecule in which
oligonucleotide 1 is 35 nucleotides in length (not including the 3' overhang), is 2'-O-methylated on all Cs and Us, contains 2'-O-methyl on nucleotide positions 17 and 18 (counting from the 5' end of the molecule), and has a 2'-O-methyl modified UU overhang,
oligonucleotide 2 is 21 nucleotides in length, with all Cs and Us being 2' F modified, and has phosphorothioate internucleotide linkages between the last three nucleotides on the 3' terminus, and
oligonucleotide 3 is 14 nucleotides in length, is the reverse complement of the non-targeting region of oligonucleotide 1, is fully 2'-O-methylated, has phosphorothioate internucleotiide linkages between the last three nucleotides on the 3' terminus, and has cholesterol linked to the 3' terminus of the oligonucleotide using a C5 linker.

B. A tripartite molecule in which
oligonucleotide 1 is 35 nucleotides in length (not including the 3' overhang), is 2'-O-methylated on all Cs and Us, contains 2'-O-methyl on nucleotide positions 17 and 18

(counting from the 5' end of the molecule), and has a 2'-O-methyl modified UU overhang, oligonucleotide 2 is 21 nucleotides in length, with all Cs and Us being 2' F modified, and oligonucleotide 3 is 14 nucleotides in length, is the reverse complement of the non-targeting region of oligonucleotide 1, is fully 2'-O-methylated, and has cholesterol linked to the 3' terminus of the oligonucleotide using a C5 linker.

C. A tripartite molecule in which oligonucleotide 1 is 35 nucleotides in length (not including the 3' overhang), is 2'-O-methylated on all Cs and Us, contains 2'-O-methyl on nucleotide positions 17 and 18 (counting from the 5' end of the molecule), and has a 2'-O-methyl modified UU overhang, oligonucleotide 2 is 21 nucleotides in length, with all Cs and Us being 2' F modified, and has phosphorothioate internucleotide linkages between the last three nucleotides on the 3' terminus, and oligonucleotide 3 is 14 nucleotides in length, is the reverse complement of the non-targeting region of oligonucleotide 1, is fully 2'-O-methylated, and has cholesterol linked to the 3' terminus of the oligonucleotide using a C5 linker.

D. A tripartite molecule in which oligonucleotide 1 is 35 nucleotides in length (not including the 3' overhang), is 2'-O-methylated on all Cs and Us, contains 2'-O-methyl on nucleotide positions 17 and 18 (counting from the 5' end of the molecule), and has a 2'-O-methyl modified UU overhang, oligonucleotide 2 is 21 nucleotides in length, with all Cs and Us being 2' F modified, and has phosphorothioate internucleotide linkages between the last three nucleotides on the 3' terminus, and oligonucleotide 3 is 14 nucleotides in length, is the reverse complement of the non-targeting region of oligonucleotide 1, and has cholesterol linked to the 3' terminus of the oligonucleotide using a C5 linker Another nine designs provided 70% or greater knockdown and an additional dozen designs provided between 60% and 70% silencing. In addition, seven designs provided between 50% and 60% silencing. These experiments clearly identify the best modification patterns that can be applied to tripartite molecules intended for lipid-independent RNAi where the first oligonucleotide has the 35+2 configuration, the second oligonucleotide has the 19+2 configuration, and the third oligonucleotide has the 14 nucleotide+3' cholesterol conjugate configuration.

Table 5 provides a description of each tripartite design tested in HeLa cells to identify modification patterns that provide optimal levels of silencing. "Exp" is the level of expression of PPIB following targeting by each design relative to untreated cells.

TABLE 5

|  | Oligo #1 | Oligo #2 | Oligo #3 | Exp |
| --- | --- | --- | --- | --- |
| ~70% KD or more | PPIB3_35 + 2OMe_2OMe_UU | PPIB3_19 + 2_2F_PS | 5pmiR_arm_RC_2OMe_PS | 0.172 |
|  | PPIB3_35 + 2OMe_2OMe_UU | PPIB3_19 + 2_2F | 5pmiR_arm_RC_2OMe | 0.178 |
|  | PPIB3_35 + 2OMe_2OMe_UU | PPIB3_19 + 2_2F_PS | 5pmiR_arm_RC_2OMe | 0.190 |
|  | PPIB3_35 + 2OMe_2OMe_UU | PPIB3_19 + 2_2F_PS | 5pmiR_arm_RC_naked | 0.211 |
|  | PPIB3_35 + 2_2OMe_UU | PPIB3_19 + 2_2F_PS | 5pmiR_arm_RC_2OMe | 0.215 |
|  | PPIB3_35 + 2_PS_UU | PPIB3_19 + 2_2F_PS | 5pmiR_arm_RC_2OMe | 0.242 |
|  | PPIB3_35 + 2_2OMe_UU | PPIB3_19 + 2_2F_PS | 5pmiR_arm_RC_2OMe_PS | 0.257 |
|  | PPIB3_35 + 2_PS_UU | PPIB3_19 + 2_2F_PS | 5pmiR_arm_RC_2OMe_PS | 0.257 |
|  | PPIB3_35 + 2OMe_2OMe_UU | PPIB3_19 + 2_2F | 5pmiR_arm_RC_2OMe_PS | 0.269 |
|  | PPIB3_35 + 2_unmod_UU | PPIB3_19 + 2_2F_PS | 5pmiR_arm_RC_2OMe_PS | 0.269 |
|  | PPIB3_35 + 2_PS_UU | PPIB3_19 + 2_2F_PS | 5pmiR_arm_RC_naked | 0.294 |
|  | PPIB3_35 + 2_unmod_UU | PPIB3_19 + 2_2F_PS | 5pmiR_arm_RC_2OMe | 0.294 |
|  | PPIB3_35 + 2OMe_2OMe_UU | PPIB3_19 + 2_2F_PS | 5pmiR_arm_RC_PS | 0.309 |
| 60-70% KD | PPIB3_35 + 2_PS_UU | PPIB3_19 + 2_2F | 5pmiR_arm_RC_2OMe | 0.313 |
|  | PPIB3_35 + 2_PS_UU | PPIB3_19 + 2_2F | 5pmiR_arm_RC_2OMe_PS | 0.316 |
|  | PPIB3_35 + 2_unmod_UU | PPIB3_19 + 2_2F_PS | 5pmiR_arm_RC_naked | 0.327 |
|  | PPIB3_35 + 2_2OMe_UU | PPIB3_19 + 2_2F | 5pmiR_arm_RC_2OMe | 0.339 |
|  | PPIB3_35 + 2_2OMe_UU | PPIB3_19 + 2_2F_PS | 5pmiR_arm_RC_naked | 0.342 |
|  | PPIB3_35 + 2OMe_2OMe_UU | PPIB3_19 + 2_2F | 5pmiR_arm_RC_naked | 0.346 |
|  | PPIB3_35 + 2_2OMe_UU | PPIB3_19 + 2_2F | 5pmiR_arm_RC_naked | 0.353 |
|  | PPIB3_35 + 2_unmod_UU | PPIB3_19 + 2_2F | 5pmiR_arm_RC_2OMe | 0.368 |
|  | PPIB3_35 + 2_unmod_UU | PPIB3_19 + 2_2F | 5pmiR_arm_RC_naked | 0.372 |
|  | PPIB3_35 + 2OMe_2OMe_UU | PPIB3_19 + 2_2F | 5pmiR_arm_RC_PS | 0.373 |
|  | PPIB3_35 + 2_2OMe_UU | PPIB3_19 + 2_2F | 5pmiR_arm_RC_2OMe_PS | 0.390 |
|  | PPIB3_35 + 2_PS_UU | PPIB3_19 + 2_2F | 5pmiR_arm_RC_naked | 0.390 |
| 50-60% KD | PPIB3_35 + 2_2OMe_UU | PPIB3_19 + 2_2F | 5pmiR_arm_RC_PS | 0.423 |
|  | PPIB3_35 + 2_unmod_UU | PPIB3_19 + 2_2F | 5pmiR_arm_RC_2OMe_PS | 0.434 |
|  | PPIB3_35 + 2_2OMe_UU | PPIB3_19 + 2_2F_PS | 5pmiR_arm_RC_PS | 0.434 |
|  | PPIB3_35 + 2_PS_UU | PPIB3_19 + 2_2F | 5pmiR_arm_RC_PS | 0.435 |
|  | PPIB3_35 + 2OMe_2OMe_UU | PPIB3_19 + 2_PS | 5pmiR_arm_RC_2OMe | 0.448 |
|  | PPIB3_35 + 2_PS_UU | PPIB3_19 + 2_2F_PS | 5pmiR_arm_RC_PS | 0.454 |
|  | PPIB3_35 + 2OMe_2OMe_UU | PPIB3_19 + 2 | 5pmiR_arm_RC_2OMe | 0.458 |
| 40-50% KD | PPIB3_35 + 2OMe_2OMe_UU | PPIB3_19 + 2_PS | 5pmiR_arm_RC_naked | 0.524 |
|  | PPIB3_35 + 2OMe_2OMe_UU | PPIB3_19 + 2 | 5pmiR_arm_RC_2OMe_PS | 0.549 |
|  | PPIB3_35 + 2_PS_UU | PPIB3_19 + 2_PS | 5pmiR_arm_RC_2OMe | 0.549 |
|  | PPIB3_35 + 2_unmod_UU | PPIB3_19 + 2_2F_PS | 5pmiR_arm_RC_PS | 0.552 |
|  | PPIB3_35 + 2OMe_2OMe_UU | PPIB3_19 + 2_2F_OTP_PS | 5pmiR_arm_RC_2OMe | 0.556 |
|  | PPIB3_35 + 2OMe_2OMe_UU | PPIB3_19 + 2_PS | 5pmiR_arm_RC_2OMe_PS | 0.561 |
|  | PPIB3_35 + 2_unmod_UU | PPIB3_19 + 2 | 5pmiR_arm_RC_naked | 0.573 |
|  | PPIB3_35 + 2_2OMe_UU | PPIB3_19 + 2_PS | 5pmiR_arm_RC_2OMe | 0.573 |
|  | PPIB3_35 + 2_unmod_UU | PPIB3_19 + 2_2F | 5pmiR_arm_RC_PS | 0.579 |
|  | PPIB3_35 + 2_2OMe_UU | PPIB3_19 + 2 | 5pmiR_arm_RC_naked | 0.592 |

TABLE 5-continued

| | Oligo #1 | Oligo #2 | Oligo #3 | Exp |
|---|---|---|---|---|
| 30-40% KD | PPIB3_35 + 2_2OMe_UU | PPIB3_19 + 2 | 5pmiR_arm_RC_2OMe | 0.613 |
| | PPIB3_35 + 2_unmod_UU | PPIB3_19 + 2_PS | 5pmiR_arm_RC_2OMe | 0.615 |
| | PPIB3_35 + 2_PS_UU | PPIB3_19 + 2_2F_OTP_PS | 5pmiR_arm_RC_2OMe_PS | 0.624 |
| | PPIB3_35 + 2_PS_UU | PPIB3_19 + 2 | 5pmiR_arm_RC_2OMe | 0.627 |
| | PPIB3_35 + 2_unmod_UU | PPIB3_19 + 2_PS | 5pmiR_arm_RC_2OMe_PS | 0.628 |
| | PPIB3_35 + 2_PS_UU | PPIB3_19 + 2_PS | 5pmiR_arm_RC_naked | 0.639 |
| | PPIB3_35 + 2_unmod_UU | PPIB3_19 + 2_PS | 5pmiR_arm_RC_naked | 0.642 |
| | PPIB3_35 + 2OMe_2OMe_UU | PPIB3_19 + 2_2F_OTP_PS | 5pmiR_arm_RC_2OMe_PS | 0.644 |
| | PPIB3_35 + 2_2OMe_UU | PPIB3_19 + 2_PS | 5pmiR_arm_RC_naked | 0.648 |
| | PPIB3_35 + 2OMe_2OMe_UU | PPIB3_19 + 2_2F_OTP_PS | 5pmiR_arm_RC_naked | 0.654 |
| | PPIB3_35 + 2_PS_UU | PPIB3_19 + 2_PS | 5pmiR_arm_RC_2OMe_PS | 0.657 |
| | PPIB3_35 + 2OMe_2OMe_UU | PPIB3_19 + 2_OTP_PS | 5pmiR_arm_RC_2OMe | 0.664 |
| | PPIB3_35 + 2_PS_UU | PPIB3_19 + 2 | 5pmiR_arm_RC_naked | 0.667 |
| | PPIB3_35 + 2OMe_2OMe_UU | PPIB3_19 + 2 | 5pmiR_arm_RC_PS | 0.668 |
| | PPIB3_35 + 2_2OMe_UU | PPIB3_19 + 2_2F_OTP_PS | 5pmiR_arm_RC_2OMe | 0.673 |
| | PPIB3_35 + 2_2OMe_UU | PPIB3_19 + 2 | 5pmiR_arm_RC_2OMe_PS | 0.676 |
| | PPIB3_35 + 2_unmod_UU | PPIB3_19 + 2 | 5pmiR_arm_RC_2OMe | 0.679 |
| | PPIB3_35 + 2_unmod_UU | PPIB3_19 + 2_2F_OTP | 5pmiR_arm_RC_naked | 0.681 |
| | PPIB3_35 + 2_PS_UU | PPIB3_19 + 2_2F_OTP_PS | 5pmiR_arm_RC_2OMe | 0.685 |
| | PPIB3_35 + 2OMe_2OMe_UU | PPIB3_19 + 2_PS | 5pmiR_arm_RC_PS | 0.685 |
| Less than 30% KD (Inactive) | PPIB3_35 + 2_unmod_UU | PPIB3_19 + 2_2F_OTP_PS | 5pmiR_arm_RC_naked | 0.712 |
| | PPIB3_35 + 2_2OMe_UU | PPIB3_19 + 2_2F_OTP_PS | 5pmiR_arm_RC_naked | 0.719 |
| | PPIB3_35 + 2_2OMe_UU | PPIB3_19 + 2_PS | 5pmiR_arm_RC_2OMe_PS | 0.750 |
| | PPIB3_35 + 2_unmod_UU | PPIB3_19 + 2_OTP | 5pmiR_arm_RC_naked | 0.750 |
| | PPIB3_35 + 2_2OMe_UU | PPIB3_19 + 2_PS | 5pmiR_arm_RC_PS | 0.753 |
| | PPIB3_35 + 2OMe_2OMe_UU | PPIB3_19 + 2_2F_OTP | 5pmiR_arm_RC_2OMe_PS | 0.763 |
| | PPIB3_35 + 2_unmod_UU | PPIB3_19 + 2_2F_OTP_PS | 5pmiR_arm_RC_2OMe_PS | 0.774 |
| | PPIB3_35 + 2OMe_2OMe_UU | PPIB3_19 + 2_2F_OTP | 5pmiR_arm_RC_2OMe | 0.775 |
| | PPIB3_35 + 2_unmod_UU | PPIB3_19 + 2_OTP_PS | 5pmiR_arm_RC_naked | 0.775 |
| | PPIB3_35 + 2_2OMe_UU | PPIB3_19 + 2_OTP | 5pmiR_arm_RC_naked | 0.786 |
| | PPIB3_35 + 2_unmod_UU | PPIB3_19 + 2_OTP | 5pmiR_arm_RC_2OMe_PS | 0.786 |
| | PPIB3_35 + 2OMe_2OMe_UU | PPIB3_19 + 2_OTP | 5pmiR_arm_RC_PS | 0.788 |
| | PPIB3_35 + 2_unmod_UU | PPIB3_19 + 2_2F_OTP_PS | 5pmiR_arm_RC_2OMe | 0.797 |
| | PPIB3_35 + 2_PS_UU | PPIB3_19 + 2_OTP | 5pmiR_arm_RC_naked | 0.801 |
| | PPIB3_35 + 2_unmod_UU | PPIB3_19 + 2_2F_OTP_PS | 5pmiR_arm_RC_PS | 0.807 |
| | PPIB3_35 + 2_2OMe_UU | PPIB3_19 + 2_2F_OTP_PS | 5pmiR_arm_RC_2OMe_PS | 0.810 |
| | PPIB3_35 + 2OMe_2OMe_UU | PPIB3_19 + 2_OTP | 5pmiR_arm_RC_2OMe_PS | 0.815 |
| | PPIB3_35 + 2_unmod_UU | PPIB3_19 + 2_OTP_PS | 5pmiR_arm_RC_PS | 0.816 |
| | PPIB3_35 + 2_PS_UU | PPIB3_19 + 2 | 5pmiR_arm_RC_PS | 0.819 |
| | PPIB3_35 + 2OMe_2OMe_UU | PPIB3_19 + 2_OTP_PS | 5pmiR_arm_RC_naked | 0.825 |
| | PPIB3_35 + 2_PS_UU | PPIB3_19 + 2_2F_OTP | 5pmiR_arm_RC_naked | 0.826 |
| | PPIB3_35 + 2_PS_UU | PPIB3_19 + 2_PS | 5pmiR_arm_RC_PS | 0.828 |
| | PPIB3_35 + 2OMe_2OMe_UU | PPIB3_19 + 2_2F_OTP_PS | 5pmiR_arm_RC_PS | 0.829 |
| | PPIB3_35 + 2_PS_UU | PPIB3_19 + 2_2F_OTP_PS | 5pmiR_arm_RC_naked | 0.833 |
| | PPIB3_35 + 2_2OMe_UU | PPIB3_19 + 2_2F_OTP | 5pmiR_arm_RC_naked | 0.833 |
| | PPIB3_35 + 2_2OMe_UU | PPIB3_19 + 2_2F_OTP | 5pmiR_arm_RC_2OMe | 0.843 |
| | PPIB3_35 + 2_2OMe_UU | PPIB3_19 + 2_OTP | 5pmiR_arm_RC_2OMe_PS | 0.852 |
| | PPIB3_35 + 2_2OMe_UU | PPIB3_19 + 2_2F_OTP_PS | 5pmiR_arm_RC_PS | 0.858 |
| | PPIB3_35 + 2_unmod_UU | PPIB3_19 + 2_PS | 5pmiR_arm_RC_PS | 0.858 |
| | PPIB3_35 + 2_2OMe_UU | PPIB3_19 + 2_OTP_PS | 5pmiR_arm_RC_naked | 0.859 |
| | PPIB3_35 + 2OMe_2OMe_UU | PPIB3_19 + 2_2F_OTP | 5pmiR_arm_RC_PS | 0.867 |
| | PPIB3_35 + 2_unmod_UU | PPIB3_19 + 2 | 5pmiR_arm_RC_2OMe_PS | 0.868 |
| | PPIB3_35 + 2OMe_2OMe_UU | PPIB3_19 + 2_OTP_PS | 5pmiR_arm_RC_2OMe_PS | 0.893 |
| | PPIB3_35 + 2_2OMe_UU | PPIB3_19 + 2_OTP_PS | 5pmiR_arm_RC_2OMe | 0.899 |
| | PPIB3_35 + 2_2OMe_UU | PPIB3_19 + 2_2F_OTP | 5pmiR_arm_RC_2OMe_PS | 0.902 |
| | PPIB3_35 + 2_PS_UU | PPIB3_19 + 2_OTP_PS | 5pmiR_arm_RC_2OMe | 0.904 |
| | PPIB3_35 + 2_2OMe_UU | PPIB3_19 + 2_OTP_PS | 5pmiR_arm_RC_PS | 0.911 |
| | PPIB3_35 + 2_PS_UU | PPIB3_19 + 2_OTP_PS | 5pmiR_arm_RC_PS | 0.913 |
| | PPIB3_35 + 2_PS_UU | PPIB3_19 + 2_OTP_PS | 5pmiR_arm_RC_naked | 0.918 |
| | PPIB3_35 + 2_unmod_UU | PPIB3_19 + 2_OTP_PS | 5pmiR_arm_RC_2OMe | 0.932 |
| | PPIB3_35 + 2OMe_2OMe_UU | PPIB3_19 + 2 | 5pmiR_arm_RC_naked | 0.936 |
| | PPIB3_35 + 2_PS_UU | PPIB3_19 + 2_2F_OTP_PS | 5pmiR_arm_RC_PS | 0.937 |
| | PPIB3_35 + 2_2OMe_UU | PPIB3_19 + 2_OTP | 5pmiR_arm_RC_2OMe | 0.947 |
| | PPIB3_35 + 2_2OMe_UU | PPIB3_19 + 2 | 5pmiR_arm_RC_PS | 0.953 |
| | PPIB3_35 + 2_PS_UU | PPIB3_19 + 2_OTP_PS | 5pmiR_arm_RC_2OMe | 0.954 |
| | PPIB3_35 + 2_PS_UU | PPIB3_19 + 2_OTP | 5pmiR_arm_RC_PS | 0.960 |
| | PPIB3_35 + 2_PS_UU | PPIB3_19 + 2_2F_OTP | 5pmiR_arm_RC_PS | 0.968 |
| | PPIB3_35 + 2_unmod_UU | PPIB3_19 + 2_OTP | 5pmiR_arm_RC_2OMe | 0.975 |
| | PPIB3_35 + 2OMe_2OMe_UU | PPIB3_19 + 2_OTP_PS | 5pmiR_arm_RC_PS | 0.985 |
| | PPIB3_35 + 2_unmod_UU | PPIB3_19 + 2_2F_OTP | 5pmiR_arm_RC_2OMe | 0.991 |
| | PPIB3_35 + 2_PS_UU | PPIB3_19 + 2_OTP | 5pmiR_arm_RC_2OMe | 1.005 |
| | PPIB3_35 + 2_unmod_UU | PPIB3_19 + 2 | 5pmiR_arm_RC_PS | 1.019 |
| | PPIB3_35 + 2_2OMe_UU | PPIB3_19 + 2_OTP | 5pmiR_arm_RC_PS | 1.024 |
| | PPIB3_35 + 2_unmod_UU | PPIB3_19 + 2_OTP | 5pmiR_arm_RC_PS | 1.047 |
| | PPIB3_35 + 2_2OMe_UU | PPIB3_19 + 2_2F_OTP | 5pmiR_arm_RC_PS | 1.075 |
| | PPIB3_35 + 2OMe_2OMe_UU | PPIB3_19 + 2_OTP | 5pmiR_arm_RC_2OMe | 1.084 |
| | PPIB3_35 + 2OMe_2OMe_UU | PPIB3_19 + 2_OTP | 5pmiR_arm_RC_naked | 1.092 |
| | PPIB3_35 + 2_PS_UU | PPIB3_19 + 2_OTP_PS | 5pmiR_arm_RC_2OMe_PS | 1.105 |

TABLE 5-continued

| Oligo #1 | Oligo #2 | Oligo #3 | Exp |
|---|---|---|---|
| PPIB3_35 + 2_unmod_UU | PPIB3_19 + 2_2F_OTP | 5pmiR_arm_RC_PS | 1.117 |
| PPIB3_35 + 2OMe_2OMe_UU | PPIB3_19 + 2_2F_OTP | 5pmiR_arm_RC_naked | 1.126 |
| PPIB3_35 + 2_unmod_UU | PPIB3_19 + 2_2F_OTP | 5pmiR_arm_RC_2OMe_PS | 1.141 |
| PPIB3_35 + 2_unmod_UU | PPIB3_19 + 2_OTP_PS | 5pmiR_arm_RC_2OMe_PS | 1.200 |
| PPIB3_35 + 2_PS_UU | PPIB3_19 + 2_OTP | 5pmiR_arm_RC_2OMe_PS | 1.203 |
| PPIB3_35 + 2_2OMe_UU | PPIB3_19 + 2_OTP_PS | 5pmiR_arm_RC_2OMe_PS | 1.213 |
| PPIB3_35 + 2_PS_UU | PPIB3_19 + 2 | 5pmiR_arm_RC_2OMe_PS | 1.313 |
| PPIB3_35 + 2_PS_UU | PPIB3_19 + 2_2F_OTP | 5pmiR_arm_RC_2OMe_PS | 1.548 |

Table 6 provides examples of the target dependent region sequences of oligonucleotide 1 which can be employed in the tripartite design of the present disclosure:

TABLE 6

| Gene Name | Sequence 5' to 3' | SEQ ID NO: |
|---|---|---|
| TNFRSF1A | GAAGAGAGAUAGUGUGUGU | 8 |
|  | GUGUGUGGCUGCAGGAAGA | 9 |
|  | GAACCUACUUGUACAAUGA | 10 |
|  | GGGAGAAGAGAGAUAGUGU | 11 |
|  | GAGUGUGUCUCCUGUAGUA | 12 |
| CA2 | AAUCAAAGCUUCCUUCAAA | 13 |
|  | CAACAAUGGUCAUGCUUUC | 14 |
|  | GCACUUACAGAUUGAUUCA | 15 |
| RAN | GCAACAAAGUGGAUAUUAA | 16 |
|  | GAAAUUCGGUGGACUGAGA | 17 |
|  | UCAUUUGACUGGUGAAUUU | 18 |
|  | CUAGGAAGCUCAUUGGAGA | 19 |
|  | GCAUAGAGAUCUGGUACGA | 20 |
|  | CAGAGGACCUAUUAAGUUC | 21 |
|  | GACCCUAACUUGGAAUUUG | 22 |
|  | GUGUGCCACCUCAUUAUUA | 23 |
|  | GAGAGUUACUUACAAGAAU | 24 |
|  | CAACAGAGGACCUAUUAAG | 25 |
|  | ACAGGAAAGUGAAGGCGAA | 26 |
| HIF1A | GGACACAGAUUUAGACUUG | 27 |
|  | GCAGUAACCUUUCAUCAUG | 28 |
|  | GAUGUUAGCUCCCUAUAUC | 29 |
|  | GCAUAUAUCUAGAAGGUAU | 30 |
|  | GAGACACAAUCAUAUCUUU | 31 |
|  | CUACAUCACUUUCUUGGAA | 32 |
|  | GGAUAUGUCUGGGUUGAAA | 33 |
|  | CAAACAGAAUGUGUCCUUA | 34 |
|  | CAAGUAGCCUCUUUGACAA | 35 |
|  | CGUGUUAUCUGUCGCUUUG | 36 |

TABLE 6-continued

| Gene Name | Sequence 5' to 3' | SEQ ID NO: |
|---|---|---|
|  | GAAGGAACCUGAUGCUUUA | 37 |
|  | GAAGGUAUGUGGCAUUUAU | 38 |
| MCL1 | CGAAGGAAGUAUCGAAUUU | 39 |
|  | ACGGAAGGCUCAGUAAUUA | 40 |
|  | AGAACGAAUUGAUGUGUAA | 41 |
|  | GGGACUGGCUAGUUAAACA | 42 |
|  | GCAAGAGGAUUAUGGCUAA | 43 |
|  | GAAUUGAUGUGUAACUGUA | 44 |
|  | GGAAUGUGCUGCUGGCUUU | 45 |
|  | ACAAGGAUCUUAGUUGAUA | 46 |
|  | GAAGGAAGUAUCGAAUUUA | 47 |
|  | CCAAGAAAGCUGCAUCGAA | 48 |
|  | GCUCAGUAAUUAGUUAUGA | 49 |
|  | AUUAGGAACCUGUUUCUUA | 50 |
| BCL2L1 | AAAGUGCAGUUCAGUAAUA | 51 |
|  | GGAAAUGACCAGACACUGA | 52 |
|  | GGAUACAGCUGGAGUCAGU | 53 |
|  | GAGACUAGAUUGCCUUUGU | 54 |
|  | GCUCUCUGCUGUACAUAUU | 55 |
|  | GGAGGCAGGCGACGAGUUU | 56 |
|  | CCAGAAAGGAGACUAGAUU | 57 |
|  | GUCCAAAUGUCCUCCAGAA | 58 |
|  | GGAGUCAGUUUAGUGAUGU | 59 |
|  | GUUAAGCGUGUCUGUAUUU | 60 |
|  | GUACAUAUUUGAGACUAGU | 61 |
|  | CCUACAAGCUUUCCCAGAA | 62 |
| BIRC5 | GAAGCAGUUUGAAGAAUUA | 63 |
|  | GCAGUGGCCUAAAUCCUUU | 64 |
|  | GCUGAAGUCUGGCGUAAGA | 65 |
|  | GGCGUAAGAUGAUGGAUUU | 66 |
|  | GAGACAGAAUAGAGUGAUA | 67 |

TABLE 6-continued

| Gene Name | Sequence 5' to 3' | SEQ ID NO: |
|---|---|---|
| | GAAAGAAUUUGAGGAAACU | 68 |
| | GUAGAUGCAUGACUUGUGU | 69 |
| | GCAGGUUCCUUAUCUGUCA | 70 |
| | GAAUUAACCCUUGGUGAAU | 71 |
| | CCACUGCUGUGUGAUUAGA | 72 |
| | GAAAGGAGAUCAACAUUUU | 73 |
| | CCAACAAUAAGAAGAAAGA | 74 |
| SYK | GAACUGGGCUCUGGUAAUU | 75 |
| | GCUGCGCAAUUACUACUAU | 76 |
| | AGAAAUGUGUUGCUAGUUA | 77 |
| | CGGAAUGCAUCAACUACUA | 78 |
| | GAAAUGUGUUGCUAGUUAC | 79 |
| | UGUACGAUCUCAUGAAUCU | 80 |
| | UGAGCAAAUUGUCCUGAUA | 81 |
| | CCAAAUCCCUUUCAUGUCU | 82 |
| | CAGCAGAACAGACAUGUCA | 83 |
| | GAACAGACAUGUCAAGGAU | 84 |
| | GGAAGAAUCUGAGCAAAUU | 85 |
| | UGAAGUCACCGCUAUGUUA | 86 |
| HRH1 | UGAUAGAGAAGUAGACAAA | 87 |
| | CUACAAGGCCGUACGCACAA | 88 |
| | AGAGGAUGAUAGAGAAGUA | 89 |
| | AAGAAGACAUUCAAGAGAA | 90 |
| | GCCAAGAGGAUGAUAGAGA | 91 |
| | AGAGACAGCACCAGGCAAA | 92 |
| | GCAAUGAGAACUUCAAGAA | 93 |
| | GAAACCUUGUCUCUACUAA | 94 |
| | UCAAGAGAAUUCUGCAUAU | 95 |
| | GCAACAAAUGAUCCUUAU | 96 |
| CFB | UGAUCAAGCUCAAGAAUAA | 97 |
| | ACACGUACCUGCAGAUCUA | 98 |
| | GGAUUUGGGUUUUCUAUAA | 99 |
| | GAAAGACAAUGAGCAACAU | 100 |
| | GGAGCACCCUGAAGACUCA | 101 |
| | GCCAAGAUCUCAGUCAUUC | 102 |
| | GGGCUGUGGUGUCUGAGUA | 103 |
| | GCAGCUCAAUGAAAUCAAU | 104 |
| | CAAGAGAAGUCGUUUCAUU | 105 |
| | CGAAGCAGCUCAAUGAAAU | 106 |

TABLE 6-continued

| Gene Name | Sequence 5' to 3' | SEQ ID NO: |
|---|---|---|
| | GAUGAAAGCCAGUCUCUGA | 107 |
| | CUACAACAUUAAUGGGAAA | 108 |
| AQP4 | GGAGUCAGGUAGAGACGGA | 109 |
| | GGUAUUGUCUUCAGUAUGA | 110 |
| | GGAAAACCAUUGGAUAUAU | 111 |
| | GUGCAGUGCUUUGGCCAUA | 112 |
| | UGAUGUCACUGGCUCAAUA | 113 |
| | GAGGUAUUGUCUUCAGUAU | 114 |
| | UUAGAACUGUCCUCAGAUU | 115 |
| | GAAUUUCUGGCCAUGCUUA | 116 |
| | CUCAAUAGCUUUAGCAAUU | 117 |
| | AGACCAAUCUGGAGAGGUA | 118 |
| | CGGAUGACCUGAUUCUAAA | 119 |
| | UUAGAAAUGUGCAGGUUUG | 120 |
| PDE4D | AGACUAUGGUUGAAACUAA | 121 |
| | GGGAAGAAGAGGAAAGCCA | 122 |
| | GAUCAGUGGAGUCAAGAAA | 123 |
| | GGAAGAAAACUGUGACAUU | 124 |
| | CCAAGGAACUAGAAGAUGU | 125 |
| | GCAGUCAAGUGGAAGAAGA | 126 |
| TIE-1 | GUGCAGAACUCUACGAGAA | 127 |
| | AGACAAUGCUGGCGGGAGA | 128 |
| | GAAUGUUAGAGGAGCGAAA | 129 |
| | AGAAGAAGAUGCAGUGAUU | 130 |
| KRAS | CGAAUAUGAUCCAACAAUA | 131 |
| | GGACGAAUAUGAUCCAACA | 132 |
| | UAAGGACUCUGAAGAUGUA | 133 |
| | GGAAGCAAGUAGUAAUUGA | 134 |
| | GCAAGAAGUUAUGGAAUUC | 135 |
| | GAUGAUGCCUUCUAUACAU | 136 |
| | AAACCUGUCUCUUGGAUAU | 137 |
| | GGGCUUUCUUUGUGUAUUU | 138 |
| | GCAUGCAGUUGAUUACUUC | 139 |
| | UGCAGUUGAUUACUUCUUA | 140 |
| | CGAUACAGCUAAUUCAGAA | 141 |
| | GAAGUUAUGGAAUUCCUUU | 142 |

In Table 6, the following abbreviations are used: TNFRSF1A:tumor necrosis factor receptor superfamily member 1A; CA2:canbonic anhydrase II; RAN:ras-related nuclear protein; HIF1A:hypoxia-inducible factor 1, alpha subunit; MCL1:myeloid cell leukemia sequence 1; BCL2L1:

Bcl2-like 1; BIRC5:survivin; SYK:splenn tyrosine kinase; HRH1:histamine receptor H1; CFB:complement factor B; AQP4:aquaporin 4; TIE-1:TEK tyrosine kinase, endothelial; PDE4D:phosphodiesterase 4D; KRAS:v-Ki-ras2 Kirsten rat sarcoma viral oncogene homolog.

Example 59

Figure 13A:
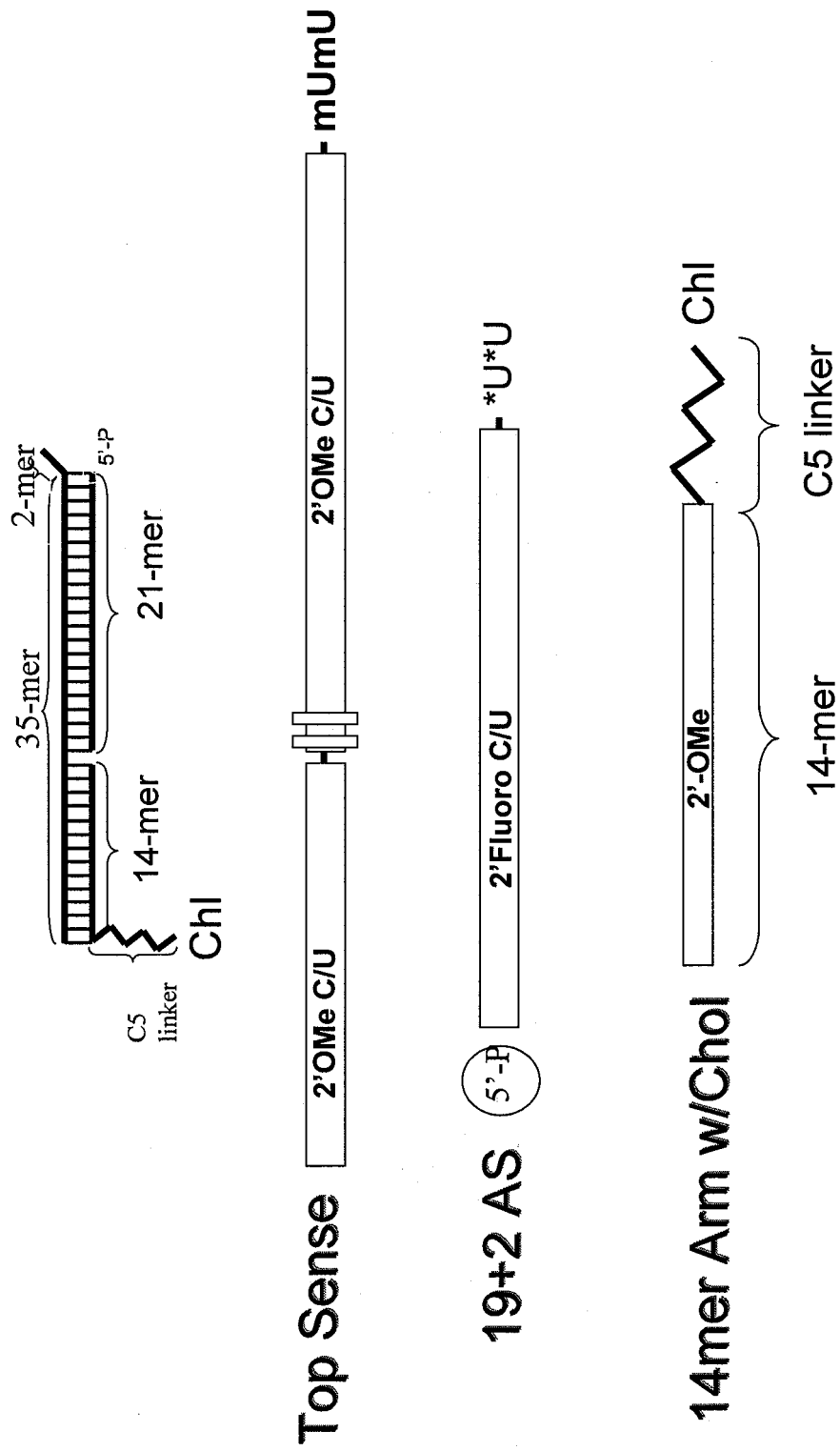
FIG. 13A provides schematic of a tripartite molecule and with modifications on each of the 3 oligonucleotides. Specifically, the top (sense) strand (oligonucleotide 1) has 2'-O-methyl on all Cs and Us and on the first two (5'-most) nucleotides of the region that is complementary to the antisense strand (see vertical bars). The antisense strand (oligonucleotide 2) has a 5' phosphate, 2' fluoro on all Cs and Us, and a 3' UU overhang with phosphorothioate modifications. The 14 nucleotide oligonucleotide 3 has 2' O-methyl modifications on all nucleotides, a 3' C5 linker, and a cholesterol conjugate.

A Comparison of Gene Knockdown Induced by Duplex and Tripartite Molecules Targeting Multiple Genes Forty gene targeting sequences (10 genes×4 sequences per gene; CDC2, LMNA, GAPDH, TP53, AKT, RBI, DBI, MAP2K, HRI, and MET) were constructed to test the efficacy of the tripartite molecule. The design used in these experiments is presented in FIG. 13A and includes:

Oligonucleotide 1: 37 nucleotides in length, with (from 5' to 3') a 14 nucleotide target independent region, and 19 nucleotide target dependent region, and a 2 nucleotide UU overhang at the 3' end. Oligonucleotide 1 is fully 2'-O-methylated on all Cs and Us across the length of the oligonucleotide. In addition, the two 5'-most nucleotides of the target dependent region are 2' O-methylated, as is the UU overhang. In FIG. 13A, oligonucleotide 1 is labeled as the "top sense" strand.

Oligonucleotide 2: 21 nucleotides in length, including a UU overhang at the 3' end. 2' F groups are present on all Cs and Us, and a phosphate group is present on the 5' terminus. The overhang contains phosphorothioate internucleotide linkages ("*"). In FIG. 13A, oligonucleotide 2 is labelled as "19+2 AS."

Oligonucleotide 3: 14 nucleotides in length, fully 2'-O-methylated, and has a C5 linker on the 3' terminus, and is conjugated through the linker to a cholesterol molecule. In FIG. 13A, oligonucleotide 3 is labelled as "14 mer Arm w/Chol."

The tripartite design was directly compared with a simple duplex design having the same targeting sequence. The duplex design comprises:

Sense strand: 19 nucleotides in length with 2'-O-methyl modification on nucleotides 1 and 2 (counting from the 5' terminus of the molecule) and on all Cs and Us, and a cholesterol conjugate associated with the 3' terminus via a C5 linker.

Antisense strand: 19 nucleotides in length plus a two-nucleotide 3' UU overhang with phosphorothioate internucleotide linkages, all Cs and Us are 2' F, and a phosphate group is present on the 5' end of the molecule.

To introduce the molecules into cells, 2.5 K HeLa S3 cells were first plated and subsequently exposed to the respective tripartite molecule or duplex in reduced serum media (1 micromolar). Seventy-two hours later, target knockdown was measured using a branched DNA (bDNA) assay.

Figure 13B:
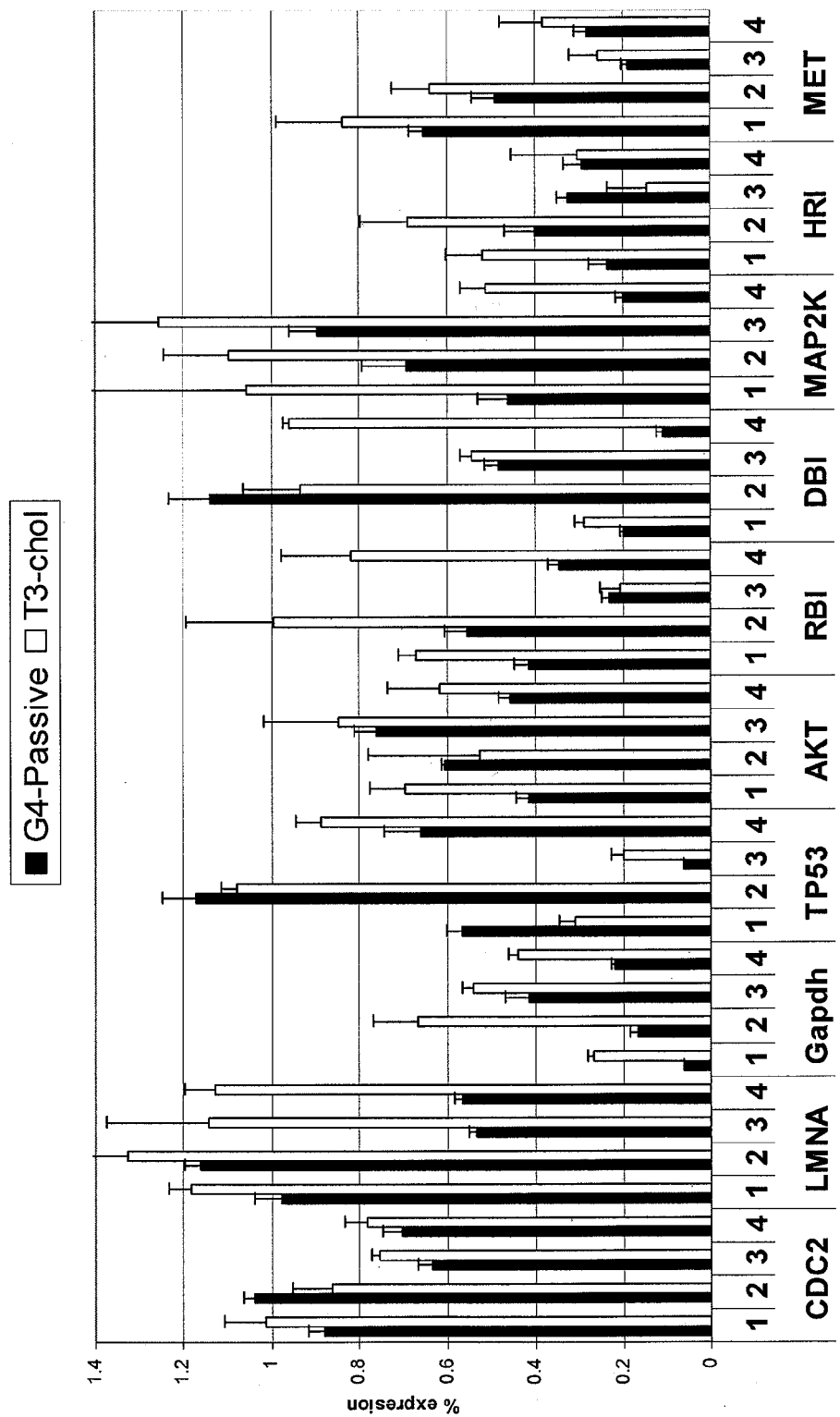
FIG. 13B provides a graph which shows a comparison of forty different sequences targeting ten different genes using passively delivered tripartite (design described in FIG. 14A) and duplex molecules. "G4" represents duplex molecules containing the following modification pattern: the sense strand has 2'-O-methyl modifications on positions 1 and 2 (counting from the 5' terminus of the molecule), and 2'-O-methyl modifications on all Cs and Us. In addition, the sense strand has a C5 linker on the 3' terminus and is conjugated to cholesterol. The antisense strand has 2' F on all Cs and Us, a phosphate group on the 5' terminus, and a 2 nucleotide overhang on the 3' end of the oligonucleotide containing phophorothioate internucleotide linkages. "T3-chol" represents the tripartite molecule described in detail in FIG. 14A. Y axis represents the fraction of gene expression as compared with untreated cells.

The results of this study are presented in FIG. 13B and show that in the majority of cases, the performance of the tripartite design was roughly equivalent to the duplex.

Figure 13C:
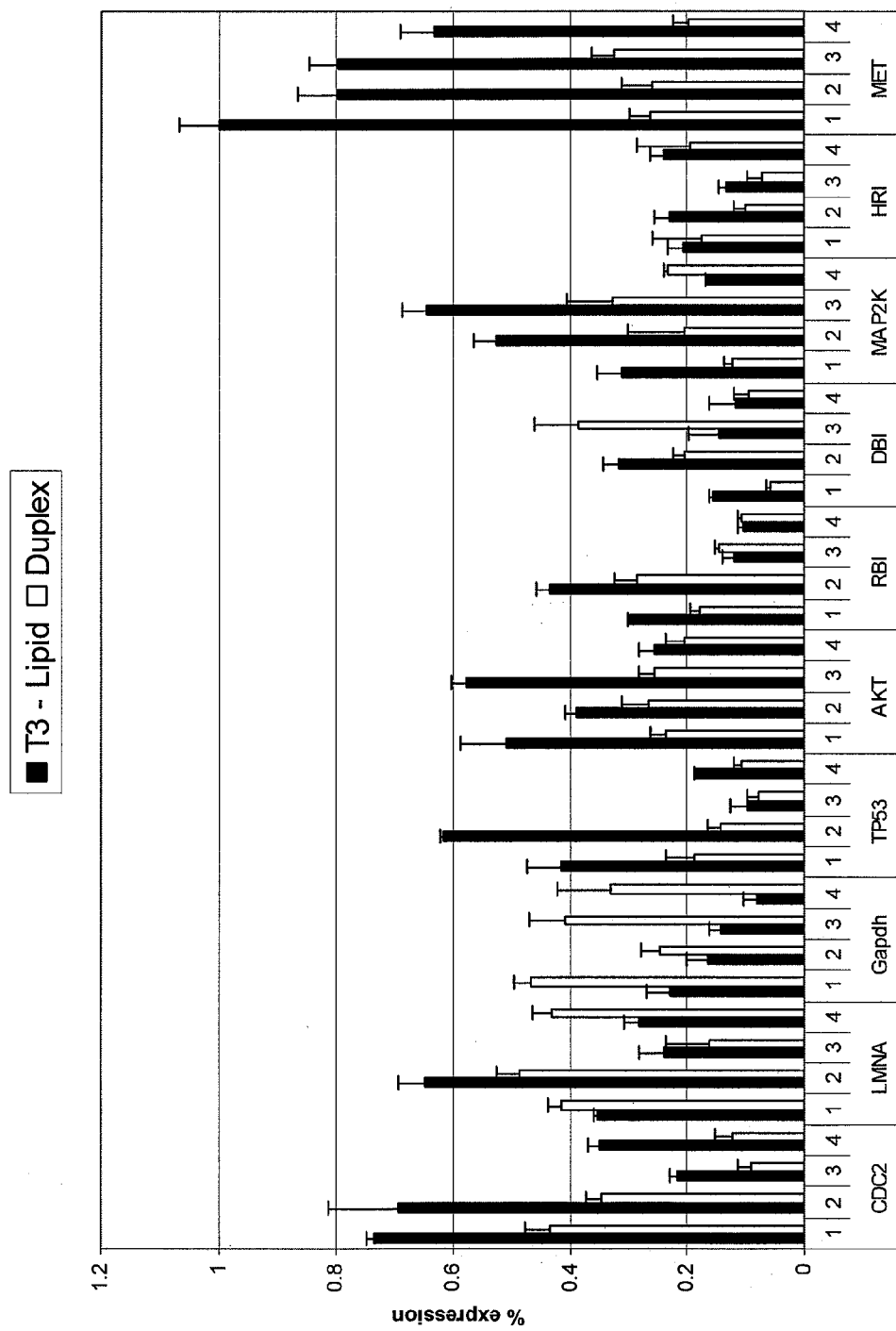
FIG. 13C provides a graph which shows a comparison of forty different sequences targeting ten different genes using tripartite and duplex molecules (without cholesterol) delivered by lipid transfection. "duplex" represents the double stranded molecule with previously described chemical modifications (without cholesterol or the C5 linker). "T3-lipid" represents the tripartite molecule with the previously described chemical modifications without the linker or the cholesterol conjugate. Y axis represents the fraction of gene expression as compared with untreated cells.

Additional studies were performed to determine whether the tripartite design could be used in conjunction with lipid transfection reagents. HeLa S3 cells (10K) were plated and subsequently transfected with tripartite molecules (100 nM, DharmaFECT4 lipid, 0.2 ul/well) that had the same sequence and design as those described above, with the exception that they lacked both the C5 linker and the cholesterol conjugate. In a side-by-side experiment, the targeting sequences were also introduced as modified 19 bp duplexes. Specifically, sequences having sense strand modifications (2'-O-methyl on all Cs and Us) and antisense strand modifications (2'F on all Cs and Us, and a phosphate on the 5' terminus) were transfected into cells under equivalent conditions. Forty-eight hours after transfection, gene knockdown by each class of molecules was measured using a bDNA assay. The results for these experiments are presented in FIG. 13C and demonstrate that in roughly half of the cases the tripartite structures performed as well or better than the duplexes when transfected using DharmaFECT4 lipids.

Example 60

Testing an Alternative Tripartite Oligonucleotide Complex Configuration

A second configuration of the tripartite molecule was tested to determine the flexibility of the design. In this design, oligonucleotide 1 includes target dependent sequence that will form the antisense strand of the post Dicer-processed duplex (rather than the sense strand as in the foregoing examples), and also includes a target independent sequence that anneals to oligonucleotide 3. Oligonucleotide 2 includes sequence that will form the sense strand of the post-Dicer processed duplex. The second design used in these studies is shown in FIG. 14A. In more detail, this alternative tripartite oligonucleotide complex has the following design:

Oligonucleotide 1 is 35 nucleotides in length and consists of a 19 nt target dependent region (antisense strand) targeting PPIB, linked to a 16 nucleotide non-targeting sequence (which is located 3' of the target dependent region). The nucleotide sequence of oligonucleotide 1 is:

```
                                           SEQ ID NO: 143
   5' ACACGAUGGAAUUUGCUGUUUGUACCUACUCUCGA 3'
```

The 5' terminus of this oligonucleotide is phosphorylated and nucleotides 20 and 21 (counting from the 5' end) are Us. Four different modification patterns were tested for oligonucleotide 1. These include:
  2' F on all Cs and Us in the target dependent region
  2' F on all Cs and Us in the target dependent region plus phorphorthioate internucleotide linkages between nucleotides 19 and 20 as well as 20 and 21 (counting from the 5' end).
  2' F on all Cs and Us (except nucleotides 20 and 21)
  2' F on all Cs and Us (except nucleotides 20 and 21) plus phosphorothioate internucleotide linkages between nucleotides 19 and 20 as well as 20 and 21 (counting from the 5' end).

Oligonucleotide 2 is 21 nucleotides in length and consists of 19 nucleotides that are complementary to the target dependent region of oligonucleotide 1, plus two, unpaired UU nucleotides:

```
   5' ACAGCAAAUUCCAUCGUGUUU 3'    SEQ ID NO: 144
```

In all of these experiments, the UU overhangs on oligonucleotide 2 are 2'-O methylated.

Oligonucleotide 3 is 16 nucleotides in length and has the following sequence:

```
   5' UCGAGAGUAGGUACAA 3'    SEQ ID NO: 145
```

Figure 14B:
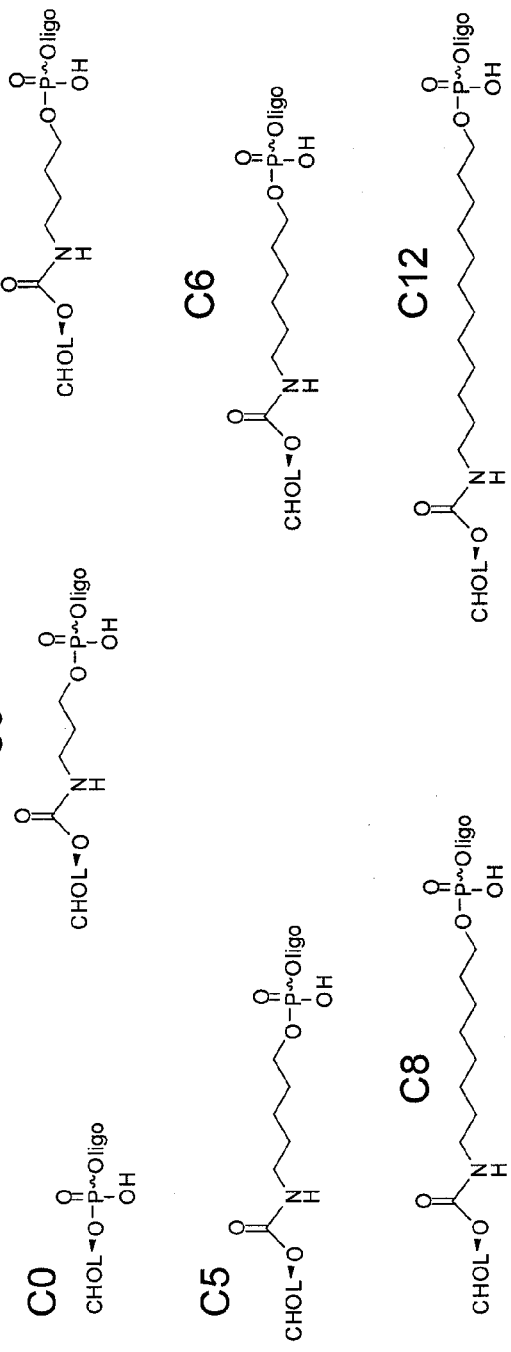
FIG. 14B shows a range of linker structures that were tested in the context of the design provided in FIG. 14A.
Figure 14B:
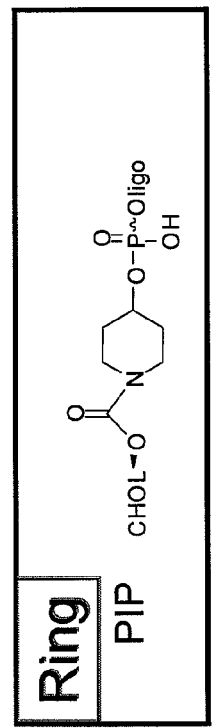
Figure 14C:
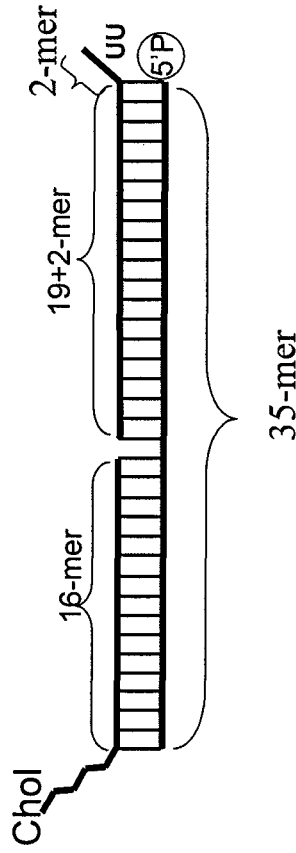
FIG. 14C provides a list of chemical modifications tested in the context of the design provided in FIG. 14A.

Oligonucleotide 3 was formulated with cholesterol linked to the 5' terminus using a variety of different linkers as shown in FIG. 14B. In all of these experiments, oligonucleotide 3 is fully 2'-O-methylated.

Figure 14D:
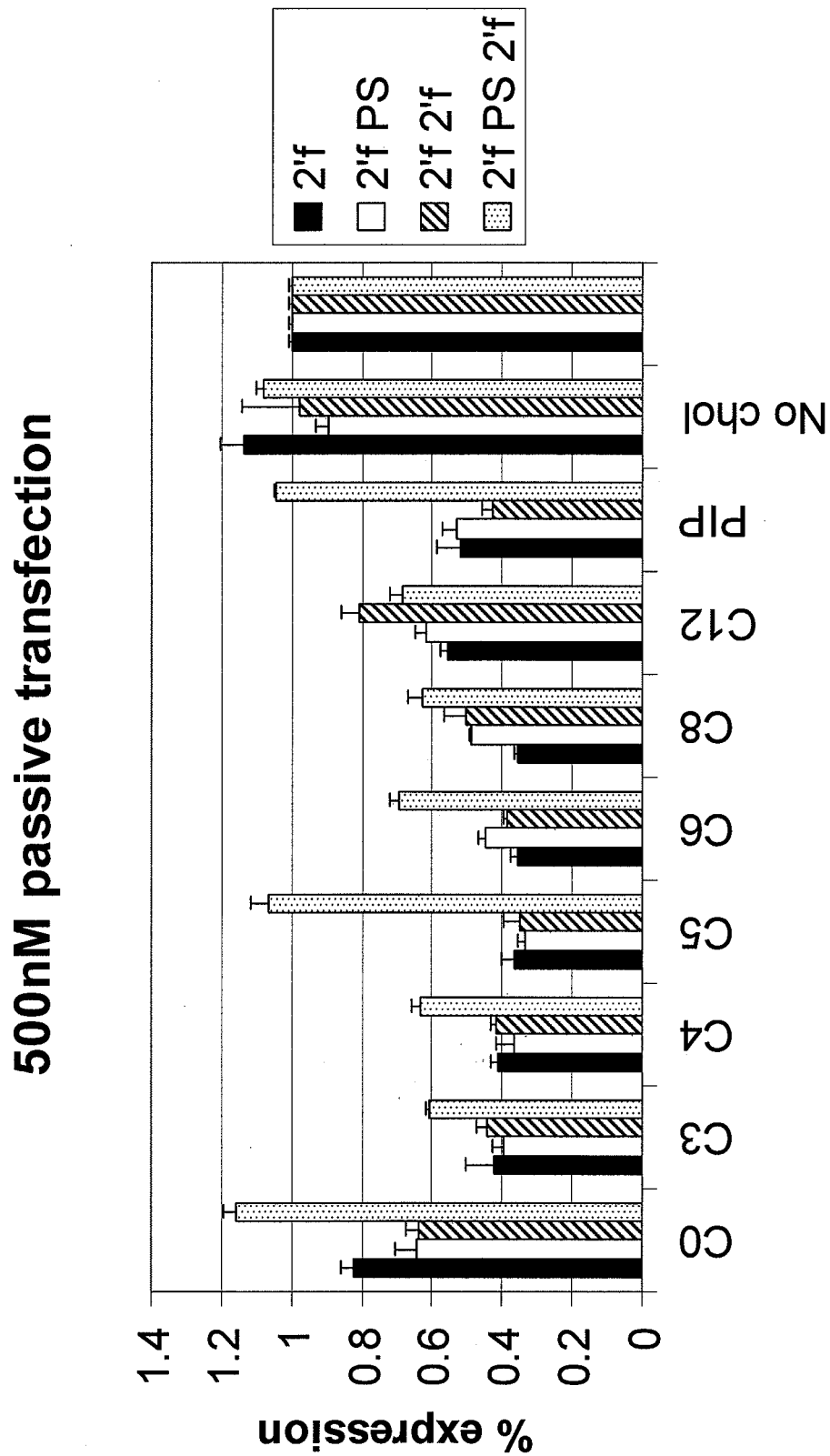
FIG. 14D shows the functionality of each of the designs at 500 nM concentrations.

Each of the molecules was synthesized as described previously and passively transfected into HeLa S3 cells (2.5K cells per well, 500 nM concentrations) in reduced serum media. Gene knockdown was measured using branched DNA technologies at 72 hr post transfection. The results of these studies are provided in FIG. 14D and show that the level of potency varies upon the modification pattern. Preferred linker lengths were found to be between 3 and 6 carbons while the best modification pattern on oligonucleotide 1 was found to contain 2'F on Cs and Us in the portion of the oligonucleotide that is complementary to oligonucleotide 2. Phosphorothioate modifications in the positions tested were not found to be essential.

What is claimed is:

1. A tripartite oligonucleotide complex comprising:
   i) a first oligonucleotide between 29 nucleotides and 37 nucleotides in length having a target-dependent region and a target-independent region that is 5' to the target-dependent region,
   ii) a second oligonucleotide between 19 nucleotides and 23 nucleotides in length comprising an antisense region that has greater than 70% complementarity to a target gene of an organism, and
   iii) a third oligonucleotide between 10 nucleotides and 14 nucleotides in length, wherein the target-dependent region of the first oligonucleotide is greater than 80% complementary to the second oligonucleotide and the target-independent region of the first oligonucleotide is greater than 80% complementary to the third oligonucleotide, such that the first, second and third oligonucleotides are capable of forming a tripartite complex having at least two regions of duplex, and the third oligonucleotide is a non-targeting sequence.

2. The tripartite oligonucleotide complex of claim 1 wherein the first oligonucleotide has a 3' overhang of 1-6 nucleotides.

3. The tripartite oligonucleotide complex of claim 2 wherein the first oligonucleotide has a 3' overhang of 2 nucleotides.

4. The tripartite oligonucleotide complex of claim 3 wherein the first oligonucleotide is 37 nucleotides in length including said 3' overhang of 2 nucleotides, the second oligonucleotide is 21 nucleotides in length including a UU dinucleotide sequence at the 3' end, and the third oligonucleotide is 14 nucleotides in length.

5. The tripartite oligonucleotide complex of claim 1 wherein about 40% to about 90% of all nucleotides in each of the first, second and third oligonucleotides are chemically modified and wherein the 5' terminus of the second oligonucleotide is phosphorylated.

6. The tripartite oligonucleotide complex of claim 5 wherein all the Us and Cs in the first oligonucleotide are 2' O-methyl modified, all Us and Cs of the second oligonucleotide are 2' F modified, and all the nucleotides of the third oligonucleotide are 2' O-methyl modified.

7. The tripartite oligonucleotide complex of claim 4 wherein nucleotide positions in the target-dependent region of the first oligonucleotide that are opposite nucleotide positions 18 and 19 of the second oligonucleotide counting from the 5' end are 2' O-methyl modified.

8. The tripartite oligonucleotide complex of claim 4 wherein a mismatch exists between position 10, 11, 12, 13, or 14 on the second oligonucleotide counting from the 5' end and the opposite nucleotide in the target-dependent region of the first oligonucleotide.

9. The tripartite oligonucleotide complex of claim 8 wherein a mismatch exists between position 14 on the second oligonucleotide counting from the 5' end and the opposite nucleotide in the target-dependent region of the first oligonucleotide.

10. The tripartite oligonucleotide complex of claim 2 wherein the sequence of the boundary between the target-independent region of the first oligonucleotide and the target-dependent region of region of the first oligonucleotide is 5' G/AA 3'.

11. The tripartite oligonucleotide complex of claim 2 further comprising at least one conjugate moiety attached to the third oligonucleotide.

12. The tripartite oligonucleotide complex of claim 11 wherein said conjugate moiety is attached to the 3' terminus of the third oligonucleotide.

13. The tripartite oligonucleotide complex of claim 12 wherein said conjugate moiety is attached to the 3' terminus of the third oligonucleotide via a linker.

14. The tripartite oligonucleotide complex of claim 13 wherein said conjugate moiety is selected from the group consisting of a steroid molecule, a vitamin, and a peptide.

15. The tripartite oligonucleotide complex of claim 14 wherein said conjugate moiety is a steroid molecule selected from the group consisting of cholesterol, cholestanol, stigmasterol, cholanic acid, and ergosterol.

16. The tripartite oligonucleotide complex of claim 15 wherein said conjugate moiety is cholesterol, wherein said linker is a C5 linker molecule, and wherein the third oligonucleotide has the structure:

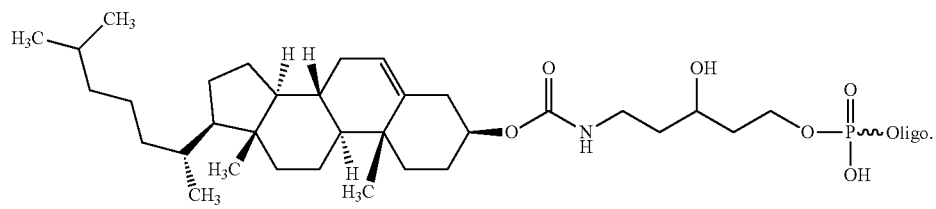

17. The tripartite oligonucleotide complex of claim 2 further comprising at least one detectable label attached to the third oligonucleotide.

18. The tripartite oligonucleotide complex of claim 17 further comprising at least one conjugate moiety.

19. The tripartite oligonucleotide of claim 17 wherein said detectable label is a dye molecule.

20. A pharmaceutical composition comprising a tripartite oligonucleotide complex, said tripartite oligonucleotide complex comprising:
   i) a first oligonucleotide between 29 nucleotides and 37 nucleotides in length having a target-dependent region and a target-independent region that is 5' to the target-dependent region,
   ii) a second oligonucleotide between 19 nucleotides and 23 nucleotides in length comprising an antisense region that has greater than 70% complementarity to a target gene of an organism, and
   iii) a third oligonucleotide between 10 nucleotides and 14 nucleotides in length,
wherein the target-dependent region of the first oligonucleotide is greater than 80% complementary to the second oligonucleotide nucleotide and the sequence of the target-independent region of the first oligonucleotide is greater than 80% complementary to the third oligonucleotide, such that the first, second and third oligonucleotides are capable of forming a tripartite complex having at least two regions of duplex, and the third oligonucleotide is a non-targeting sequence.

21. The pharmaceutical composition of claim 20 wherein the first oligonucleotide is 37 nucleotides in length and includes a 3' overhang of 2 nucleotides, the second oligonucleotide is 21 nucleotides in length including a UU dinucleotide sequence at the 3' end, and the third oligonucleotide is 14 nucleotides in length.

22. The pharmaceutical composition of claim 20 wherein about 40% to about 90% of all nucleotides in each of the first, second and third oligonucleotides are chemically modified and wherein the 5' terminus of the second oligonucleotide is phosphorylated.

23. The pharmaceutical composition of claim 21 wherein nucleotide positions in the target-dependent region of the first oligonucleotide that are opposite nucleotide positions 18 and 19 of the second oligonucleotide counting from the 5' end are 2' O-methyl modified.

24. The pharmaceutical composition of claim 23 wherein a mismatch exists between position 10, 11, 12, 13, or 14 on the second oligonucleotide counting from the 5' end and the opposite nucleotide in the target-dependent region of the first oligonucleotide.

25. The pharmaceutical composition of claim 20 wherein said tripartite oligonucleotide complex further comprises at least one conjugate moiety attached to the third oligonucleotide.

* * * * *

SEQUENCE LISTING

```
<160> NUMBER OF SEQ ID NOS: 145

<210> SEQ ID NO 1
<211> LENGTH: 14
<212> TYPE: RNA
<213> ORGANISM: Artificial sequence
<220> FEATURE:
<223> OTHER INFORMATION: oligo

<400> SEQUENCE: 1
agcucucauc caug                                                      14

<210> SEQ ID NO 2
<211> LENGTH: 14
<212> TYPE: RNA
<213> ORGANISM: Artificial sequence
<220> FEATURE:
<223> OTHER INFORMATION: oligo

<400> SEQUENCE: 2
cauggaugag agcu                                                      14

<210> SEQ ID NO 3
<211> LENGTH: 19
<212> TYPE: RNA
<213> ORGANISM: Artificial sequence
<220> FEATURE:
<223> OTHER INFORMATION: oligo

<400> SEQUENCE: 3
acagcaaauu ccaucgugu                                                 19

<210> SEQ ID NO 4
<211> LENGTH: 19
<212> TYPE: RNA
<213> ORGANISM: Artificial sequence
<220> FEATURE:
<223> OTHER INFORMATION: oligo

<400> SEQUENCE: 4
cacucaagau ugucagcaa                                                 19

<210> SEQ ID NO 5
<211> LENGTH: 35
<212> TYPE: RNA
<213> ORGANISM: Artificial sequence
<220> FEATURE:
<223> OTHER INFORMATION: oligo

<400> SEQUENCE: 5
agcucucauc caugaaacag caaauuccau cgugu                               35

<210> SEQ ID NO 6
<211> LENGTH: 21
<212> TYPE: RNA
<213> ORGANISM: Artificial sequence
<220> FEATURE:
<223> OTHER INFORMATION: oligo
```

-continued

```
<400> SEQUENCE: 6
acacgaugga auuugcuguu u                                              21

<210> SEQ ID NO 7
<211> LENGTH: 14
<212> TYPE: RNA
<213> ORGANISM: Artificial sequence
<220> FEATURE:
<223> OTHER INFORMATION: oligo

<400> SEQUENCE: 7
cauggaugag agcu                                                      14

<210> SEQ ID NO 8
<211> LENGTH: 19
<212> TYPE: RNA
<213> ORGANISM: Artificial sequence
<220> FEATURE:
<223> OTHER INFORMATION: oligo

<400> SEQUENCE: 8
gaagagagau agugugugu                                                 19

<210> SEQ ID NO 9
<211> LENGTH: 19
<212> TYPE: RNA
<213> ORGANISM: Artificial sequence
<220> FEATURE:
<223> OTHER INFORMATION: oligo

<400> SEQUENCE: 9
guguguggcu gcaggaaga                                                 19

<210> SEQ ID NO 10
<211> LENGTH: 19
<212> TYPE: RNA
<213> ORGANISM: Artificial sequence
<220> FEATURE:
<223> OTHER INFORMATION: oligo

<400> SEQUENCE: 10
gaaccuacuu guacaauga                                                 19

<210> SEQ ID NO 11
<211> LENGTH: 19
<212> TYPE: RNA
<213> ORGANISM: Artificial sequence
<220> FEATURE:
<223> OTHER INFORMATION: oligo

<400> SEQUENCE: 11
gggagaagag agauagugu                                                 19

<210> SEQ ID NO 12
<211> LENGTH: 19
<212> TYPE: RNA
<213> ORGANISM: Artificial sequence
<220> FEATURE:
<223> OTHER INFORMATION: oligo

<400> SEQUENCE: 12
gagugugucu ccuguagua                                                 19

<210> SEQ ID NO 13
<211> LENGTH: 19
```

```
<212> TYPE: RNA
<213> ORGANISM: Artificial sequence
<220> FEATURE:
<223> OTHER INFORMATION: oligo

<400> SEQUENCE: 13
aaucaaagcu uccuucaaa                                                19

<210> SEQ ID NO 14
<211> LENGTH: 19
<212> TYPE: RNA
<213> ORGANISM: Artificial sequence
<220> FEATURE:
<223> OTHER INFORMATION: oligo

<400> SEQUENCE: 14
caacaauggu caugcuuuc                                                19

<210> SEQ ID NO 15
<211> LENGTH: 19
<212> TYPE: RNA
<213> ORGANISM: Artificial sequence
<220> FEATURE:
<223> OTHER INFORMATION: oligo

<400> SEQUENCE: 15
gcacuuacag auugauuca                                                19

<210> SEQ ID NO 16
<211> LENGTH: 19
<212> TYPE: RNA
<213> ORGANISM: Artificial sequence
<220> FEATURE:
<223> OTHER INFORMATION: oligo

<400> SEQUENCE: 16
gcaacaaagu ggauauuaa                                                19

<210> SEQ ID NO 17
<211> LENGTH: 19
<212> TYPE: RNA
<213> ORGANISM: Artificial sequence
<220> FEATURE:
<223> OTHER INFORMATION: oligo

<400> SEQUENCE: 17
gaaauucggu ggacugaga                                                19

<210> SEQ ID NO 18
<211> LENGTH: 19
<212> TYPE: RNA
<213> ORGANISM: Artificial sequence
<220> FEATURE:
<223> OTHER INFORMATION: oligo

<400> SEQUENCE: 18
ucauuugacu ggugaauuu                                                19

<210> SEQ ID NO 19
<211> LENGTH: 19
<212> TYPE: RNA
<213> ORGANISM: Artificial sequence
<220> FEATURE:
<223> OTHER INFORMATION: oligo

<400> SEQUENCE: 19
```
cuaggaagcu cauuggaga                                                    19

<210> SEQ ID NO 20
<211> LENGTH: 19
<212> TYPE: RNA
<213> ORGANISM: Artificial sequence
<220> FEATURE:
<223> OTHER INFORMATION: oligo

<400> SEQUENCE: 20
gcauagagau cugguacga                                                    19

<210> SEQ ID NO 21
<211> LENGTH: 19
<212> TYPE: RNA
<213> ORGANISM: Artificial sequence
<220> FEATURE:
<223> OTHER INFORMATION: oligo

<400> SEQUENCE: 21
cagaggaccu auuaaguuc                                                    19

<210> SEQ ID NO 22
<211> LENGTH: 19
<212> TYPE: RNA
<213> ORGANISM: Artificial sequence
<220> FEATURE:
<223> OTHER INFORMATION: oligo

<400> SEQUENCE: 22
gacccuaacu uggaauuug                                                    19

<210> SEQ ID NO 23
<211> LENGTH: 19
<212> TYPE: RNA
<213> ORGANISM: Artificial sequence
<220> FEATURE:
<223> OTHER INFORMATION: oligo

<400> SEQUENCE: 23
gugugccacc ucauuauua                                                    19

<210> SEQ ID NO 24
<211> LENGTH: 19
<212> TYPE: RNA
<213> ORGANISM: Artificial sequence
<220> FEATURE:
<223> OTHER INFORMATION: oligo

<400> SEQUENCE: 24
gagaguuacu uacaagaau                                                    19

<210> SEQ ID NO 25
<211> LENGTH: 19
<212> TYPE: RNA
<213> ORGANISM: Artificial sequence
<220> FEATURE:
<223> OTHER INFORMATION: oligo

<400> SEQUENCE: 25
caacagagga ccuauuaag                                                    19

<210> SEQ ID NO 26
<211> LENGTH: 19
<212> TYPE: RNA
<213> ORGANISM: Artificial sequence -continued

```
<220> FEATURE:
<223> OTHER INFORMATION: oligo

<400> SEQUENCE: 26
acaggaaagu gaaggcgaa                                                19

<210> SEQ ID NO 27
<211> LENGTH: 19
<212> TYPE: RNA
<213> ORGANISM: Artificial sequence
<220> FEATURE:
<223> OTHER INFORMATION: oligo

<400> SEQUENCE: 27
ggacacagau uuagacuug                                                19

<210> SEQ ID NO 28
<211> LENGTH: 19
<212> TYPE: RNA
<213> ORGANISM: Artificial sequence
<220> FEATURE:
<223> OTHER INFORMATION: oligo

<400> SEQUENCE: 28
gcaguaaccu uucaucaug                                                19

<210> SEQ ID NO 29
<211> LENGTH: 19
<212> TYPE: RNA
<213> ORGANISM: Artificial sequence
<220> FEATURE:
<223> OTHER INFORMATION: oligo

<400> SEQUENCE: 29
gauguuagcu cccuauauc                                                19

<210> SEQ ID NO 30
<211> LENGTH: 19
<212> TYPE: RNA
<213> ORGANISM: Artificial sequence
<220> FEATURE:
<223> OTHER INFORMATION: oligo

<400> SEQUENCE: 30
gcauauaucu agaagguau                                                19

<210> SEQ ID NO 31
<211> LENGTH: 19
<212> TYPE: RNA
<213> ORGANISM: Artificial sequence
<220> FEATURE:
<223> OTHER INFORMATION: oligo

<400> SEQUENCE: 31
gagacacaau cauaucuuu                                                19

<210> SEQ ID NO 32
<211> LENGTH: 19
<212> TYPE: RNA
<213> ORGANISM: Artificial sequence
<220> FEATURE:
<223> OTHER INFORMATION: oligo

<400> SEQUENCE: 32
cuacaucacu uucuuggaa                                                19
```

```
<210> SEQ ID NO 33
<211> LENGTH: 19
<212> TYPE: RNA
<213> ORGANISM: Artificial sequence
<220> FEATURE:
<223> OTHER INFORMATION: oligo

<400> SEQUENCE: 33
ggauaugucu ggguugaaa                                                    19

<210> SEQ ID NO 34
<211> LENGTH: 19
<212> TYPE: RNA
<213> ORGANISM: Artificial sequence
<220> FEATURE:
<223> OTHER INFORMATION: oligo

<400> SEQUENCE: 34
caaacagaau guguccuua                                                    19

<210> SEQ ID NO 35
<211> LENGTH: 19
<212> TYPE: RNA
<213> ORGANISM: Artificial sequence
<220> FEATURE:
<223> OTHER INFORMATION: oligo

<400> SEQUENCE: 35
caaguagccu cuuugacaa                                                    19

<210> SEQ ID NO 36
<211> LENGTH: 19
<212> TYPE: RNA
<213> ORGANISM: Artificial sequence
<220> FEATURE:
<223> OTHER INFORMATION: oligo

<400> SEQUENCE: 36
cguguuaucu gucgcuuug                                                    19

<210> SEQ ID NO 37
<211> LENGTH: 19
<212> TYPE: RNA
<213> ORGANISM: Artificial sequence
<220> FEATURE:
<223> OTHER INFORMATION: oligo

<400> SEQUENCE: 37
gaaggaaccu gaugcuuua                                                    19

<210> SEQ ID NO 38
<211> LENGTH: 19
<212> TYPE: RNA
<213> ORGANISM: Artificial sequence
<220> FEATURE:
<223> OTHER INFORMATION: oligo

<400> SEQUENCE: 38
gaagguaugu ggcauuuau                                                    19

<210> SEQ ID NO 39
<211> LENGTH: 19
<212> TYPE: RNA
<213> ORGANISM: Artificial sequence
<220> FEATURE:
<223> OTHER INFORMATION: oligo
```

```
<400> SEQUENCE: 39
cgaaggaagu aucgaauuu                                          19

<210> SEQ ID NO 40
<211> LENGTH: 19
<212> TYPE: RNA
<213> ORGANISM: Artificial sequence
<220> FEATURE:
<223> OTHER INFORMATION: oligo

<400> SEQUENCE: 40
acggaaggcu caguaauua                                          19

<210> SEQ ID NO 41
<211> LENGTH: 19
<212> TYPE: RNA
<213> ORGANISM: Artificial sequence
<220> FEATURE:
<223> OTHER INFORMATION: oligo

<400> SEQUENCE: 41
agaacgaauu gauguguaa                                          19

<210> SEQ ID NO 42
<211> LENGTH: 19
<212> TYPE: RNA
<213> ORGANISM: Artificial sequence
<220> FEATURE:
<223> OTHER INFORMATION: oligo

<400> SEQUENCE: 42
gggacuggcu aguuaaaca                                          19

<210> SEQ ID NO 43
<211> LENGTH: 19
<212> TYPE: RNA
<213> ORGANISM: Artificial sequence
<220> FEATURE:
<223> OTHER INFORMATION: oligo

<400> SEQUENCE: 43
gcaagaggau uauggcuaa                                          19

<210> SEQ ID NO 44
<211> LENGTH: 19
<212> TYPE: RNA
<213> ORGANISM: Artificial sequence
<220> FEATURE:
<223> OTHER INFORMATION: oligo

<400> SEQUENCE: 44
gaauugaugu guaacugua                                          19

<210> SEQ ID NO 45
<211> LENGTH: 19
<212> TYPE: RNA
<213> ORGANISM: Artificial sequence
<220> FEATURE:
<223> OTHER INFORMATION: oligo

<400> SEQUENCE: 45
ggaaugugcu gcuggcuuu                                          19

<210> SEQ ID NO 46
```

```
<211> LENGTH: 19
<212> TYPE: RNA
<213> ORGANISM: Artificial sequence
<220> FEATURE:
<223> OTHER INFORMATION: oligo

<400> SEQUENCE: 46
acaaggaucu aguugaua                                                  19

<210> SEQ ID NO 47
<211> LENGTH: 19
<212> TYPE: RNA
<213> ORGANISM: Artificial sequence
<220> FEATURE:
<223> OTHER INFORMATION: oligo

<400> SEQUENCE: 47
gaaggaagua ucgaauuua                                                 19

<210> SEQ ID NO 48
<211> LENGTH: 19
<212> TYPE: RNA
<213> ORGANISM: Artificial sequence
<220> FEATURE:
<223> OTHER INFORMATION: oligo

<400> SEQUENCE: 48
ccaagaaagc ugcaucgaa                                                 19

<210> SEQ ID NO 49
<211> LENGTH: 19
<212> TYPE: RNA
<213> ORGANISM: Artificial sequence
<220> FEATURE:
<223> OTHER INFORMATION: oligo

<400> SEQUENCE: 49
gcucaguaau uaguuauga                                                 19

<210> SEQ ID NO 50
<211> LENGTH: 19
<212> TYPE: RNA
<213> ORGANISM: Artificial sequence
<220> FEATURE:
<223> OTHER INFORMATION: oligo

<400> SEQUENCE: 50
auuaggaacc uguuucuua                                                 19

<210> SEQ ID NO 51
<211> LENGTH: 19
<212> TYPE: RNA
<213> ORGANISM: Artificial sequence
<220> FEATURE:
<223> OTHER INFORMATION: oligo

<400> SEQUENCE: 51
aaagugcagu ucaguaaua                                                 19

<210> SEQ ID NO 52
<211> LENGTH: 19
<212> TYPE: RNA
<213> ORGANISM: Artificial sequence
<220> FEATURE:
<223> OTHER INFORMATION: oligo

<400> SEQUENCE: 52
```

```
ggaaaugacc agacacuga                                               19

<210> SEQ ID NO 53
<211> LENGTH: 19
<212> TYPE: RNA
<213> ORGANISM: Artificial sequence
<220> FEATURE:
<223> OTHER INFORMATION: oligo

<400> SEQUENCE: 53
ggauacagcu ggagucagu                                               19

<210> SEQ ID NO 54
<211> LENGTH: 19
<212> TYPE: RNA
<213> ORGANISM: Artificial sequence
<220> FEATURE:
<223> OTHER INFORMATION: oligo

<400> SEQUENCE: 54
gagacuagau ugccuuugu                                               19

<210> SEQ ID NO 55
<211> LENGTH: 19
<212> TYPE: RNA
<213> ORGANISM: Artificial sequence
<220> FEATURE:
<223> OTHER INFORMATION: oligo

<400> SEQUENCE: 55
gcucucugcu guacauauu                                               19

<210> SEQ ID NO 56
<211> LENGTH: 19
<212> TYPE: RNA
<213> ORGANISM: Artificial sequence
<220> FEATURE:
<223> OTHER INFORMATION: oligo

<400> SEQUENCE: 56
ggaggcaggc gacgaguuu                                               19

<210> SEQ ID NO 57
<211> LENGTH: 19
<212> TYPE: RNA
<213> ORGANISM: Artificial sequence
<220> FEATURE:
<223> OTHER INFORMATION: oligo

<400> SEQUENCE: 57
ccagaaagga gacuagauu                                               19

<210> SEQ ID NO 58
<211> LENGTH: 19
<212> TYPE: RNA
<213> ORGANISM: Artificial sequence
<220> FEATURE:
<223> OTHER INFORMATION: oligo

<400> SEQUENCE: 58
guccaaaugu ccuccagaa                                               19

<210> SEQ ID NO 59
<211> LENGTH: 19
<212> TYPE: RNA
```

```
<213> ORGANISM: Artificial sequence
<220> FEATURE:
<223> OTHER INFORMATION: oligo

<400> SEQUENCE: 59
ggagucaguu uagugaugu                                                      19

<210> SEQ ID NO 60
<211> LENGTH: 19
<212> TYPE: RNA
<213> ORGANISM: Artificial sequence
<220> FEATURE:
<223> OTHER INFORMATION: oligo

<400> SEQUENCE: 60
guuaagcgug ucuguauuu                                                      19

<210> SEQ ID NO 61
<211> LENGTH: 19
<212> TYPE: RNA
<213> ORGANISM: Artificial sequence
<220> FEATURE:
<223> OTHER INFORMATION: oligo

<400> SEQUENCE: 61
guacauauuu gagacuagu                                                      19

<210> SEQ ID NO 62
<211> LENGTH: 19
<212> TYPE: RNA
<213> ORGANISM: Artificial sequence
<220> FEATURE:
<223> OTHER INFORMATION: oligo

<400> SEQUENCE: 62
ccuacaagcu uucccagaa                                                      19

<210> SEQ ID NO 63
<211> LENGTH: 19
<212> TYPE: RNA
<213> ORGANISM: Artificial sequence
<220> FEATURE:
<223> OTHER INFORMATION: oligo

<400> SEQUENCE: 63
gaagcaguuu gaagaauua                                                      19

<210> SEQ ID NO 64
<211> LENGTH: 19
<212> TYPE: RNA
<213> ORGANISM: Artificial sequence
<220> FEATURE:
<223> OTHER INFORMATION: oligo

<400> SEQUENCE: 64
gcaguggccu aaauccuuu                                                      19

<210> SEQ ID NO 65
<211> LENGTH: 19
<212> TYPE: RNA
<213> ORGANISM: Artificial sequence
<220> FEATURE:
<223> OTHER INFORMATION: oligo

<400> SEQUENCE: 65
gcugaagucu ggcguaaga                                                      19
```

<210> SEQ ID NO 66
<211> LENGTH: 19
<212> TYPE: RNA
<213> ORGANISM: Artificial sequence
<220> FEATURE:
<223> OTHER INFORMATION: oligo

<400> SEQUENCE: 66
ggcguaagau gauggauuu                                                19

<210> SEQ ID NO 67
<211> LENGTH: 19
<212> TYPE: RNA
<213> ORGANISM: Artificial sequence
<220> FEATURE:
<223> OTHER INFORMATION: oligo

<400> SEQUENCE: 67
gagacagaau agagugaua                                                19

<210> SEQ ID NO 68
<211> LENGTH: 19
<212> TYPE: RNA
<213> ORGANISM: Artificial sequence
<220> FEATURE:
<223> OTHER INFORMATION: oligo

<400> SEQUENCE: 68
gaaagaauuu gaggaaacu                                                19

<210> SEQ ID NO 69
<211> LENGTH: 19
<212> TYPE: RNA
<213> ORGANISM: Artificial sequence
<220> FEATURE:
<223> OTHER INFORMATION: oligo

<400> SEQUENCE: 69
guagaugcau gacuugugu                                                19

<210> SEQ ID NO 70
<211> LENGTH: 19
<212> TYPE: RNA
<213> ORGANISM: Artificial sequence
<220> FEATURE:
<223> OTHER INFORMATION: oligo

<400> SEQUENCE: 70
gcagguuccu uaucuguca                                                19

<210> SEQ ID NO 71
<211> LENGTH: 19
<212> TYPE: RNA
<213> ORGANISM: Artificial sequence
<220> FEATURE:
<223> OTHER INFORMATION: oligo

<400> SEQUENCE: 71
gaauuaaccc uuggugaau                                                19

<210> SEQ ID NO 72
<211> LENGTH: 19
<212> TYPE: RNA
<213> ORGANISM: Artificial sequence
<220> FEATURE:

<223> OTHER INFORMATION: oligo

<400> SEQUENCE: 72
ccacugcugu gugauuaga                                                    19

<210> SEQ ID NO 73
<211> LENGTH: 19
<212> TYPE: RNA
<213> ORGANISM: Artificial sequence
<220> FEATURE:
<223> OTHER INFORMATION: oligo

<400> SEQUENCE: 73
gaaaggagau caacauuuu                                                    19

<210> SEQ ID NO 74
<211> LENGTH: 19
<212> TYPE: RNA
<213> ORGANISM: Artificial sequence
<220> FEATURE:
<223> OTHER INFORMATION: oligo

<400> SEQUENCE: 74
ccaacaauaa gaagaaaga                                                    19

<210> SEQ ID NO 75
<211> LENGTH: 19
<212> TYPE: RNA
<213> ORGANISM: Artificial sequence
<220> FEATURE:
<223> OTHER INFORMATION: oligo

<400> SEQUENCE: 75
gaacugggcu cugguaauu                                                    19

<210> SEQ ID NO 76
<211> LENGTH: 19
<212> TYPE: RNA
<213> ORGANISM: Artificial sequence
<220> FEATURE:
<223> OTHER INFORMATION: oligo

<400> SEQUENCE: 76
gcugcgcaau uacuacuau                                                    19

<210> SEQ ID NO 77
<211> LENGTH: 19
<212> TYPE: RNA
<213> ORGANISM: Artificial sequence
<220> FEATURE:
<223> OTHER INFORMATION: oligo

<400> SEQUENCE: 77
agaaaugugu ugcuaguua                                                    19

<210> SEQ ID NO 78
<211> LENGTH: 19
<212> TYPE: RNA
<213> ORGANISM: Artificial sequence
<220> FEATURE:
<223> OTHER INFORMATION: oligo

<400> SEQUENCE: 78
cggaaugcau caacuacua                                                    19

-continued

```
<210> SEQ ID NO 79
<211> LENGTH: 19
<212> TYPE: RNA
<213> ORGANISM: Artificial sequence
<220> FEATURE:
<223> OTHER INFORMATION: oligo

<400> SEQUENCE: 79
gaaauguguu gcuaguuac                                                    19

<210> SEQ ID NO 80
<211> LENGTH: 19
<212> TYPE: RNA
<213> ORGANISM: Artificial sequence
<220> FEATURE:
<223> OTHER INFORMATION: oligo

<400> SEQUENCE: 80
uguacgaucu caugaaucu                                                    19

<210> SEQ ID NO 81
<211> LENGTH: 19
<212> TYPE: RNA
<213> ORGANISM: Artificial sequence
<220> FEATURE:
<223> OTHER INFORMATION: oligo

<400> SEQUENCE: 81
ugagcaaauu guccugaua                                                    19

<210> SEQ ID NO 82
<211> LENGTH: 19
<212> TYPE: RNA
<213> ORGANISM: Artificial sequence
<220> FEATURE:
<223> OTHER INFORMATION: oligo

<400> SEQUENCE: 82
ccaaaucccu uucaugucu                                                    19

<210> SEQ ID NO 83
<211> LENGTH: 19
<212> TYPE: RNA
<213> ORGANISM: Artificial sequence
<220> FEATURE:
<223> OTHER INFORMATION: oligo

<400> SEQUENCE: 83
cagcagaaca gacauguca                                                    19

<210> SEQ ID NO 84
<211> LENGTH: 19
<212> TYPE: RNA
<213> ORGANISM: Artificial sequence
<220> FEATURE:
<223> OTHER INFORMATION: oligo

<400> SEQUENCE: 84
gaacagacau gucaaggau                                                    19

<210> SEQ ID NO 85
<211> LENGTH: 19
<212> TYPE: RNA
<213> ORGANISM: Artificial sequence
<220> FEATURE:
<223> OTHER INFORMATION: oligo
```

```
<400> SEQUENCE: 85
ggaagaaucu gagcaaauu                                                  19

<210> SEQ ID NO 86
<211> LENGTH: 19
<212> TYPE: RNA
<213> ORGANISM: Artificial sequence
<220> FEATURE:
<223> OTHER INFORMATION: oligo

<400> SEQUENCE: 86
ugaagucacc gcuauguua                                                  19

<210> SEQ ID NO 87
<211> LENGTH: 19
<212> TYPE: RNA
<213> ORGANISM: Artificial sequence
<220> FEATURE:
<223> OTHER INFORMATION: oligo

<400> SEQUENCE: 87
ugauagagaa guagacaaa                                                  19

<210> SEQ ID NO 88
<211> LENGTH: 19
<212> TYPE: RNA
<213> ORGANISM: Artificial sequence
<220> FEATURE:
<223> OTHER INFORMATION: oligo

<400> SEQUENCE: 88
cuacaaggcc guacgacaa                                                  19

<210> SEQ ID NO 89
<211> LENGTH: 19
<212> TYPE: RNA
<213> ORGANISM: Artificial sequence
<220> FEATURE:
<223> OTHER INFORMATION: oligo

<400> SEQUENCE: 89
agaggaugau agagaagua                                                  19

<210> SEQ ID NO 90
<211> LENGTH: 19
<212> TYPE: RNA
<213> ORGANISM: Artificial sequence
<220> FEATURE:
<223> OTHER INFORMATION: oligo

<400> SEQUENCE: 90
aagaagacau ucaagagaa                                                  19

<210> SEQ ID NO 91
<211> LENGTH: 19
<212> TYPE: RNA
<213> ORGANISM: Artificial sequence
<220> FEATURE:
<223> OTHER INFORMATION: oligo

<400> SEQUENCE: 91
gccaagagga ugauagaga                                                  19

<210> SEQ ID NO 92
<211> LENGTH: 19
```

```
<212> TYPE: RNA
<213> ORGANISM: Artificial sequence
<220> FEATURE:
<223> OTHER INFORMATION: oligo

<400> SEQUENCE: 92
agagacagca ccaggcaaa                                                    19

<210> SEQ ID NO 93
<211> LENGTH: 19
<212> TYPE: RNA
<213> ORGANISM: Artificial sequence
<220> FEATURE:
<223> OTHER INFORMATION: oligo

<400> SEQUENCE: 93
gcaaugagaa cuucaagaa                                                    19

<210> SEQ ID NO 94
<211> LENGTH: 19
<212> TYPE: RNA
<213> ORGANISM: Artificial sequence
<220> FEATURE:
<223> OTHER INFORMATION: oligo

<400> SEQUENCE: 94
gaaaccuugu cucuacuaa                                                    19

<210> SEQ ID NO 95
<211> LENGTH: 19
<212> TYPE: RNA
<213> ORGANISM: Artificial sequence
<220> FEATURE:
<223> OTHER INFORMATION: oligo

<400> SEQUENCE: 95
ucaagagaau ucugcauau                                                    19

<210> SEQ ID NO 96
<211> LENGTH: 19
<212> TYPE: RNA
<213> ORGANISM: Artificial sequence
<220> FEATURE:
<223> OTHER INFORMATION: oligo

<400> SEQUENCE: 96
gcaacaaaau gauccuuau                                                    19

<210> SEQ ID NO 97
<211> LENGTH: 19
<212> TYPE: RNA
<213> ORGANISM: Artificial sequence
<220> FEATURE:
<223> OTHER INFORMATION: oligo

<400> SEQUENCE: 97
ugaucaagcu caagaauaa                                                    19

<210> SEQ ID NO 98
<211> LENGTH: 19
<212> TYPE: RNA
<213> ORGANISM: Artificial sequence
<220> FEATURE:
<223> OTHER INFORMATION: oligo

<400> SEQUENCE: 98
```

```
acacguaccu gcagaucua                                                    19

<210> SEQ ID NO 99
<211> LENGTH: 19
<212> TYPE: RNA
<213> ORGANISM: Artificial sequence
<220> FEATURE:
<223> OTHER INFORMATION: oligo

<400> SEQUENCE: 99
ggauuugggu uuucuauaa                                                    19

<210> SEQ ID NO 100
<211> LENGTH: 19
<212> TYPE: RNA
<213> ORGANISM: Artificial sequence
<220> FEATURE:
<223> OTHER INFORMATION: oligo

<400> SEQUENCE: 100
gaaagacaau gagcaacau                                                    19

<210> SEQ ID NO 101
<211> LENGTH: 19
<212> TYPE: RNA
<213> ORGANISM: Artificial sequence
<220> FEATURE:
<223> OTHER INFORMATION: oligo

<400> SEQUENCE: 101
ggagcacccu gaagacuca                                                    19

<210> SEQ ID NO 102
<211> LENGTH: 19
<212> TYPE: RNA
<213> ORGANISM: Artificial sequence
<220> FEATURE:
<223> OTHER INFORMATION: oligo

<400> SEQUENCE: 102
gccaagaucu cagucauuc                                                    19

<210> SEQ ID NO 103
<211> LENGTH: 19
<212> TYPE: RNA
<213> ORGANISM: Artificial sequence
<220> FEATURE:
<223> OTHER INFORMATION: oligo

<400> SEQUENCE: 103
gggcuguggu gucugagua                                                    19

<210> SEQ ID NO 104
<211> LENGTH: 19
<212> TYPE: RNA
<213> ORGANISM: Artificial sequence
<220> FEATURE:
<223> OTHER INFORMATION: oligo

<400> SEQUENCE: 104
gcagcucaau gaaaucaau                                                    19

<210> SEQ ID NO 105
<211> LENGTH: 19
<212> TYPE: RNA
<213> ORGANISM: Artificial sequence
```

```
<220> FEATURE:
<223> OTHER INFORMATION: oligo

<400> SEQUENCE: 105
caagagaagu cguuucauu                                                19

<210> SEQ ID NO 106
<211> LENGTH: 19
<212> TYPE: RNA
<213> ORGANISM: Artificial sequence
<220> FEATURE:
<223> OTHER INFORMATION: oligo

<400> SEQUENCE: 106
cgaagcagcu caaugaaau                                                19

<210> SEQ ID NO 107
<211> LENGTH: 19
<212> TYPE: RNA
<213> ORGANISM: Artificial sequence
<220> FEATURE:
<223> OTHER INFORMATION: oligo

<400> SEQUENCE: 107
gaugaaagcc agucucuga                                                19

<210> SEQ ID NO 108
<211> LENGTH: 19
<212> TYPE: RNA
<213> ORGANISM: Artificial sequence
<220> FEATURE:
<223> OTHER INFORMATION: oligo

<400> SEQUENCE: 108
cuacaacauu aaugggaaa                                                19

<210> SEQ ID NO 109
<211> LENGTH: 19
<212> TYPE: RNA
<213> ORGANISM: Artificial sequence
<220> FEATURE:
<223> OTHER INFORMATION: oligo

<400> SEQUENCE: 109
ggagucaggu agagacgga                                                19

<210> SEQ ID NO 110
<211> LENGTH: 19
<212> TYPE: RNA
<213> ORGANISM: Artificial sequence
<220> FEATURE:
<223> OTHER INFORMATION: oligo

<400> SEQUENCE: 110
gguauugucu ucaguauga                                                19

<210> SEQ ID NO 111
<211> LENGTH: 19
<212> TYPE: RNA
<213> ORGANISM: Artificial sequence
<220> FEATURE:
<223> OTHER INFORMATION: oligo

<400> SEQUENCE: 111
ggaaaaccau uggauauau                                                19
```

```
<210> SEQ ID NO 112
<211> LENGTH: 19
<212> TYPE: RNA
<213> ORGANISM: Artificial sequence
<220> FEATURE:
<223> OTHER INFORMATION: oligo

<400> SEQUENCE: 112
gugcagugcu uuggccaua                                              19

<210> SEQ ID NO 113
<211> LENGTH: 19
<212> TYPE: RNA
<213> ORGANISM: Artificial sequence
<220> FEATURE:
<223> OTHER INFORMATION: oligo

<400> SEQUENCE: 113
ugaugucacu ggcucaaua                                              19

<210> SEQ ID NO 114
<211> LENGTH: 19
<212> TYPE: RNA
<213> ORGANISM: Artificial sequence
<220> FEATURE:
<223> OTHER INFORMATION: oligo

<400> SEQUENCE: 114
gagguauugu cuucaguau                                              19

<210> SEQ ID NO 115
<211> LENGTH: 19
<212> TYPE: RNA
<213> ORGANISM: Artificial sequence
<220> FEATURE:
<223> OTHER INFORMATION: oligo

<400> SEQUENCE: 115
uuagaacugu ccucagauu                                              19

<210> SEQ ID NO 116
<211> LENGTH: 19
<212> TYPE: RNA
<213> ORGANISM: Artificial sequence
<220> FEATURE:
<223> OTHER INFORMATION: oligo

<400> SEQUENCE: 116
gaauuucugg ccaugcuua                                              19

<210> SEQ ID NO 117
<211> LENGTH: 19
<212> TYPE: RNA
<213> ORGANISM: Artificial sequence
<220> FEATURE:
<223> OTHER INFORMATION: oligo

<400> SEQUENCE: 117
cucaauagcu uuagcaauu                                              19

<210> SEQ ID NO 118
<211> LENGTH: 19
<212> TYPE: RNA
<213> ORGANISM: Artificial sequence
<220> FEATURE:
<223> OTHER INFORMATION: oligo
```

```
<400> SEQUENCE: 118
agaccaaucu ggagaggua                                          19

<210> SEQ ID NO 119
<211> LENGTH: 19
<212> TYPE: RNA
<213> ORGANISM: Artificial sequence
<220> FEATURE:
<223> OTHER INFORMATION: oligo

<400> SEQUENCE: 119
cggaugaccu gauucuaaa                                          19

<210> SEQ ID NO 120
<211> LENGTH: 19
<212> TYPE: RNA
<213> ORGANISM: Artificial sequence
<220> FEATURE:
<223> OTHER INFORMATION: oligo

<400> SEQUENCE: 120
uuagaaaugu gcagguuug                                          19

<210> SEQ ID NO 121
<211> LENGTH: 19
<212> TYPE: RNA
<213> ORGANISM: Artificial sequence
<220> FEATURE:
<223> OTHER INFORMATION: oligo

<400> SEQUENCE: 121
agacuauggu ugaaacuaa                                          19

<210> SEQ ID NO 122
<211> LENGTH: 19
<212> TYPE: RNA
<213> ORGANISM: Artificial sequence
<220> FEATURE:
<223> OTHER INFORMATION: oligo

<400> SEQUENCE: 122
gggaagaaga ggaaagcca                                          19

<210> SEQ ID NO 123
<211> LENGTH: 19
<212> TYPE: RNA
<213> ORGANISM: Artificial sequence
<220> FEATURE:
<223> OTHER INFORMATION: oligo

<400> SEQUENCE: 123
gaucagugga gucaagaaa                                          19

<210> SEQ ID NO 124
<211> LENGTH: 19
<212> TYPE: RNA
<213> ORGANISM: Artificial sequence
<220> FEATURE:
<223> OTHER INFORMATION: oligo

<400> SEQUENCE: 124
ggaagaaaac ugugacauu                                          19

<210> SEQ ID NO 125
```

```
<211> LENGTH: 19
<212> TYPE: RNA
<213> ORGANISM: Artificial sequence
<220> FEATURE:
<223> OTHER INFORMATION: oligo

<400> SEQUENCE: 125
ccaaggaacu agaagaugu                                              19

<210> SEQ ID NO 126
<211> LENGTH: 19
<212> TYPE: RNA
<213> ORGANISM: Artificial sequence
<220> FEATURE:
<223> OTHER INFORMATION: oligo

<400> SEQUENCE: 126
gcagucaagu ggaagaaga                                              19

<210> SEQ ID NO 127
<211> LENGTH: 19
<212> TYPE: RNA
<213> ORGANISM: Artificial sequence
<220> FEATURE:
<223> OTHER INFORMATION: oligo

<400> SEQUENCE: 127
gugcagaacu cuacgagaa                                              19

<210> SEQ ID NO 128
<211> LENGTH: 19
<212> TYPE: RNA
<213> ORGANISM: Artificial sequence
<220> FEATURE:
<223> OTHER INFORMATION: oligo

<400> SEQUENCE: 128
agacaaugcu ggcgggaga                                              19

<210> SEQ ID NO 129
<211> LENGTH: 19
<212> TYPE: RNA
<213> ORGANISM: Artificial sequence
<220> FEATURE:
<223> OTHER INFORMATION: oligo

<400> SEQUENCE: 129
gaauguuaga ggagcgaaa                                              19

<210> SEQ ID NO 130
<211> LENGTH: 19
<212> TYPE: RNA
<213> ORGANISM: Artificial sequence
<220> FEATURE:
<223> OTHER INFORMATION: oligo

<400> SEQUENCE: 130
agaagaagau gcagugauu                                              19

<210> SEQ ID NO 131
<211> LENGTH: 19
<212> TYPE: RNA
<213> ORGANISM: Artificial sequence
<220> FEATURE:
<223> OTHER INFORMATION: oligo

<400> SEQUENCE: 131
```

-continued

```
cgaauaugau ccaacaaua                                           19

<210> SEQ ID NO 132
<211> LENGTH: 19
<212> TYPE: RNA
<213> ORGANISM: Artificial sequence
<220> FEATURE:
<223> OTHER INFORMATION: oligo

<400> SEQUENCE: 132
ggacgaauau gauccaaca                                           19

<210> SEQ ID NO 133
<211> LENGTH: 19
<212> TYPE: RNA
<213> ORGANISM: Artificial sequence
<220> FEATURE:
<223> OTHER INFORMATION: oligo

<400> SEQUENCE: 133
uaaggacucu gaagaugua                                           19

<210> SEQ ID NO 134
<211> LENGTH: 19
<212> TYPE: RNA
<213> ORGANISM: Artificial sequence
<220> FEATURE:
<223> OTHER INFORMATION: oligo

<400> SEQUENCE: 134
ggaagcaagu aguaauuga                                           19

<210> SEQ ID NO 135
<211> LENGTH: 19
<212> TYPE: RNA
<213> ORGANISM: Artificial sequence
<220> FEATURE:
<223> OTHER INFORMATION: oligo

<400> SEQUENCE: 135
gcaagaaguu auggaauuc                                           19

<210> SEQ ID NO 136
<211> LENGTH: 19
<212> TYPE: RNA
<213> ORGANISM: Artificial sequence
<220> FEATURE:
<223> OTHER INFORMATION: oligo

<400> SEQUENCE: 136
gaugaugccu ucuauacau                                           19

<210> SEQ ID NO 137
<211> LENGTH: 19
<212> TYPE: RNA
<213> ORGANISM: Artificial sequence
<220> FEATURE:
<223> OTHER INFORMATION: oligo

<400> SEQUENCE: 137
aaaccugucu cuuggauau                                           19

<210> SEQ ID NO 138
<211> LENGTH: 19
<212> TYPE: RNA
```

```
<213> ORGANISM: Artificial sequence
<220> FEATURE:
<223> OTHER INFORMATION: oligo

<400> SEQUENCE: 138
gggcuuucuu uguguauuu                                                    19

<210> SEQ ID NO 139
<211> LENGTH: 19
<212> TYPE: RNA
<213> ORGANISM: Artificial sequence
<220> FEATURE:
<223> OTHER INFORMATION: oligo

<400> SEQUENCE: 139
gcaugcaguu gauuacuuc                                                    19

<210> SEQ ID NO 140
<211> LENGTH: 19
<212> TYPE: RNA
<213> ORGANISM: Artificial sequence
<220> FEATURE:
<223> OTHER INFORMATION: oligo

<400> SEQUENCE: 140
ugcaguugau uacuucuua                                                    19

<210> SEQ ID NO 141
<211> LENGTH: 19
<212> TYPE: RNA
<213> ORGANISM: Artificial sequence
<220> FEATURE:
<223> OTHER INFORMATION: oligo

<400> SEQUENCE: 141
cgauacagcu aauucagaa                                                    19

<210> SEQ ID NO 142
<211> LENGTH: 19
<212> TYPE: RNA
<213> ORGANISM: Artificial sequence
<220> FEATURE:
<223> OTHER INFORMATION: oligo

<400> SEQUENCE: 142
gaaguuaugg aauuccuuu                                                    19

<210> SEQ ID NO 143
<211> LENGTH: 35
<212> TYPE: RNA
<213> ORGANISM: Artificial sequence
<220> FEATURE:
<223> OTHER INFORMATION: oligo

<400> SEQUENCE: 143
acacgaugga auugcuguu uguaccuacu cucga                                   35

<210> SEQ ID NO 144
<211> LENGTH: 21
<212> TYPE: RNA
<213> ORGANISM: Artificial sequence
<220> FEATURE:
<223> OTHER INFORMATION: oligo

<400> SEQUENCE: 144 acagcaaaauu ccaucguguu u                                                21
```

```
<210> SEQ ID NO 145
<211> LENGTH: 16
<212> TYPE: RNA
<213> ORGANISM: Artificial sequence
<220> FEATURE:
<223> OTHER INFORMATION: oligo

<400> SEQUENCE: 145
ucgagaguag guacaa                                                    16
```